United States Patent
Esteves et al.

(10) Patent No.: US 10,711,270 B2
(45) Date of Patent: Jul. 14, 2020

(54) HIGH EFFICIENCY LIBRARY-IDENTIFIED AAV VECTORS

(71) Applicant: University of Massachusetts, Boston, MA (US)

(72) Inventors: Miguel Sena Esteves, Westford, MA (US); Sourav Roy Choudhury, Newton, MA (US)

(73) Assignee: University of Massachusetts, Boston, MA (US)

( * ) Notice: Subject to any disclaimer, the term of this patent is extended or adjusted under 35 U.S.C. 154(b) by 126 days.

(21) Appl. No.: 15/516,585

(22) PCT Filed: Oct. 2, 2015

(86) PCT No.: PCT/US2015/053804
§ 371 (c)(1),
(2) Date: Apr. 3, 2017

(87) PCT Pub. No.: WO2016/054557
PCT Pub. Date: Apr. 7, 2016

(65) Prior Publication Data
US 2018/0265863 A1   Sep. 20, 2018

Related U.S. Application Data

(60) Provisional application No. 62/059,769, filed on Oct. 3, 2014.

(51) Int. Cl.
*C12N 15/10* (2006.01)
*C07K 14/005* (2006.01)
*C40B 40/08* (2006.01)

(52) U.S. Cl.
CPC ........ *C12N 15/1065* (2013.01); *C07K 14/005* (2013.01); *C40B 40/08* (2013.01); *C12N 2750/14122* (2013.01); *C12N 2750/14143* (2013.01); *C12N 2750/14151* (2013.01); *C12N 2750/14171* (2013.01)

(58) Field of Classification Search
CPC .... C07K 14/005; C40B 40/08; C12N 15/1065
See application file for complete search history.

(56) References Cited

U.S. PATENT DOCUMENTS

| | | | |
|---|---|---|---|
| 5,478,745 A | 12/1995 | Samulski et al. |
| 5,871,982 A | 2/1999 | Wilson et al. |
| 6,001,650 A | 12/1999 | Colosi |
| 6,156,303 A | 12/2000 | Russell et al. |
| 6,251,677 B1 | 6/2001 | Wilson et al. |
| 6,485,966 B2 | 11/2002 | Gao et al. |
| 6,498,244 B1 | 12/2002 | Patel et al. |
| 6,544,786 B1 | 4/2003 | Xiao et al. |
| 6,953,690 B1 | 10/2005 | Gao et al. |
| 6,962,815 B2 | 11/2005 | Bartlett |
| 7,022,519 B2 | 4/2006 | Gao et al. |
| 7,198,951 B2 | 4/2007 | Gao et al. |
| 7,235,393 B2 | 6/2007 | Gao et al. |
| 7,238,526 B2 | 7/2007 | Wilson et al. |
| 7,282,199 B2 | 10/2007 | Gao et al. |
| 7,427,396 B2 | 9/2008 | Arbetman et al. |
| 7,456,015 B2 | 11/2008 | Bohn et al. |
| 7,906,111 B2 | 3/2011 | Wilson et al. |
| 8,222,221 B2 | 7/2012 | Corey et al. |
| 8,524,446 B2 | 9/2013 | Gao et al. |
| 8,734,809 B2 | 5/2014 | Gao et al. |
| 9,217,155 B2 | 12/2015 | Gao et al. |
| 9,249,424 B2 | 2/2016 | Wolf et al. |
| 2001/0016355 A1 | 8/2001 | Samulski et al. |
| 2002/0019050 A1 | 2/2002 | Gao et al. |
| 2002/0164783 A1 | 11/2002 | Feldhaus |
| 2002/0192823 A1 | 12/2002 | Bartlett |
| 2003/0040101 A1 | 2/2003 | Wilson et al. |
| 2003/0103939 A1 | 6/2003 | Engelhardt et al. |
| 2003/0110526 A1 | 6/2003 | Brown et al. |
| 2003/0119191 A1 | 6/2003 | Gao et al. |
| 2003/0138772 A1 | 7/2003 | Gao et al. |

(Continued)

FOREIGN PATENT DOCUMENTS

| | | |
|---|---|---|
| EP | 2261242 A1 | 12/2010 |
| EP | 2468891 A2 | 6/2012 |

(Continued)

OTHER PUBLICATIONS

Taganov et al., NF-kappaB-dependent induction of microRNA miR-146, an inhibitor targeted to signaling proteins of innate immune responses. Proc Natl Acad Sci U S A. Aug. 15, 2006;103(33):12481-6. Epub Aug. 2, 2006.

Aartsma-Rus et al., New insights in gene-derived therapy: the example of Duchenne muscular dystrophy. Ann N Y Acad Sci. Dec. 2010;1214:199-212. doi: 10.1111/j.1749-6632.2010.05836.x. Epub Dec. 1, 2010.

Adachi et al., Drawing a high-resolution functional map of adeno-associated virus capsid by massively parallel sequencing. Nat Commun. 2014;5:3075. doi: 10.1038/ncomms4075.

Afione et al., In vivo model of adeno-associated virus vector persistence and rescue. J Virol. May 1996;70(5):3235-41.

Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].

(Continued)

*Primary Examiner* — Antonio Galisteo Gonzalez
(74) *Attorney, Agent, or Firm* — Wolf, Greenfield & Sacks, P.C.

(57) ABSTRACT

Aspects of the disclosure relate to barcoded chimeric adeno-associated virus (AAV) capsid libraries, chimeric capsids and related recombinant AAVs (rAAVs) identified using the libraries. Specifically, the chimeric AAV capsid libraries comprise a plurality of nucleic adds encoding AAV capsid proteins, wherein each nucleic acid (i) encodes a unique AAV capsid protein having distinct polypeptide regions of greater than six amino acids in length that are derived from at least two different AAV serotypes, and (ii) comprises a unique barcode sequence. Further disclosed are methods of preparing an AAV library and identifying AAV capsids tropic for a target tissue.

4 Claims, 65 Drawing Sheets

Specification includes a Sequence Listing.

(56) References Cited

U.S. PATENT DOCUMENTS

| | | |
|---|---|---|
| 2003/0207259 A1 | 11/2003 | Gao et al. |
| 2003/0228282 A1 | 12/2003 | Gao et al. |
| 2004/0101514 A1 | 5/2004 | Liu et al. |
| 2005/0014262 A1 | 1/2005 | Gao et al. |
| 2005/0032219 A1 | 2/2005 | Aubourg et al. |
| 2005/0197313 A1 | 9/2005 | Roelvink |
| 2005/0255086 A1 | 11/2005 | Davidson et al. |
| 2005/0255089 A1 | 11/2005 | Chiorini et al. |
| 2005/0287122 A1 | 12/2005 | Bartlett et al. |
| 2006/0018841 A1 | 1/2006 | Arbetman et al. |
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189515 A1 | 8/2006 | Beliveau et al. |
| 2006/0189564 A1 | 8/2006 | Burright et al. |
| 2006/0228800 A1 | 10/2006 | Lin et al. |
| 2006/0292117 A1 | 12/2006 | Loiler et al. |
| 2007/0004042 A1 | 1/2007 | Gao et al. |
| 2007/0036760 A1 | 2/2007 | Wilson et al. |
| 2007/0243526 A1 | 10/2007 | Kay et al. |
| 2007/0253936 A1 | 11/2007 | Kay et al. |
| 2008/0075737 A1 | 3/2008 | Gao et al. |
| 2008/0075740 A1 | 3/2008 | Gao et al. |
| 2008/0292595 A1 | 11/2008 | Arbetman et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0197338 A1 | 8/2009 | Vandenberghe et al. |
| 2009/0239240 A1 | 9/2009 | Chu |
| 2010/0104561 A1 | 4/2010 | Zhong et al. |
| 2010/0186103 A1 | 7/2010 | Gao et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2011/0306550 A1 | 12/2011 | Vitek et al. |
| 2012/0077870 A1 | 3/2012 | Blanks et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0281516 A1 | 10/2013 | Gao et al. |
| 2013/0323226 A1 | 12/2013 | Wilson et al. |
| 2014/0010861 A1 | 1/2014 | Bancel et al. |
| 2014/0142161 A1 | 5/2014 | Flotte et al. |
| 2014/0142288 A1 | 5/2014 | Davidson et al. |
| 2014/0179770 A1 | 6/2014 | Zhang et al. |
| 2014/0201857 A1 | 7/2014 | Fahrenkrug et al. |
| 2014/0205599 A1 | 7/2014 | Willemsen et al. |
| 2014/0335054 A1 | 11/2014 | Gao et al. |
| 2015/0065560 A1 | 3/2015 | Bjorklund et al. |
| 2015/0258180 A1 | 9/2015 | Mahuran et al. |
| 2016/0000794 A1 | 1/2016 | Chiorini et al. |
| 2016/0017005 A1 | 1/2016 | Asokan et al. |
| 2016/0060624 A1 | 3/2016 | Davidson et al. |
| 2016/0153005 A1 | 6/2016 | Zhang et al. |

FOREIGN PATENT DOCUMENTS

| | | |
|---|---|---|
| JP | 2008-538286 | 10/2008 |
| WO | WO 2003/042397 | 5/2003 |
| WO | WO 2003/093460 | 11/2003 |
| WO | WO 2004/108922 A2 | 12/2004 |
| WO | WO 2005/033321 | 4/2005 |
| WO | WO 2006/031267 A2 | 3/2006 |
| WO | WO 2006/066066 A2 | 6/2006 |
| WO | WO 2006/119432 A2 | 11/2006 |
| WO | WO 2007/127264 A2 | 11/2007 |
| WO | WO 2008/091703 | 7/2008 |
| WO | WO 2008/125846 A2 | 10/2008 |
| WO | WO 2008/150897 A2 | 12/2008 |
| WO | WO 2009/043936 | 4/2009 |
| WO | WO 2009/146178 A1 | 12/2009 |
| WO | WO 2010/027446 A2 | 3/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2012/123430 A1 | 9/2012 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 12/2013 |
| WO | WO 2014/160092 A1 | 10/2014 |
| WO | WO 2014/186746 A1 | 11/2014 |
| WO | WO 2014/197748 A2 | 11/2014 |
| WO | WO 2015/121501 A1 | 8/2015 |
| WO | WO 2015/164786 A1 | 10/2015 |
| WO | WO 2015/168666 A2 | 11/2015 |
| WO | WO 2016/065001 A1 | 4/2016 |
| WO | WO 2017/023724 A1 | 2/2017 |

OTHER PUBLICATIONS

Akache et al., The 37/67-kilodalton laminin receptor is a receptor for adeno-associated virus serotypes 8, 2, 3, and 9. J Virol. Oct. 2006;80(19):9831-6.

Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.

Arbuthnot et al., Hepatic delivery of RNA interference activators for therapeutic application. Curr Gene Ther. Apr. 2009;9(2):91-103.

Asokan et al., The AAV vector toolkit: poised at the clinical crossroads. Mol Ther. Apr. 2012;20(4):699-708. doi: 10.1038/mt.2011.287. Epub Jan. 24, 2012.

Baek et al., AAV-mediated gene delivery in adult GM1-gangliosidosis mice corrects lysosomal storage in CNA and improves survival. PLoS One. Oct. 18, 2010;5(10):e13468. doi: 10.1371/journal.pone.0013468.

Berns et al., Biology of adeno-associated virus. Curr Top Microbiol Immunol. 1996;218:1-23.

Berns et al., Detection of adeno-associated virus (AAV)-specific nucleotide sequences in DNA isolated from latently infected Detroit 6 cells. Virology. Dec. 1975;68(2):556-60.

Beutler et al., AAV for pain: steps towards clinical translation. Gene Ther. Apr. 2009;16(4):461-9. Epub Mar. 5, 2009.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.

Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.

Brantly et al., Phase I trial of intramuscular injection of a recombinant adeno-associated virus serotype 2 alpha1-antitrypsin (AAT) vector in AAT-deficient adults. Hum Gene Ther. Dec. 2006;17(12):1177-86.

Buning et al., Receptor targeting of adeno-associated virus vectors. Gene Ther. Jul. 2003;10(14):1142-51.

Calcedo et al., Worldwide epidemiology of neutralizing antibodies to adeno-associated viruses. J Infect Dis. Feb. 1, 2009;199(3):381-90.

Carter et al., Adeno-associated virus gene expression and regulation. CRC Handbook of parvoviruses. 1990:227-54.

Carter, in "Handbook of Parvoviruses", ed., P. Tijsser, CRC Press, pp. 155-168 (1990).

Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.

Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.

(56) References Cited

OTHER PUBLICATIONS

Chadderton et al., Improved retinal function in a mouse model of dominant retinitis pigmentosa following AAV-delivered gene therapy. Mol Ther. Apr. 2009;17(4):593-9. Epub Jan. 27, 2009.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Efficient transduction of vascular endothelial cells with recombinant adeno-associated virus serotype 1 and 5 vectors. Hum Gene Ther. Feb. 2005;16(2):235-47.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.
Chiorini et al., Cloning and characterization of adeno-associated virus type 5. J Virol. Feb. 1999;73(2):1309-19.
Chirmule et al., Humoral immunity to adeno-associated virus type 2 vectors following administration to murine and nonhuman primate muscle. J Virol. Mar. 2000;74(5):2420-5.
Choi et al., Effects of adeno-associated virus DNA hairpin structure on recombination. J Virol. Jun. 2005;79(11):6801-7.
Choudhury et al., Identification of Novel vectors capable of CNS transduction in adult mice after single round selection using DNA shuffled AAV capsid library. Mol Ther. May 1, 2003;21(1):S1.
Choudhury et al., In Vivo Selection Yields AAV-B1 Capsid for Central Nervous System and Muscle Gene Therapy. Mol Ther. Aug. 2016;24(7):1247-57. doi: 10.1038/mt.2016.84. Epub Apr. 27, 2016.
Cideciyan et al., Human RPE65 gene therapy for Leber congenital amaurosis: persistence of early visual improvements and safety at 1 year. Hum Gene Ther. Sep. 2009;20(9):999-1004.
Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.
Conlon et al., Ribozyme Approaches towards Down-Regulation of Pi*Z Mutant Human a-1 Anti-Trypsin. Mol. Therapy. 2004;9:S333. Abstract 875.
Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.
Cruz et al., The promise of gene therapy for the treatment of alpha-1 antitrypsin deficiency. Pharmacogenomics. Sep. 2007;8(9):1191-8.
Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.
Daya et al., Gene therapy using adeno-associated virus vectors. Clin Microbiol Rev. Oct. 2008;21(4):583-93. doi: 10.1128/CMR.00008-08.
Dominov et al., A novel dysferlin mutant pseudoexon bypassed with antisense oligonucleotides. Ann Clin Transl Neurol. Sep. 2014;1(9):703-20. doi: 10.1002/acn3.96. Epub Sep. 27, 2014.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Ehlert et al., Cellular toxicity following application of adeno-associated viral vector-mediated RNA interference in the nervous system. BMC Neurosci. Feb. 18, 2010;11:20.
Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.

Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fischer et al., Successful transgene expression with serial doses of aerosolized rAAV2 vectors in rhesus macaques. Mol Ther. Dec. 2003;8(6):918-26.
Fisher et al., Transduction with recombinant adeno-associated virus for gene therapy is limited by leading-strand synthesis. J Virol. Jan. 1996;70(1):520-32.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Flotte, Recombinant adeno-associated virus (AAV) gene therapy vectors for, cystic fibrosis (CF), alpha-1-antitrypsin deficiency (AAT) and fatty oxidation disorders (FAO). Umass Medical School. Interdisciplinary Graduate Program. Last accessed at http://www.umassmed.edu/igp/faculty/flotte.cfm?start=0& on Aug. 27, 2009.
Foust et al., Intravascular AAV9 preferentially targets neonatal-neurons and adult-astrocytes. Nature Biotechnology, 27; 59-65 2009.
Foust et al., Over the barrier and through the blood: to CNS delivery we go. Cell Cycle. Dec. 15, 2009;8(24):4017-8.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Fu et al., Self-complementary adeno-associated virus serotype 2 vector: global distribution and broad dispersion of AAV-mediated transgene expression in mouse brain. Mol Ther. Dec. 2003;8(6):911-7.
Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.
Gao et al., Adeno-associated viruses undergo substantial evolution in primates during natural infections. Proc Natl Acad Sci U S A. May 13, 2003;100(10):6081-6. Epub Apr. 25, 2003.
Gao et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060.
Gao et al., Biology of AAV serotype vectors in liver-directed gene transfer to nonhuman primates. Mol Ther. Jan. 2006;13(1):77-87. Epub Oct. 10, 2005.
Gao et al., Clades of Adeno-associated viruses are widely disseminated in human tissues. J Virol. Jun. 2004;78(12):6381-8.
Gao et al., Erythropoietin gene therapy leads to autoimmune anemia in macaques. Blood. May 1, 2004;103(9):3300-2. Epub Dec. 24, 2003.
Gao et al., Inadvertent gene transfer of co-packaged rep and cap sequences during the production of AAV vector and its potential impact on vector performance. Molecular Therapy. May 2008;16(Suppl. 1):S105-S106. Abstract 279.
Gao et al., New recombinant serotypes of AAV vectors. Curr Gene Ther. Jun. 2005;5(3):285-97.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Gao et al., Purification of recombinant adeno-associated virus vectors by column chromatography and its performance in vivo. Hum Gene Ther. Oct. 10, 2000;11(15):2079-91.
Gao et al., RAAV-mediated targeting in adult mice and its potential in generating animal models of tissue-specific somatic transgenics or knock down. Molecular Therapy. May 2008;16(1):S118-S119. Abstract 316.
Genbank Submission; Accession No. ADZ26851; Wilson et al.; Jun. 30, 2005.
Genbank Submission; Accession No. AF028705.1; Rutledge et al.; Jan. 12, 1998.

(56) References Cited

OTHER PUBLICATIONS

Genbank Submission; NCBI, Accession No. AAB95450; Rutledge et al.; Jan. 12, 1998.
Genbank Submission; NCBI, Accession No. AAS99264; Gao et al.; Jun. 24, 2004.
Genbank Submission; NCBI, Accession No. ABA71701; Schmidt et al.; May 10, 2006.
Genbank Submission; NCBI, Accession No. ACB55301; Vandenberghe et al.; Jul. 31, 2008.
Genbank Submission; NCBI, Accession No. ACB55310; Vandenberghe et al.; Jul. 31, 2008.
Genbank Submission; NCBI, Accession No. NP_049542; Xiao et al.; Mar. 11, 2010.
Genbank Submission; NCBI, Accession No. YP_680426; Ruffing et al.; Nov. 19, 2010.
Grimm et al., Fatality in mice due to oversaturation of cellular microRNA/short hairpin RNA pathways. Nature. May 25, 2006;441(7092):537-41.
Grimm, Small silencing RNAs: state-of-the-art. Adv Drug Deliv Rev. Jul. 25, 2009;61(9):672703. doi: 10.1016/j.addr.2009.05.002. Epub May 7, 2009.
Hauswirth et al., Treatment of leber congenital amaurosis due to RPE65 mutations by ocular subretinal injection of adeno-associated virus gene vector: short-term results of a phase I trial. Hum Gene Ther. Oct. 2008;19(10):979-90.
Hernandez et al., Latent adeno-associated virus infection elicits humoral but not cell-mediated immune responses in a nonhuman primate model. J Virol. Oct. 1999;73(10):8549-58.
Hildinger et al., Hybrid vectors based on adeno-associated virus serotypes 2 and 5 for muscle-directed gene transfer. J Virol. Jul. 2001;75(13):6199-203.
Iida et al., Systemic Delivery of Tyrosine-Mutant AAV Vectors Results in Robust Transduction of Neurons in Adult Mice. BioMed Res Int. 2013;2013.
Iwamoto et al., Global diffuse distribution in the brain and efficient gene delivery to the dorsal root ganglia by intrathecal injection of adeno-associated viral vector serotype 1. J Gene Med. Jun. 2009;11(6):498-505. doi: 10.1002/jgm.1325.
Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.
Kaspar et al., Retrograde viral delivery of IGF-1 prolongs survival in a mouse ALS model. Science. Aug. 8, 2003;301(5634):839-42.
Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.
Kotin et al., Organization of adeno-associated virus DNA in latently infected Detroit 6 cells. Virology. Jun. 1989;170(2):460-7.
Kotin et al., Site-specific integration by adeno-associated virus. Proc Natl Acad Sci U S A. Mar. 1990;87(6):2211-5.
Lawlor et al., Efficient gene delivery and selective transduction of glial cells in the mammalian brain by AAV serotypes isolated from nonhuman primates. Mol Ther. Oct. 2009;17(10):1692-702. doi: 10.1038/mt.2009.170.
Lebherz et al., Gene therapy with novel adeno-associated virus vectors substantially diminishes atherosclerosis in a murine model of familial hypercholesterolemia. J Gene Med. Jun. 2004;6(6):663-72.
Leone et al., Aspartoacylase gene transfer to the mammalian central nervous system with therapeutic implications for Canavan disease. Ann Neurol. Jul. 2000;48(1):27-38. Erratum in: Ann Neurol Sep. 2000;48(3):398. Bilianuk L [corrected to Bilaniuk L].
Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.
Li et al., Ex vivo transduction and transplantation of bone marrow cells for liver gene delivery of alpha1-antitrypsin. Mol Ther. Aug. 2010;18(8):1553-8. Epub Jun. 15, 2010.
Li et al., Protein trans-splicing as a means for viral vector-mediated in vivo gene therapy. Hum Gene Ther. Sep. 2008;19(9):958-64. doi: 10.1089/hum.2008.009.
Lin et al., Impact of preexisting vector immunity on the efficacy of adeno-associated virus-based HIV-1 Gag vaccines. Hum Gene Ther. Jul. 2008;19(7):663-9.
Liu et al., Biological Differences in rAAV Transduction of Airway Epithelia in Humans and in Old World Non-human Primates. Mol Ther. Dec. 2007;15(12):2114-23. Epub Jul. 31, 2007.
Liu et al., Comparative biology of rAAV transduction in ferret, pig and human airway epithelia. Gene Ther. Nov. 2007;14(21):1543-8. Epub Aug. 30, 2007.
Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.
Loiler et al., Targeting recombinant adeno-associated virus vectors to enhance gene transfer to pancreatic islets and liver. Gene Ther. Sep. 2003;10(18):1551-8.
Lowenstein, Crossing the rubicon. Nat Biotechnol. Jan. 2009;27(1):42-4.
Lux et al., Green fluorescent protein-tagged adeno-associated virus particles allow the study of cytosolic and nuclear trafficking. J Virol. Sep. 2005;79(18):11776-87.
Maguire et al., Directed evolution of adeno-associated virus for glioma cell transduction. J Neurooncol. Feb. 2010;96(3):337-47. doi:10.1007/s11060-009-9972-7. Epub Jul. 19, 2009.
Maguire et al., Gene therapy for the nervous system: challenges and new strategies. Neurotherapeutics. Oct. 2014;11(4):817-39. doi: 10.1007/s13311-014-0299-5.
Mandel et al., Recombinant adeno-associated viral vectors as therapeutic agents to treat neurological disorders. Mol Ther. Mar. 2006;13(3):463-83. Epub Jan. 18, 2006.
Manfredsson et al., AAV9: a potential blood-brain barrier buster. Mol Ther. Mar. 2009;17(3):403-5.
Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592. Rasko, John [corrected to Rasko, John JE]; Rustagi, Pradip K [added].
Matalon et al., Adeno-associated virus-mediated aspartoacylase gene transfer to the brain of knockout mouse for canavan disease. Mol Ther. May 2003;7(5 Pt 1):580-7.
McCarty et al., Adeno-associated virus terminal repeat (TR) mutant generates self-complementary vectors to overcome the rate-limiting step to transduction in vivo. Gene Ther. Dec. 2003;10(26):2112-8.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
McCarty, Self-complementary AAV vectors; advances and applications. Mol Ther. Oct. 2008;16(10):1648-56. Epub Aug. 5, 2008.
Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.
Mingozzi et al., CD8(+) T-cell responses to adeno-associated virus capsid in humans. Nat Med. Apr. 2007;13(4):419-22. Epub Mar. 18, 2007.
Moffett et al., N-Acetylaspartate in the CNS: from neurodiagnostics to neurobiology. Prog Neurobiol. Feb. 2007;81(2):89-131. Epub Jan. 5, 2007.
Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.

(56) References Cited

OTHER PUBLICATIONS

Mueller et al., In Vivo AAV Delivered Allele Specific shRNA for the Knockdown of Alpha-1 Antitrypsin. Molecular Therapy May 2010;18(1):S22. Abstract 53.
Mueller et al., In Vivo Allele Specific Knockdown of Mutant Alpha-1 Antitrypsin Using Recombinant AAV Delivered shRNA. Molecular Therapy May 2009;17(1):S313. Abstract 817.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., The pros and cons of immunomodulatory IL-10 gene therapy with recombinant AAV in a Cftr−/−-dependent allergy mouse model. Gene Ther. Feb. 2009;16(2):172-83. Epub Sep. 25, 2008.
Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.
NCBI BLAST Protein Sequence. RID-09JSKF33114. Alignment of Seq ID Nos. 87, 179. 2016.
O'Reilly et al., RNA interference-mediated suppression and replacement of human rhodopsin in vivo. Am J Hum Genet. Jul. 2007;81(1):127-35. Epub May 23, 2007.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.
Scallan et al., Human immunoglobulin inhibits liver transduction by AAV vectors at low AAV2 neutralizing titers in SCID mice. Blood. Mar. 1, 2006;107(5):1810-7. Epub Oct. 25, 2005.
Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi:10.4049/jimmunol.1501048.
Schnepp et al., Characterization of adeno-associated virus genomes isolated from human tissues. J Virol. Dec. 2005;79(23):14793-803.
Seiler et al., Adeno-associated virus types 5 and 6 use distinct receptors for cell entry. Hum Gene Ther. Jan. 2006;17(1):10-9.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.
Song et al., Intramuscular administration of recombinant adeno-associated virus 2 alpha-1 antitrypsin (rAAV-SERPINA1) vectors in a nonhuman primate model: safety and immunologic aspects. Mol Ther. Sep. 2002;6(3):329-35.
Stoica et al., Targeting Human SOD1 Using AAV mediated RNAi in a mouse model of amyotrophic lateral sclerosis. Mol ther. Jun. 2013;21(1):S149.
Storek et al., Intrathecal long-term gene expression by self-complementary adeno-associated virus type 1 suitable for chronic pain studies in rats. Mol Pain. Jan. 30, 2006;2:4.
Tenenbaum et al., Recombinant AAV-mediated gene delivery to the central nervous system. J Gene Med. Feb. 2004;6 Suppl 1:S212-22.
Tomar et al., Use of adeno-associated viral vector for delivery of small interfering RNA. Oncogene. Aug. 28, 2003;22(36):5712-5.
Towne et al., Systemic AAV6 delivery mediating RNA interference against SOD1: neuromuscular transduction does not alter disease progression in fALS mice. Mol Ther. Jun. 2008;16(6):1018-25. doi:10.1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
UNIPROT Submission; Accession No. A8IGP7; Nov. 13, 2013.
UNIPROT Submission; Accession No. H3GK32; Feb. 6, 2013.
UNIPROT Submission; Accession No. T2BRA8; Nov. 13, 2013.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.
Virella-Lowell et al., Enhancing rAAV vector expression in the lung. J Gene Med. Jul. 2005;7(7):842-50.
Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.
Wang et al., Somatically Repairing Compound Heterozygous Recessive Mutations by Chromosomal Cut-and-Paste for in Vivo Gene Therapy. May 2016. 24(1):S289. Abstract 733.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wang et al., The design of vectors for RNAi delivery system. Curr Pharm Des. 2008;14(13):1327-40.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.
Wein et al., Efficient bypass of mutations in dysferlin deficient patient cells by antisense-induced exon skipping. Hum Mutat. Feb. 2010;31(2):136-42. doi: 10.1002/humu.21160.
Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.
Weismann, Approaches and Considerations Towards a Safe and Effective Adeno-Associated Virus Mediated Therapeutic Intervention for GM 1-Gangliosidosis: A Dissertation. University Massachusetts Medical School. Aug. 5, 2014.
Wu et al., Alpha2,3 and alpha2,6 N-linked sialic acids facilitate efficient binding transduction by adeno-associated virus types 1 and 6. J Virol. Sep. 2006;80(18):9093-103.
Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.
Xie et al., Characterization of positioning effect of pol III-shRNA transcription unit in scAAV vector genome on the packaging efficiency and functionality of shRNA silencing. Molecular Therapy. May 2010;18(1): S262. Abstract 671.
Xie et al., MicroRNA regulated tissue specific transduction by rAAV vector. Molecular Therapy. May 2009;17(1): S279. Abstract 732.

(56) References Cited

OTHER PUBLICATIONS

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.
Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.
Xu et al., Delivery of MDR1 small interfering RNA by self-complementary recombinant adeno-associated virus vector. Mol Ther. Apr. 2005;11(4):523-30.
Yan et al., Unique biologic properties of recombinant AAV1 transduction in polarized human airway epithelia. J Biol Chem. Oct. 6, 2006;281(40):29684-92. Epub Aug. 9, 2006.
Zabner et al., Adeno-associated virus type 5 (AAV5) but not AAV2 binds to the apical surfaces of airway epithelia and facilitates gene transfer. J Virol. Apr. 2000;74(8):3852-8.
Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.
Zhong et al., Chimpanzee-derived novel natural variants of aav9: vector development and interrogation of correlations between capsid structure and vector biology. Molecular Therapy. May 2010;18(1): S24. Abstract 58.
Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.
Zolotukhin et al., Production and purification of serotype 1, 2, and 5 recombinant adeno-associated viral vectors. Methods. Oct. 2002;28(2):158-67.
Lisowski et al., Selection and evaluation of clinically relevant AAV variants in a xenograft liver model. Nature. Feb. 20, 2014;506(7488):382-6. doi: 10.1038/nature12875. Epub Dec. 25, 2013.
Ward et al., Chimeric AAV Cap sequences alter gene transduction. Virology. Apr. 10, 2009;386(2):237-48. doi: 10.1016/j.virol.2009.01.012. Epub Feb. 15, 2009.

AAV9

B1

B2

AAV9

B2

AAV9 rAAV-B1 rAAV-B2

Cerebrum

Liver

AAV9 rAAV-B1 rAAV-B2 rAAV-B1 rAAV-B2

```
       1,910      1,920      1,930      1,940      1,950      1,960      1,970      1,980      1,990      2,000      2,010      2,020
GATGGGGCGGGCTTTGGCCTGAAACATCCTGCGCCTCAGATCCTGATCAAGAACACGGCCTGTACTGGCGATCCTCGGACCACCTTCAACCAGTCAAAGCTCAAACTCTTTCATCACGCAAT
}AAV8/rh43{
       2,030      2,040      2,050      2,060      2,070      2,080      2,090      2,100      2,110      2,120      2,130      2,140
ACAGCACCGGACAGTCAGCCTGGAAATCGAGTGGGAGCTGCAGAGAAGAAAAACAGCCTGAAGCCCTGAGATCCAGTACCAGTACCAGTACCTTCCAACTCCAACTACAACTACAAATCTACAAATGTGGACTTT
}AAV8/rh43{   }AAVrh8/rh10{                                        }AAV8/rh43{                                  }AAVrh8{
       2,150      2,160      2,170      2,180      2,190      2,200  2,210 2,214
GCTGTCAACACGGAGGGGTTTATAGCCGAGCCCTTCGCGCCCCATTGGCACCCCGTTACCTTCACCCGCAACCTGTAA
}AAVrh8{
```

GCGGCGTTGGCCTCAAACGTGATCCTCGGACCGGCTGGGCGCTCAATGAACAACGTCAGTTCTTCAATCGGAGGAATCA

CGACCGGAGGAGCTCAGCGCTGTGAATTGAATGGGAGCTCAGAGGAAACAGAAGTCGGAGATCCAGATCCTCAATCTCGA

GTTAATTACAGAAGGGTGTACTACTCTGAACCCGCCATTGGCACCCGGTTTCCTTCCTCACCCGGTAATCTGTAA

Triceps

Quadriceps

Heart

Pancreas

Fold change 2.0 over AAV9

AAV-B1
AAV9

Fold change 14.1 over AAV9

Lung

Brain

Pairwise homology 97.3%

Liver

Nucleotide alignment

Amino acid alignment 88.6%

- ☐ AAV1
- ☐ AAV2
- ☐ AAV4
- ☐ AAV6
- ☐ AAV8
- ☐ AAV9
- ☒ AAVrh8
- ☐ AAVrh10
- ☐ AAVrh39
- ☒ AAVrh43

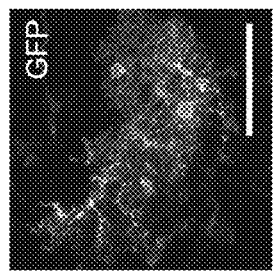
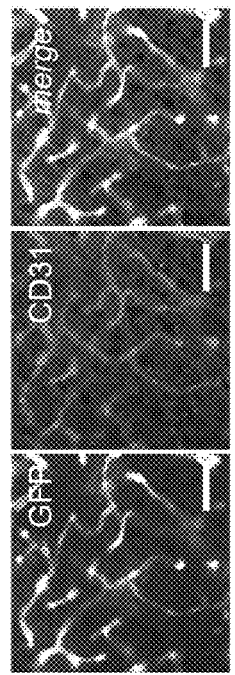
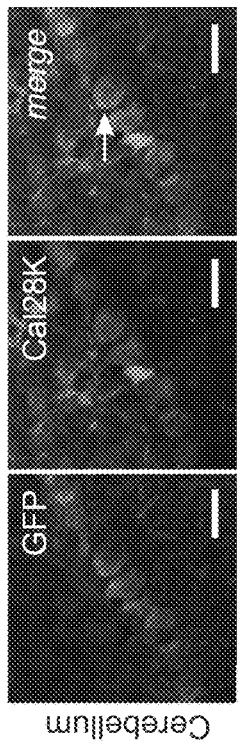
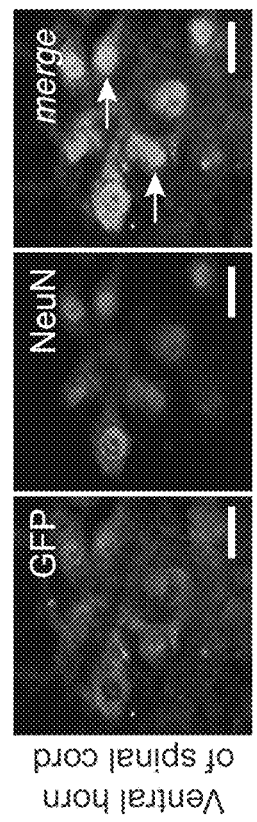
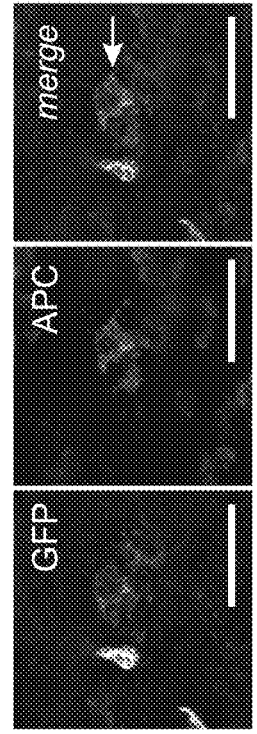
FIG. 32G
FIG. 32E
FIG. 32C
FIG. 32F
FIG. 32D

FIG. 33A

```
AAV8    161 GKKGQQPARKRLNFGQTGDSESVPDPQPLGEPPAAPSG-VGPNTMAAGGGAPMADNNEGADGVGSSSGNWHCDSTWLGDR 239
AAV-B1  160 GKKGQQPARKRLNFGQTGDSESVPDPQPLGEPPAAPSG-VGPNTMAAGGGAPMADNNEGADGVGNSSGNWHCDSTWMGDR 238
AAV1    160 GKTGQQPAKKRLNFGQTGDSESVPDPQPLGEPPATPAA-VGPTTMASGGGAPMADNNEGADGVGNASGNWHCDSTWLGDR 238
AAV2    160 GKAGQQPARKRLNFGQTGDADSVPDPQPLGQPPAAPSG-VGPTTMASGGGAPMADNNEGADGVGNSSGNWHCDSTWMGDR 238
AAV5    157 ---EEDSKP----STSSDAEAGPSGSQQLIPAQPASSLGADTMSAGGGGPLGDNNQGADGVGNASGDWHCDSTWMGDR 228
AAV6    160 GKTGQQPAKKRLNFGQTGDSESVPDPQPLGEPPATPAA-VGPTTMASGGGAPMADNNEGADGVGNASGNWHCDSTWLGDR 238
AAV7    161 GKTGQQPAKKRLNFGQTGDSESVPDPQPLGEPPAAPSS-VGSGTVAAGGGGAPMADNNEGADGVGNSSGNWHCDSTWLGDR 239
AAV9    160 GKSGAQPAKKRLNFGQTGDTESVPDPQPIGEPPAAPSG-VGSLTMASGGGAPVADNNEGADGVGSSSGNWHCDSQWLGDR 238
AAVrh10 161 GKKGQAPAKKRLNFGQTGDSESVPDPQPIGEPPAGPSG-LGSGTMAAGGGGAPMADNNEGADGVGSSSGNWHCDSTWLGDR 239

βB                           i                      βC              α1         βD
AAV8    240 VITTSTRTWALPTYNNHLYKQISNGTSGGATNDNTYFGYSTPWGYFDFNRFHCHFSPRDWQRLINNNWGFRPKRLSFKLF 319
AAV-B1  239 VITTSTRTWALPTYNNHLYKQISNGTSGGSTNDNTYFGYSTPWGYFDFNRFHCHFSPRDWQRLINNNWGFRPKRLSFKLF 318
AAV1    239 VITTSTRTWALPTYNNHLYKQISSASTG-ASNDNHYFGYSTPWGYFDFNRFHCHFSPRDWQRLINNNWGFRPKRLNFKLF 317
AAV2    239 VITTSTRTWALPTYNNHLYKQISSQS-G-ASNDNHYFGYSTPWGYFDFNRFHCHFSPRDWQRLINNNWGFRPKRLNFKLF 316
AAV5    229 VVTKSTRTWVLPSYNNHQYREIKSGSVD-GSNANAYFGYSTPWGYFDFNRFHSHWSPRDWQRLINNYWGFRPRSLRVKIF 307
AAV6    239 VITTSTRTWALPTYNNHLYKQISSASTG-ASNDNHYFGYSTPWGYFDFNRFHCHFSPRDWQRLINNNWGFRPKRLNFKLF 317
AAV7    240 VITTSTRTWALPTYNNHLYKQISSETA-GSTNDNTYFGYSTPWGYFDFNRFHCHFSPRDWQRLINNNWGFRPKKLRFKLF 318
AAV9    239 VITTSTRTWALPTYNNHLYKQISNSTSGGSSNDNAYFGYSTPWGYFDFNRFHCHFSPRDWQRLINNNWGFRPKRLNFKLF 318
AAVrh10 240 VITTSTRTWALPTYNNHLYKQISNGTSGGSTNDNTYFGYSTPWGYFDFNRFHCHFSPRDWQRLINNNWGFRPKRLNFKLF 319
```

```
                        V                                              VI                       VII
AAV8    477 A-KNWLPGPCYRQQRVSTTTGQNNNSNFAWTAGTKYHLNGRNSLANPGIAMATHKDDEERFFPSNGILIFGKQNAARDNA 555
AAV-B1  476 A-KNWLPGPCYRQQRVSTTTGQNNNSNSAWTAGTKYHLNGRNSLANPGIAMATHKDDEERFFPSNGILIFGKQNAARDNA 554
AAV1    475 P-KNWLPGPCYRQQRVSKTKTDNNNSNFTWTGASKYNLNGRESIINPGTAMASHKDDEDKFFPMSGVMIFGKESAGASNT 553
AAV2    474 S-RNWLPGPCYRQQRVSKTSADNNNSEYSWTGATKYHLNGRDSLVNPGPAMASHKDDEEKFFPQSGVLIFGKQGSEKTNV 552
AAV5    460 TYKMWFPGPMGRTQGWNLGSGVNRASVSAFATTNRMELEGASYQVPPQPNGMTNNLQGSNTYALENTMIFNSQPANPGTT 539
AAV6    475 P-RNWLPGPCYRQQRVSKTKTDNNNSNFTWTGASKYNLNGRESIINPGTAMASHKDDKFFPMSGVMIFGKESAGASNT 553
AAV7    477 A-KNWLPGPCFRQQRVSKTLDQNNNSNFAWTGATKYHLNGRNSLVNPGVAMATHKDDEDRFFPSSGVLIFGKTGA-TNKT 554
AAV9    475 G-RNYIPGPSYRQQRVSTTVTQNNNSEFAWPGASSWALNGRNSLMNPGPAMASHKEGEDRFFPLSGSLIFGKQGTGRDNV 553
AAVrh10 477 A-KNWLPGPCYRQQRVSTTLSQNNNSNFAWTGATKYHLNGRDSLVNPGVAMATHKDDEERFFPSSGVLMFGKQGAGKDNV 555

VIII
AAV8    556 DY---SDVMLTSEEEIKTTNPVATEEYGIVADNLQQQNTAPQIGTVNSQGALPGMVWQNRDVYLQGPIWAKIPHTDGNFH 632
AAV-B1  555 DY---SDVMLTSEEEIKTTNPVATEEYGIVADNLQQQNTAPQIGTVNSQGALPGMVWQNRDVYLQGPIWAKIPHTDGNFH 631
AAV1    554 AL---DNVMITDEEEIKATNPVATERFGTVAVNFQSSSTDPATGDVHAMGALPGMVWQDRDVYLQGPIWAKIPHTDGHFH 630
AAV2    553 DI---EKVMITDEEEIRTTNPVATEQYGSVSTNLQRGNRQAATADVNTQGVLPGMVWQDRDVYLQGPIWAKIPHTDGHFH 629
AAV5    540 ATYLEGNMLITSESETQPVNRVAYNVGGQMATNNQSTTAPATGTYNLQEIVPGSVWMERDVYLPGSVWMERDVYLQGPIWAKIPETGAHFH 619
AAV6    554 AL---DNVMITDEEEIKATNPVATERFGTVAVNLQSSSTDPATGDVHVMGALPGMVWQDRDVYLQGPIWAKIPHTDGHFH 630
AAV7    555 TL---ENVLMTNEEEIRPTNPVATEEYGIVSSNLQAANTAAQTQVVNNQGALPGMVWQNRDVYLQGPIWAKIPHTDGNFH 631
AAV9    554 DA---DKVMITNEEEIKTTNPVATESYGQVATNHQSAQAQAQTGWVQNQGILPGMVWQDRDVYLPGMVWQDRDVYLQGPIWAKIPHTDGNFH 630
AAVrh10 631 DY---SSVMLTSEEEIKTTNPVATEQYGVVADNLQQQNAAPIVGAVNSQGALPGMVWQNRDVYLQGPIWAKIPHTDGNFH 632
```

FIG. 33D

|       |     | βH                                                          | β1                                                    | IX          |     |
|-------|-----|-------------------------------------------------------------|-------------------------------------------------------|-------------|-----|
| AAV8   | 633 | PSPLMGGFGLKHPPPQILIKNTPVPADPPTTFNQSKLNSFITQYSTGQVSVEIEWELQKENSKRWNPEIQYTSNYYKSTS | 712 |
| AAV-B1 | 632 | PSPLMGGFGLKHPPPQILIKNTPVPADPPTTFNQSKLNSFITQYSTGQVSVEIEWELQKENSKRWNPEIQYTSNYYKSTS | 711 |
| AAV1   | 631 | PSPLMGGFGLKHPPPQILIKNTPVPANPPAEFSATKFASFITQYSTGQVSVEIEWELQKENSKRWNPEVQYTSNYAKSAN | 710 |
| AAV2   | 630 | PSPLMGGFGLKHPPPQILIKNTPVPANPSTTFSAAKFASFITQYSTGQVSVEIEWELQKENSKRWNPEIQYTSNYNKSVN | 709 |
| AAV5   | 620 | PSPAMGGFGLKHPPPMMLIKNTPVPGN-ITSFSDVPVSSFITQYSTGQVTVEMEWELKKENSKRWNPEIQYTNNYNDPQF | 698 |
| AAV6   | 631 | PSPLMGGFGLKHPPPQILIKNTPVPANPPAEFSATKFASFITQYSTGQVSVEIEWELQKENSKRWNPEVQYTSNYAKSAN | 710 |
| AAV7   | 632 | PSPLMGGFGLKHPPPQILIKNTPVPANPPEVFTPAKFASFITQYSTGQVSVEIEWELQKENSKRWNPEIQYTSNFEKQTG | 711 |
| AAV9   | 631 | PSPLMGGFGMKHPPPQILIKNTPVPADPPTAFNKDKLNSFITQYSTGQVSVEIEWELQKENSKRWNPEIQYTSNYYKSNN | 710 |
| AAVrh10| 633 | PSPLMGGFGLKHPPPQILIKNTPVPADPPTTFSQAKLASFITQYSTGQVSVEIEWELQKENSKRWNPEIQYTSNYYKSTN | 712 |

| AAV8    | 713 | VDFAVNTEGVYSEPRPIGTRYLTRNL | 738 |
| AAV-B1  | 712 | VDFAVNTEGVYSEPRPIGTRYLTRNL | 737 |
| AAV1    | 711 | VDFTVDNNGLYTEPRPIGTRYLTRPL | 736 |
| AAV2    | 710 | VDFTVDTNGVYSEPRPIGTRYLTRNL | 736 |
| AAV5    | 699 | VDFAPDSTGEYRTTRPIGTRYLTRPL | 724 |
| AAV6    | 711 | VDFTVDNNGLYTEPRPIGTRYLTRPL | 736 |
| AAV7    | 712 | VDFAVDSQGVISEPRPIGTRYLTRNL | 737 |
| AAV9    | 711 | VEFAVNTEGVYSEPRPIGTRYLTRNL | 736 |
| AAVrh10 | 713 | VDFAVNTDGTYSEPRPIGTRYLTRNL | 739 |

FIG. 33E

HIGH EFFICIENCY LIBRARY-IDENTIFIED AAV VECTORS

RELATED APPLICATIONS

This application is a National Stage Application of PCT/US2015/053804, filed Oct. 2, 2015, entitled "NOVEL HIGH EFFICIENCY LIBRARY-IDENTIFIED AAV VECTORS", which claims the benefit under 35 U.S.C. § 119(e) of U.S. Provisional Application Ser. No. 62/059,769, filed on Oct. 3, 2014, entitled, "NOVEL HIGH EFFICIENCY LIBRARY-IDENTIFIED AAV VECTORS", the entire content of each application which is incorporated herein by reference.

FEDERALLY SPONSORED RESEARCH

This invention was made with government support under grant no. R01 NS066310 awarded by the National Institutes of Health. The government has certain rights in the invention.

FIELD

In some aspects, the disclosure provides novel AAV capsid sequences and methods of use thereof as well as related kits.

BACKGROUND

Effective gene transfer is important for development of new therapies for certain diseases (e.g., neurological diseases). AAV vectors have emerged as an effective platform for in vivo gene transfer. However, a need remains for new vectors for gene delivery.

SUMMARY OF INVENTION

The disclosure relates to compositions, kits and methods of useful for identifying adeno-associated viruses (AAVs). In some embodiments, the disclosure relates to identification of AAV capsid genes with useful targeting properties. For example, in some embodiments, AAV capsid genes are provided that have been identified using a chimeric AAV library. In some embodiments, the chimeric AAV capsid library comprises a plurality of nucleic acids encoding AAV capsid proteins. In some embodiments, each nucleic acid encodes a unique chimeric AAV capsid protein. In some embodiments, each nucleic acid encodes a unique chimeric AAV capsid protein having distinct polypeptide regions of different AAV serotypes (e.g., at least three serotypes). In some embodiments, each nucleic acid comprises a unique barcode sequence. In some embodiments, barcodes sequences in the library have the formula $(NNM)_n$. In some embodiments, n is an integer in the range of is 3 to 20. In some embodiments, N is independently selected from A, G, T and C. In some embodiments, M is independently A or C.

In some embodiments, the barcoded chimeric AAV capsid library comprises a plurality of nucleic acids, wherein each nucleic acid (i) encodes a unique AAV capsid protein having distinct polypeptide regions of greater than six amino acids in length that are derived from at least two different AAV serotypes; and (ii) comprises a unique barcode sequence. In some embodiments, the nucleic acid sequences encoding the chimeric AAV capsid proteins comprise capsid sequence fragments from at least 2 different AAV serotypes.

In some embodiments, the barcode sequence comprises a single contiguous stretch of nucleotides inserted into an untranslated region (UTR) (e.g., the 5' or 3' UTR) of the nucleic acid sequence encoding the chimeric AAV capsid protein, thereby allowing identification of the capsid protein by detection of the barcode sequence.

In some embodiments, the barcode sequence of the barcoded chimeric AAV capsid library is not interrupted by a primer sequence or other sequence. In some embodiments, each barcode sequence of the barcoded chimeric AAV capsid library does not comprise a restriction endonuclease cleavage site.

In some embodiments, each unique barcode sequence has a length of between about 10 nucleotides and about 50 nucleotides. In some embodiments, each unique barcode sequence has a length of between about 20 and about 40 nucleotides. In some embodiments, each unique barcode sequence has a length of 30 nucleotides.

In some embodiments, the disclosure relates to a chimeric AAV capsid protein identified by the methods disclosed herein. In some embodiments, the chimeric AAV capsid protein comprises distinct polypeptide regions derived from at least two, at least three, at least four, at least five or more different AAV serotypes selected from the group consisting of: AAV1, AAV2, AAV4, AAV5, AAV6, AAV8, AAV9, AAVrh8, AAVrh10, AAVrh39, and AAVrh43. In some embodiments, the chimeric AAV capsid protein comprises distinct polypeptide regions of greater than four, greater than five, greater than six, greater than seven or more amino acids in length that are derived from different AAV serotypes (e.g., at least two) selected from the group consisting of: AAV1, AAV2, AAV4, AAV5, AAV6, AAV8, AAV9, AAVrh8, AAVrh10, AAVrh39, and AAVrh43. In some embodiments, the chimeric AAV capsid protein comprises the amino acid sequence represented by SEQ ID NO: 5-8 or SEQ ID NO: 13-16. In some embodiments, the chimeric AAV capsid protein comprises an amino acid sequence encoded by a nucleic acid sequence as set forth in SEQ ID NO: 1-4 or SEQ ID NO: 9-12. In some embodiments, isolated nucleic acids encoding such capsid proteins are provided.

In some embodiments, the disclosure relates to a rAAV comprising the capsid identified by the methods disclosed herein. In some embodiments, the rAAV selectively targets the CNS tissue or another tissue of a subject. In some embodiments, the rAAV further comprises a transgene (e.g., a protein coding gene or functional RNA encoding gene)

In another aspect, the disclosure relates to methods of producing a chimeric AAV capsid encoding nucleic acid library. In some embodiments, the method of producing a chimeric AAV capsid encoding nucleic acid library comprises preparing a set of chimeric AAV capsid encoding nucleic acids. In some embodiments, the methods comprise preparing a set of constrained, randomized barcode nucleic acids such that number of unique barcode nucleic acids is greater than the number of chimeric AAV capsid encoding nucleic acids. In some embodiments, the methods comprise combining each chimeric AAV capsid encoding nucleic acid with a unique barcode nucleic acid (e.g., of a set prepared according to methods disclosed herein).

In some embodiments, a method of generating a chimeric AAV capsid encoding nucleic acid library is provided. In some embodiments, the method comprises shuffling AAV capsid encoding nucleic acids to obtain a set of chimeric AAV capsid encoding nucleic acids. In some embodiments, each nucleic acid of the set encodes a unique chimeric AAV capsid protein having distinct polypeptide regions of at least three different AAV serotypes. In some embodiments, the methods further comprise tagging each chimeric AAV capsid encoding nucleic acid with a unique barcode nucleic acid from a set of constrained, randomized barcode nucleic acids.

In some embodiments, the disclosure relates to a method of preparing an AAV library, the method comprising: (i) transfecting AAV packaging cells with a chimeric AAV capsid encoding nucleic acid library of disclosed herein; and/or (ii) maintaining the cells under conditions that permit production of AAVs incorporating chimeric AAV capsids; and/or (iii) preparing an AAV library comprising AAVs produced in step (ii).

In some embodiments, the disclosure relates to a method of identifying AAV capsids tropic for a target tissue. In some embodiments, methods are provided that comprise administering to a subject AAVs of an AAV library produced by a method disclosed herein. In some embodiments, the methods comprise isolating nucleic acids from cells of the target tissue. In some embodiments, the methods comprise detecting AAV capsid encoding nucleic acids in the isolated nucleic acids. In some embodiments methods of identifying AAV capsids tropic for a target tissue, further comprises amplifying the nucleic acids isolated from the target tissue to facilitate detection of the AAV capsid encoding nucleic acids. In some embodiments, methods further comprises confirming that the AAV capsid encoding nucleic acids are from the library by detecting barcode sequences. In some embodiments, barcode sequences are detected by colony hybridization. In some embodiments, barcode sequences are detected by deep sequencing. In some embodiments, barcode sequences are detected by PCR. In some embodiments, PCR amplifies only the barcode sequence. In some embodiments, PCR amplifies the at least a portion of a capsid encoding sequence and a barcode sequence.

BRIEF DESCRIPTION OF DRAWINGS

Figure 15A:
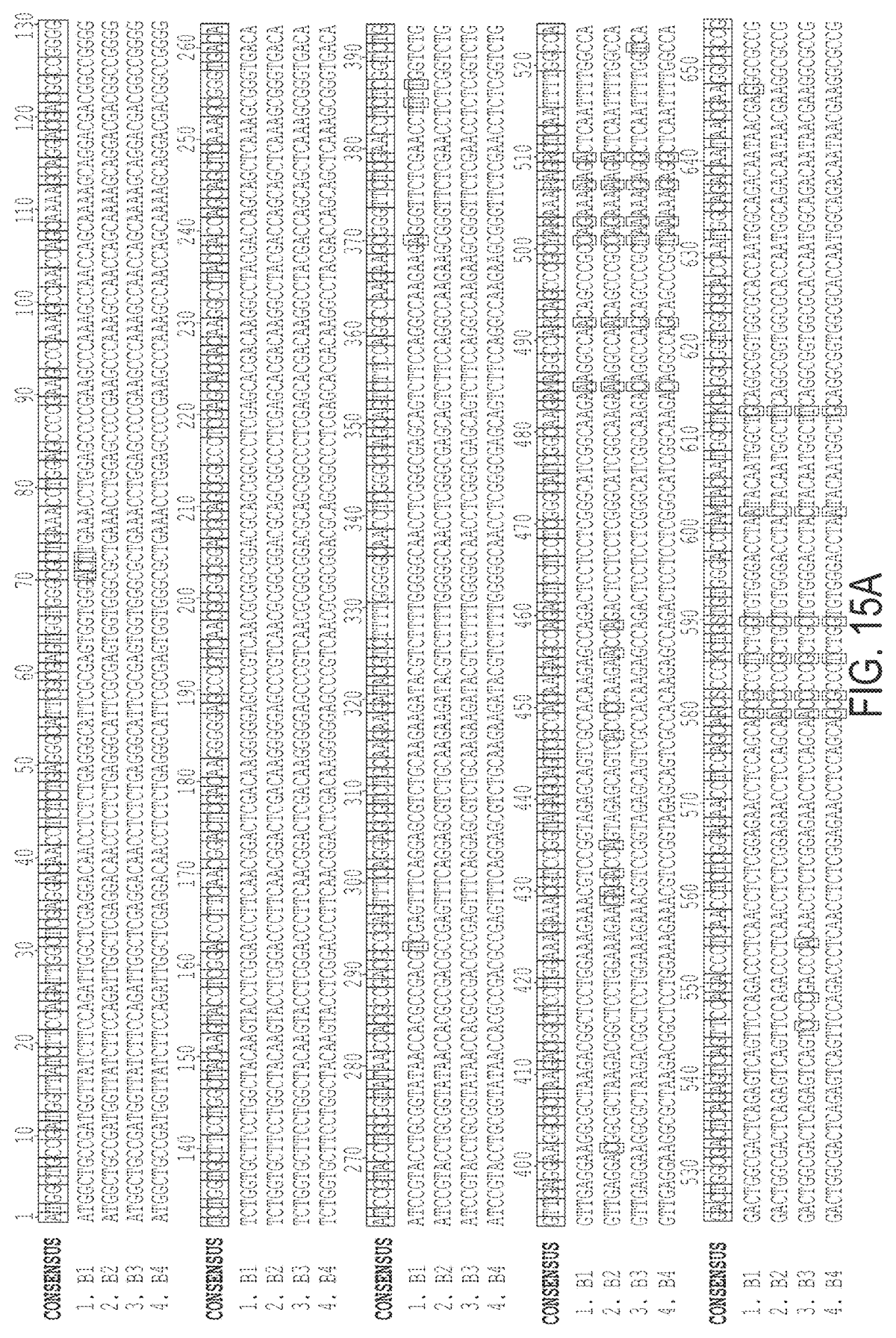
Figure 15B:
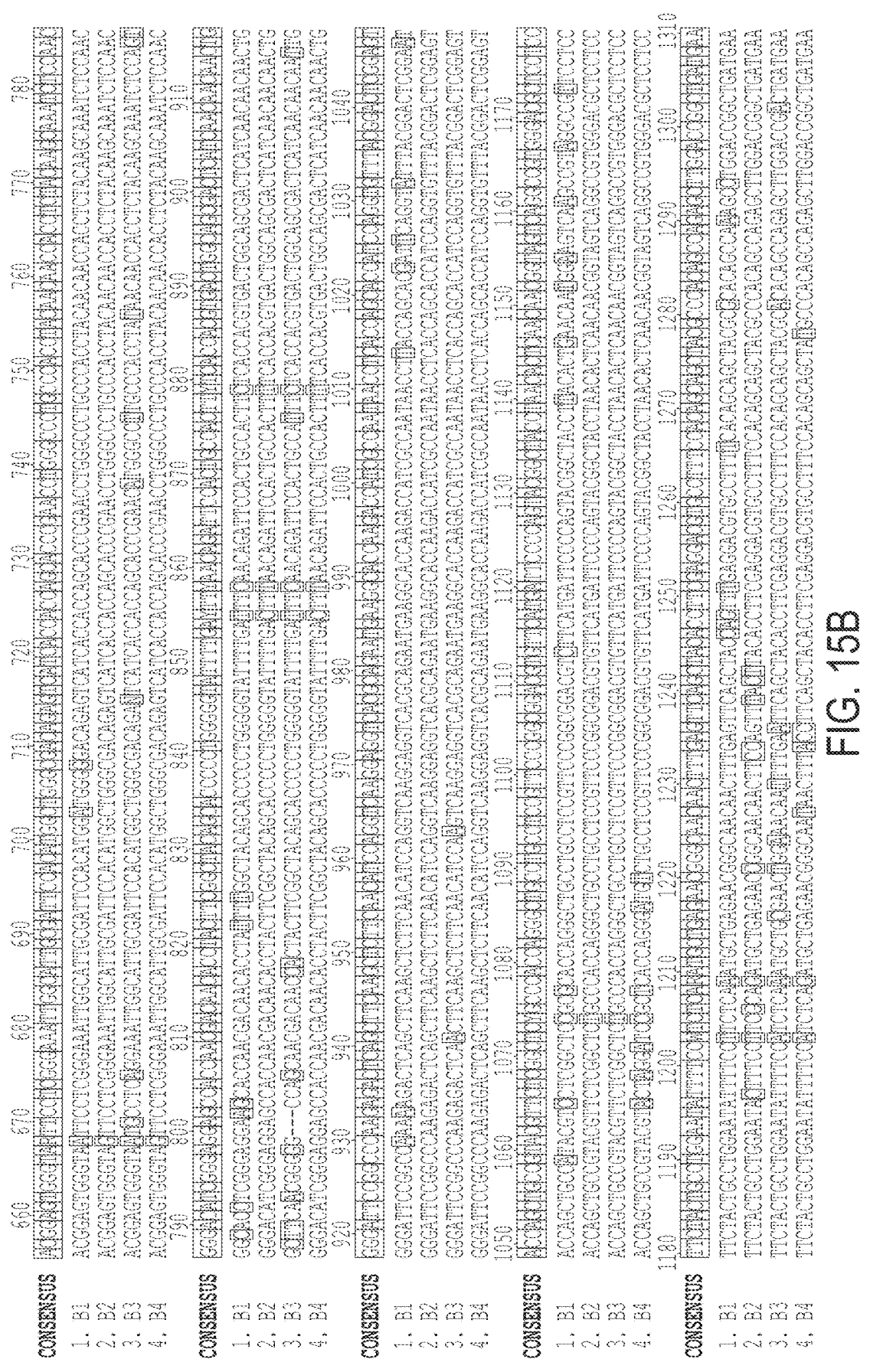
Figure 15C:
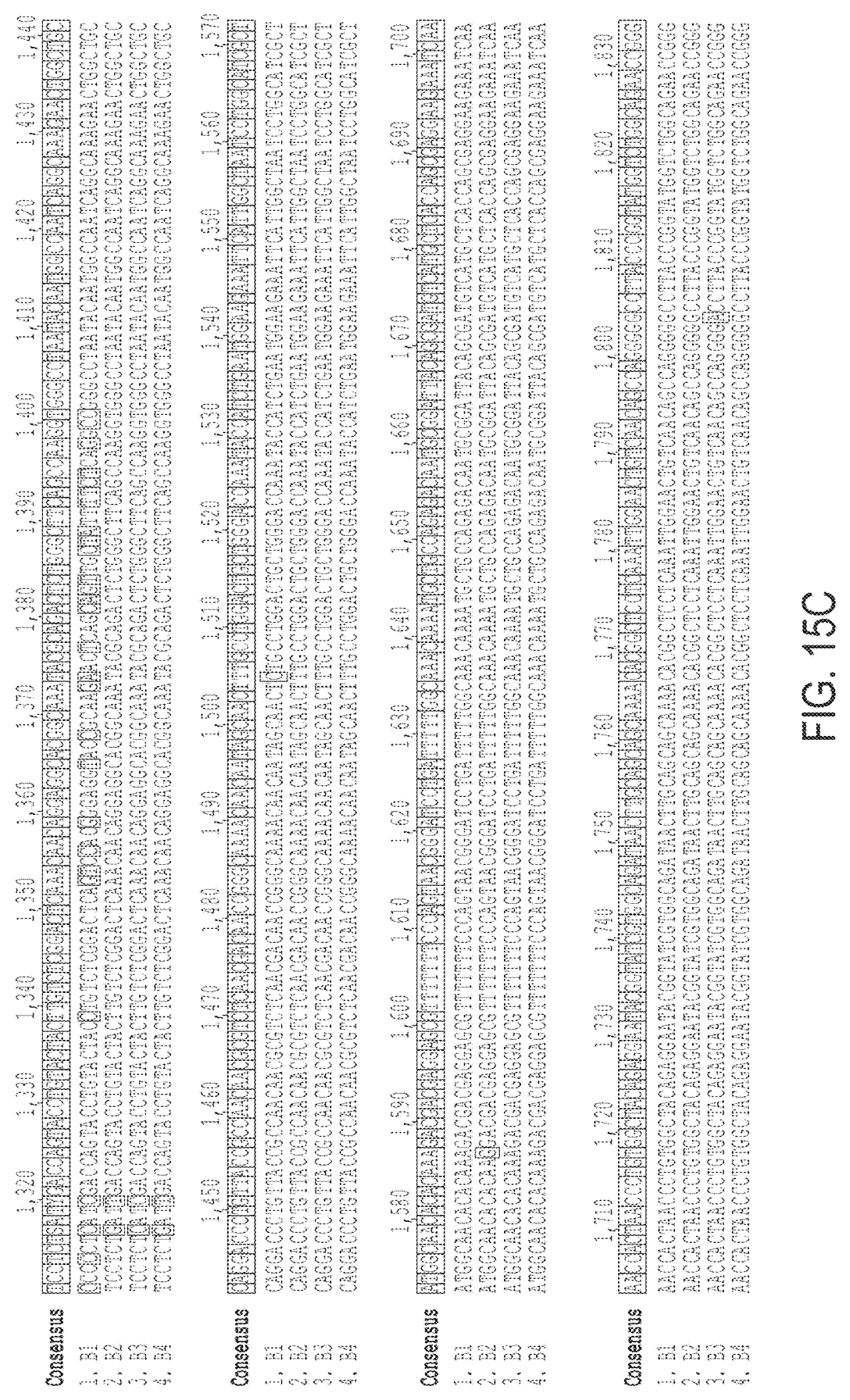
Figure 15D:
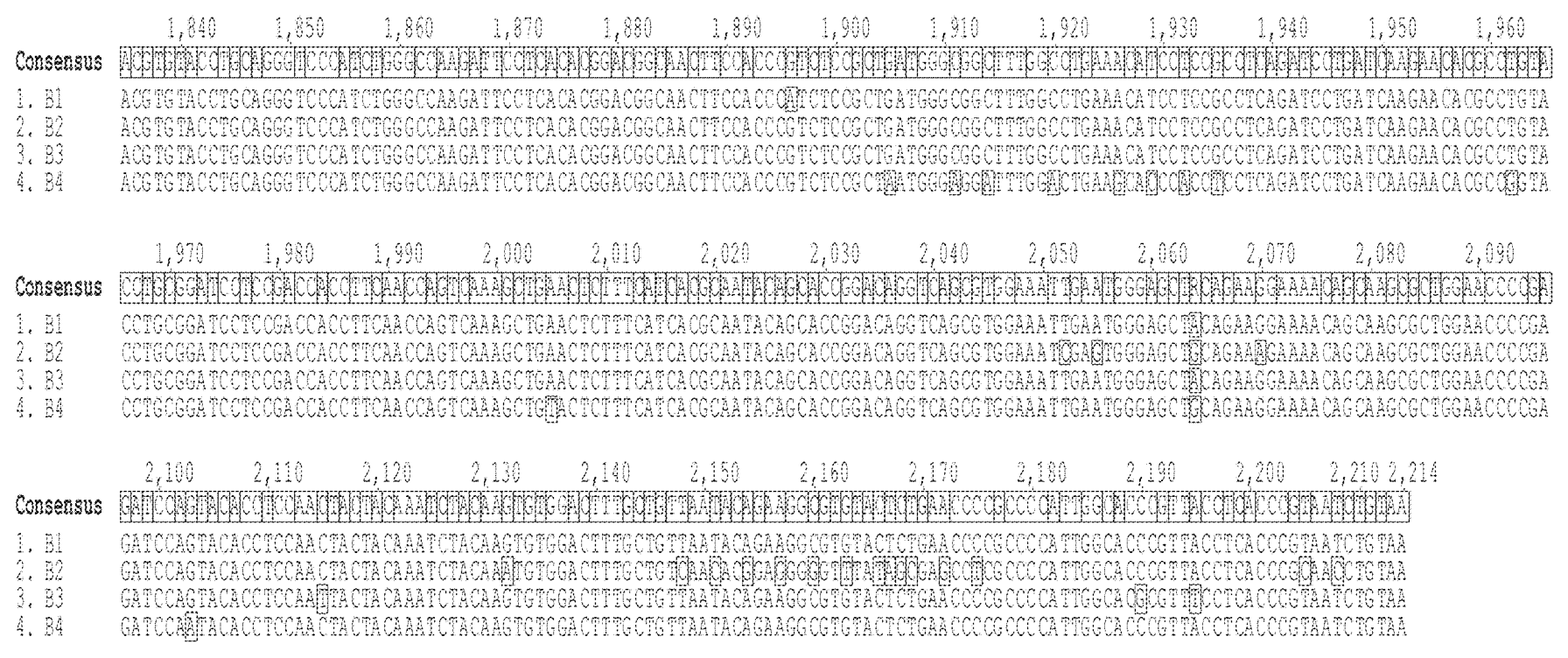

FIGS. 15A-15D depict a multiple sequence alignment. The consensus sequence is shown as the top line of the alignment. Variant bases are shaded. The 'consensus' strand corresponds to SEQ ID NO: 96. The '1. B1' strand corresponds to SEQ ID NO: 1. The '2. B2' strand corresponds to SEQ ID NO: 2. The '3. B3' strand corresponds to SEQ ID NO: 4. The '1. B4' strand corresponds to SEQ ID NO: 4.

FIGS. 16A-16B depict a multiple sequence alignment. Variant residues are shaded. The '1. B1 translation' strand corresponds to SEQ ID NO: 5. The '2. B2 translation' strand corresponds to SEQ ID NO: 6. The '3. B3 translation' strand corresponds to SEQ ID NO: 7. The '4. B4 translation' strand corresponds to SEQ ID NO: 8.

Figure 17C:
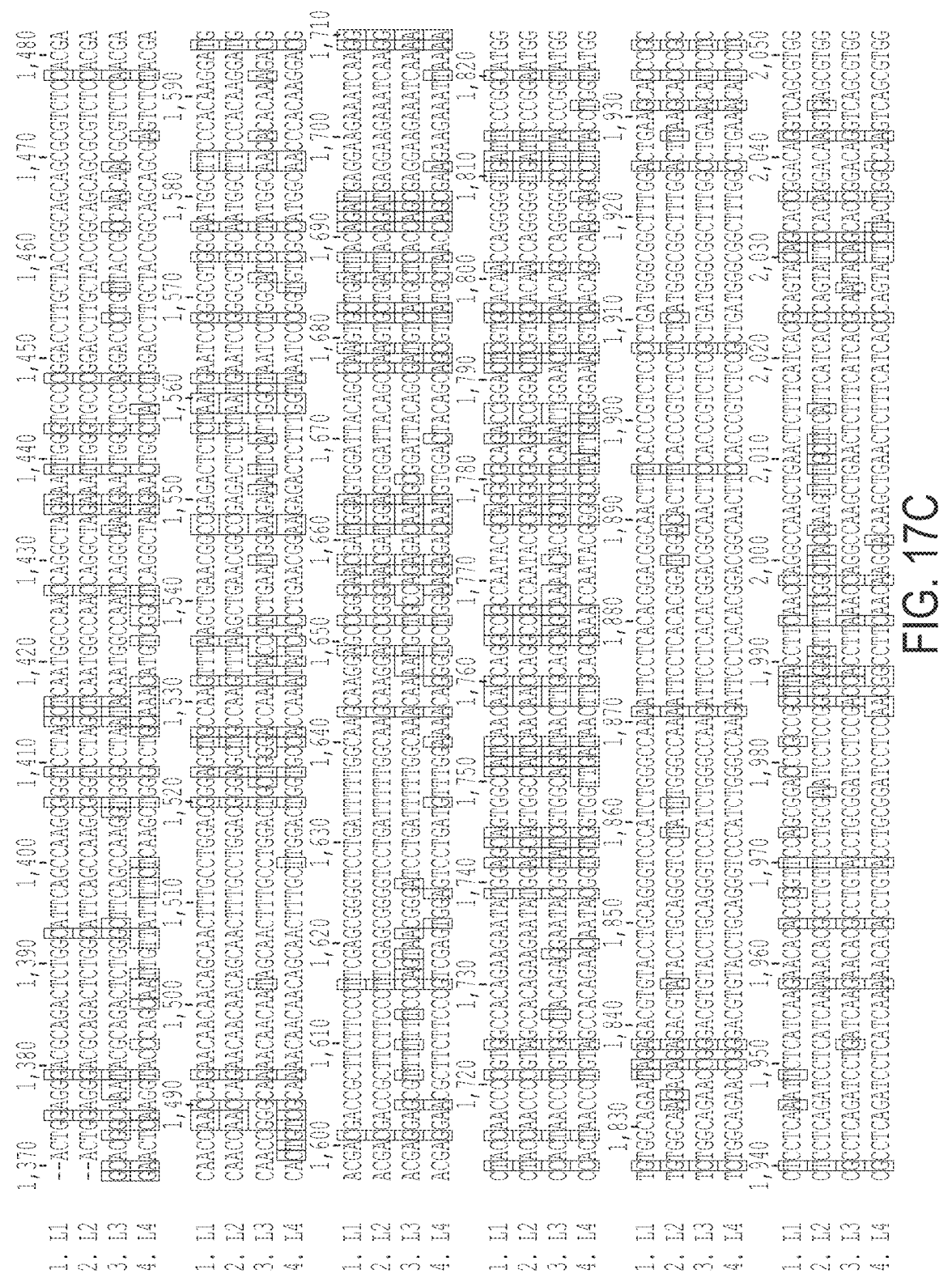
Figure 17D:
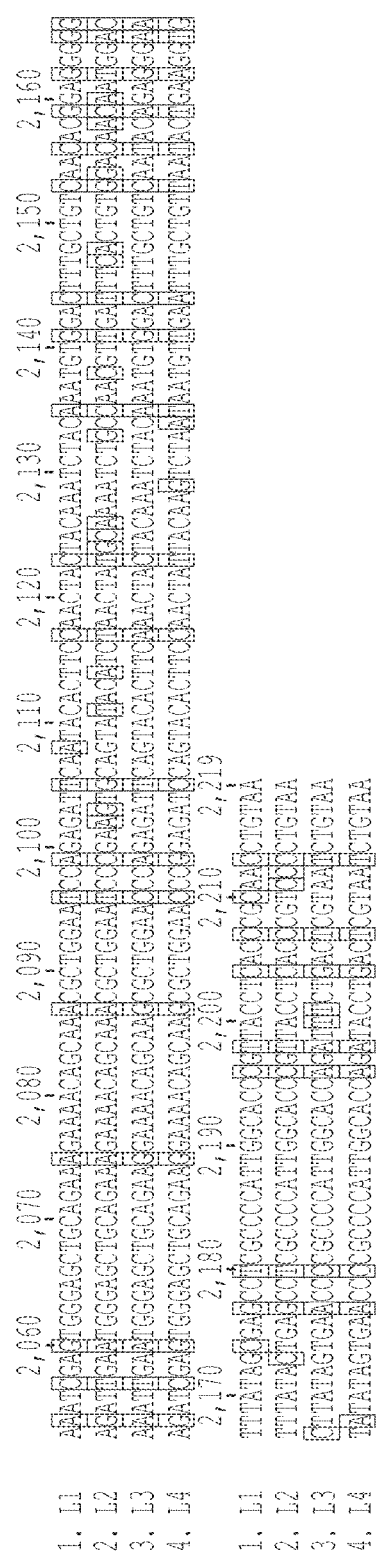

FIGS. 17A-17D depict a multiple sequence alignment. The consensus sequence is shown as the top line of the alignment. Variant bases are shaded. The '1. L1' strand corresponds to SEQ ID NO: 9. The '2. L2' strand corresponds to SEQ ID NO: 10. The '3. L3' strand corresponds to SEQ ID NO: 11. The '4. L4' strand corresponds to SEQ ID NO: 12.

FIGS. 18A-18B depict a multiple sequence alignment. Variant residues are shaded. The '1. L1 translation' strand corresponds to SEQ ID NO: 13. The '2. L2 translation' strand corresponds to SEQ ID NO: 14. The '3. L3 translation' strand corresponds to SEQ ID NO: 15. The '4. L4 translation' strand corresponds to SEQ ID NO: 16.

FIGS. 19A-19B depict a schematic representation of native capsid contributions to B1. Capsid contributors to B1 are AAV1, AAVrh.8, AAVrh.10, AAV6, AAVrh.43, AAV2, and AAVrh.39. The sequence depicted corresponds to SEQ ID NO: 1.

Figure 20A:
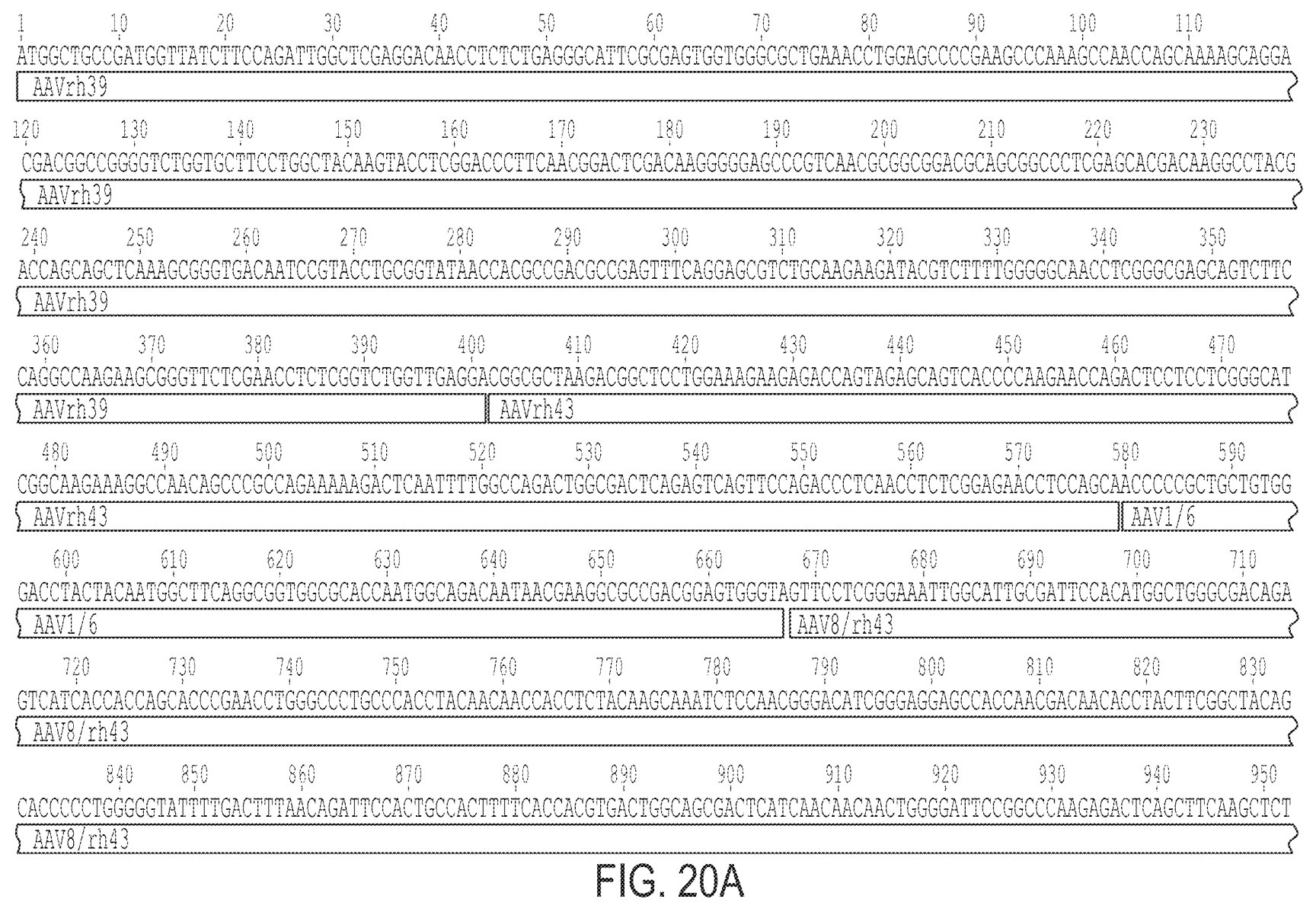
Figure 20B:
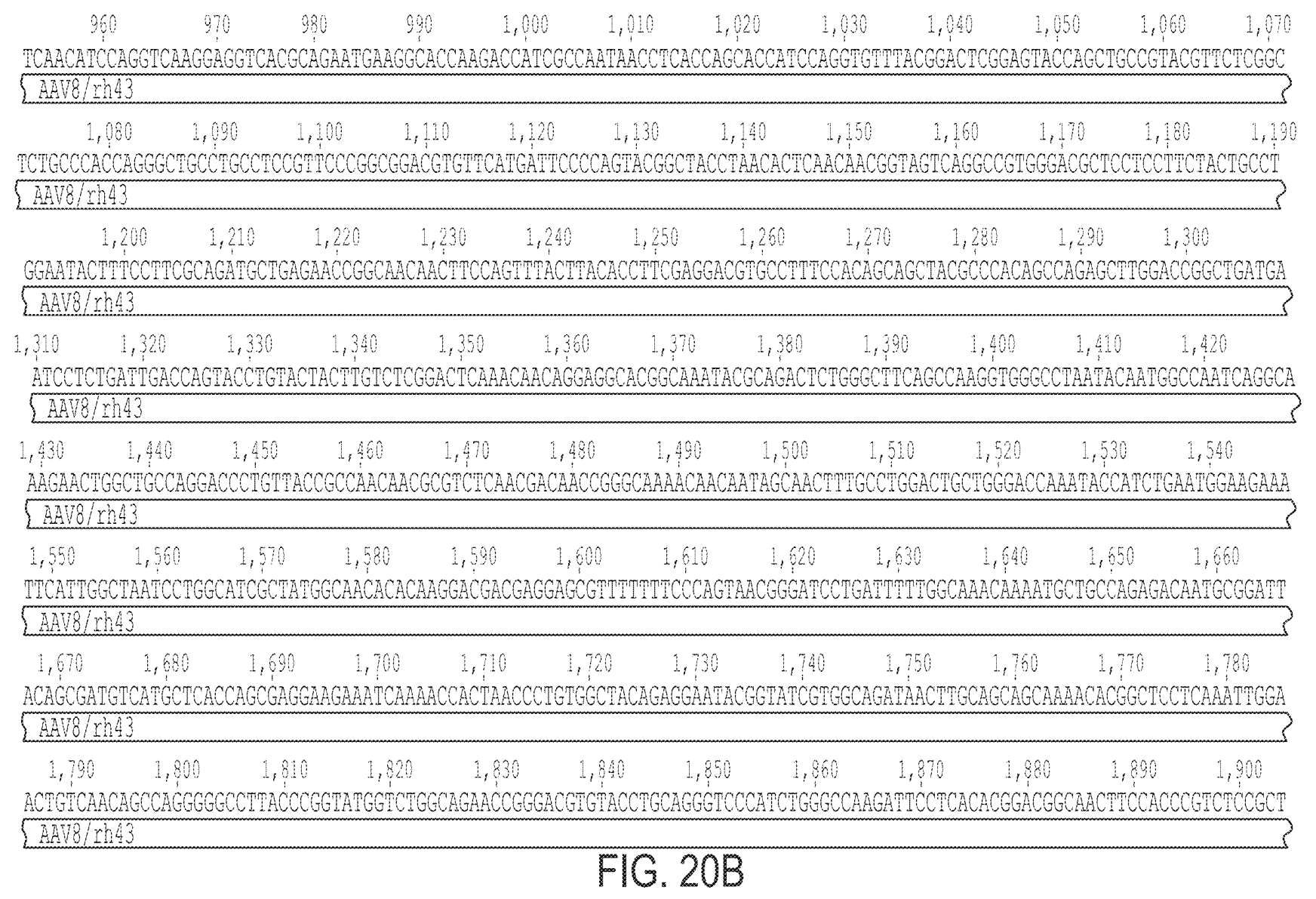

FIGS. 20A-20C depict a schematic representation of native capsid contributions to B2. Capsid contributors to B2 are AAVrh.39, AAVrh.43, AAV1, AAV6, AAV8, AAVrh.10, and AAVrh.8. The sequence depicted corresponds to SEQ ID NO: 2.

Figure 21A:
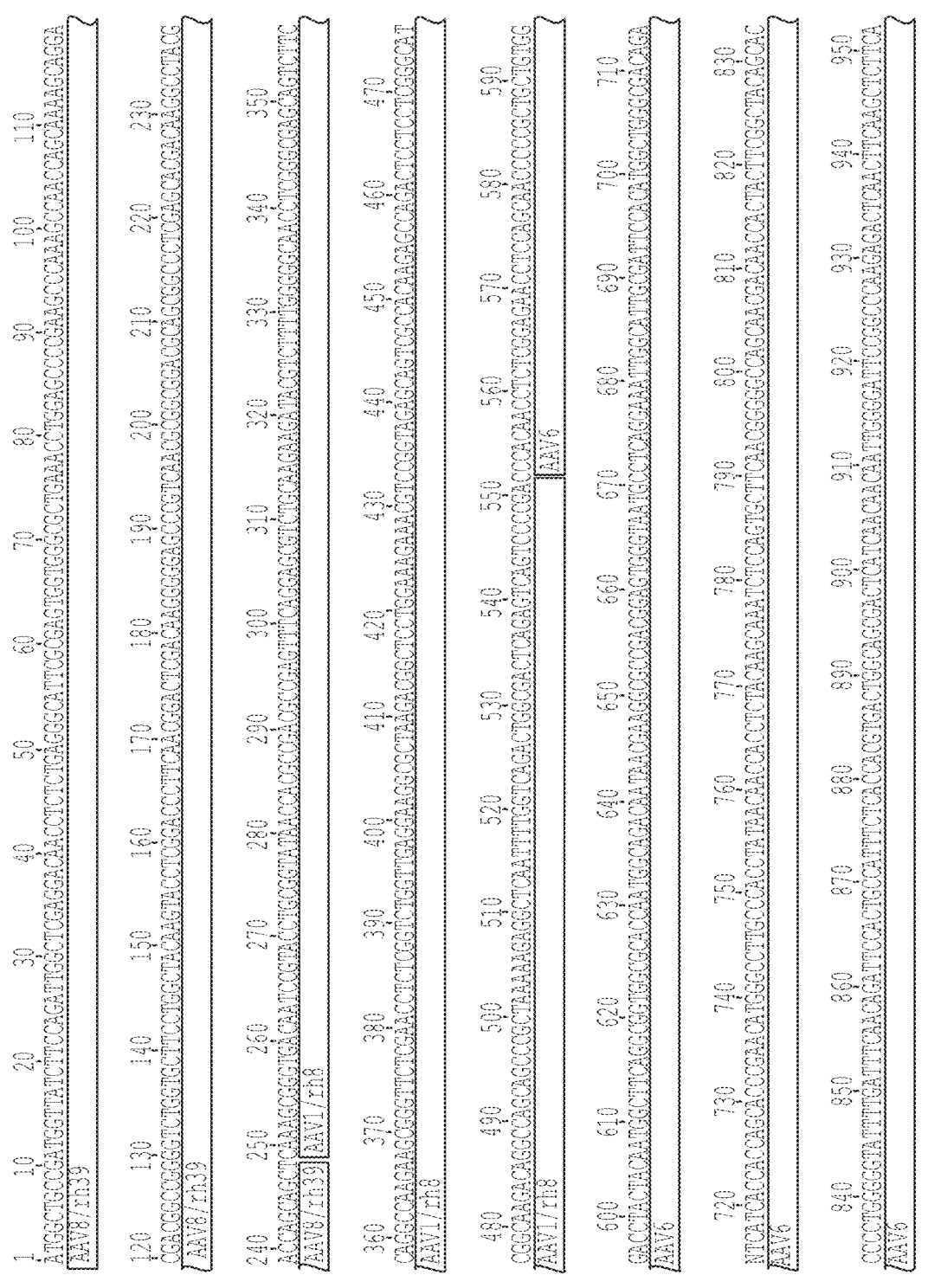
Figure 21B:
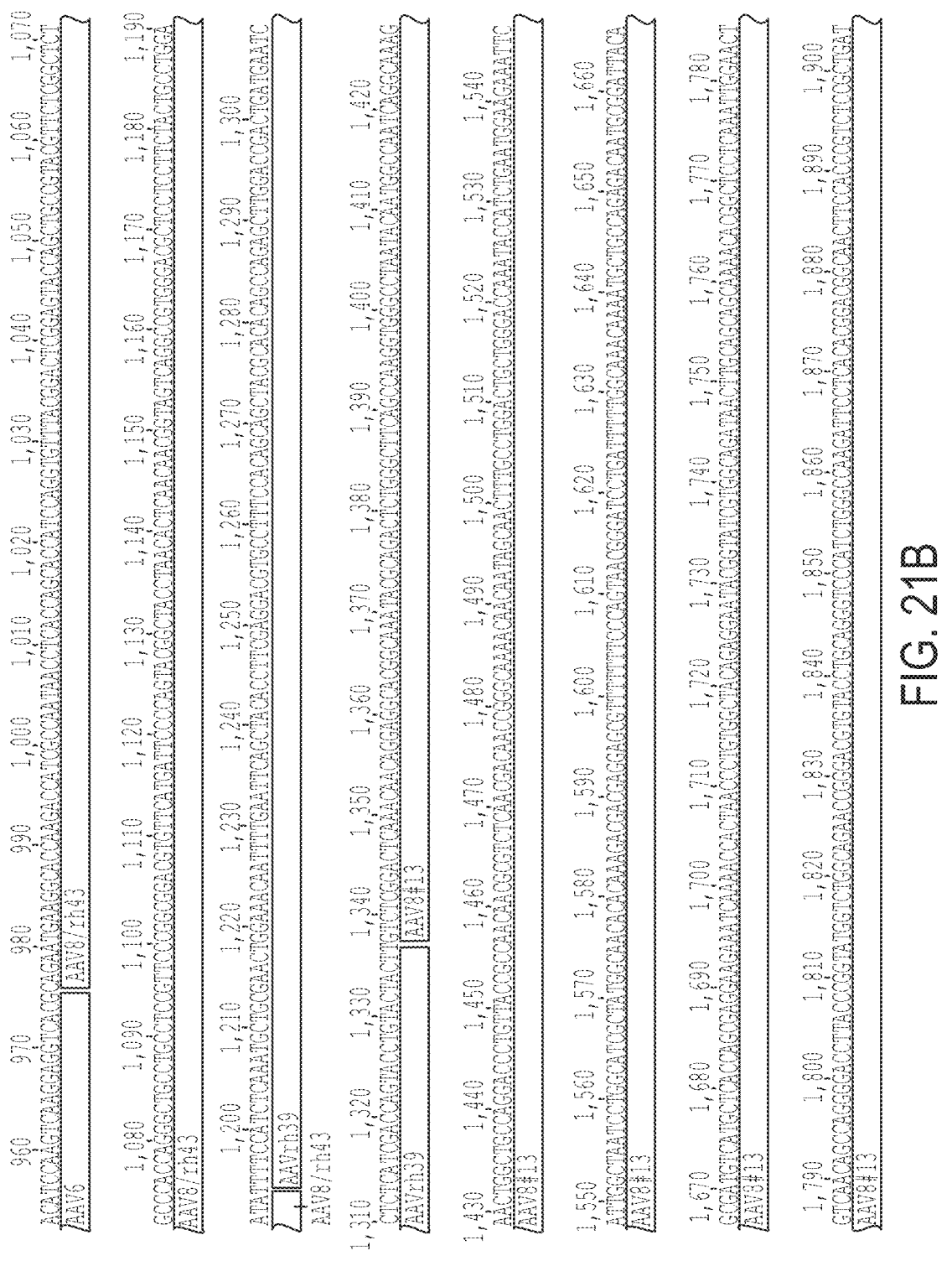

FIGS. 21A-21C depict a schematic representation of native capsid contributions to B3. Capsid contributors to B3 are AAV8, AAVrh.39, AAV1, AAVrh.8, AAV6, and AAVrh.43. The sequence depicted corresponds to SEQ ID NO: 3.

FIGS. 22A-22D depict a schematic representation of native capsid contributions to B4. Capsid contributors to B4 are AAVrh.39, AAV1, AAVrh.43, AAVrh.8, AAV6, and AAV8. The sequence depicted corresponds to SEQ ID NO: 4.

FIG. 23A provides an overview of GFP distribution in brains of AAV-B1 and AAV9 injected mice ($2 \times 10^{12}$ vg/mouse). Representative images of coronal brain sections located at +0.5 mm, −1.80 mm and −3.00 mm (left to right) in relation to bregma are shown. Transduction of neuronal populations in different CNS regions of AAV-B1 injected mice ($2 \times 10^{12}$ vg/mouse) is shown in FIG. 23B. Black arrows indicate examples of GFP-positive neurons identified by morphology. Bar=50 μm. FIG. 23C shows AAV vector genome content in cerebrum, cerebellum and spinal cords (N=4 animals per group) ($5 \times 10^{11}$ vg/mouse). Age matched non-injected mice were included as controls (not shown). FIG. 23D shows Western blot analysis of GFP expression in cerebrum, cerebellum and spinal cord of 2 animals per group ($5 \times 10^{11}$ vg/mouse). Signal intensity of GFP was normalized to corresponding β-actin signal intensity for quantitative comparison. $p<0.01$, *$p<0.001$, ****$p<0.0001$ by Student's unpaired t-test.

FIG. 25E muscle groups) and Western blot analysis of GFP expression (N=2 animals per group) (FIG. 25C, liver; FIG. 25F muscle groups) are shown ($5 \times 10^{11}$ vg/mouse). Signal intensity of GFP was normalized to corresponding β-actin signal intensity for quantitative comparison. *$p<0.05$, **$p<0.01$, by Student's unpaired t-test.

FIG. 26E lung) and FIG. 26C. Western blot analysis of GFP expression (N=2 animals per group) (FIG. 26C, pancreas; FIG. 26E lung) are shown. Signal intensity of GFP was normalized to corresponding β-actin signal intensity for quantitative comparison. *$p<0.05$, ****$p<0.0001$ by Student's unpaired t-test.

FIG. 27A shows a predicted molecular model of AAV-B1 capsid. FIG. 27B shows a surface exposed variable region-IV (VR-IV) of AAV-B1 (left) and AAV8 (right). FIG. 27C shows pooled human IVIg neutralization assay and FIG. 27D shows a CHO cell binding assay of AAV-B1 and AAV9 vectors. Data shown as mean±SEM in FIG. 27C, and as mean±SD in FIG. 27D. Experiment was performed with N=3 biological replicates. *$p<0.05$ by one-way ANOVA.

FIGS. 30A-30D show the chimeric and homologous nature of brain-resident capsids. Parental capsid contribution to (FIG. 30A) brain-selected capsids AAV-B1, -B2, -B3 and -B4, and (FIG. 30B) 4 liver-resident variants chosen at random. Homology among (FIG. 31C) brain and (FIG. 30D) liver clones at the amino acid level. Grey areas indicate homology; black lines indicate non-homologous amino acids. % homology is calculated for amino acid composition.

FIGS. 32A-32G show phenotyping of GFP positive cells in CNS after systemic delivery of AAV-B1. Transduced cells were identified by double immunofluorescence staining with antibodies to GFP, pan-neuronal marker NeuN (FIG. 32A, FIG. 32B and FIG. 32D), striatal medium spiny neuron marker DARPP32 (FIG. 32A), dopaminergic neuron marker tyrosine hydroxylase (TH) (FIG. 32B), Purkinje neuron marker calbindin-D-28k (Cal28K) (FIG. 32C), endothelial marker CD31 (FIG. 32E), and mature oligodendrocyte marker APC (FIG. 32F). The large size, morphology and location of GFP-positive neurons in the ventral spinal cord suggest a motor neuron identity. GFP-positive astrocytes (FIG. 32G) were identified based on their morphology. White arrows indicate examples of co-localization. Bar=10 µm.

FIGS. 33A-33E show a comparison of AAV-B1 capsid protein sequence to AAV8 and other natural AAV isolates. The top two lines highlight the similarities and differences between amino acid sequences of AAV8 and AAV-B1, with singleton residue variants relative to AAV8 highlighted in red. The residue highlighted in green indicates a variant residue with no corresponding orthologs in the nine AAV species presented in the alignment. Translation start sites for VP1, VP2, and VP3 are indicated with filled triangles. The conserved parvovirus phospholipase A2 domain (approximately residues 44 to 104) in the VP1 unique region with the conserved AAV calcium-binding motif (Y-X-G-P-G/F) and catalytic residues (H-D-X-X-Y) are indicated with filled rectangles. The secondary structural elements are labeled with the corresponding text and the following symbols: β sheets B, C, D, E, F, G, and I are indicated with a horizontal overlined arrow. The positions of the variable loops (VR), I through IX, are indicated. The position of the conserved a helix is indicated with three parallel horizontal lines. The 'AAV8' strand corresponds to SEQ ID NO: 88. The 'AAV-B1' strand corresponds to SEQ ID NO: 5. The 'AAV1' strand corresponds to SEQ ID NO: 89. The 'AAV2' strand corresponds to SEQ ID NO: 90. The 'AAV5' strand corresponds to SEQ ID NO: 91. The 'AAV6' strand corresponds to SEQ ID NO: 92. The 'AAV7' strand corresponds to SEQ ID NO: 93. The 'AAV9' strand corresponds to SEQ ID NO: 94. The 'AAVrh10' strand corresponds to SEQ ID NO: 95.

DETAILED DESCRIPTION OF INVENTION

Figure 1:
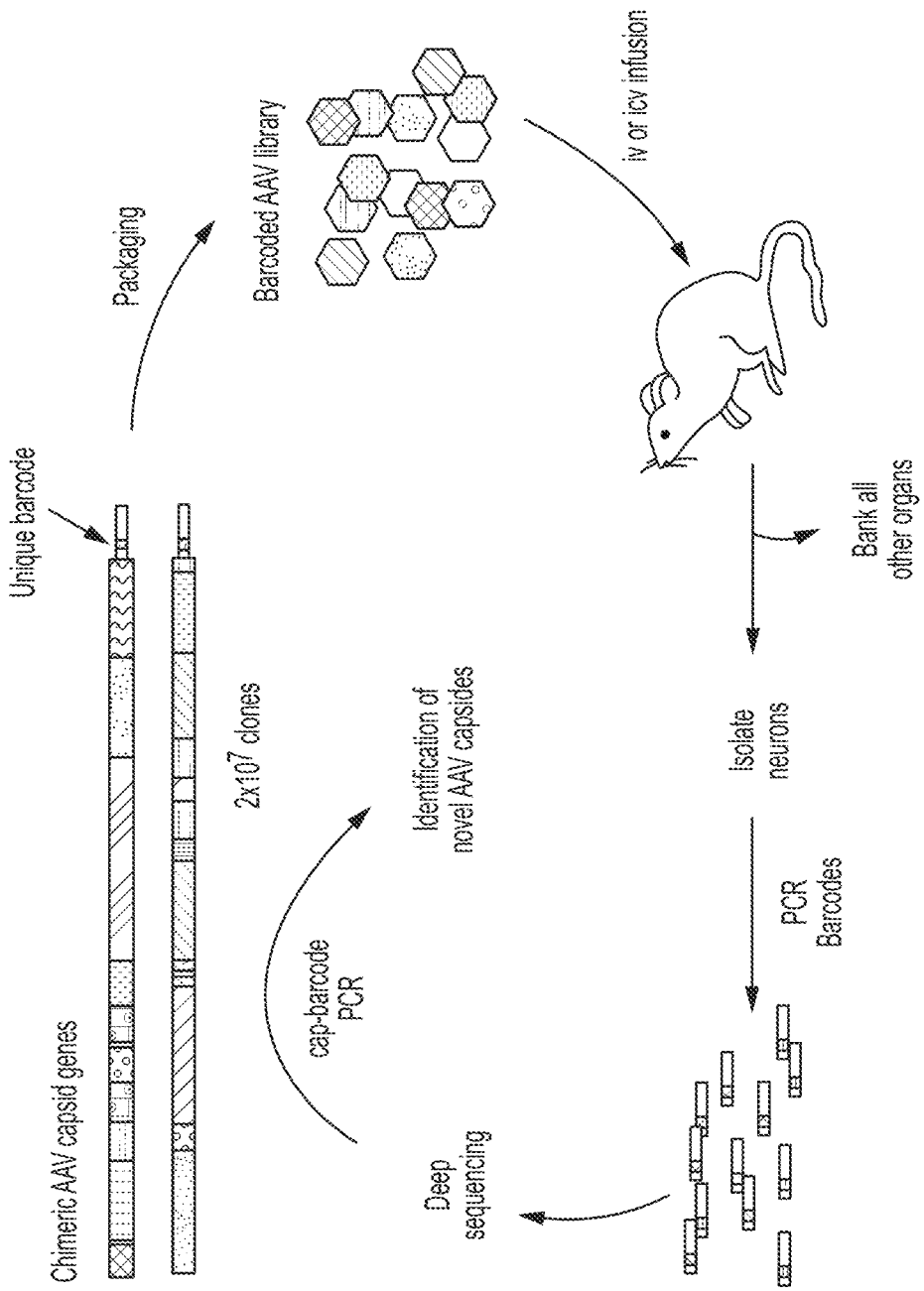
FIG. 1 provides a schematic representation of an approach for in vivo selection of AAV capsid libraries by using unique barcodes in the 3'UTR of each clone in the library and deep sequencing to determine their frequency in target cells/tissue followed by PCR amplification of capsid/barcode pairs from the plasmid library.

In some aspects, provided herein are recombinant AAVs having desirable tissue targeting and transduction properties that make them useful for certain gene therapy and research applications. In some embodiments, the disclosure relates to chimeric AAV capsids that are useful for transducing various target tissues. The disclosure provides in some aspects novel AAV capsid proteins that have been identified from a barcoded chimeric AAV capsid library. As used herein, the term "library" refers to an collection of entities, such as, for example, viral particles (e.g., rAAVs), molecules (e.g., nucleic acids), etc. A library may comprise at least two, at least three, at least four, at least five, at least ten, at least 25, at least 50, at least $10^2$, at least $10^3$, at least $10^4$, at least $10^5$, at least $10^6$, at least $10^7$, at least $10^8$, at least $10^9$, or more different entities (e.g., viral particles, molecules (e.g., nucleic acids)). In some embodiments, a library entity (e.g., a viral particle, a nucleic acid) can be associated with or linked to a tag (e.g., a barcode), which can facilitate recovery or identification of the entity. For example, in some embodiments, libraries provided herein comprise a collection of barcoded nucleic acids. In some embodiments, a library refers to a collection of nucleic acids that are propagatable, e.g., through a process of clonal amplification. Library entities can be stored, maintained or contained separately or as a mixture.

As used herein, "barcode sequence" refers to a sequence of a biological molecule (e.g., nucleic acid, protein, etc.) that when combined with the sequence another biological molecule serves to identify the other biological molecule. Typically, a barcode sequence is a heterologous sequence that is incorporated within or appended to a sequence of a target biological molecule and utilized as a reference in order to identify a target molecule of interest. In some embodiments, a barcode sequence is a sequence of a nucleic acid (e.g., a heterologous or synthetic nucleic acid) that is incorporated within or appended to a target nucleic acid and utilized as a reference in order to identify the target nucleic acid. In some embodiments, a barcode sequence is of the formula $(NNM)_n$. In some embodiments, n is an integer in the range of 5 to 20, 5 to 10, 10 to 20, 7 to 20, or 7 to 30. In some embodiments, n is 2, 3, 4, 5, 6, 7, 8, 9, 10, 11, 12, 13, 14, 15, 16, 17, 18, 19, 20, 21, 22, 23, 24, 25, 26, 27, 28, 29, 30 or more. In some embodiments, N are each nucleotides that are independently selected from A, G, T and C and M is a nucleotide that is either A or C. Thus, in some embodiments, the disclosure provides nucleic acids that (i) have a target sequence of interest (e.g., a coding sequence (e.g., that encodes a protein or functional RNA)); and (ii) comprises a unique barcode sequence. In some embodiments, the target sequence of interest encodes an AAV capsid (e.g., a chimeric AAV capsid).

In some aspects, the disclosure provides barcoded chimeric AAV capsid libraries. DNA shuffling may be used to create a library of nucleic acid sequences encoding chimeric AAV capsid proteins. In some embodiments, each nucleic acid sequence of the library comprises nucleic acid fragments from the capsid genes of multiple AAV serotypes. Thus, new AAV variants having altered tissue tropism may be created. In some embodiments, AAV capsid genes having altered tissue tropism are identified using a barcoded chimeric AAV library. In some embodiments, the altered tissue tropism allows for targeting of a particular tissue by the AAV capsid protein. In some embodiments, the target tissue is a tissue selected from the group consisting of heart, lung, spleen, pancreas, skeletal muscle, kidney, intestine, and stomach. In some embodiments, the tissue targeted by the AAV capsid protein is the central nervous system (CNS). In some embodiments, the target tissue is the brain. In some embodiments, the target tissue is the liver.

In some embodiments, the barcoded chimeric AAV capsid library comprises a plurality of nucleic acids, wherein each nucleic acid (i) encodes a unique chimeric AAV capsid protein having distinct polypeptide regions of at least three different AAV serotypes; and/or (ii) comprises a unique barcode sequence. In some embodiments, the barcoded chimeric AAV capsid library comprises a plurality of nucleic acids. In some embodiments, each nucleic acid (i) encodes a unique chimeric AAV capsid protein; and/or (ii) comprises a unique barcode sequence. In some embodiments, barcodes sequences in the library have the formula $(NNM)_n$. In some embodiments, n is an integer in the range of is 5 to 20, 5 to 10, 10 to 20, 7 to 20, or 7 to 30. In some embodiments, n is 2, 3, 4, 5, 6, 7, 8, 9, 10, 11, 12, 13, 14, 15, 16, 17, 18, 19, 20, 21, 22, 23, 24, 25, 26, 27, 28, 29, 30 or more. In some embodiments, N are each nucleotides that are independently selected from A, G, T and C and M is a nucleotide that is either A or C.

In some embodiments, the barcoded chimeric AAV capsid library comprises a plurality of nucleic acids, wherein each nucleic acid (i) encodes a unique AAV capsid protein having distinct polypeptide regions of greater than six amino acids in length that are derived from at least two different AAV serotypes; and (ii) comprises a unique barcode sequence. In some embodiments, the nucleic acid sequences encoding the chimeric AAV capsid proteins comprise capsid sequence fragments from at least 2 different AAV serotypes.

In some embodiments, the barcode sequence comprises a single contiguous stretch of nucleotides inserted into the 3' untranslated region (UTR) of the nucleic acid sequence encoding the chimeric AAV capsid protein, thereby allowing identification of the capsid protein by detection of the barcode sequence.

In some embodiments, the barcode sequence of the barcoded chimeric AAV capsid library is not interrupted by a primer sequence. In some embodiments, each barcode sequence of the barcoded chimeric AAV capsid library does not comprise a restriction endonuclease cleavage site.

In some embodiments, each unique barcode sequence has a length of between about 10 nucleotides and about 50 nucleotides. In some embodiments, each unique barcode sequence has a length of between about 20 and about 40 nucleotides. In some embodiments, each unique barcode sequence has a length of 30 nucleotides.

Construction of the chimeric AAV capsid libraries of the disclosure maybe carried out by any suitable means known in the art, for example DNA family shuffling (Crameri et al., Nature, 391: 288-291 (1998), the contents of which are incorporated herein by reference in their entirety). Methods of incorporating nucleic acid barcodes into libraries are also known in the art, for example through the addition of adapter sequences.

In another aspect, the disclosure relates to methods of producing a chimeric AAV capsid encoding nucleic acid library. In some embodiments, the method of producing a chimeric AAV capsid encoding nucleic acid library comprises (i) preparing a set of chimeric AAV capsid encoding nucleic acids; (ii) preparing a set of constrained, randomized barcode nucleic acids such that number of unique barcode nucleic acids is greater than the number of chimeric AAV capsid encoding nucleic acids; and (iii) combining each chimeric AAV capsid encoding nucleic acid with a unique barcode nucleic acid of the set prepared in (ii).

In some embodiments, methods of generating a chimeric AAV capsid encoding nucleic acid library are provided that comprise shuffling AAV capsid encoding nucleic acids to obtain a set of chimeric AAV capsid encoding nucleic acids. In some embodiments, the methods further comprise tagging each chimeric AAV capsid encoding nucleic acid with a unique barcode nucleic acid from a set of constrained, randomized barcode nucleic acids. In some embodiments, each nucleic acid of a set encodes a unique chimeric AAV capsid protein having distinct polypeptide regions of at least three different AAV serotypes.

In some embodiments, barcode nucleic acids in a library produced by methods disclosed herein have the formula: $(NNM)_n$. In some embodiments, n is an integer in the range of is 5 to 20, 5 to 10, 10 to 20, 7 to 20, or 7 to 30. In some embodiments, n is 2, 3, 4, 5, 6, 7, 8, 9, 10, 11, 12, 13, 14, 15, 16, 17, 18, 19, 20, 21, 22, 23, 24, 25, 26, 27, 28, 29, 30 or more. In some embodiments, N are each nucleotides that are independently selected from A, G, T and C and M is a nucleotide that is either A or C. In some embodiments, the chimeric AAV capsid encoding nucleic acids each encode a unique chimeric AAV capsid protein having distinct polypeptide regions of at least three different AAV serotypes. In some embodiments, the chimeric AAV capsid encoding nucleic acids each encode a unique chimeric AAV capsid protein having distinct polypeptide regions of greater than six amino acids in length that are derived from at least two different AAV serotypes. In some embodiments, each barcode nucleic acid comprises a single contiguous stretch of nucleotides inserted into the 3' untranslated region (UTR) of the nucleic acid sequence encoding the chimeric AAV capsid protein, thereby allowing identification of the capsid protein by detection of the barcode sequence.

In some embodiments, the disclosure relates to a method of preparing an AAV library, in which the method comprises (i) transfecting AAV packaging cells with the chimeric AAV capsid encoding nucleic acid library disclosed herein; and/or (ii) maintaining the cells under conditions that permit production of AAVs incorporating chimeric AAV capsids; and/or (iii) preparing an AAV library comprising AAVs produced in step (ii).

In some embodiments, the disclosure relates to methods of identifying AAV capsids tropic for a target tissue, in which the methods comprise: (i) administering to a subject AAVs of an AAV library produced by a method disclosed herein; and/or (ii) isolating nucleic acids from cells of the target tissue; and/or (iii) detecting AAV capsid encoding nucleic acids in the isolated nucleic acids. In some embodiments, methods of identifying AAV capsids tropic for a target tissue, further comprise amplifying nucleic acids isolated from a target tissue to facilitate detection of the AAV capsid encoding nucleic acids. In some embodiments, methods further comprise confirming that the AAV capsid encoding nucleic acids are from the library by detecting barcode sequences. In some embodiments, the barcode sequences are detected by colony hybridization. In some embodiments, barcode sequences are detected by deep sequencing. In some embodiments, barcode sequences are detected by PCR. In some embodiments, PCR amplifies only the barcode sequence. In some embodiments, the PCR amplifies the entire capsid sequence and the barcode sequence.

Isolated AAV Capsid Proteins and Nucleic Acids Encoding the Same

AAVs isolated from mammals, particularly non-human primates, are useful for creating gene transfer vectors for clinical development and human gene therapy applications. In some embodiments, recombinant AAVs (rAAVs) disclosed herein have a tropism for the CNS. Accordingly, in some embodiments, the rAAV vectors of the instant disclosure are particularly useful for gene therapy of CNS disorders. In some embodiments, AAV capsid proteins are provided that have been obtained using barcoded chimeric AAV capsid libraries. Protein and amino acid sequences as well as other information regarding the AAVs capsid are set forth in the sequence listing. In some embodiments, a fragment (portion) of an isolated nucleic acid encoding a AAV capsid sequence may be useful for constructing a nucleic acid encoding a desired capsid sequence. Fragments may be of any appropriate length (e.g., at least 6, at least 9, at least 18, at least 36, at least 72, at least 144, at least 288, at least 576, at least 1152 or more nucleotides in length). For example, a fragment of nucleic acid sequence encoding a polypeptide of a first AAV capsid protein may be used to construct, or may be incorporated within, a nucleic acid sequence encoding a second AAV capsid sequence to alter the properties of the AAV capsid. In some embodiments, AAV capsid proteins that comprise capsid sequence fragments from multiple AAV serotypes are referred to as chimeric AAV capsids.

In some embodiments, the disclosure provides chimeric capsid proteins comprising distinct polypeptide regions derived from at least 2, at least 3, at least 4, at least 5, at least 6, or more different AAV serotypes. In some embodiments, AAV serotypes are selected from the group consisting of: AAV1, AAV2, AAV4, AAV5, AAV6, AAV8, AAV9, AAVrh8, AAVrh10, AAVrh39, and AAVrh43. In some embodiments, the chimeric capsid proteins comprise contributions from the native capsid serotypes listed above. In some embodiments, the capsid contributors are AAV1, AAVrh.8, AAVrh.10, AAV6, AAVrh.43, AAV2, and AAVrh.39. In some embodiments, the capsid contributors are AAVrh.39, AAVrh.43, AAV1, AAV6, AAV8, AAVrh.10, and AAVrh.8. In some embodiments, the capsid contributors are AAV8, AAVrh.39, AAV1, AAVrh.8, AAV6, and AAVrh.43. In some embodiments, the capsid contributors to B4 are AAVrh.39, AAV1, AAVrh.43, AAVrh.8, AAV6, and AAV8. In some embodiments, the chimeric capsid proteins comprise distinct polypeptide regions of greater than 3, 4, 5, 6, 7, 8, 9, 10, 11, 12, 13, 14, 15, 16, 17, 18, 19, 20, 25, 50, 75, 100 or more amino acids in length that are derived from different AAV serotypes. In some embodiments, the AAV serotypes are selected from the group consisting of AAV1, AAV2, AAV4, AAV5, AAV6, AAV8, AAV9, AAVrh8, AAVrh10, AAVrh39, and AAVrh43.

In some embodiments, the disclosure provides for chimeric AAV capsid proteins that are identified by the methods disclosed herein. In some embodiments, the amino acid sequences of the identified chimeric AAV capsid proteins are represented by SEQ ID NO: 5-8 or SEQ ID NO: 13-16. In some embodiments, the chimeric AAV capsid proteins are encoded by nucleic acids represented by SEQ ID NO: 1-4 or SEQ ID NO: 9-12.

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

As used herein, the term "nucleic acid" refers to polymers of linked nucleotides, such as DNA, RNA, etc. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been artificially produced (e.g., by chemical synthesis, by recombinant DNA technology, etc.).

"Homology" refers to the percent identity between two polynucleotides or two polypeptides. The term "substantial homology" when referring to a nucleic acid, or fragment thereof, indicates that, when optimally aligned with appropriate nucleotide insertions or deletions with another nucleic acid (or its complementary strand), there is nucleotide sequence identity in about 90 to 100% of the aligned sequences. When referring to a polypeptide, or fragment thereof, the term "substantial homology" indicates that, when optimally aligned with appropriate gaps, insertions or deletions with another polypeptide, there is nucleotide sequence identity in about 90 to 100% of the aligned sequences. The term "highly conserved" means at least 80% identity, preferably at least 90% identity, and more preferably, over 97% identity. In some cases, highly conserved may refer to 100% identity. Identity is readily determined by one of skill in the art by, for example, the use of algorithms and computer programs known by those of skill in the art.

As described herein, alignments between sequences of nucleic acids or polypeptides are performed using any of a variety of publicly or commercially available Multiple Sequence Alignment Programs, such as "Clustal W", accessible through Web Servers on the internet. Alternatively, Vector NTI utilities may also be used. There are also a number of algorithms known in the art which can be used to measure nucleotide sequence identity, including those contained in the programs described above. As another example, polynucleotide sequences can be compared using BLASTN, which provides alignments and percent sequence identity of the regions of the best overlap between the query and search sequences. Similar programs are available for the comparison of amino acid sequences, e.g., the "Clustal X" program, BLASTP. Typically, any of these programs are used at default settings, although one of skill in the art can alter these settings as needed. Alternatively, one of skill in the art can utilize another algorithm or computer program which provides at least the level of identity or alignment as that provided by the referenced algorithms and programs. Alignments may be used to identify corresponding amino acids between two proteins or peptides. A "corresponding amino acid" is an amino acid of a protein or peptide sequence that has been aligned with an amino acid of another protein or peptide sequence. Corresponding amino acids may be identical or non-identical. A corresponding amino acid that is a non-identical amino acid may be referred to as a variant amino acid.

Alternatively for nucleic acids, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art.

Recombinant AAVs

In some aspects, the disclosure provides isolated AAVs. As used herein with respect to AAVs, the term "isolated" refers to an AAV that has been artificially obtained or produced. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected. In some embodiments, the rAAV comprises a capsid protein having an amino acid sequence as set forth in any one of SEQ ID NOs 5-8 or SEQ ID NO: 13-16, or a protein having substantial homology thereto.

In some embodiments, the rAAVs of the disclosure are pseudotyped rAAVs. Pseudotyping is the process of producing viruses or viral vectors in combination with foreign viral envelope proteins. The result is a pseudotyped virus particle. With this method, the foreign viral envelope proteins can be used to alter host tropism or an increased/decreased stability of the virus particles. In some aspects, a pseudotyped rAAV comprises nucleic acids from two or more different AAVs, wherein the nucleic acid from one AAV encodes a capsid protein and the nucleic acid of at least one other AAV encodes other viral proteins and/or the viral genome. In some embodiments, a pseudotyped rAAV refers to an AAV comprising an inverted terminal repeats (ITRs) of one AAV serotype and an capsid protein of a different AAV serotype. For example, a pseudotyped AAV vector containing the ITRs of serotype X encapsidated with the proteins of Y will be designated as AAVX/Y (e.g., AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein (e.g., a nucleic acid having a sequence as set forth in any one of SEQ ID NOs: 1-4 or SEQ ID NO: 9-12, or fragment thereof; a functional rep gene; a recombinant AAV vector composed of, AAV inverted terminal repeats (ITRs) and a transgene; and sufficient helper functions to permit packaging of the recombinant AAV vector into the AAV capsid proteins.

In some embodiments, the disclosure relates to a rAAV comprising a chimeric capsid protein identified by the methods disclosed herein. In some embodiments, the rAAV targets the CNS tissue of a subject. In some embodiments, the rAAV further comprises a transgene. In some embodiments, the transgene is a CNS-associated gene. In some embodiments, the rAAV targets the liver tissue of a subject. In some embodiments, the transgene is a Liver- or CNS-associated miRNA.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the disclosure. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA, miRNA inhibitor) from a transcribed gene.

The foregoing methods for packaging recombinant vectors in desired AAV capsids to produce the rAAVs of the disclosure are not meant to be limiting and other suitable methods will be apparent to the skilled artisan.

Recombinant AAV Vectors

"Recombinant AAV (rAAV) vectors" of the disclosure are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In some embodiments, the rAAVs of the disclosure are pseudotyped rAAVs. For example, a pseudotyped AAV vector containing the ITRs of serotype X encapsidated with the proteins of Y will be designated as AAVX/Y (e.g., AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA, miRNA inhibitor).

For nucleic acids encoding proteins, a polyadenylation sequence generally is inserted following the transgene sequences and before the 3' AAV ITR sequence. A rAAV construct useful in the disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (, Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, one or more binding sites for one or more of miRNAs are incorporated in a transgene of a rAAV vector, to inhibit the expression of the transgene in one or more tissues of a subject harboring the transgene. The skilled artisan will appreciate that binding sites may be selected to control the expression of a transgene in a tissue specific manner. For example, binding sites for the liver-specific miR-122 may be incorporated into a transgene to inhibit expression of that transgene in the liver. The target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

Recombinant AAV Vector: Transgene Coding Sequences

The composition of the transgene sequence of the rAAV vector will depend upon the use to which the resulting vector will be put. For example, one type of transgene sequence includes a reporter sequence, which upon expression produces a detectable signal. In another example, the transgene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

Reporter sequences that may be provided in a transgene include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer. Such reporters can, for example, be useful in verifying the tissue-specific targeting capabilities and tissue specific promoter regulatory activity of an rAAV.

In some aspects, the disclosure provides rAAV vectors for use in methods of preventing or treating one or more genetic deficiencies or dysfunctions in a mammal, such as for example, a polypeptide deficiency or polypeptide excess in a mammal, and particularly for treating or reducing the severity or extent of deficiency in a human manifesting one or more of the disorders linked to a deficiency in such polypeptides in cells and tissues. The method involves administration of an rAAV vector that encodes one or more therapeutic peptides, polypeptides, siRNAs, microRNAs, antisense nucleotides, etc. in a pharmaceutically-acceptable carrier to the subject in an amount and for a period of time sufficient to treat the deficiency or disorder in the subject suffering from such a disorder.

Thus, the disclosure embraces the delivery of rAAV vectors encoding one or more peptides, polypeptides, or proteins, which are useful for the treatment or prevention of disease states in a mammalian subject. Exemplary therapeutic proteins include one or more polypeptides selected from the group consisting of growth factors, interleukins, interferons, anti-apoptosis factors, cytokines, anti-diabetic factors, anti-apoptosis agents, coagulation factors, anti-tumor factors. Other non-limiting examples of therapeutic proteins include BDNF, CNTF, CSF, EGF, FGF, G-SCF, GM-CSF, gonadotropin, IFN, IFG-1, M-CSF, NGF, PDGF, PEDF, TGF, VEGF, TGF-B2, TNF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16 IL-17, and IL-18.

The rAAV vectors may comprise a gene to be transferred to a subject to treat a disease associated with reduced expression, lack of expression or dysfunction of the gene. Exemplary genes and associated disease states include, but are not limited to: glucose-6-phosphatase, associated with glycogen storage deficiency type 1A; phosphoenolpyruvate-carboxykinase, associated with Pepck deficiency; galactose-1 phosphate uridyl transferase, associated with galactosemia; phenylalanine hydroxylase, associated with phenylketonuria; branched chain alpha-ketoacid dehydrogenase, associated with Maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; ornithine transcarbamylase, associated with ornithine transcarbamylase deficiency; argininosuccinic acid synthetase, associated with citrullinemia; low density lipoprotein receptor protein, associated with familial hypercholesterolemia; UDP-glucouronosyltransferase, associated with Crigler-Najjar disease; adenosine deaminase, associated with severe combined immunodeficiency disease; hypoxanthine guanine phosphoribosyl transferase, associated with Gout and Lesch-Nyan syndrome; biotinidase, associated with biotinidase deficiency; beta-galactosidase, associated with GM1 gangliosidosis; beta-hexosaminidase A and B, associated with Tay-Sachs disease and Sandhoff disease; beta-glucocerebrosidase, associated with Gaucher disease; beta-glucuronidase, associated with Sly syndrome; peroxisome membrane protein 70 kDa, associated with Zellweger syndrome; porphobilinogen deaminase, associated with acute intermittent porphyria; alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the beta adrenergic receptor, anti-sense to, or a mutant form of, phospholamban, the sarco(endo)plasmic reticulum adenosine triphosphatase-2 (SERCA2), and the cardiac adenylyl cyclase for the treatment of congestive heart failure; a tumor suppessor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; and, insulin for the treatment of diabetes.

In some embodiments, The rAAV vectors may comprise a gene encoding an antigen-binding protein, such as an immunoglobulin heavy chain or light chain or fragment thereof, e.g., that may be used for therapeutic purposes. In some embodiments, the protein is a single chain Fv fragment or Fv-Fc fragment. Accordingly, in some embodiments, the rAAV can be used to infect cells are of target tissue (e.g., muscle tissue) to engineer cells of the tissue to express an antigen-binding protein, such as an antibody or fragment thereof. In some embodiments, to generate rAAVs that express the antibodies or antigen binding fragments, cDNAs engineered to express such proteins will be sucloned into an appropriate plasmid backbone and packaged into an rAAV.

In some embodiments, the rAAV vectors may comprise a gene or genes encoding genome editing enzymes or related molecules. As used herein, "genome editing" refers to adding, disrupting or changing genomic sequences (e.g., a gene sequence). In some embodiments, genome editing is performed using engineered proteins and related molecules. In some aspects, genome editing comprises the use of engineered nucleases to cleave a target genomic locus. In some embodiments, genome editing further comprises inserting, deleting, mutating or substituting nucleic acid residues at a cleaved locus. In some embodiments, inserting, deleting, mutating or substituting nucleic acid residues at a cleaved locus is accomplished through endogenous cellular mechanisms such as homologous recombination (HR) and non-homologous end joining (NHEJ). Exemplary genome editing technologies include, but are not limited to Transcription Activator-like Effector Nucleases (TALENs), Zinc Finger Nucleases (ZFNs), engineered meganuclease re-engineered homing endonucleases and the CRISPR/Cas system. In some embodiments, the rAAV may comprise a gene or genes encoding proteins or molecules related to TALENs, including but not limited to transcription activator-like effectors (TALEs) and restriction endonucleases (e.g., FokI). In some embodiments, the rAAV may comprise a gene or genes encoding proteins or molecules related to ZFNs, including but not limited to proteins comprising the Cys2His2 fold group (for example Zif268 (EGR1)), and restriction endonucleases (e.g., FokI). In some embodiments, the rAAV may comprise a gene or genes encoding proteins or molecules related to the CRISPR/Cas system, including but not limited to Cas9, Cas6, dCas9, CRISPR RNA (crRNA) and trans-activating crRNA (tracrRNA).

The rAAVs of the disclosure can be used to restore the expression of genes that are reduced in expression, silenced, or otherwise dysfunctional in a subject (e.g., a tumor suppressor that has been silenced in a subject having cancer). The rAAVs of the disclosure can also be used to knockdown the expression of genes that are aberrantly expressed in a subject (e.g., an oncogene that is expressed in a subject having cancer). In some embodiments, an rAAV vector comprising a nucleic acid encoding a gene product associated with cancer (e.g., tumor suppressors) may be used to treat the cancer, by administering a rAAV harboring the rAAV vector to a subject having the cancer. In some embodiments, an rAAV vector comprising a nucleic acid encoding a small interfering nucleic acid (e.g., shRNAs, miRNAs) that inhibits the expression of a gene product associated with cancer (e.g., oncogenes) may be used to treat the cancer, by administering a rAAV harboring the rAAV vector to a subject having the cancer. In some embodiments, an rAAV vector comprising a nucleic acid encoding a gene product associated with cancer (or a functional RNA that inhibits the expression of a gene associated with cancer) may be used for research purposes, e.g., to study the cancer or to identify therapeutics that treat the cancer. The following is a non-limiting list of exemplary genes known to be associated with the development of cancer (e.g., oncogenes and tumor suppressors): AAR5, ABCB1, ABCC4, ABI2, ABL1, ABL2, ACK1, ACP2, ACY1, ADSL, AK1, AKR1C2, AKT1, ALB, ANPEP, ANXA5, ANXA7, AP2M1, APC, ARHGAP5, ARHGEF5, ARID4A, ASNS, ATF4, ATM, ATP5B, ATP5O, AXL, BARD1, BAX, BCL2, BHLHB2, BLMH, BRAF, BRCA1, BRCA2, BTK, CANX, CAP1, CAPN1, CAPNS1, CAV1, CBFB, CBLB, CCL2, CCND1, CCND2, CCND3, CCNE1, CCT5, CCYR61, CD24, CD44, CD59, CDC20, CDC25, CDC25A, CDC25B, CDC2L5, CDK10, CDK4, CDK5, CDK9, CDKL1, CDKN1A, CDKN1B, CDKN1C, CDKN2A, CDKN2B, CDKN2D, CEBPG, CENPC1, CGRRF1, CHAF1A, CIB1, CKMT1, CLK1, CLK2, CLK3, CLNS1A, CLTC, COL1A1, COL6A3, COX6C, COX7A2, CRAT, CRHR1, CSF1R, CSK, CSNK1G2, CTNNA1, CTNNB1, CTPS, CTSC, CTSD, CUL1, CYR61, DCC, DCN, DDX10, DEK, DHCR7, DHRS2, DHX8, DLG3, DVL1, DVL3, E2F1, E2F3, E2F5, EGFR, EGR1, EIF5, EPHA2, ERBB2, ERBB3, ERBB4, ERCC3, ETV1, ETV3, ETV6, F2R, FASTK, FBN1, FBN2, FES, FGFR1, FGR, FKBP8, FN1, FOS, FOSL1, FOSL2, FOXG1A, FOXO1A, FRAP1, FRZB, FTL, FZD2, FZD5, FZD9, G22P1, GAS6, GCN5L2, GDF15, GNA13, GNAS, GNB2, GNB2L1, GPR39, GRB2, GSK3A, GSPT1, GTF2I, HDAC1, HDGF, HMMR, HPRT1, HRB, HSPA4, HSPA5, HSPA8, HSPB1, HSPH1, HYAL1, HYOU1, ICAM1, ID1, ID2, IDUA, IER3, IFITM1, IGF1R, IGF2R, IGFBP3, IGFBP4, IGFBP5, IL1B, ILK, ING1, IRF3, ITGA3, ITGA6, ITGB4, JAK1, JARID1A, JUN, JUNB, JUND, K-ALPHA-1, KIT, KITLG, KLK10, KPNA2, KRAS2, KRT18, KRT2A, KRT9, LAMB1, LAMP2, LCK, LCN2, LEP, LITAF, LRPAP1, LTF, LYN, LZTR1, MADH1, MAP2K2, MAP3K8, MAPK12, MAPK13, MAPKAPK3, MAPRE1, MARS, MAS1, MCC, MCM2, MCM4, MDM2, MDM4, MET, MGST1, MICB, MLLT3, MME, MMP1, MMP14, MMP17, MMP2, MNDA, MSH2, MSH6, MT3, MYB, MYBL1, MYBL2, MYC, MYCL1, MYCN, MYD88, MYL9, MYLK, NEO1, NF1, NF2, NFKB1, NFKB2, NFSF7, NID, NINJ1, NMBR, NME1, NME2, NME3, NOTCH1, NOTCH2, NOTCH4, NPM1, NQO1, NR1D1, NR2F1, NR2F6, NRAS, NRG1, NSEP1, OSM, PA2G4, PABPC1, PCNA, PCTK1, PCTK2, PCTK3, PDGFA, PDGFB, PDGFRA, PDPK1, PEA15, PFDN4, PFDN5, PGAM1, PHB, PIK3CA, PIK3CB, PIK3CG, PIM1, PKM2, PKMYT1, PLK2, PPARD, PPARG, PPIH, PPP1CA, PPP2R5A, PRDX2, PRDX4, PRKAR1A, PRKCBP1, PRNP, PRSS15, PSMA1, PTCH, PTEN, PTGS1, PTMA, PTN, PTPRN, RAB5A, RAC1, RAD50, RAF1, RALBP1, RAP1A, RARA, RARB, RASGRF1, RB1, RBBP4, RBL2, REA, REL, RELA, RELB, RET, RFC2, RGS19, RHOA, RHOB, RHOC, RHOD, RIPK1, RPN2, RPS6KB1, RRM1, SARS, SELENBP1, SEMA3C, SEMA4D, SEPP1, SERPINH1, SFN, SFPQ, SFRS7, SHB, SHH, SIAH2, SIVA, SIVA TP53, SKI, SKIL, SLC16A1, SLC1A4, SLC20A1, SMO, SMPD1, SNAI2, SND1, SNRPB2, SOCS1, SOCS3, SOD1, SORT1, SPINT2, SPRY2, SRC, SRPX, STAT1, STAT2, STAT3, STAT5B, STC1, TAF1, TBL3, TBRG4, TCF1, TCF7L2, TFAP2C, TFDP1, TFDP2, TGFA, TGFB1, TGFBI, TGFBR2, TGFBR3, THBS1, TIE, TIMP1, TIMP3, TJP1, TK1, TLE1, TNF, TNFRSF10A, TNFRSF10B, TNFRSF1A, TNFRSF1B, TNFRSF6, TNFSF7, TNK1, TOB1, TP53, TP53BP2, TP53I3, TP73, TPBG, TPT1, TRADD, TRAM1, TRRAP, TSG101, TUFM, TXNRD1, TYRO3, UBC, UBE2L6, UCHL1, USP7, VDAC1, VEGF, VHL, VIL2, WEE1, WNT1, WNT2, WNT2B, WNT3, WNT5A, WT1, XRCC1, YES1, YWHAB, YWHAZ, ZAP70, and ZNF9.

A rAAV vector may comprise as a transgene, a nucleic acid encoding a protein or functional RNA that modulates apoptosis. The following is a non-limiting list of genes associated with apoptosis and nucleic acids encoding the products of these genes and their homologues and encoding small interfering nucleic acids (e.g., shRNAs, miRNAs) that inhibit the expression of these genes and their homologues are useful as transgenes in certain embodiments of the disclosure: RPS27A, ABL1, AKT1, APAF1, BAD, BAG1, BAG3, BAG4, BAK1, BAX, BCL10, BCL2, BCL2A1, BCL2L1, BCL2L10, BCL2L11, BCL2L12, BCL2L13, BCL2L2, BCLAF1, BFAR, BID, BIK, NAIP, BIRC2, BIRC3, XIAP, BRCS, BIRC6, BIRC7, BIRC8, BNIP1, BNIP2, BNIP3, BNIP3L, BOK, BRAF, CARD10, CARD11, NLRC4, CARD14, NOD2, NOD1, CARD6, CARD8, CARD9, CASP1, CASP10, CASP14, CASP2, CASP3, CASP4, CASP5, CASP6, CASP7, CASP8, CASP9, CFLAR, CIDEA, CIDEB, CRADD, DAPK1, DAPK2, DFFA, DFFB, FADD, GADD45A, GDNF, HRK, IGF1R, LTA, LTBR, MCL1, NOL3, PYCARD, RIPK1, RIPK2, TNF, TNFRSF10A, TNFRSF10B, TNFRSF10C, TNFRSF10D, TNFRSF11B, TNFRSF12A, TNFRSF14, TNFRSF19, TNFRSF1A, TNFRSF1B, TNFRSF21, TNFRSF25, CD40, FAS, TNFRSF6B, CD27, TNFRSF9, TNFSF10, TNFSF14, TNFSF18, CD40LG, FASLG, CD70, TNFSF8, TNFSF9, TP53, TP53BP2, TP73, TP63, TRADD, TRAF1, TRAF2, TRAF3, TRAF4, and TRAF5.

In some aspects, the disclosure relates to methods and compositions for treating CNS-related disorders. As used herein, a "CNS-related disorder" is a disease or condition of the central nervous system. A CNS-related disorder may affect the spinal cord (e.g., a myelopathy), brain (e.g., a encephalopathy) or tissues surrounding the brain and spinal cord. A CNS-related disorder may be of a genetic origin, either inherited or acquired through a somatic mutation. A CNS-related disorder may be a psychological condition or disorder, e.g., Attention Deficit Hyperactivity Disorder, Autism Spectrum Disorder, Mood Disorder, Schizophrenia, Depression, Rett Syndrome, etc. A CNS-related disorder may be an autoimmune disorder. A CNS-related disorder may also be a cancer of the CNS, e.g., brain cancer. A CNS-related disorder that is a cancer may be a primary cancer of the CNS, e.g., an astrocytoma, glioblastomas, etc., or may be a cancer that has metastasized to CNS tissue, e.g., a lung cancer that has metastasized to the brain. Further non-limiting examples of CNS-related disorders, include Parkinson's Disease, Lysosomal Storage Disease, Ischemia, Neuropathic Pain, Amyotrophic lateral sclerosis (ALS), Multiple Sclerosis (MS), and Canavan disease (CD).

In some embodiments, the disclosure relates to a rAAV vector comprising a transgene, a nucleic acid encoding a protein or functional RNA useful for the treatment of a condition, disease or disorder associated with the central nervous system (CNS). The following is a non-limiting list of genes associated with CNS disease: DRD2, GRIA1, GRIA2, GRIN1, SLC1A1, SYP, SYT1, CHRNA7, 3Rtau/4rTUS, APP, BAX, BCL-2, GRIK1, GFAP, IL-1, AGER, associated with Alzheimer's Disease; UCH-L1, SKP1, EGLN1, Nurr-1, BDNF, TrkB, gstml, S106β, associated with Parkinson's Disease; IT15, PRNP, JPH3, TBP, ATXN1, ATXN2, ATXN3, Atrophin 1, FTL, TITF-1, associated with Huntington's Disease; FXN, associated with Freidrich's ataxia; ASPA, associated with Canavan's Disease; DMD, associated with muscular dystrophy; and SMN1, UBE1, DYNC1H1 associated with spinal muscular atrophy.

The skilled artisan will also realize that in the case of transgenes encoding proteins or polypeptides, that mutations that results in conservative amino acid substitutions may be made in a transgene to provide functionally equivalent variants, or homologs of a protein or polypeptide. In some aspects the disclosure embraces sequence alterations that result in conservative amino acid substitution of a transgene. In some embodiments, the transgene comprises a gene having a dominant negative mutation. For example, a transgene may express a mutant protein that interacts with the same elements as a wild-type protein, and thereby blocks some aspect of the function of the wild-type protein.

Useful transgene products also include miRNAs. miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

The following non-limiting list of miRNA genes, and their homologues, are useful as transgenes or as targets for small interfering nucleic acids encoded by transgenes (e.g., miRNA sponges, antisense oligonucleotides, TuD RNAs) in certain embodiments of the methods: hsa-let-7a, hsa-let-7a*, hsa-let-7b, hsa-let-7b*, hsa-let-7c, hsa-let-7c*, hsa-let-7d, hsa-let-7d*, hsa-let-7e, hsa-let-7e*, hsa-let-7f, hsa-let-7f-1*, hsa-let-7f-2*, hsa-let-7g, hsa-let-7g*, hsa-let-7i, hsa-let-7i*, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-1207-3p, hsa-miR-1207-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR-1246, hsa-miR-1247, hsa-miR-1248, hsa-miR-1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1*, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-127-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsa-miR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsa-miR-1299, hsa-miR-1300, hsa-miR-1301, hsa-miR-1302, hsa-miR-1303, hsa-miR-1304, hsa-miR-1305, hsa-miR-1306, hsa-miR-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-1*, hsa-miR-16-2*, hsa-miR-17, hsa-miR-17*, hsa-miR-181a, hsa-miR-181a*, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-miR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-29b-1*, hsa-miR-29b-2*, hsa-miR-29c, hsa-miR-29c*, hsa-miR-300, hsa-miR-301a, hsa-miR-301b, hsa-miR-302a, hsa-miR-302a*, hsa-miR-302b, hsa-miR-302b*, hsa-miR-302c, hsa-miR-302c*, hsa-miR-302d, hsa-miR-302d*, hsa-miR-302e, hsa-miR-302f, hsa-miR-30a, hsa-miR-30a*, hsa-miR-30b, hsa-miR-30b*, hsa-miR-30c, hsa-miR-30c-1*, hsa-miR-30c-2*, hsa-miR-30d, hsa-miR-30d*, hsa-miR-30e, hsa-miR-30e*, hsa-miR-31, hsa-miR-31*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsa-miR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR-518b, hsa-miR-518c, hsa-miR-518c*, hsa-miR-518d-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR-519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-548b-5p, hsa-miR-548c-3p, hsa-miR-548c-5p, hsa-miR-548d-3p, hsa-miR-548d-5p, hsa-miR-548e, hsa-miR-548f, hsa-miR-548g, hsa-miR-548h, hsa-miR-548i, hsa-miR-548j, hsa-miR-548k, hsa-miR-5481, hsa-miR-548m, hsa-miR-548n, hsa-miR-548o, hsa-miR-548p, hsa-miR-549, hsa-miR-550, hsa-miR-550*, hsa-miR-551a, hsa-miR-551b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-miR-589, hsa-miR-589*, hsa-miR-590-3p, hsa-miR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR-885-5p, hsa-miR-886-3p, hsa-miR-886-5p, hsa-miR-887, hsa-miR-888, hsa-miR-888*, hsa-miR-889, hsa-miR-890, hsa-miR-891a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*.

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, an small interfering nucleic acid that is substantially complementary to a miRNA is one that is capable of hybridizing with a miRNA, and blocking the miRNA's activity. In some embodiments, an small interfering nucleic acid that is substantially complementary to a miRNA is an small interfering nucleic acid that is complementary with the miRNA at all but 1, 2, 3, 4, 5, 6, 7, 8, 9, 10, 11, 12, 13, 14, 15, 16, 17, or 18 bases. In some embodiments, an small interfering nucleic acid sequence that is substantially complementary to a miRNA, is an small interfering nucleic acid sequence that is complementary with the miRNA at, at least, one base.

A "miRNA Inhibitor" is an agent that blocks miRNA function, expression and/or processing. For instance, these molecules include but are not limited to microRNA specific antisense, microRNA sponges, tough decoy RNAs (TuD RNAs) and microRNA oligonucleotides (double-stranded, hairpin, short oligonucleotides) that inhibit miRNA interaction with a Drosha complex. MicroRNA inhibitors can be expressed in cells from a transgenes of a rAAV vector, as discussed above. MicroRNA sponges specifically inhibit miRNAs through a complementary heptameric seed sequence (Ebert, M. S. Nature Methods, Epub Aug. 12, 2007). In some embodiments, an entire family of miRNAs can be silenced using a single sponge sequence. TuD RNAs achieve efficient and long-term-suppression of specific miR-NAs in mammalian cells (See, e.g., Takeshi Haraguchi, et al., Nucleic Acids Research, 2009, Vol. 37, No. 6 e43, the contents of which relating to TuD RNAs are incorporated herein by reference). Other methods for silencing miRNA function (derepression of miRNA targets) in cells will be apparent to one of ordinary skill in the art.

In some embodiments, the cloning capacity of the recombinant RNA vector may limited and a desired coding sequence may require the complete replacement of the virus's 4.8 kilobase genome. Large genes may, therefore, not be suitable for use in a standard recombinant AAV vector, in some cases. The skilled artisan will appreciate that options are available in the art for overcoming a limited coding capacity. For example, the AAV ITRs of two genomes can anneal to form head to tail concatamers, almost doubling the capacity of the vector. Insertion of splice sites allows for the removal of the ITRs from the transcript. Other options for overcoming a limited cloning capacity will be apparent to the skilled artisan.

Somatic Transgenic Animal Models Produced Using rAAV-Based Gene Transfer

The disclosure also involves the production of somatic transgenic animal models of disease using recombinant Adeno-Associated Virus (rAAV) based methods. The methods are based, at least in part, on the observation that AAV serotypes and variants thereof mediate efficient and stable gene transfer in a tissue specific manner in adult animals. The rAAV elements (capsid, promoter, transgene products) are combined to achieve somatic transgenic animal models that express a stable transgene in a time and tissue specific manner. The somatic transgenic animal produced by the methods of the disclosure can serve as useful models of human disease, pathological state, and/or to characterize the effects of gene for which the function (e.g., tissue specific, disease role) is unknown or not fully understood. For example, an animal (e.g., mouse) can be infected at a distinct developmental stage (e.g., age) with a rAAV comprising a capsid having a specific tissue targeting capability (e.g., liver, heart, pancreas) and a transgene having a tissue specific promoter driving expression of a gene involved in disease. Upon infection, the rAAV infects distinct cells of the target tissue and produces the product of the transgene.

In some embodiments, the sequence of the coding region of a transgene is modified. The modification may alter the function of the product encoded by the transgene. The effect of the modification can then be studied in vivo by generating a somatic transgenic animal model using the methods disclosed herein. In some embodiments, modification of the sequence of coding region is a nonsense mutation that results in a fragment (e.g., a truncated version). In other cases, the modification is a missense mutation that results in an amino acid substitution. Other modifications are possible and will be apparent to the skilled artisan.

In some embodiments, the transgene causes a pathological state. A transgene that causes a pathological state is a gene whose product has a role in a disease or disorder (e.g., causes the disease or disorder, makes the animal susceptible to the disease or disorder) and/or may induce the disease or disorder in the animal. The animal can then be observed to evaluate any number of aspects of the disease (e.g., progression, response to treatment, etc.). These examples are not meant to be limiting, other aspects and examples are disclosed herein and described in more detail below.

The disclosure in some aspects, provide methods for producing somatic transgenic animal models through the targeted destruction of specific cell types. For example, models of type 1 diabetes can be produced by the targeted destruction of pancreatic Beta-islets. In other examples, the targeted destruction of specific cell types can be used to evaluate the role of specific cell types on human disease. In this regard, transgenes that encode cellular toxins (e.g., diphtheria toxin A (DTA)) or pro-apoptotic genes (NTR, Box, etc.) can be useful as transgenes for functional ablation of specific cell types. Other exemplary transgenes, whose products kill cells are embraced by the methods disclosed herein and will be apparent to one of ordinary skill in the art.

The disclosure in some aspects, provides methods for producing somatic transgenic animal models to study the long-term effects of over-expression or knockdown of genes. The long term over expression or knockdown (e.g., by shRNA, miRNA, miRNA inhibitor, etc.) of genes in specific target tissues can disturb normal metabolic balance and establish a pathological state, thereby producing an animal model of a disease, such as, for example, cancer. The disclosure in some aspects, provides methods for producing somatic transgenic animal models to study the long-term effects of over-expression or knockdown of gene of potential oncogenes and other genes to study tumorigenesis and gene function in the targeted tissues. Useful transgene products include proteins that are known to be associated with cancer and small interfering nucleic acids inhibiting the expression of such proteins.

Other suitable transgenes may be readily selected by one of skill in the art provided that they are useful for creating animal models of tissue-specific pathological state and/or disease.

Recombinant AAV Administration Methods

The rAAVs may be delivered to a subject in compositions according to any appropriate methods known in the art. The rAAV, preferably suspended in a physiologically compatible carrier (e.g., in a composition), may be administered to a subject, e.g., host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

RAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain embodiments, $10^{12}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intrapancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 .ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (e.g., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms.

Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

In some cases, the methods involve transfecting cells with total cellular DNAs isolated from the tissues that potentially harbor proviral AAV genomes at very low abundance and supplementing with helper virus function (e.g., adenovirus) to trigger and/or boost AAV rep and cap gene transcription in the transfected cell. In some cases, RNA from the transfected cells provides a template for RT-PCR amplification of cDNA and the detection of novel AAVs. In cases where cells are transfected with total cellular DNAs isolated from the tissues that potentially harbor proviral AAV genomes, it is often desirable to supplement the cells with factors that promote AAV gene transcription. For example, the cells may also be infected with a helper virus, such as an Adenovirus or a Herpes Virus. In a specific embodiment, the helper functions are provided by an adenovirus. The adenovirus may be a wild-type adenovirus, and may be of human or non-human origin, preferably non-human primate (NHP) origin. Similarly adenoviruses known to infect non-human animals (e.g., chimpanzees, mouse) may also be employed in the methods of the disclosure (See, e.g., U.S. Pat. No. 6,083,716). In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

Cells may also be transfected with a vector (e.g., helper vector) which provides helper functions to the AAV. The vector providing helper functions may provide adenovirus functions, including, e.g., E1a, E1b, E2a, E4ORF6. The sequences of adenovirus gene providing these functions may be obtained from any known adenovirus serotype, such as serotypes 2, 3, 4, 7, 12 and 40, and further including any of the presently identified human types known in the art. Thus, in some embodiments, the methods involve transfecting the cell with a vector expressing one or more genes necessary for AAV replication, AAV gene transcription, and/or AAV packaging.

In some cases, a novel isolated capsid gene can be used to construct and package recombinant AAV vectors, using methods well known in the art, to determine functional characteristics associated with the novel capsid protein encoded by the gene. For example, novel isolated capsid genes can be used to construct and package recombinant AAV (rAAV) vectors comprising a reporter gene (e.g., B-Galactosidase, GFP, Luciferase, etc.). The rAAV vector can then be delivered to an animal (e.g., mouse) and the tissue targeting properties of the novel isolated capsid gene can be determined by examining the expression of the reporter gene in various tissues (e.g., heart, liver, kidneys) of the animal. Other methods for characterizing the novel isolated capsid genes are disclosed herein and still others are well known in the art.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

The following Examples are meant to illustrate, but in no way limit the claimed invention.

EXAMPLES

Example 1: A Novel AAV Capsid Library

Unlike peptide phage display libraries where the tissue resident phages are amplified by infection of bacteria, the multiple rounds of in vivo selection using AAV capsid libraries require PCR amplification of the entire cap gene followed by high-efficiency cloning and re-packaging. Each iteration of this process takes weeks to months. Therefore, we decided to generate a new AAV capsid library of higher diversity and based on a larger number of wild type AAV capsids, namely AAV1, AAV2, AAV4, AAV5, AAV6, AAV8, AAV9, AAVrh8, AAVrh10, AAVrh39, and AAVrh43. In addition to increasing the diversity and complexity of the new library we wanted to also investigate a new approach for in vivo selection of AAV capsid libraries by using unique barcodes in the 3'UTR of each clone in the library and deep sequencing to determine their frequency in target cells/tissue followed by PCR amplification of capsid/barcode pairs from the plasmid library (see FIG. 1).

Generation of Barcoded Capsid Library

Inclusion of unique barcodes in lentivirus-shRNA libraries dramatically accelerated genome-wide screens of gene function and pathway discovery. In these libraries with <100,000 clones, unique barcodes have been used and the relation between barcode and shRNA well characterized by high-throughput sequencing. Moreover a unique set of 240,000 microarray compatible barcodes have been developed. For the present application with a library of $2 \times 10^7$ clones, it was impossible to utilize such approach.

Figure 2:
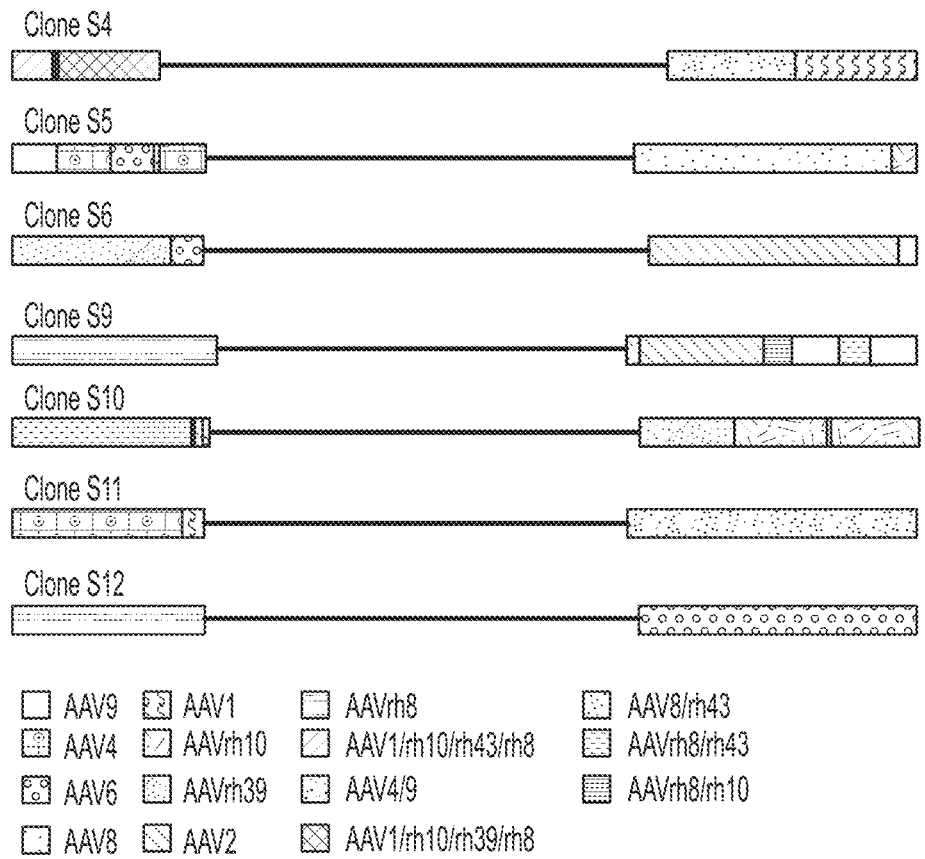
FIG. 2 depicts a sequence composition of AAV capsid clones in new barcoded library. Note that all amplified AAV genomes are chimeric.

Therefore we used a constrained randomized 30-mer $(NNM)_{10}$ designed to eliminate specific restriction site from the barcode. The number of possible barcodes in this configuration is $1.1 \times 10^{15}$. We synthesized the equivalent of $\sim 10^{12}$ barcodes and inserted it in the 3' untranslated region of the chimeric AAV genomes. Given the difference in size between the library ($2 \times 10^7$) and the synthesized barcode oligonucleotide ($\sim 10^{12}$), it is likely that each cap gene is linked to a different barcode. We have produced this new AAV capsid library and PCR amplified AAV genomes from the purified virion stock. Sequencing has shown that each clone has an individual and unrelated barcode (Table 1), and that all amplified AAV genomes are chimeric (FIG. 2). Thus far we have not observed evidence of a bias in the packaged chimeric AAV genomes.

TABLE 1

Exemplary AAV capsid library barcodes

| Clone Nb. | Barcodes | SEQ ID NO. |
|---|---|---|
| S4 | GTCTCATGCTATTGCTTCGCATCGTCAGAC | 17 |
| S5 | GCAGGAGTCTTCGGTGCAGTTTGTTACGCA | 18 |
| S6 | TGATTGGACTAGTCGTGGGAGTTAGCATGC | 19 |
| S9 | TTATCTGGCGTGTAGGCAGCGGCCTCAGAC | 20 |
| S10 | TTATACGACTCATATGTGGCATACGTCGTG | 21 |
| S11 | GGAGCCGAGGAAGACTTGTCCGGGGACTGG | 22 |
| S12 | GCCGGGGTGTTGGTCTTTGTCTACGATGGC | 23 |

This one-step in vivo AAV capsid selection approach relies on the ability to analyze simultaneously millions of sequences by deep sequencing and thus assess the frequency of individual bar codes in target cells/tissues. The second component that we will be optimizing throughout the process is how to identify the capsid sequences that correspond to each barcode. It is not feasible to sequence every single clone in a library of $2 \times 10^7$ clones by traditional methods, and deep sequencing of such large DNA molecules would require breaking them into smaller fragments, which would lead to the loss of information on the chimeric nature of these new cap genes. Therefore we will utilize the sequence variation in the barcodes to design PCR-based strategies to amplify the cap gene corresponding to each barcode using the plasmid library as template.

Cell Culture Testing of AAV Capsid Library

Figure 3A:
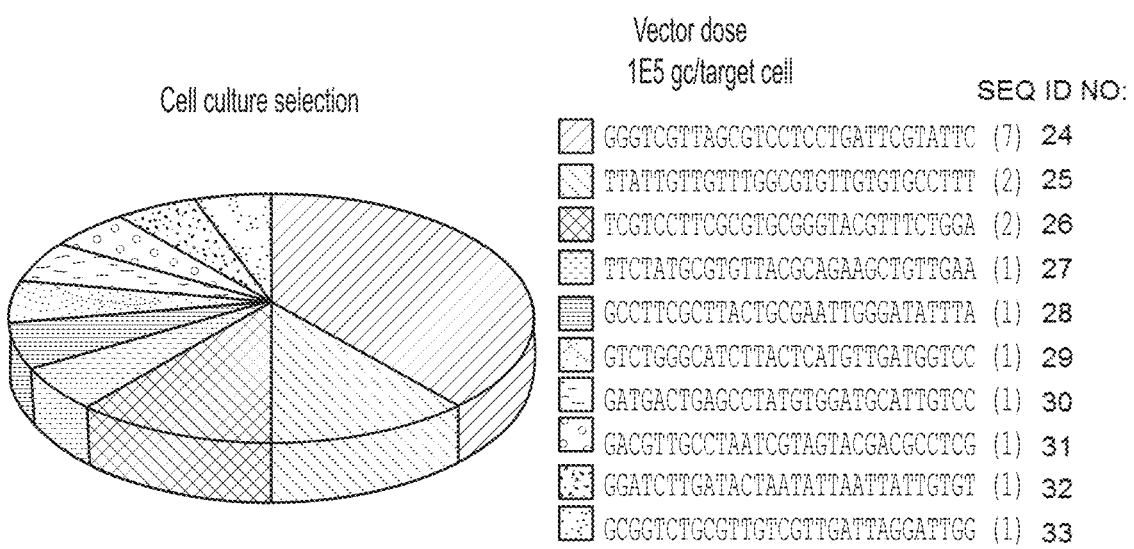
FIGS. 3A-3C depict barcode distribution after cell culture and in vivo selection of AAV capsid library. Left panel—Selection of AAV library in human U87 glioma cells at decreasing gc/target cell. Right panel—Different doses of AAV library were infused via the tail vein into 6-8 week-old C57BL/6 mice and barcodes PCR amplified from genomic DNA isolated 3 days later. Shown are the results for barcode frequency in liver from mice infused with 5E11 or 1E9 gc, and brain barcodes from the same mouse infused with 5E11 gc.
Figure 3B:
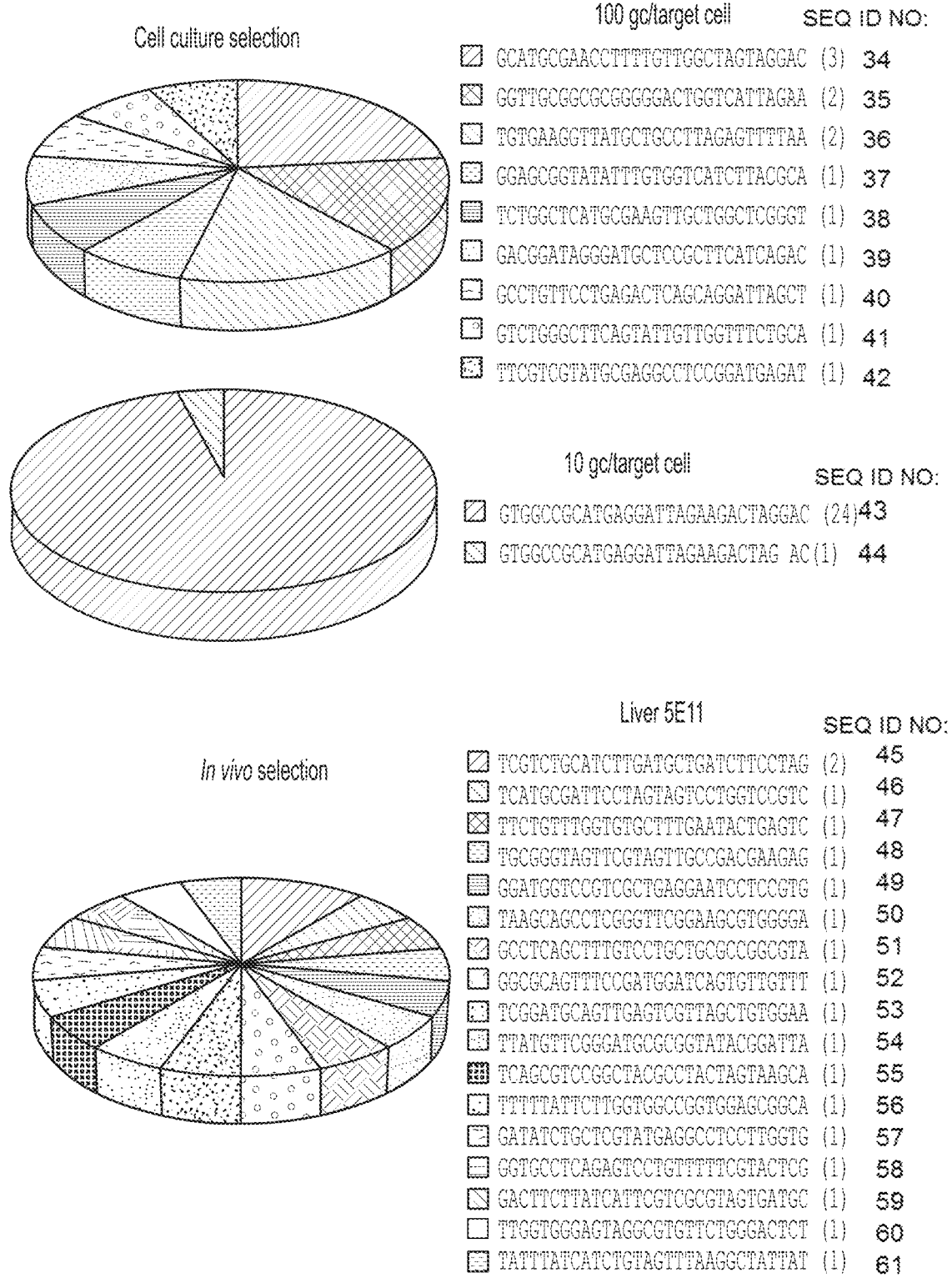
Figure 3C:
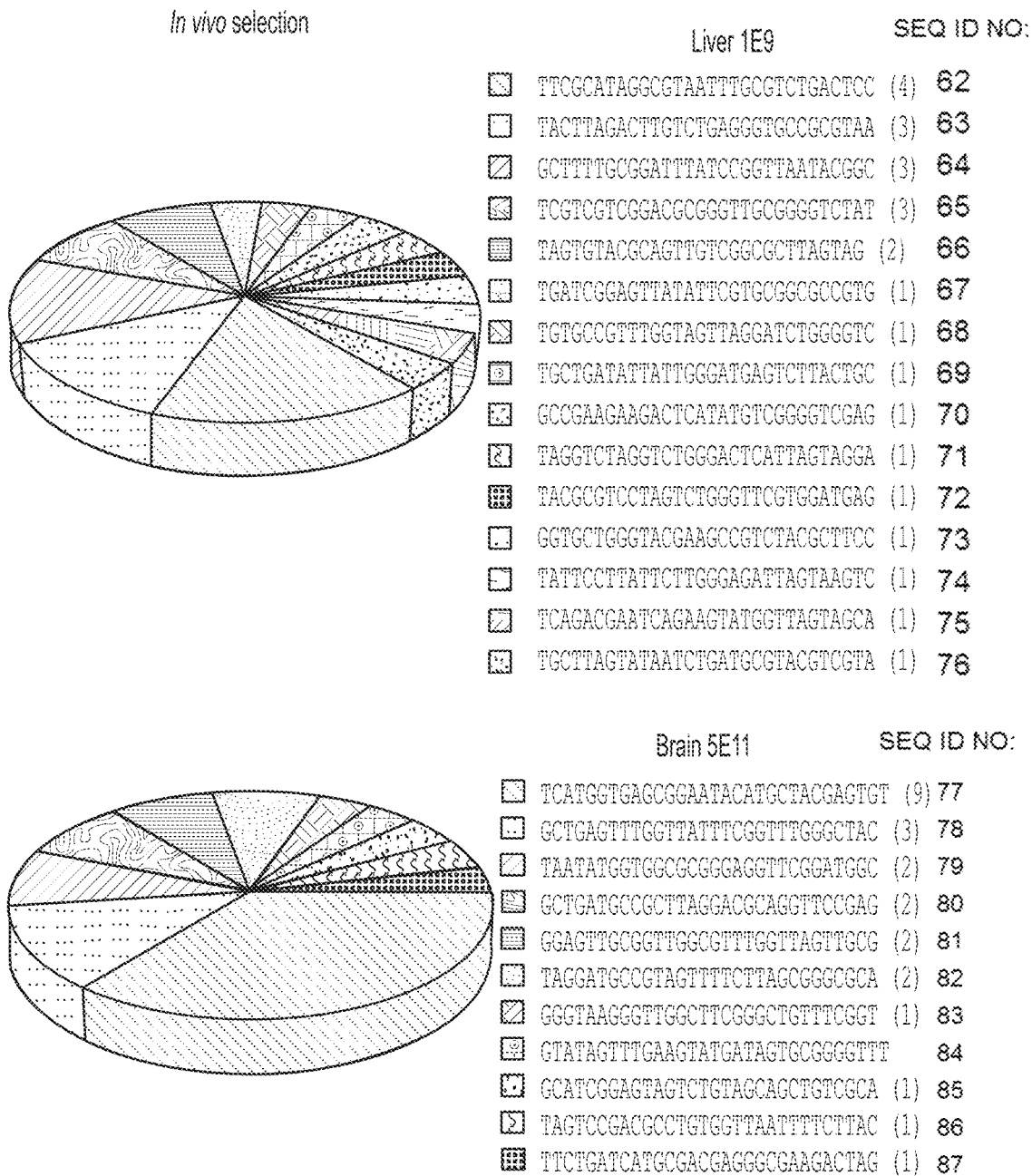

We performed experiments in human U87 glioma cells with AAV library doses of 10, $10^2$, $10^5$ genome copies (gc)/target cell. Cells were exposed to the library for 4 hrs. followed by extensive washing and incubation for 3 days. Barcodes were PCR amplified from crude cell lysates using primers specific for constant regions immediately flanking them. The PCR products were cloned into a TOPO-TA cloning plasmid and individual barcodes sequenced for a number of clones for each library dose. We found evidence of clonal dominance for all library doses, but especially at the lowest dose where 24 out of 25 clones were a single barcode (FIG. 3). The experiment was repeated with similar results of clonal dominance at the lowest library dose, albeit different barcodes were identified. These results suggest that lower AAV library doses may lead to increased stringency and identification of the most infectious clones without deep sequencing.

In Vivo Testing

Next we tested the validity of this principle in wild type mice. For this purpose we infused the AAV library via the tail vein of 6-8 week-old C57BL/6 mice at doses of $1E^9$, $1E^{10}$, $1E^{11}$, and $5E^{11}$ gc (one mouse per dose). Three days later we collected cerebrum, cerebellum, spinal cord, liver, skeletal muscle and heart from each mouse, and isolated genomic DNA. We have conducted the barcode survey in cerebrum and liver, as these two organs present very different transduction profiles for most gene transfer vectors, including AAV.

In the liver of AAV library-infused mice we found no evidence of barcode dominance at $5E^{11}$, but a considerable number of seemingly over-represented clones at $1E^9$ (FIG. 3). In contrast, in the brain we were unable to recover any barcodes at $1E^9$, but observed clear over-representation of certain barcodes at $5E^{11}$ (FIG. 3). These results are consistent with the observation that the liver is often the main depot of AAV vector genomes after systemic delivery, while the brain often has only a small percentage of the total dose, if at all. Therefore it appears that the selection stringency in vivo is dependent on library dose and target tissue. Deep sequencing of barcodes may allow identification of over-represented barcodes in all organs for the same library dose.

These results in cell culture and in vivo suggest that our principle of single-round selection/panning may be sufficient to identify novel chimeric AAV capsids with tropism for the targets of choice. These results also suggest that lower AAV doses lead to increased selection and stringency. The presence of barcodes as a diagnostic tag is critical, as the ability to estimate viral diversity and biases by deep sequencing simply does not exist for the earlier published non-barcoded AAV capsid libraries due to the chimeric nature of DNA-shuffled libraries. Deep sequencing of tissue barcode could also help bypass potential biases inherent to low-throughput sequencing screens.

In Vivo Identification of Brain-Targeting Chimeric AAVs from the Barcoded Capsid Library Traditionally, in-vivo selection of AAV libraries from target tissue has been done by either PCR amplification of full-length chimeric cap genes enriched in target tissues, or by adenoviral rescue. As an alternative strategy to our single-round in-vivo selection strategy using the barcodes as 'fishing' tags, we decided to investigate whether we could also recover enriched full-length cap genes from total DNA isolates of target tissues in a single round. An important thing to note here is although this approach does not require the use of barcodes as 'fishing' tags, they still serve to distinguish unique capsid sequences from each other; even chimeric capsid genes that differ by a single nucleotide can be readily distinguished from each other by the presence of unique barcodes.

Figure 4:
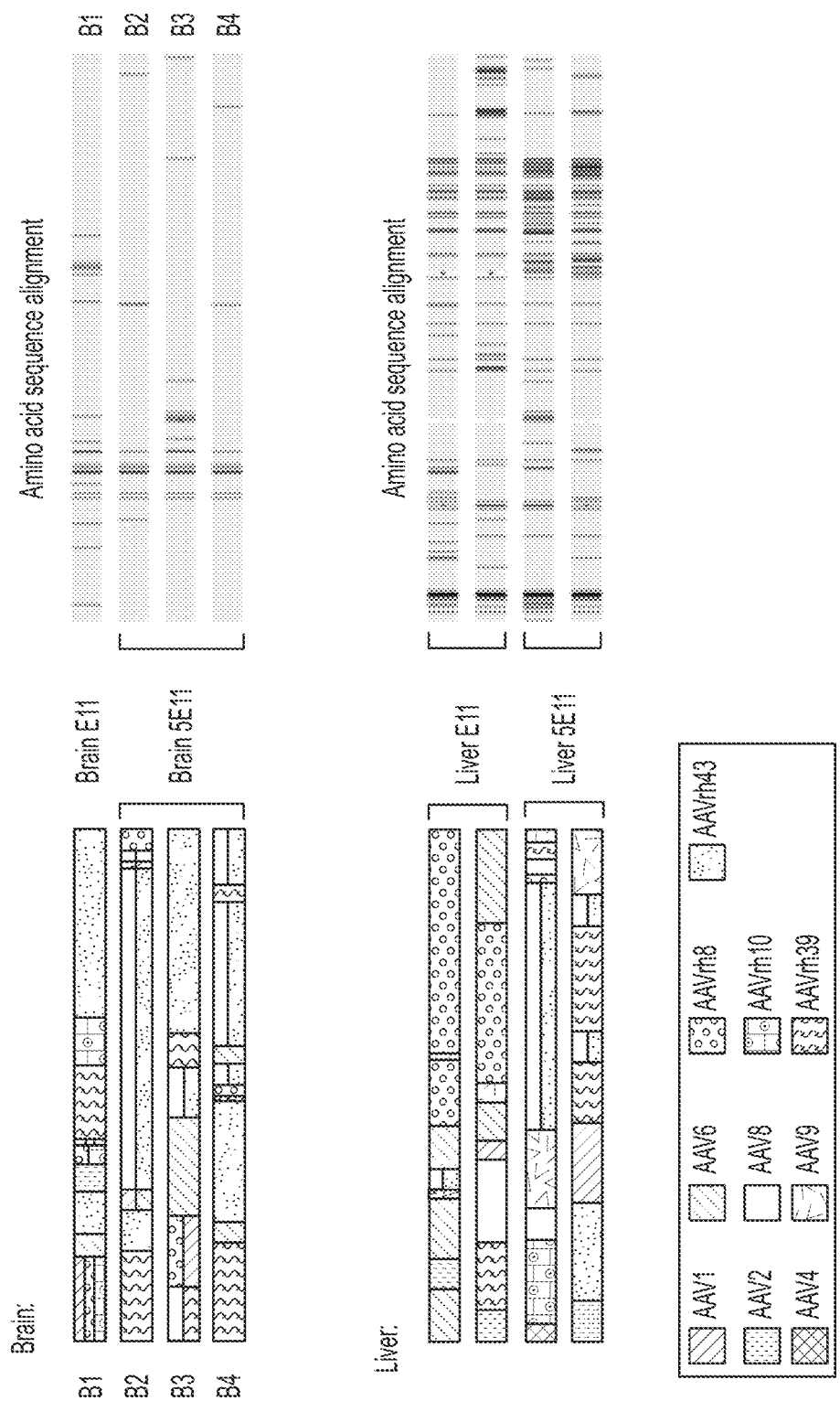
FIG. 4 depicts brain-selected capsids which are chimeric and have more translational homology than capsids pulled from liver. The colors refer to the AAV parental origin at the nucleotide level. Multiple AAV parental origins in a single cap indicate chimerism. The amino acid sequences of brain-selected capsids (B1-B4) and liver selected capsids were aligned separately amongst themselves. A non-homologous amino acid is represented by a single black bar. Homology among capsids is indicated by a relative absence of black bars.

The AAV capsid library generated above was packaged to generate a high titer viral stock and intravenously infused at two doses of 1E11 and 5E11 vg via tail vein into adult C57BL/6 mice. We performed nested PCR amplification of the full-length cap genes (including the barcode region) from total DNA isolates from brain and liver of AAV-library infused C57BL/6 mice (as mentioned earlier), using cap gene-flanking universal primers specific for constant regions across all chimeric AAV cap genes. These caps were cloned using a cloning vector and sequenced. Analogous to the aforementioned barcode dominance, evidence of dosage-dependent cap gene dominance was observed. (FIG. 4).

Figure 16A:
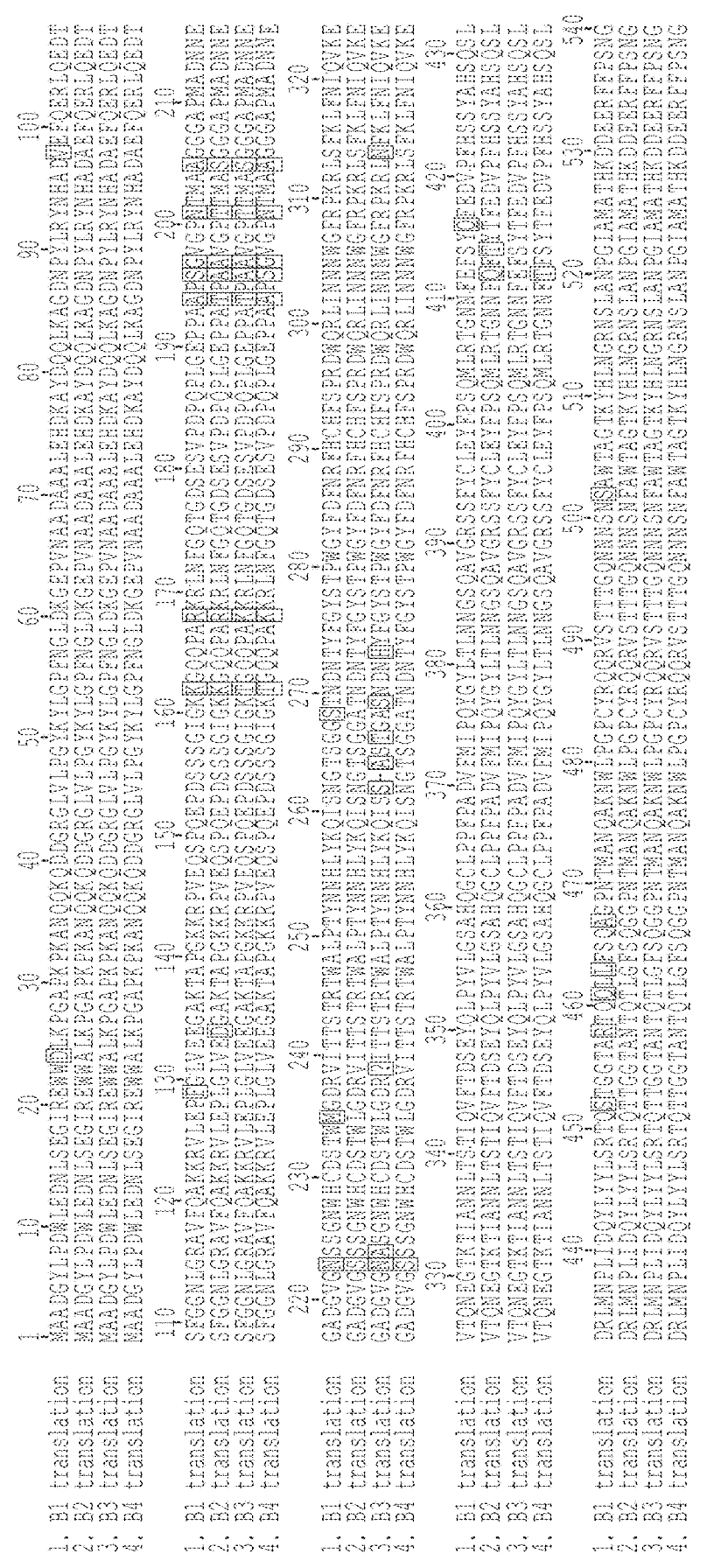
Figure 16B:
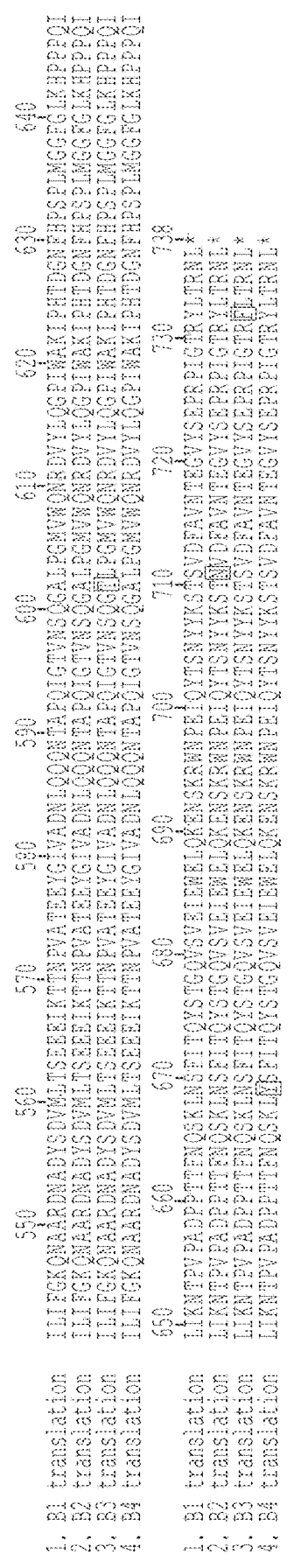
Figure 19A:
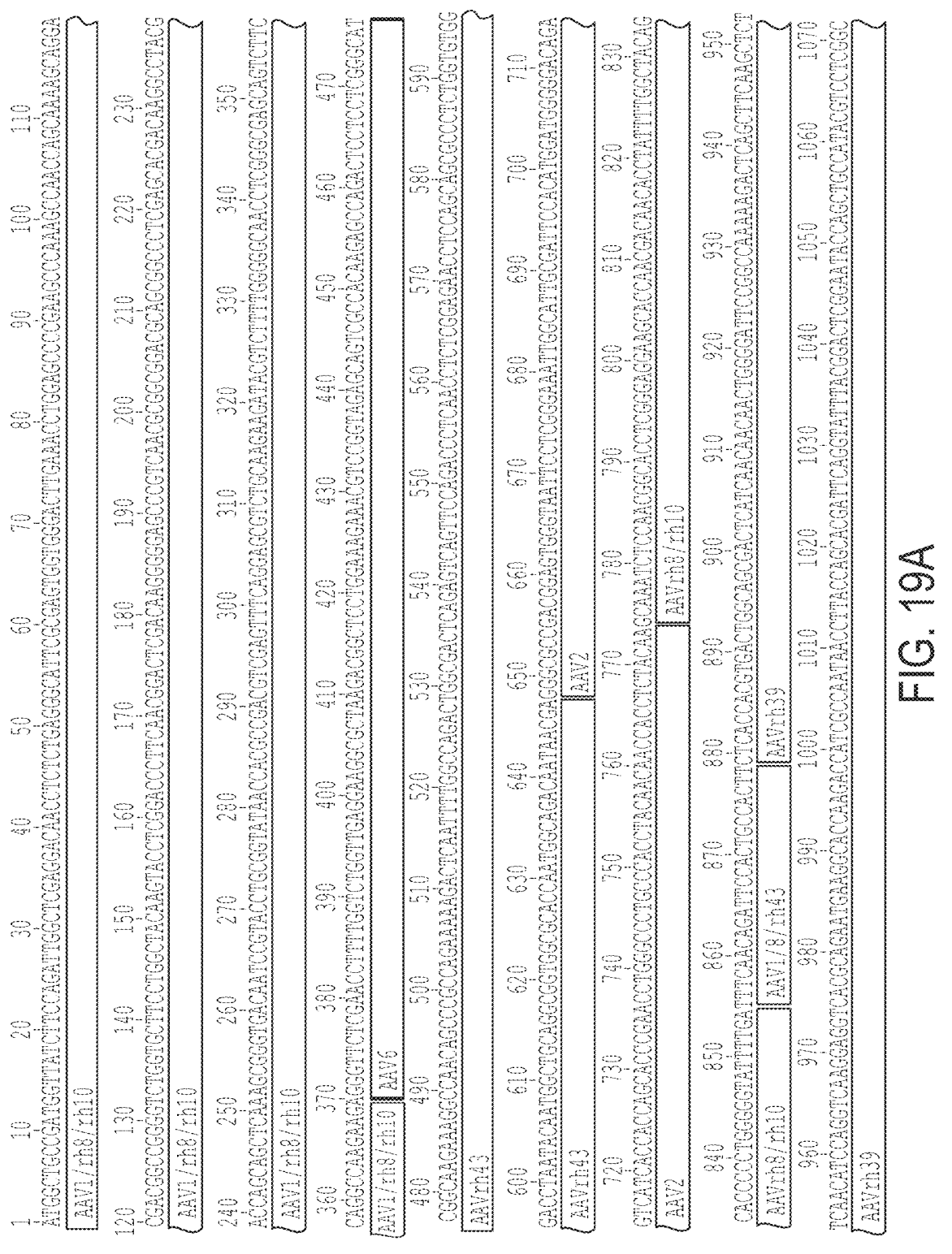
Figure 19B:
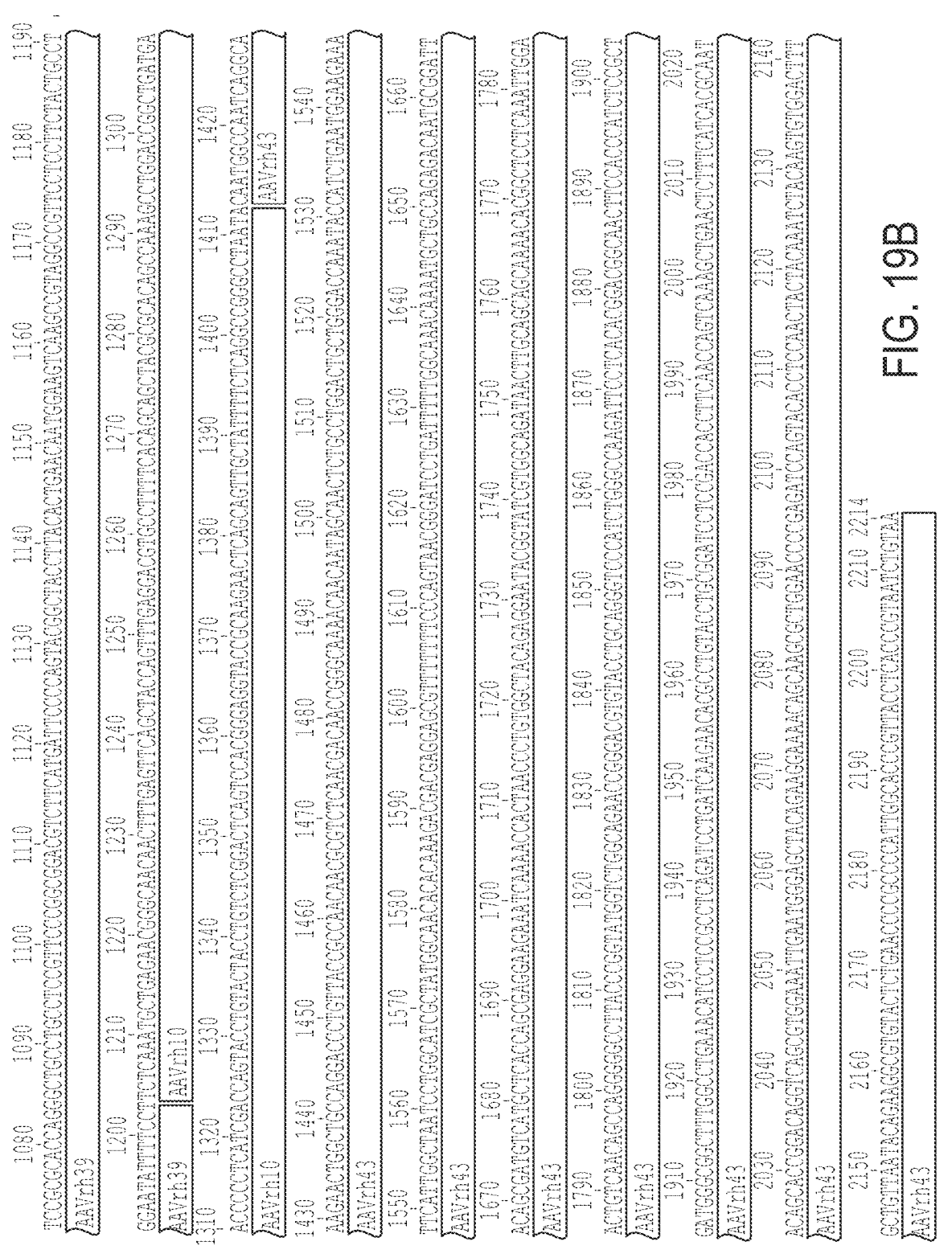
Figure 22A:
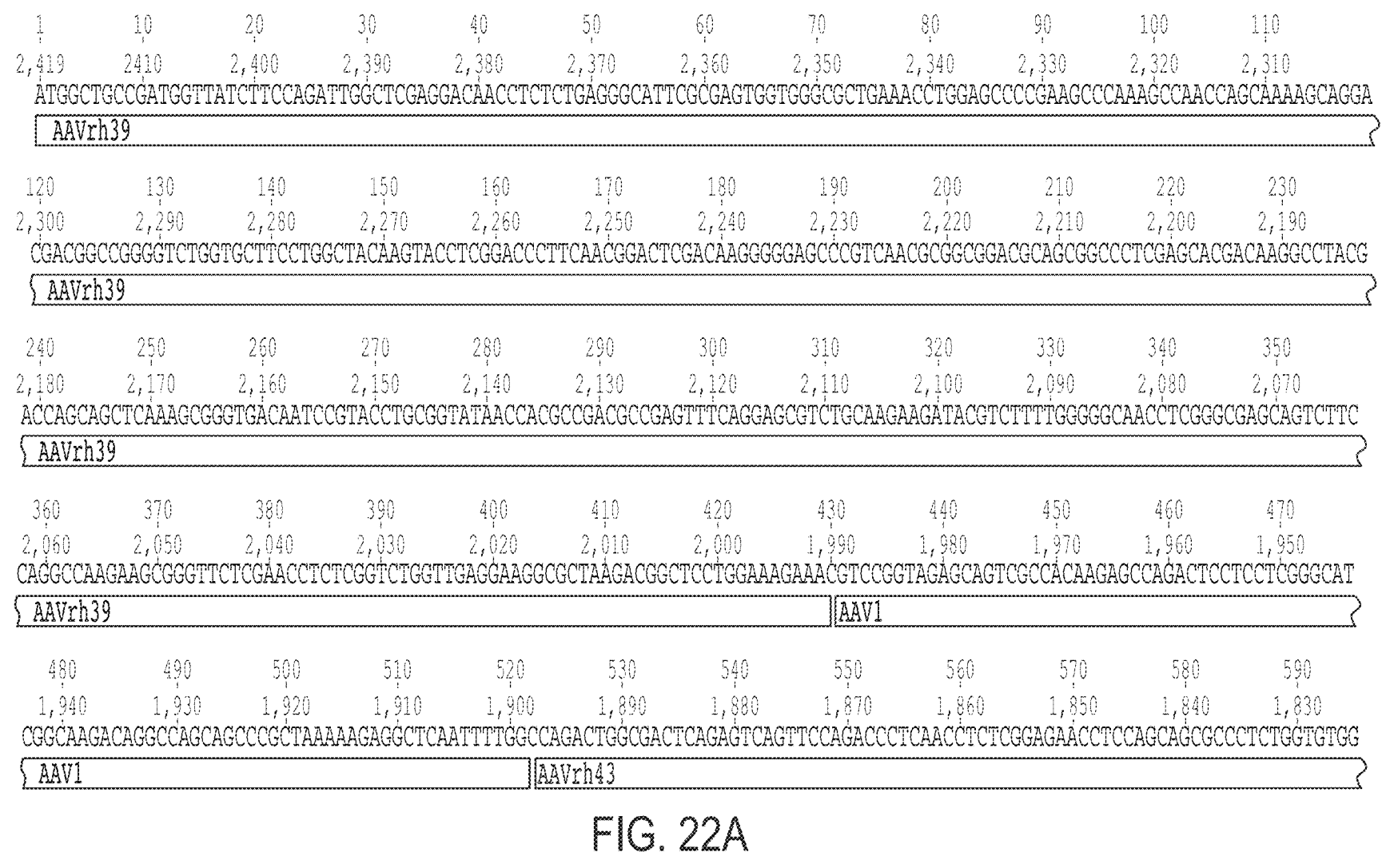
Figure 22B:
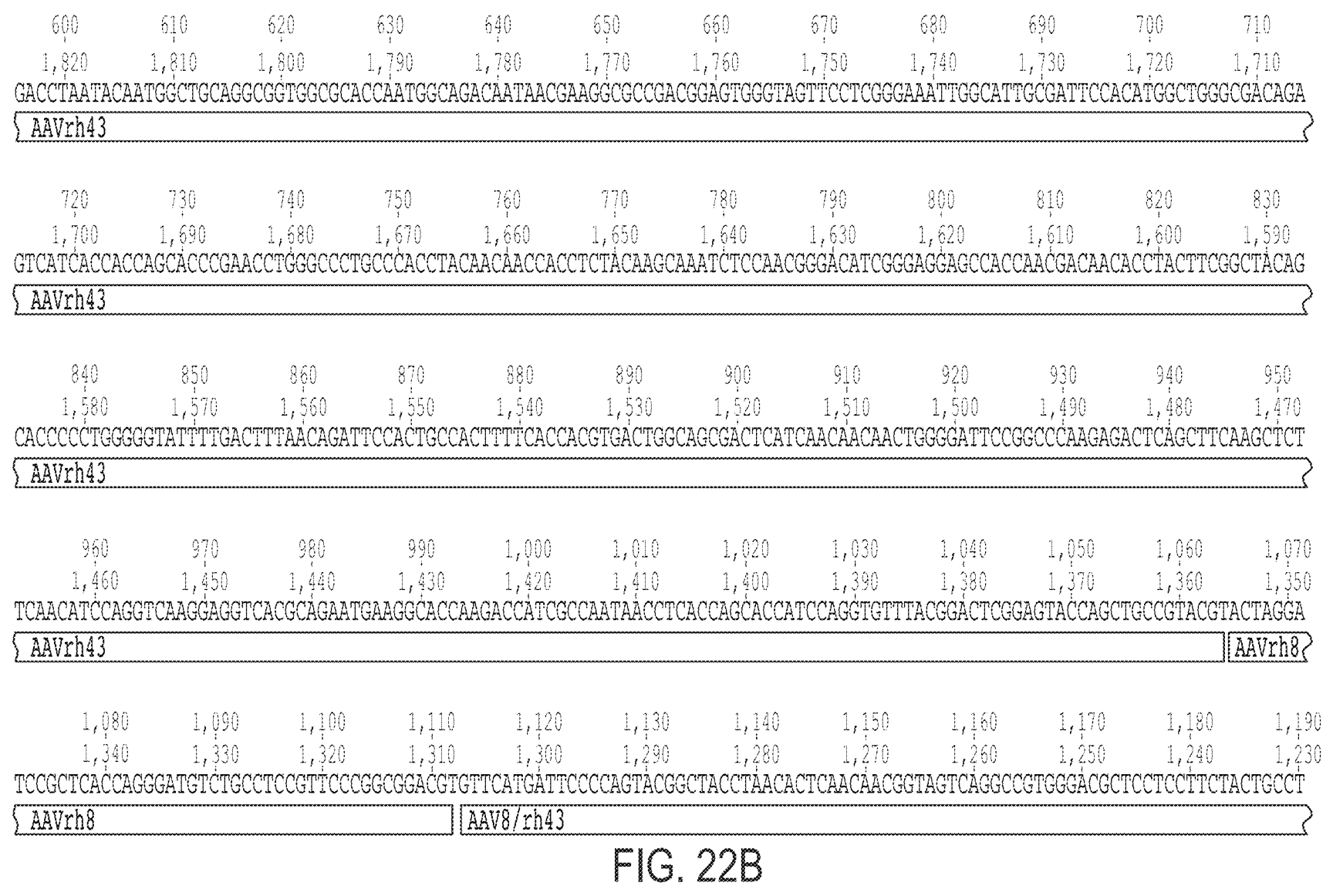
Figure 22C:
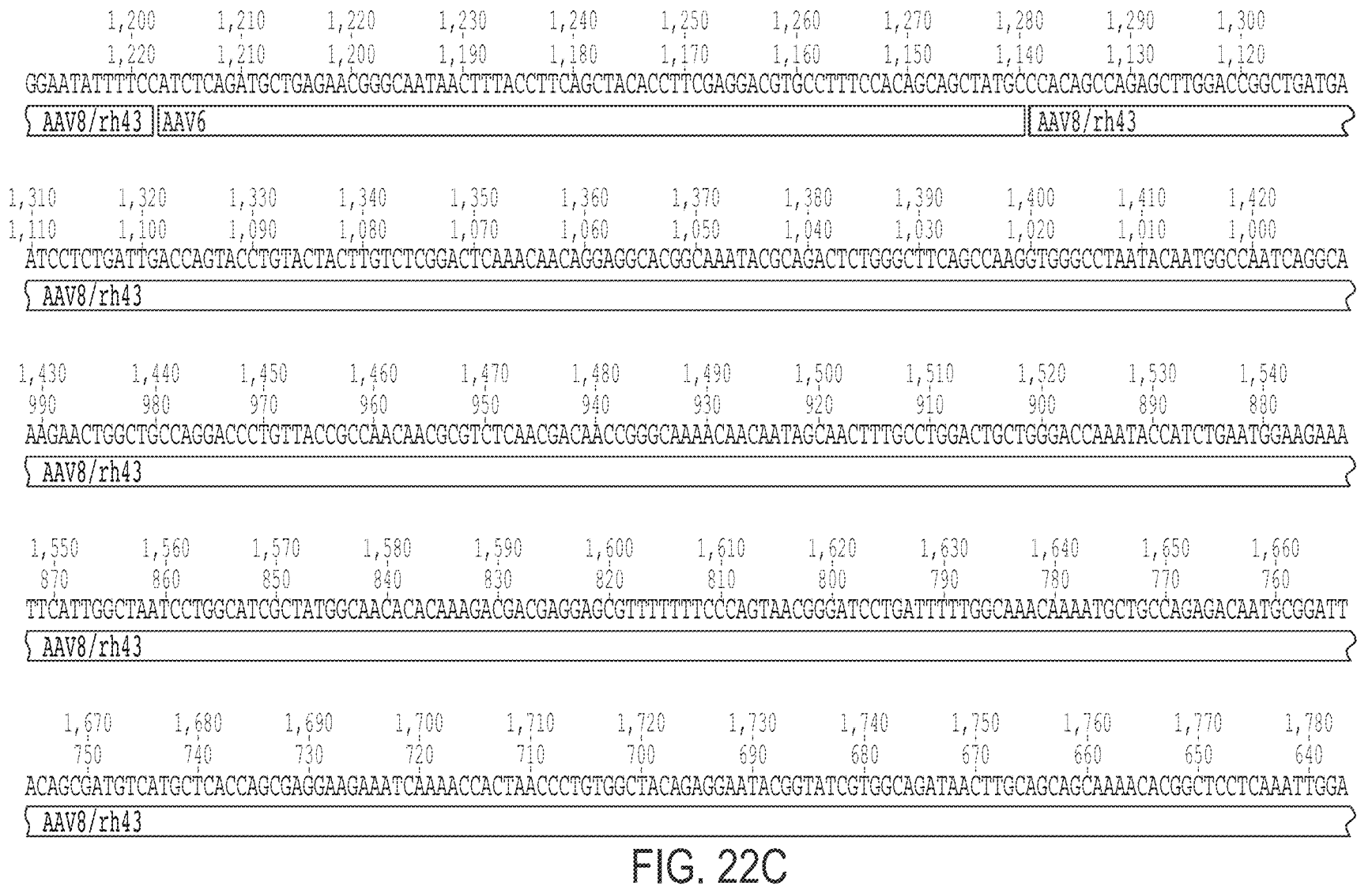
Figure 22D:
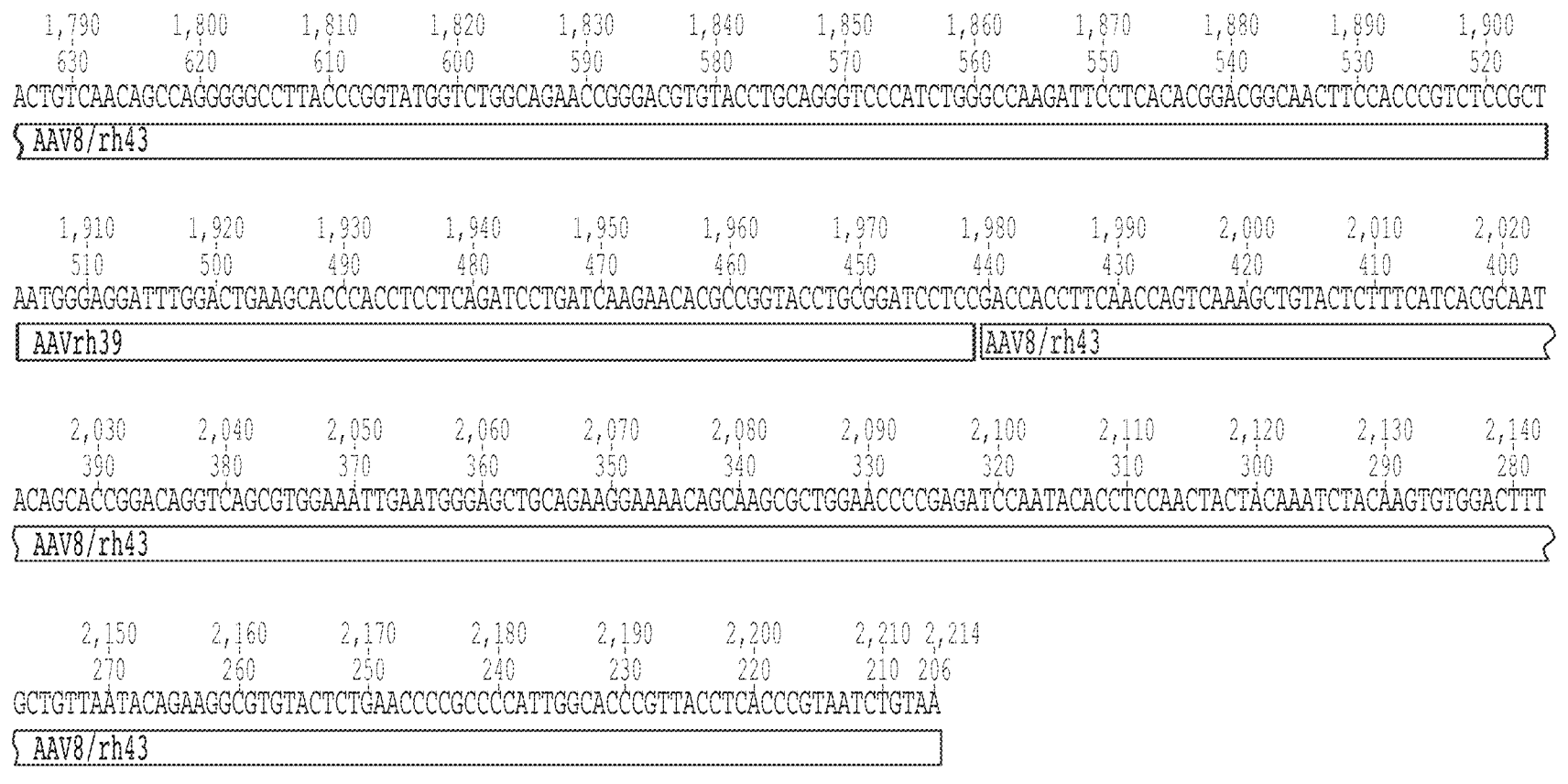

PCR amplification of library-derived AAV capsids from brain genomic DNA isolated 3 days post infusion resulted in the identification of four chimeric capsids. These were named AAV-B1 (SEQ ID NO: 1 and 5), AAV-B2 (SEQ ID NO: 2 and 6), AAV-B3 (SEQ ID NO: 3 and 7) and AAV-B4 (SEQ ID NO: 4 and 8). Native capsid contributions to AAV-B1, AAV-B2, AAV-B3 and AAV-B4 are shown in FIG. 19 FIG. 22. AAV-B1 was the only capsid isolated from the brain of 1E11 vg infused mouse and AAV-B2, AAV-B3 and AAV-B4 were the three capsids identified from the higher dose. All four capsids isolated from brain share remarkable protein sequence homology (shown in FIG. 16) despite being diverse at the nucleotide level (FIG. 4 and FIG. 15). This, coupled with the diversity of capsids isolated from the liver of the same mice, suggests selection of functional domains necessary for transducing the brain.

Figure 18A:
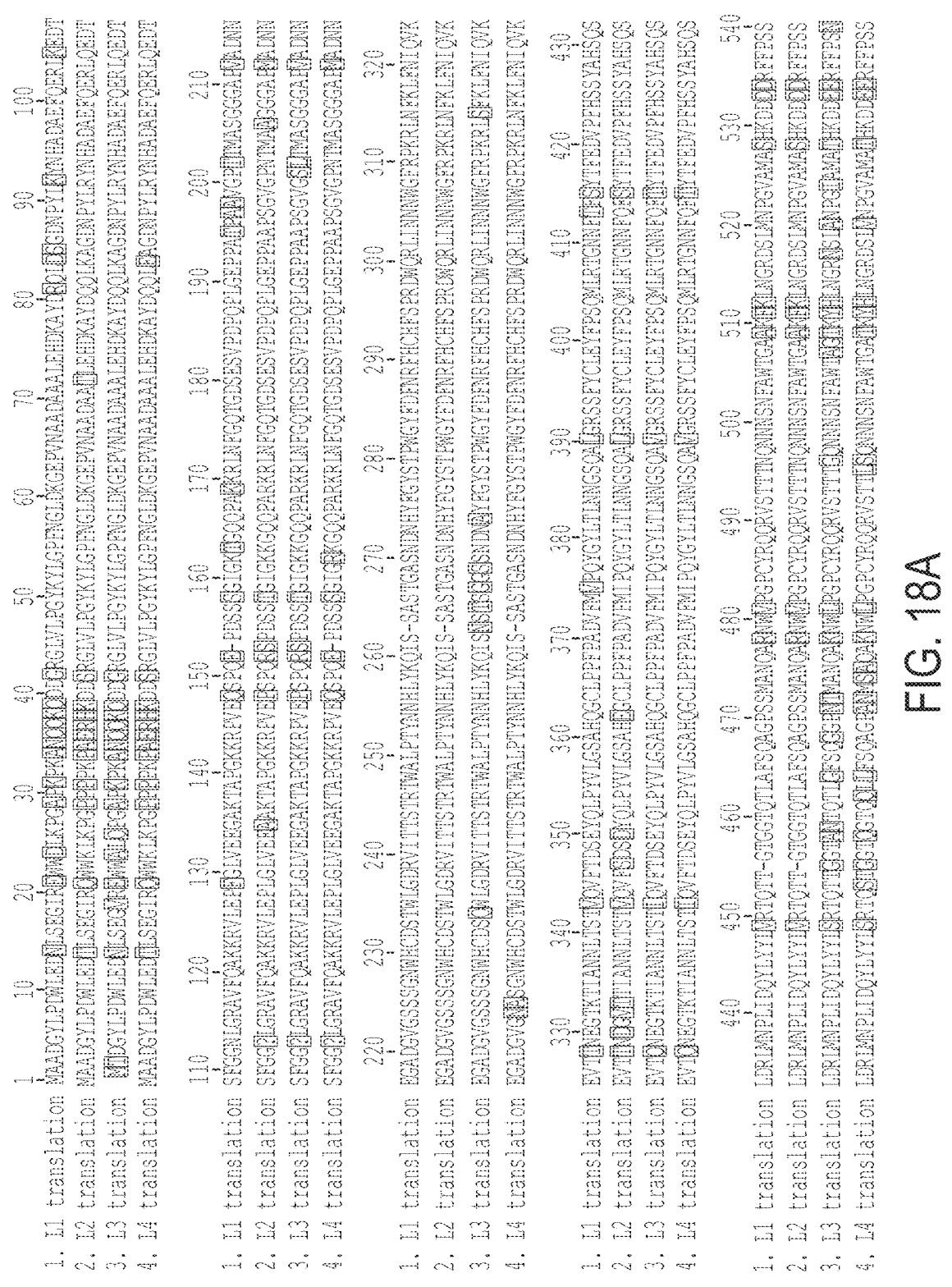
Figure 18B:
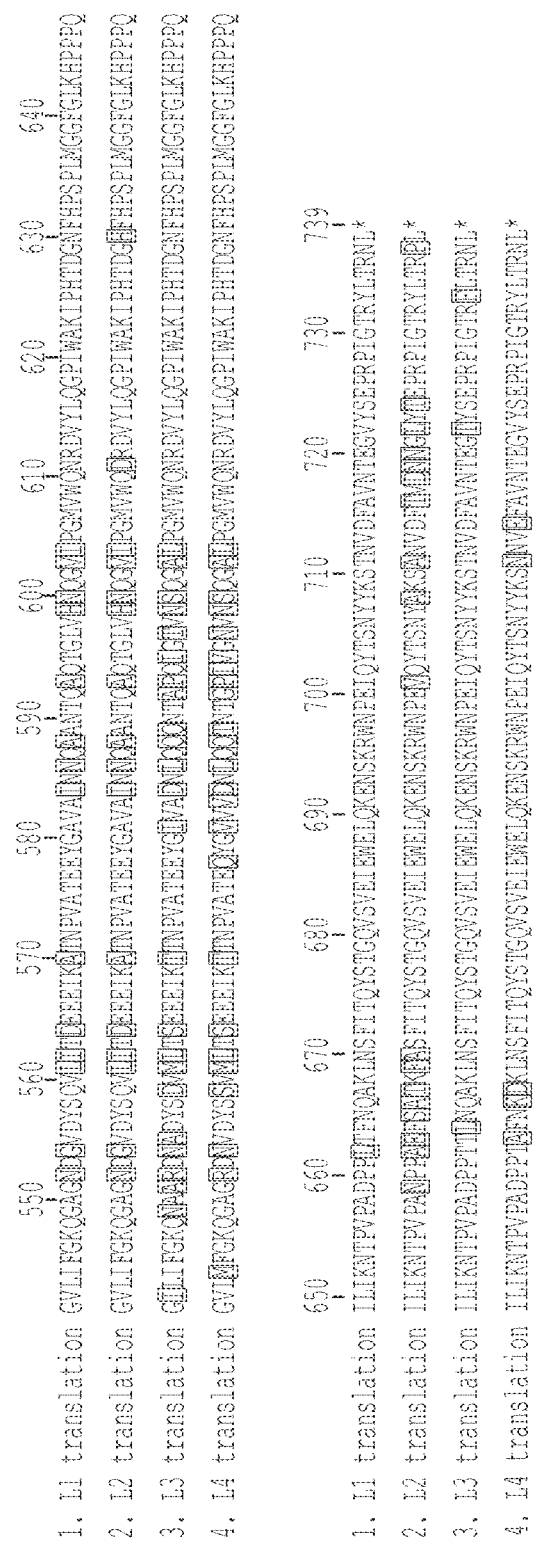

Four chimeric capsids targeting liver were also identified. These were named AAV-L1 (SEQ ID NO: 9 and 13), AAV-L2 (SEQ ID NO: 10 and 14), AAV-L3 (SEQ ID NO: 11 and 15) and AAV-L4 (SEQ ID NO: 12 and 16). All four capsids isolated from brain share remarkable protein sequence homology (shown in FIG. 18) despite being diverse at the nucleotide level (FIG. 17).

Our next goal was to determine whether these brain-selected AAV capsids demonstrate brain tropism after systemic intravenous infusion in adult mice. Self-complementary recombinant AAV vectors (rAAV-B1-B4) encoding EGFP were produced using these capsids, and also AAV9 as a control given its exceptional CNS tropism after iv infusion in neonatal and adult mice. rAAV vectors were infused into adult C57BL/6 mice at a dose of $4.6 \times 10^{11}$ vector genomes via the tail vein (N=3 mice per rAAV vector). Brain, spinal cord and peripheral tissues were harvested at 4 weeks post-injection and analyzed for GFP expression by immunofluorescence staining.

Figure 5:
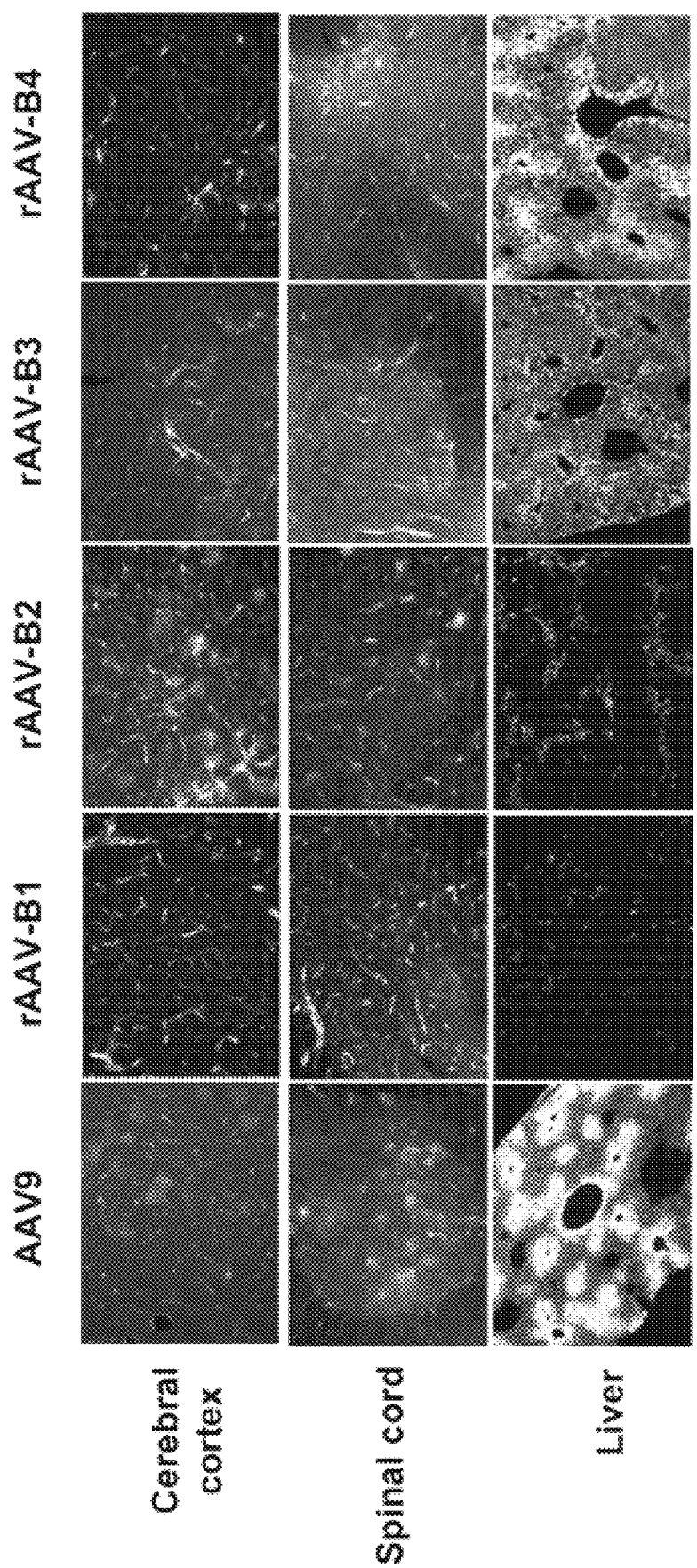
FIG. 5 depicts a biodistribution profile of rAAV-B1-B4 vectors which indicate extensive CNS transduction. GFP expression in the brain, spinal cord and liver was analyzed at 4 weeks post-intravenous injection in adult C57BL/6 mice. Detection of GFP expression in the brain and spinal cord was enhanced by immunofluorescence staining with an anti-GFP antibody (20× magnification). Native GFP fluorescence was used for liver sections (5× magnification). GFP transduction is present in CNS endothelia and glia for AAV9, B3 and B4. B1-derived rAAV vector exclusively transduces endothelia. CNS transduction for B2-B4-derived rAAV vectors is identical to AAV9. Liver transduction for B1- and B2-derived rAAV vectors appears to be considerably lower than for rAAV9, B3- or B4-derived rAAV vectors.
Figure 6:
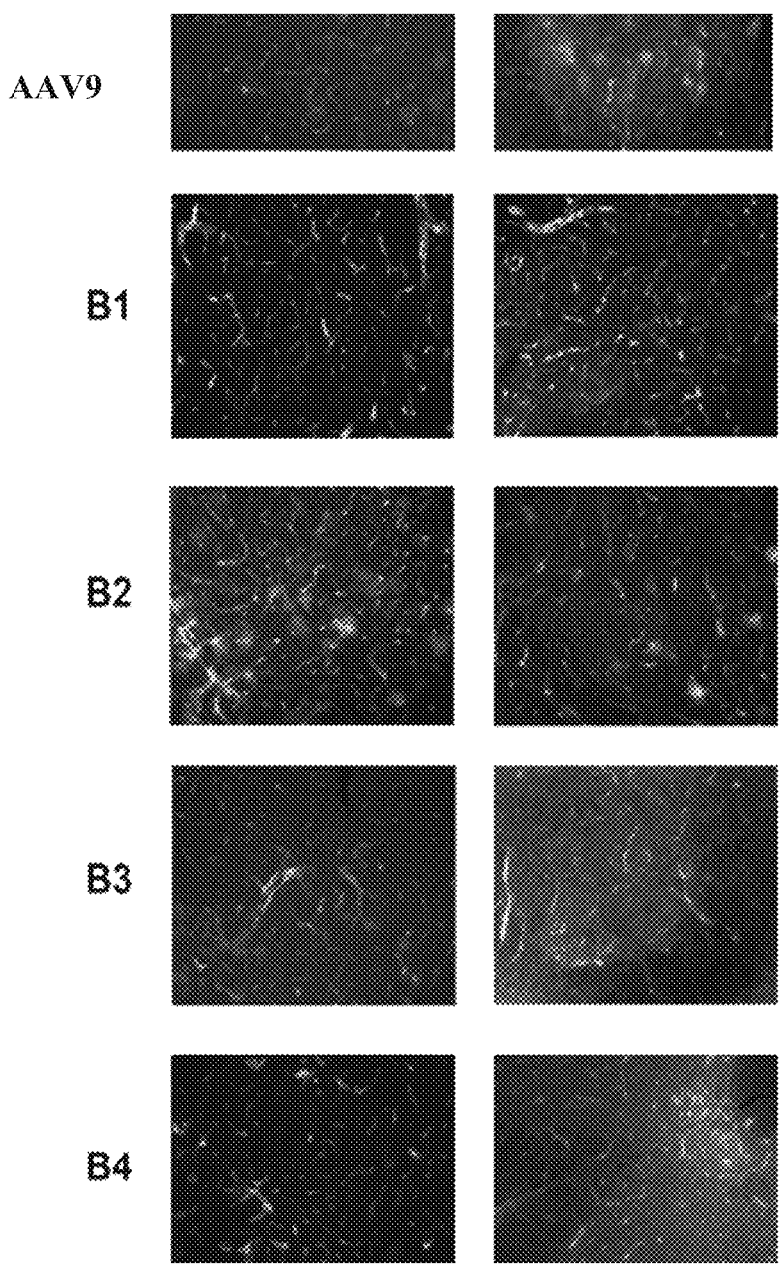
FIG. 6 depicts data showing extensive transduction of brain and spinal cord by rAAV-B 1-B4 vectors. rAAV-B1-derived rAAV vector transduces the CNS endothelium at high efficiency. rAAV-B2-B4 also transduce brain endothelial cells and glia at high efficiency. rAAV-B3 and rAAV-B4 also transduce glia at high efficiency.

All newly selected AAV vectors transduced cells in the brain and spinal cord at levels comparable to AAV9 (FIG. 5 and FIG. 6). rAAV-B1-derived rAAV vector transduced the CNS endothelium at high efficiency. rAAV-B2-B4 also transduced brain endothelial cells at high efficiency, but similar to our findings for AAV9 at this dose most transduced cells in the parenchyma appeared to be glia. The degree of glia transduction for rAAV-B2 vector appeared to be considerably superior to that observed with rAAV9 vector. The other three vectors, rAAV-B3 and rAAV-B4 also transduced glia at high efficiency. Interestingly liver transduction was considerably lower for rAAV-B1 and rAAV-B2 compared to rAAV9 (FIG. 5), but higher with rAAV-B3 and rAAV-B4.

The efficient gene transfer in the CNS in the presence of non-compromised blood-brain barrier after systemic iv delivery of DNA shuffled AAV viral vectors, coupled with significantly reduced liver transduction is novel and has not been previously observed, to the best of our knowledge. Furthermore, only one round of selection was shown to be enough for efficient selection.

Figure 7:
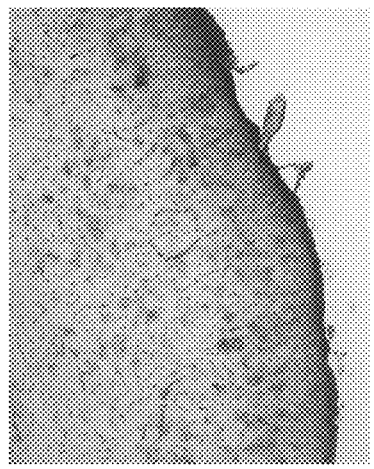
FIG. 7 depicts data showing that infusion of a higher dose (2E12 vg) of rAAV-B1 and rAAV-B2 results in increased transduction of cortical and hippocampal neurons, endothelia and astrocytes when compared to AAV9.
Figure 7:
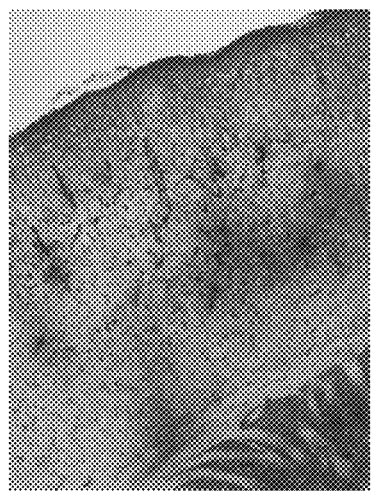
Figure 7:
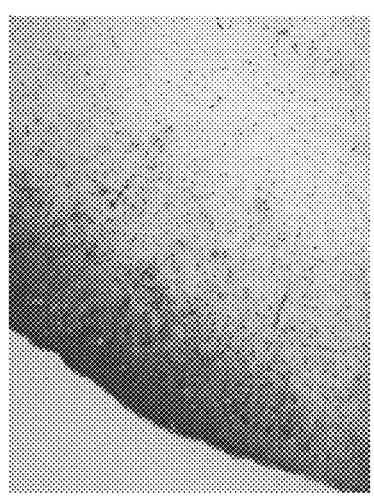
Figure 7:
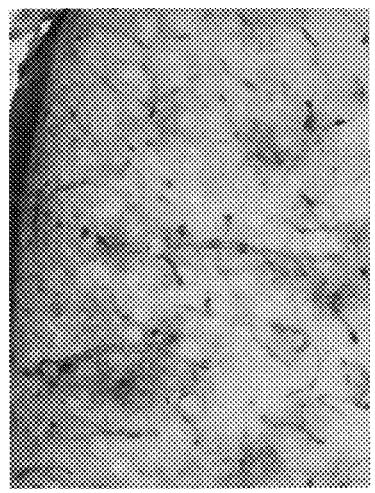
Figure 7:
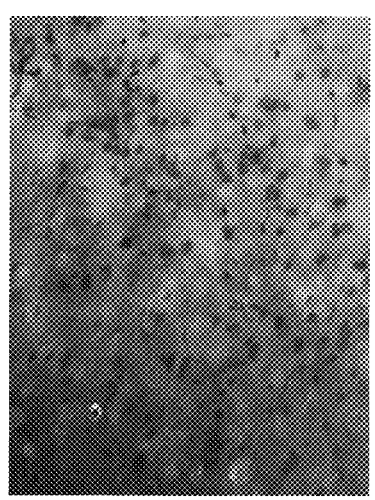
Figure 8:
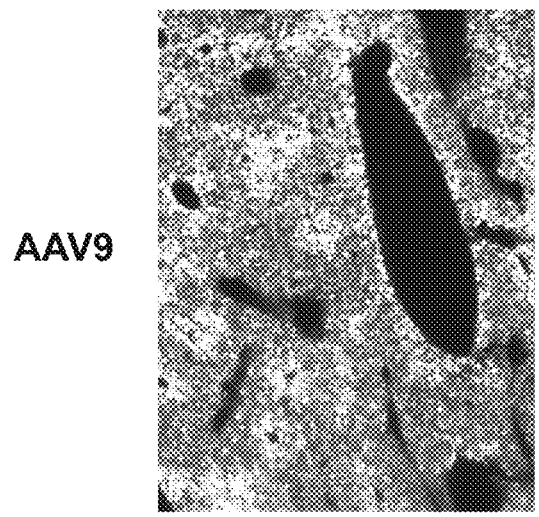
FIG. 8 depicts data showing liver transduction efficiency for rAAV-B1 and rAAV-B2 vectors is dramatically lower than AAV9, as observed by fluorescence imaging.
Figure 8:
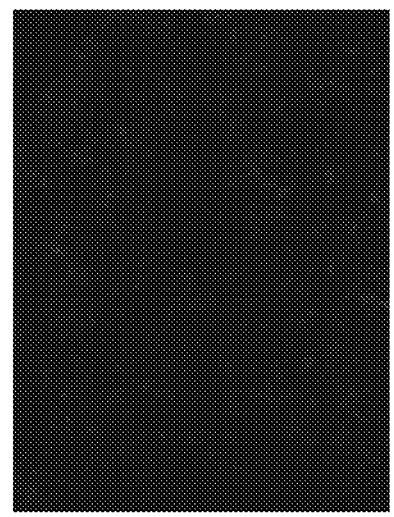
Figure 8:
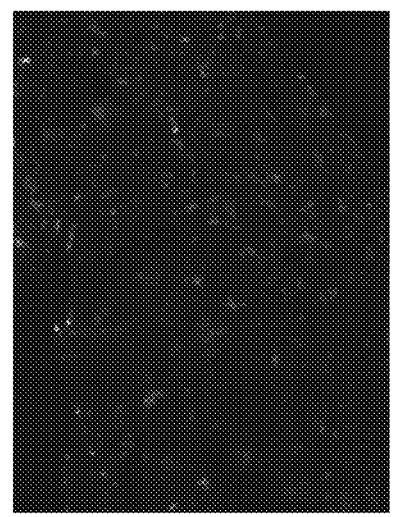

Higher doses of the two most promising vectors, AAV-B1 and AAV-B2, were used to further study their biodistribution profiles in adult mice. Infusion of a higher dose ($2E^{12}$ vg) of rAAV-B1 and rAAV-B2 resulted in transduction of cortical and hippocampal neurons, endothelia and astrocytes (FIG. 7). Importantly the liver transduction efficiency for rAAV-B1 and rAAV-B2 vectors was dramatically lower than AAV9, as observed by fluorescence imaging (FIG. 8).

Figure 9:
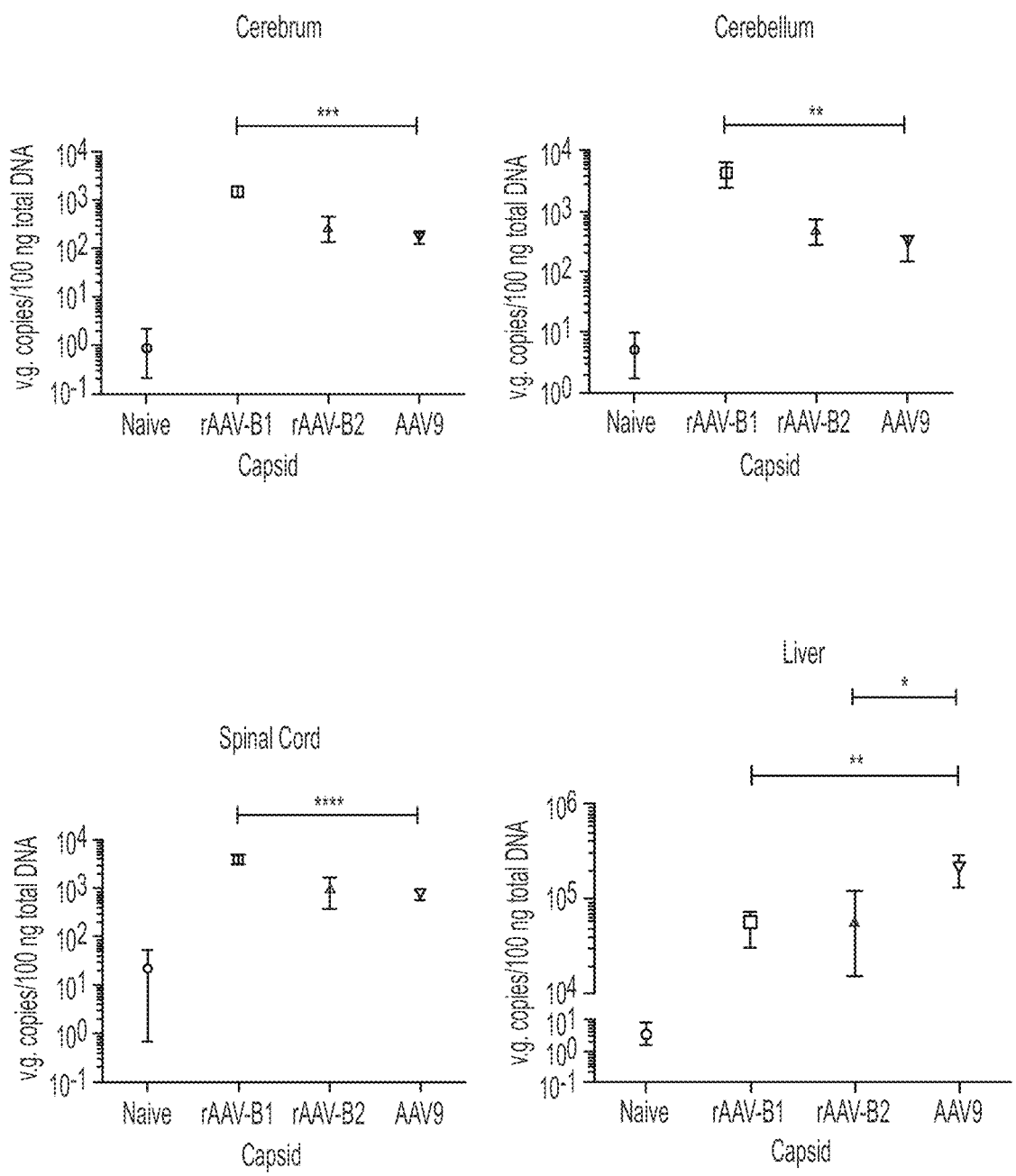
FIG. 9 depicts data showing biodistribution of rAAV-B1, rAAV-B2, and AAV9 vectors as analyzed by quantitative PCR (qPCR) of vector genomes in genomic DNA from different tissues. Analysis was performed 4 weeks post i.v. infusion of scAAV-CBA-GFP vector via the tail vein in adult C57BL/6 mice at a dose of 5E11 vg. Significantly more vector genomes are found in the cerebrum, cerebellum and spinal cord of rAAV-B1, compared to AAV9 (9-fold, 15-fold and 6-fold, respectively). However, both rAAV-B1 and rAAV-B2 have significantly lower numbers of vector genomes in the liver in comparison to AAV9 (4-fold and 3-fold, respectively).
Figure 10:
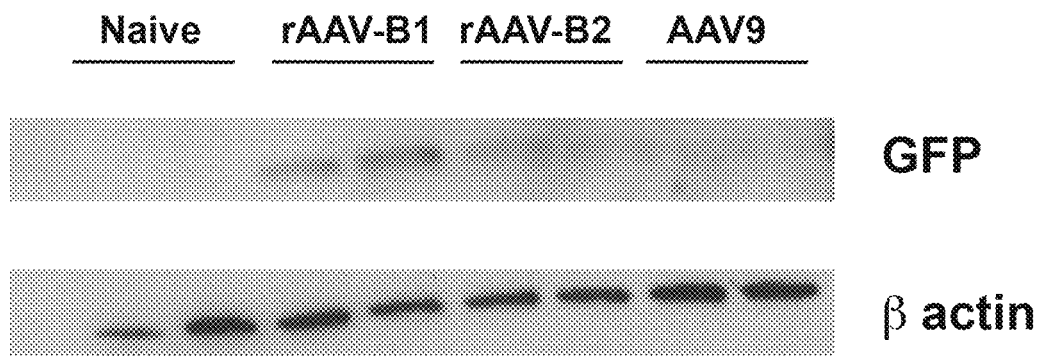
FIG. 10 depicts data showing biodistribution of rAAV-B1, rAAV-B2, and AAV9 vectors as analyzed by western blot. More GFP protein was detected in the cerebrum of adult C57BL/6 mice injected with rAAV-B1 and rAAV-B2, compared to AAV9. Less GFP protein was detected in the liver of rAAV-B1 and rAAV-B2-injected mice, in comparison to AAV9.
Figure 10:
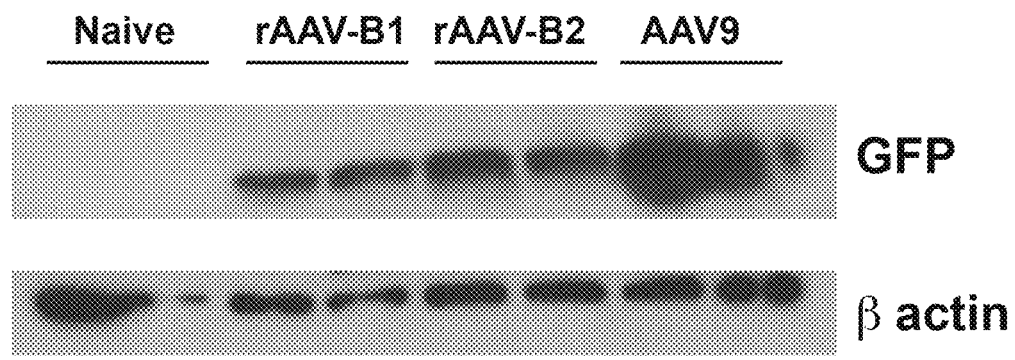

The biodistribution of rAAV-B1, rAAV-B2, and AAV9 vectors was analyzed by quantitative PCR (qPCR) of vector genomes in genomic DNA from different tissues and GFP expression levels by Western blotting. Analysis was performed 4 weeks post i.v. infusion of scAAV-CBA-GFP vector via the tail vein in adult C57BL/6 mice at a dose of $5E^{11}$ vg. Significantly more vector genomes were found in the cerebrum, cerebellum and spinal cord of rAAV-B1, compared to AAV9 (9-fold, 15-fold and 6-fold, respectively) (FIG. 9). However, both rAAV-B1 and rAAV-B2 had significantly lower vector genomes in the liver in comparison to AAV9 (4-fold and 3-fold, respectively). These observations were confirmed by detection of GFP by Western blot analysis of total tissue lysates. More GFP protein was detected in the cerebrum of adult C57BL/6 mice injected with rAAV-B1 and rAAV-B2, compared to AAV9 (FIG. 10). In contrast, less GFP protein was detected in the liver of rAAV-B1 and rAAV-B2-injected mice, in comparison to AAV9.

Figure 11:
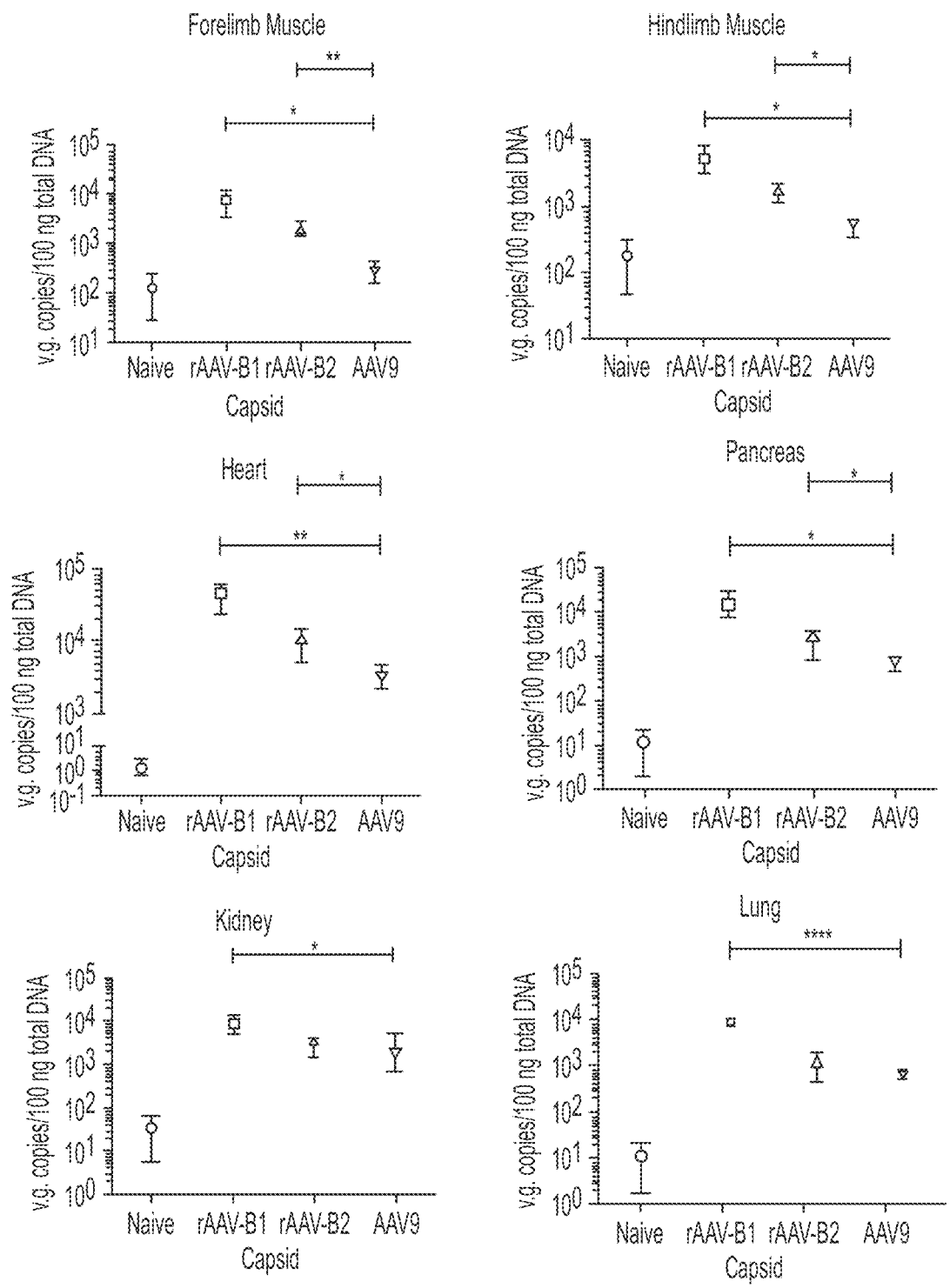
FIG. 11 depicts data showing that rAAV-B1 vector transduces peripheral tissues to a greater extent than AAV9, as determined by qPCR. Significantly more vector genomes are found in the forelimb muscle, hind limb muscle, heart and pancreas of both rAAV-B1 and rAAV-B2-injected mice, as compared to AAV9. The extent of transduction of rAAV-B1 is greater than rAAV-B2 for each of these tissues. In addition, rAAV-B1 had significantly more vector genomes in kidney and lung in comparison to AAV9.
Figure 12:
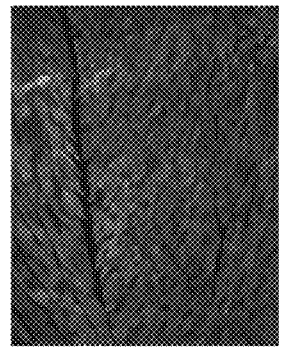
FIG. 12 depicts data showing that rAAV-B1 vector transduces peripheral tissues to a greater extent than AAV9, as determined by immunofluorescence microscopy.
Figure 12:
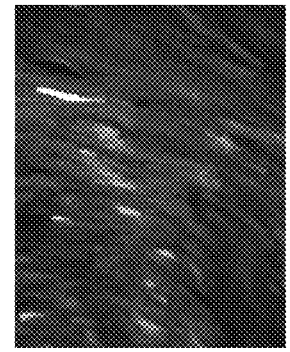
Figure 12:
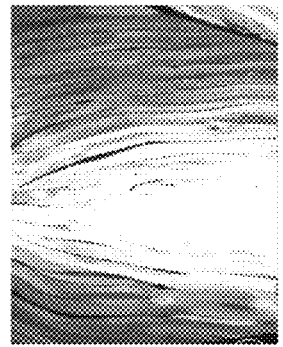
Figure 12:
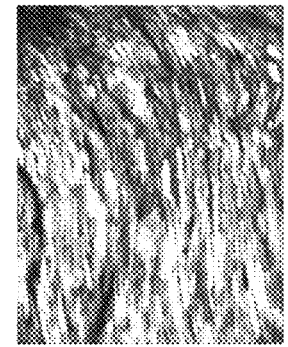
Figure 12:
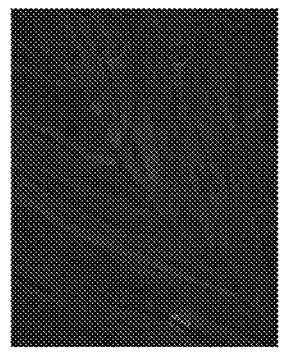
Figure 12:
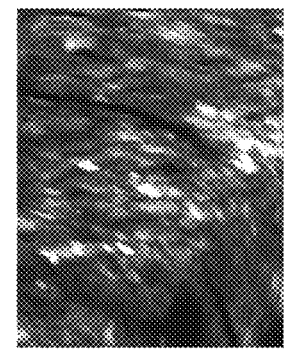
Figure 13:
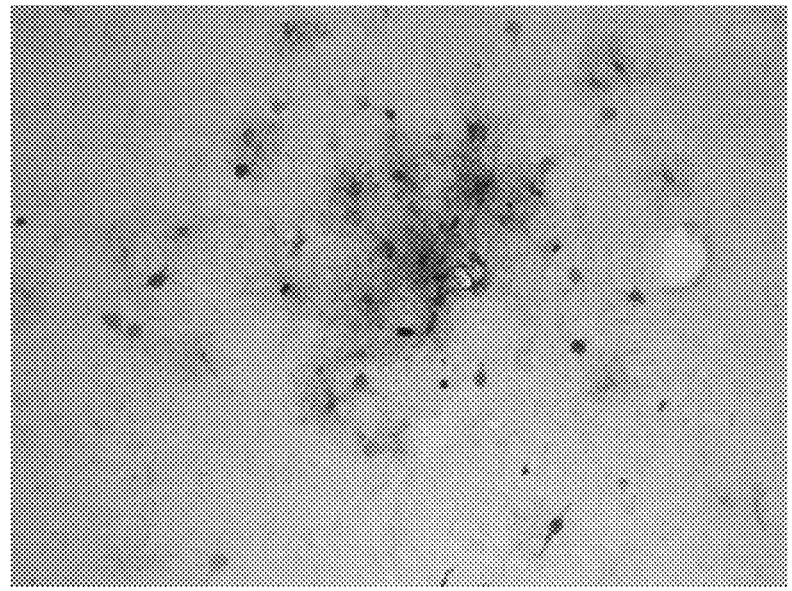
FIG. 13 depicts data showing effects of rAAV-B1-GFP and rAAV-B2-GFP vectors that were infused into 4-6 week-old kittens (n=1/vector) via the carotid artery at a dose of 3.5E12 vg. Neuronal and astrocytic populations (identified by morphology) were found to be transduced in both cat brains. rAAV-B2 has pronounced astrocytic transduction. Loci with high density of neurons were found transduced in rAAV-B1 cat brain.
Figure 13:
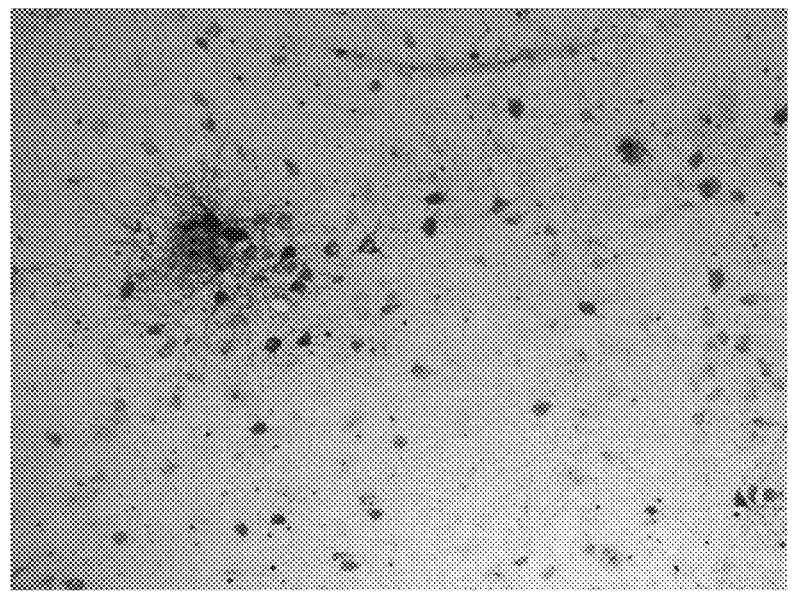

In addition, rAAV-B2, and to a greater extent, rAAV-B1, transduced peripheral tissues to a greater extent than AAV9 (FIG. 11 and FIG. 12). Significantly more vector genomes were found in the forelimb muscle, hind limb muscle, heart and pancreas of both rAAV-B1 and rAAV-B2-injected mice, as compared to AAV9, with the extent of transduction of rAAV-B1 being greater than rAAV-B2 for each of these tissues. In addition, rAAV-B1 had significantly more vector genomes in kidney and lung in comparison to AAV9.

rAAV-B1-GFP and rAAV-B2-GFP vectors were infused into 4-6 week-old kittens (n=1/vector) via the carotid artery at a dose of $3.5E^{12}$ vg. Neuronal and astrocytic populations (identified by morphology) were found to be transduced in both cat brains (FIG. 13). While rAAV-B2 has pronounced astrocytic transduction, the number of astrocytes transduced is much lower for rAAV-B1. Loci with high density of neurons were found transduced in rAAV-B1 cat brain. No endothelial transduction was observed for either vector in the feline brain.

In Vitro Identification of Cap-Barcode Pairs

Although we have now isolated novel AAV capsids targeted to broader tissues such as the CNS by full-length capsid gene PCR, this traditional method may be limited by the low number of AAV genomes that are capable of crossing the blood brain barrier to transduce neurons at high efficiency. It has been previously shown that libraries derived from PCR of smaller amplicon size contain more unique sequences and higher diversity estimates, than those derived from larger amplicons. Therefore, single-round in-vivo selection strategy of amplifying only the barcodes, instead of the entire capsid gene will thus allow us to amplify even the scarce viral genomes that may result from low frequency events, such as AAV capsids in the library capable of crossing the BBB to transduce neurons at high efficiency. This is supported by our observation that while we could pull barcodes from $1E^9$ and $1E^{10}$ brains, we were unable to isolate full-length capsid genes from brain at doses lower than $1E^{11}$.

Figure 14:
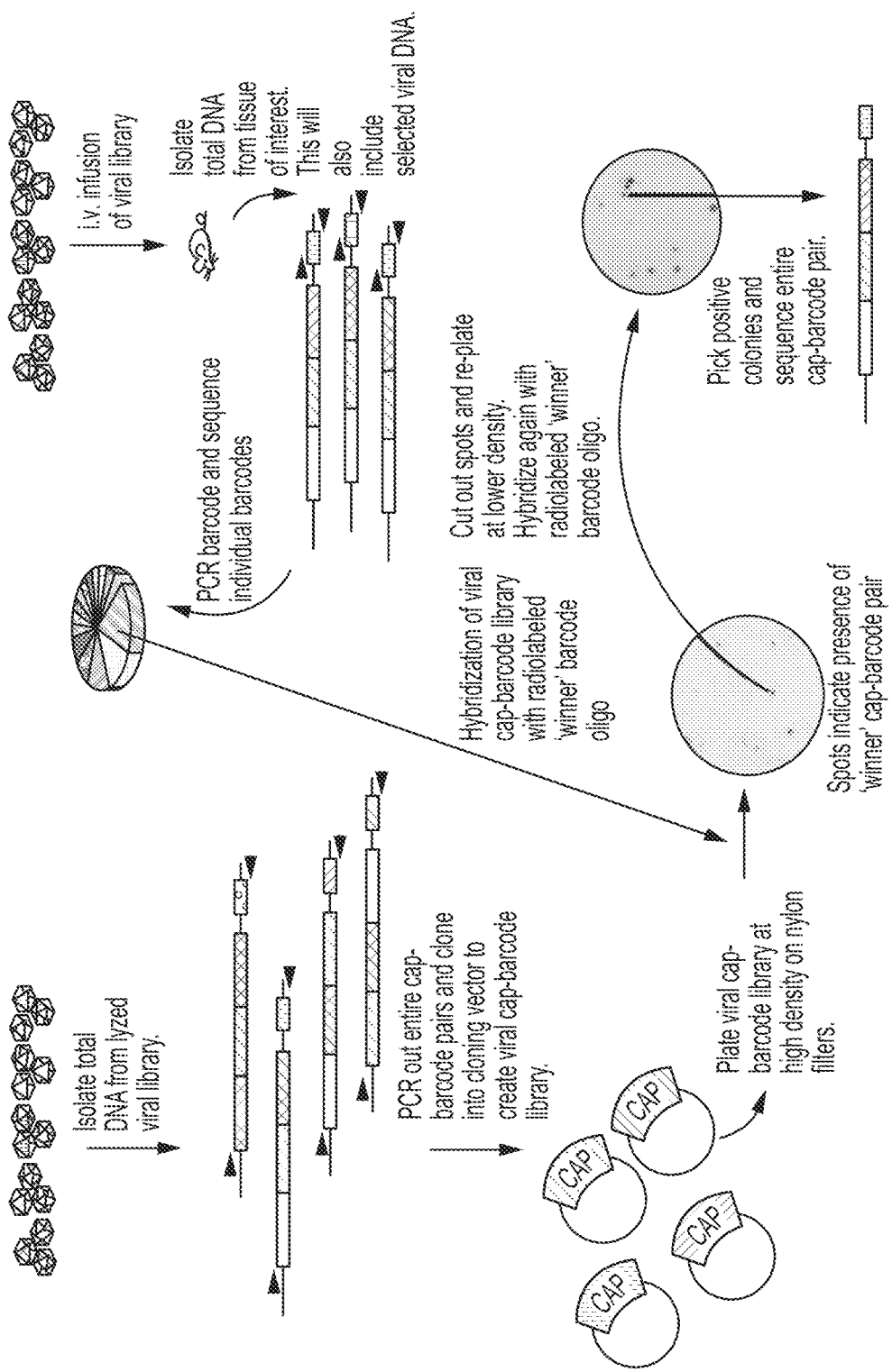
FIG. 14 depicts a schematic of a screen to identify capsid-barcode pairs. Briefly, the entire capsid-barcode pool is amplified from DNA isolated from the viral library, using universal cap-flanking primers. This pool is then cloned into a plasmid to create a cap-barcode library. This is then transformed and plated at high-density ($2.5E^5$ bacteria/filter) on nylon filters placed on 150 mm LB-agar plates. These master filters are then replica-plated, the bacteria lysed on the replica filters and DNA cross-linked by UV. These filters are then hybridized to radioactively-labeled oligos of barcodes of interest. The replica filter is then keyed back to the master filter. Since it is difficult to pick single colonies from the high-density master filter, the areas on the master filter corresponding to spots on replica filter, are cut out and the bacteria on those areas re-plated at lower density. These are then replica filtered and hybridized by regular low-density hybridization to the radiolabeled oligo probe, and subsequently positive single colonies are picked and send for sequencing of entire capsid (and barcode).

The ability to link barcodes to their unique capsid genes is key to the success of this novel approach. We now report that we have successfully developed a method to link a barcode to its corresponding capsid gene. Initially, we pulled out rAAV-B1 using its barcode for our screen, as the capsid gene and barcode for the rAAV-B1 clone were fully sequenced and thus we knew the capsid-barcode relation. Using high-density colony hybridization with a radioactively-labeled rAAV-B1 barcode-specific oligo, we were successful in identifying the rAAV-B1 capsid gene after screening a secondary plasmid library generated by PCR amplification of AAV genomes present in the packaged library. Depicted in FIG. 14 is a schematic representation of the process used to identify the rAAV-B1 capsid gene.

Example 2

Figure 23A:
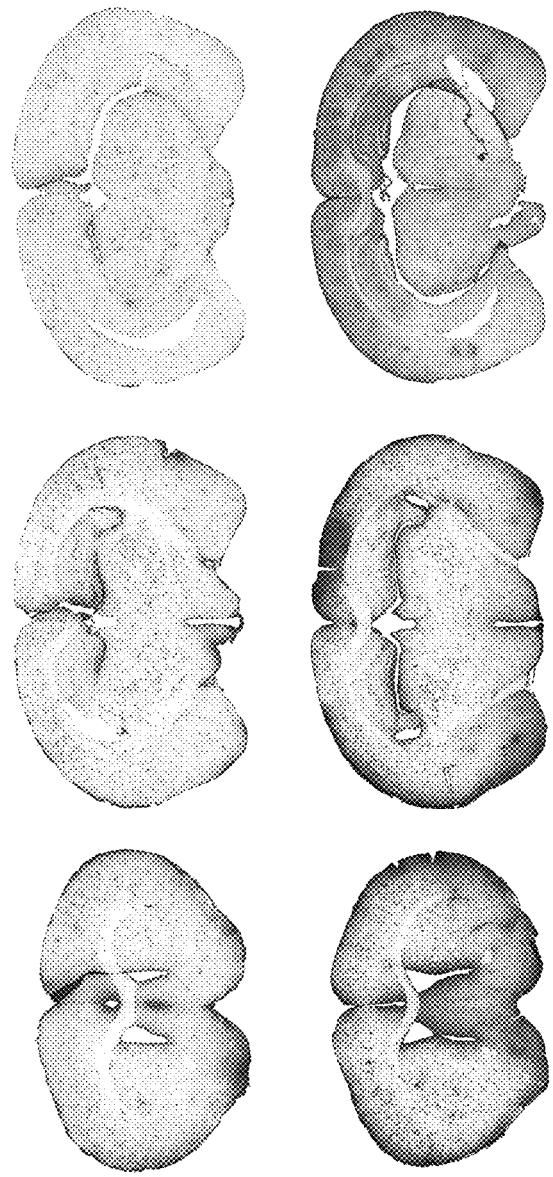
FIGS. 23A-23D show CNS transduction profile of AAV-B1 vector after intravascular infusion in adult mice.
Figure 23B:
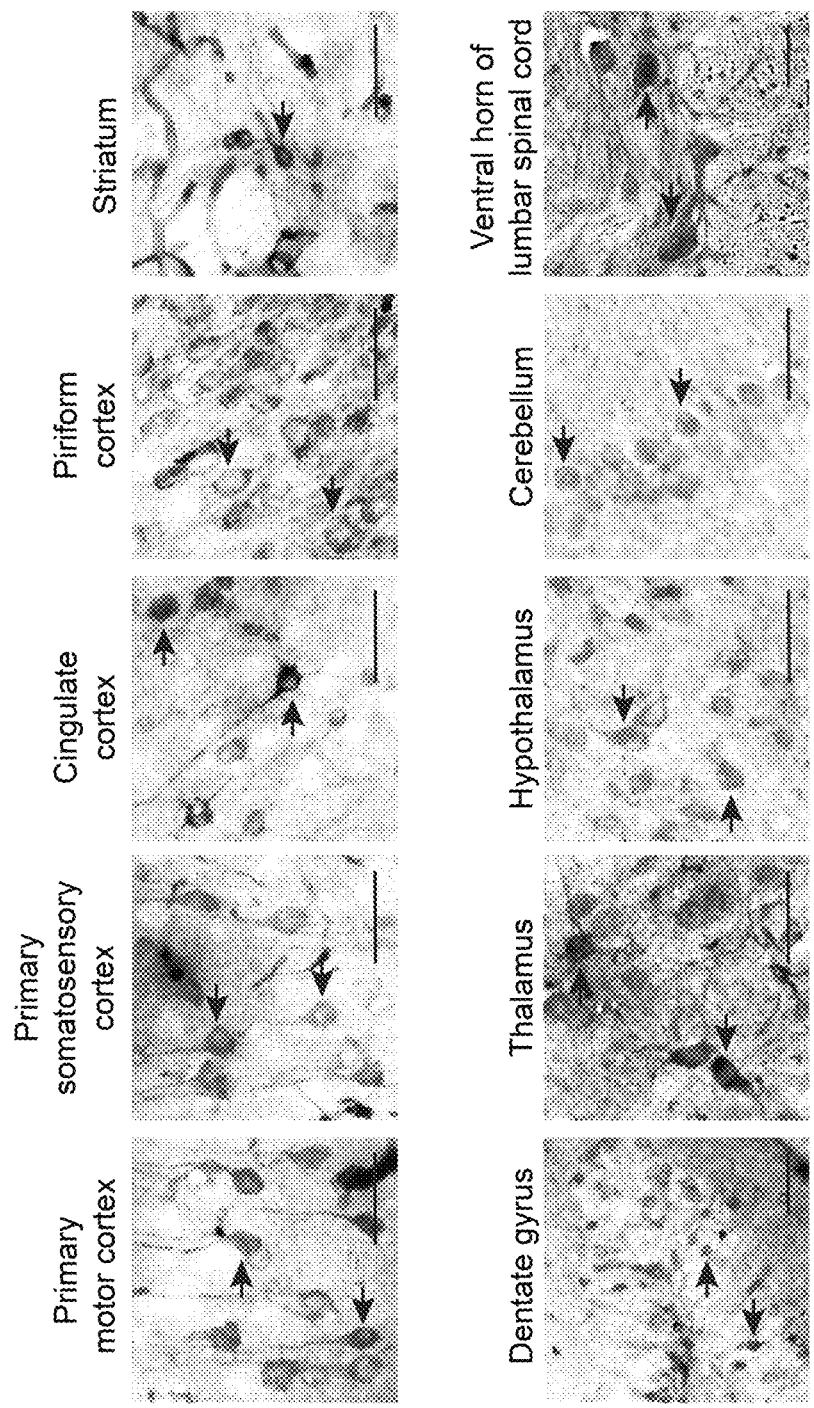
Figures 23C, 23D:
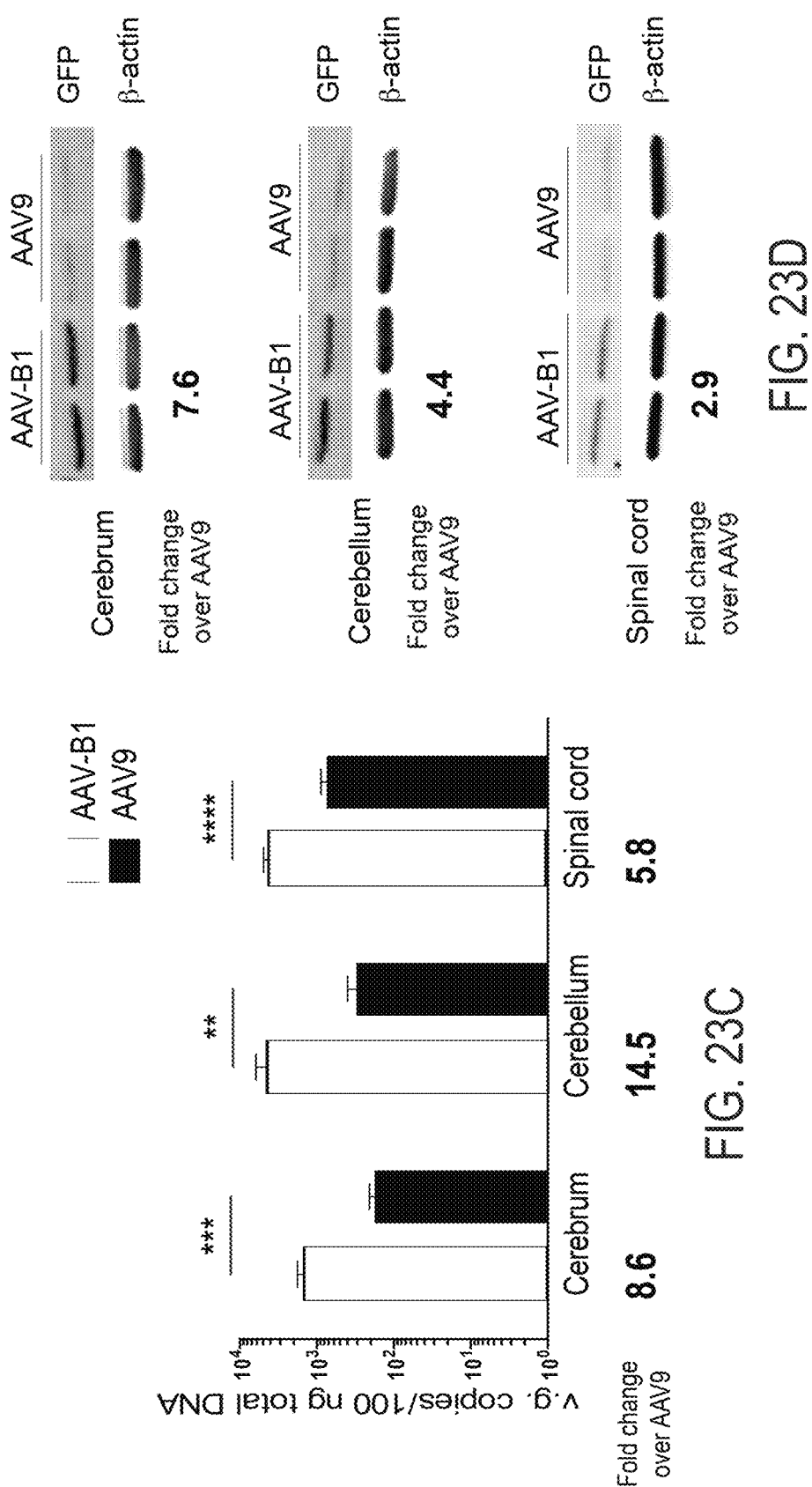

FIG. 23 shows CNS transduction profile of AAV-B1 vector after intravascular infusion in adult mice. FIG. 23A provides an overview of GFP distribution in brains of AAV-B1 and AAV9 injected mice ($2\times10^{12}$ vg/mouse). Representative images of coronal brain sections located at +0.5 mm, −1.80 mm and −3.00 mm (left to right) in relation to bregma are shown. Transduction of neuronal populations in different CNS regions of AAV-B1 injected mice ($2\times10^{12}$ vg/mouse) is shown in FIG. 23B. Black arrows indicate examples of GFP-positive neurons identified by morphology. Bar=50 μm. FIG. 23C shows AAV vector genome content in cerebrum, cerebellum and spinal cords (N=4 animals per group) ($5\times10^{11}$ vg/mouse). Age matched non-injected mice were included as controls (not shown). FIG. 23D shows Western blot analysis of GFP expression in cerebrum, cerebellum and spinal cord of 2 animals per group ($5\times10^{11}$ vg/mouse). Signal intensity of GFP was normalized to corresponding β-actin signal intensity for quantitative comparison. $p<0.01$, *$p<0.001$, ****$p<0.0001$ by Student's unpaired t-test.

Figure 24A:
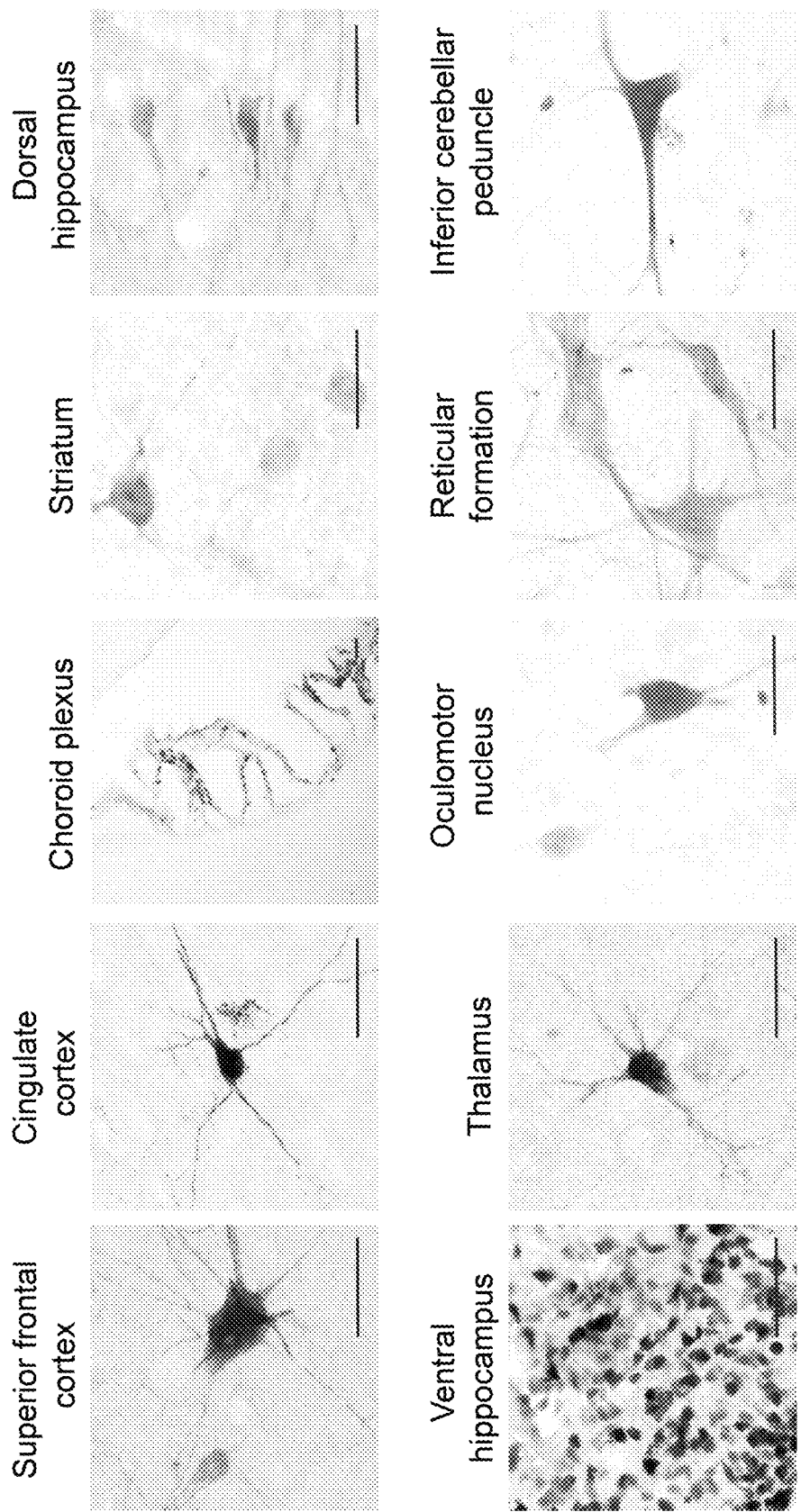
FIGS. 24A-24B show neuronal transduction in cat after systemic delivery of AAV-B1 vectors. Transduction of neurons in the cat brain after systemic delivery of AAV-B1 vector ($3.4 \times 10^{12}$ vg). Representative images show GFP-positive cells with neuronal morphology in various structures in the brain. Bar=50 μm.
Figure 24B:
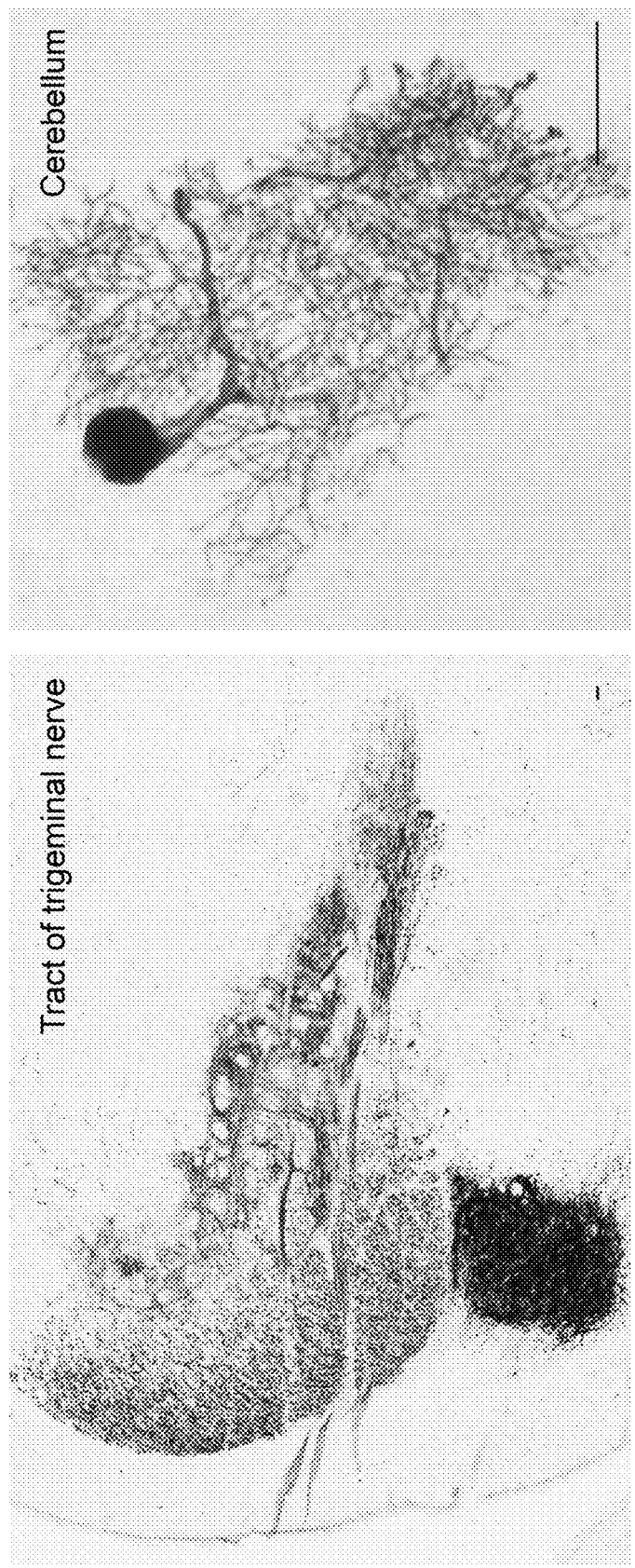
Figure 25A:
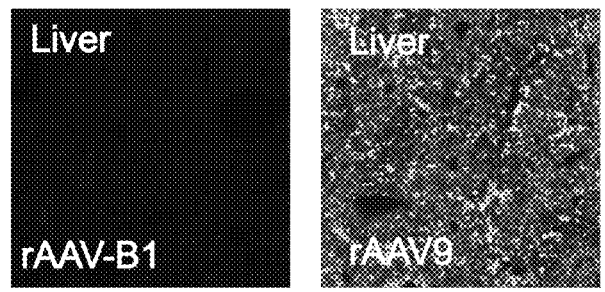
FIGS. 25A-25F show AAV-B1 biodistribution to mouse liver and muscle after intravascular delivery. Native GFP expression in (FIG. 25A) livers of AAV-B1 and AAV9 injected mice ($2 \times 10^{12}$ vg/mouse) and (FIG. 25D) skeletal muscle (triceps and quadriceps), diaphragm and heart of AAV-B1 injected mice ($5 \times 10^{11}$ vg/mouse). AAV vector genome content (N=4 animals per group) (FIG. 25B, liver.
Figure 25B:
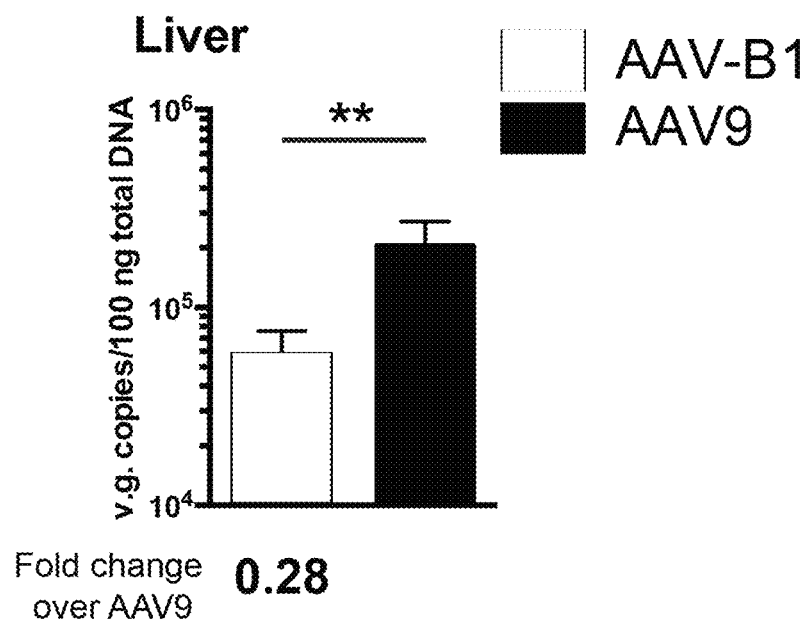
Figure 25C:
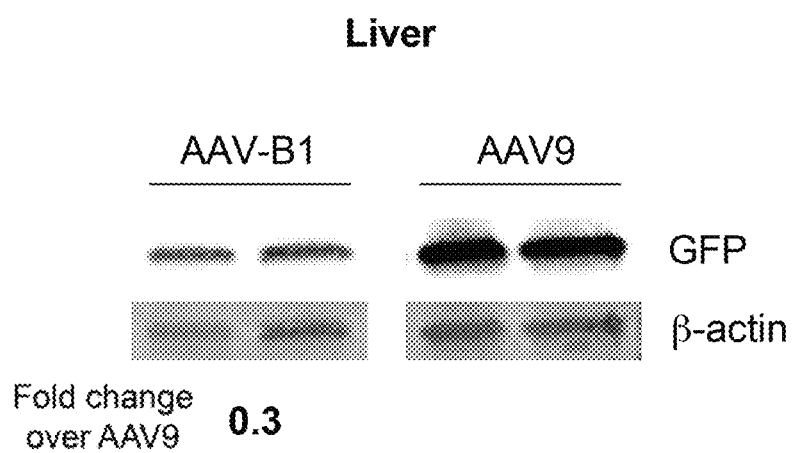
Figure 25D:
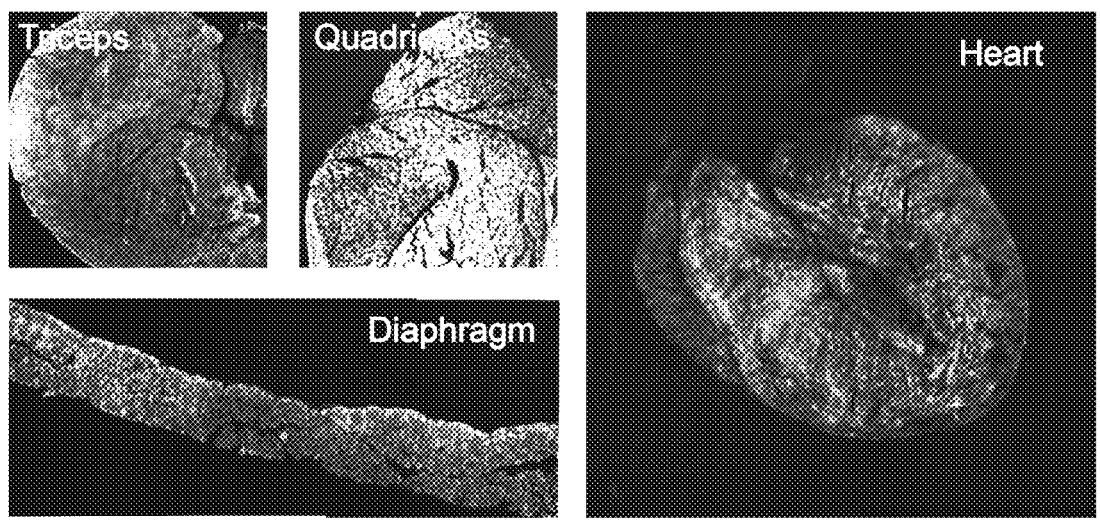
Figure 25E:
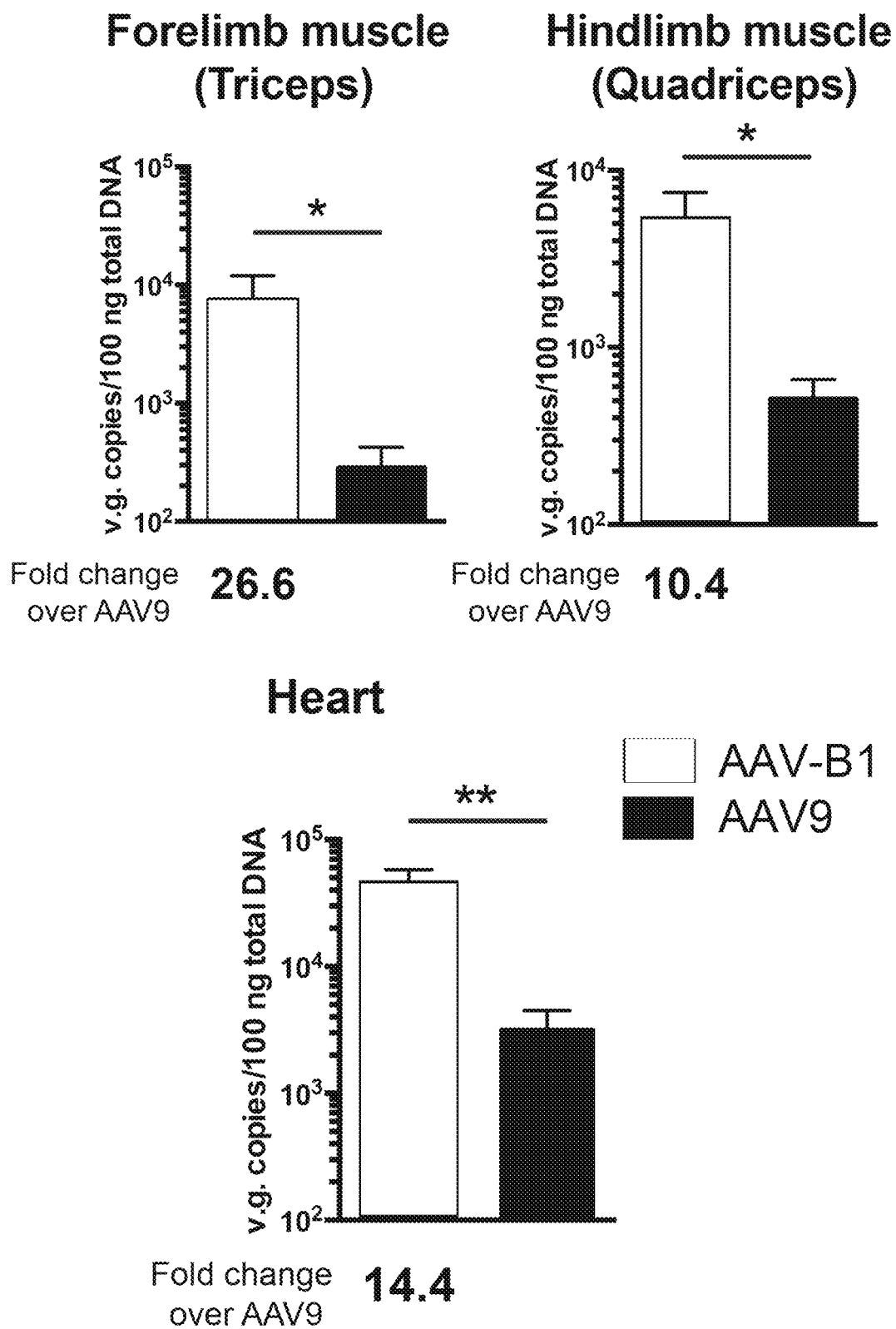
Figure 25F:
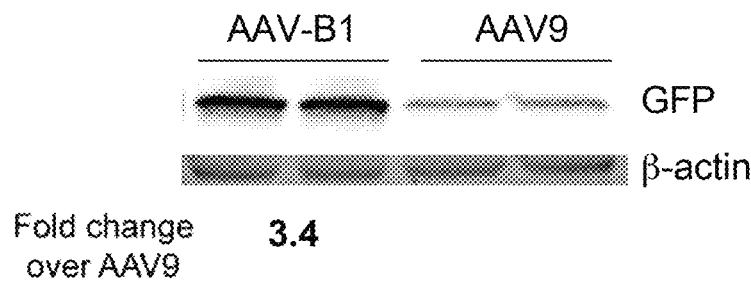
Figure 25F:
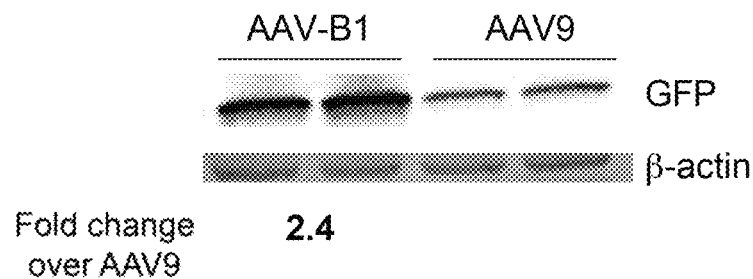
Figure 25F:
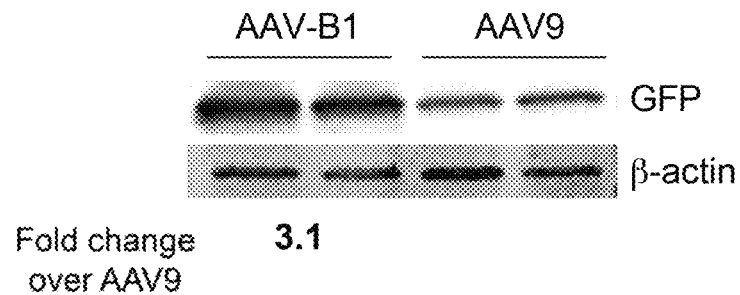
Figure 26A:
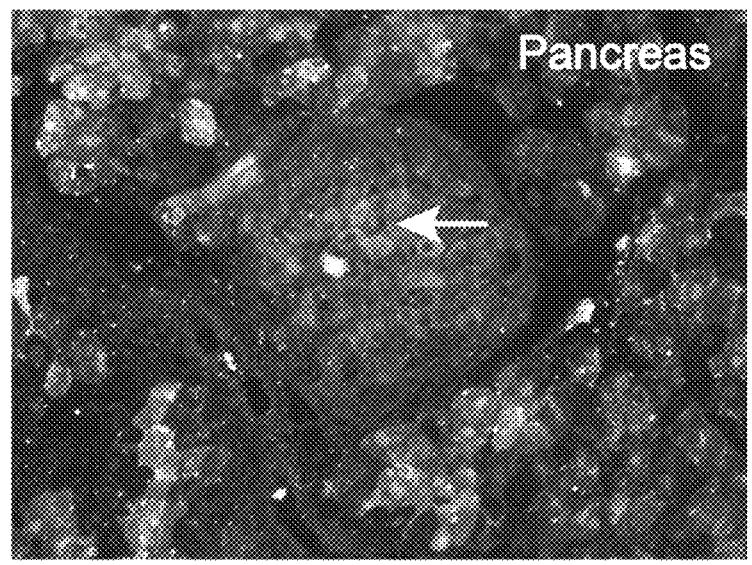
FIGS. 26A-26E show transduction of mouse beta cells, alveolar epithelium and retinal vasculature after intravenous infusion of AAV-B1. GFP expression in FIG. 26A pancreas, FIG. 26D lung, and FIG. 26G retina of AAV-B1 injected mice ($5 \times 10^{11}$ vg/mouse). White arrow in FIG. 26A indicates GFP-positive insulin-producing beta cells. Inset in FIG. 26G shows individual GFP-positive blood vessels. AAV vector genome content (N=4 animals per group) (FIG. 26B, pancreas.
Figure 26B:
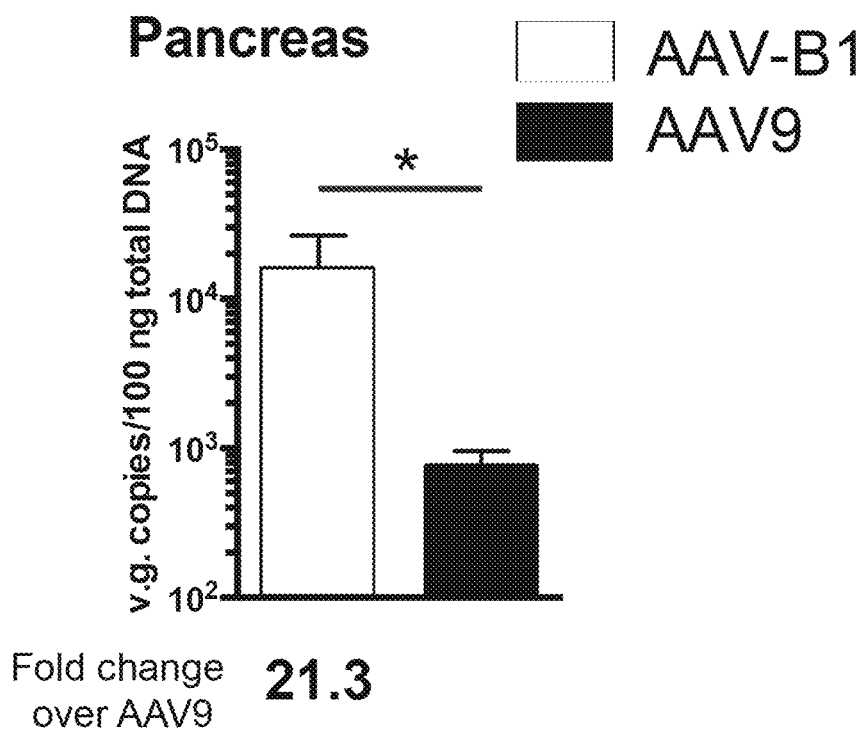
Figure 26C:
Figure 26D:
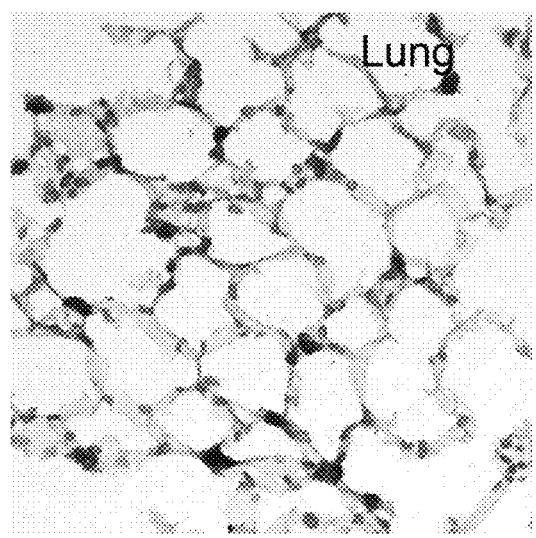
Figure 26E:
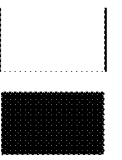
Figure 26E:
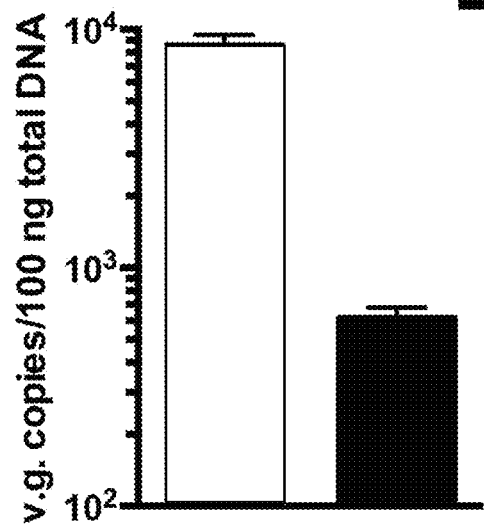
Figure 26F:
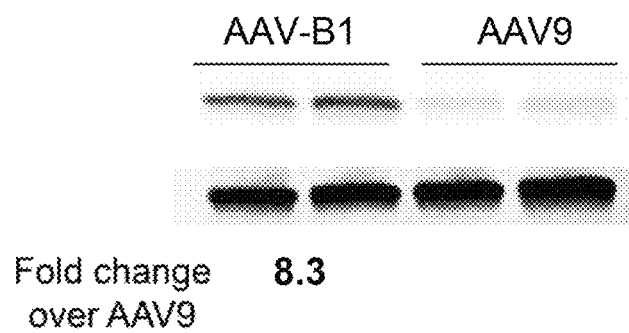
Figure 26G:
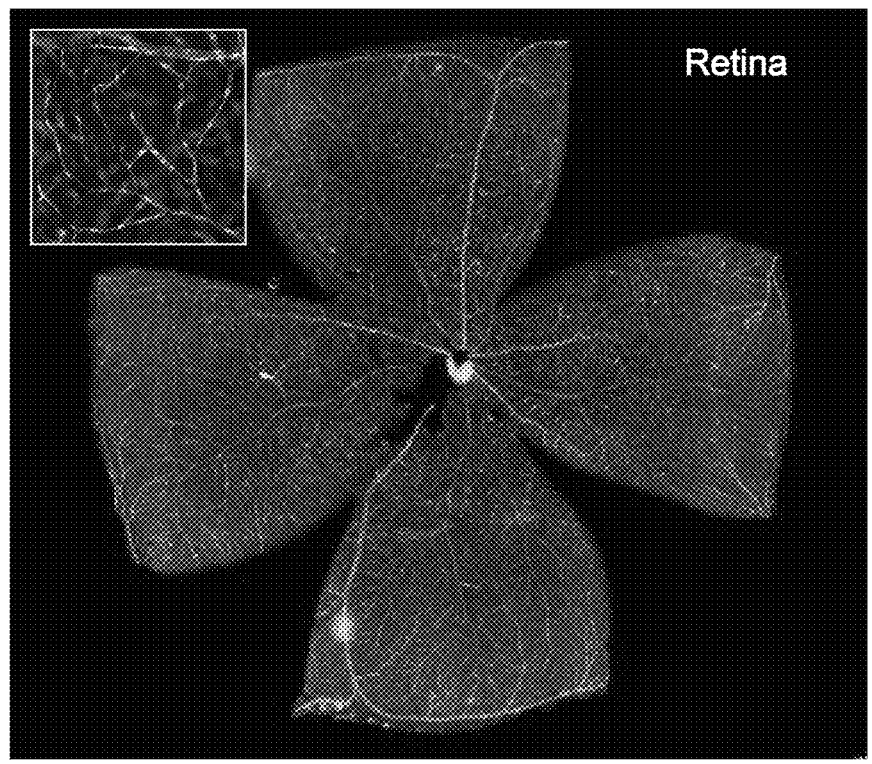
Figure 27A:
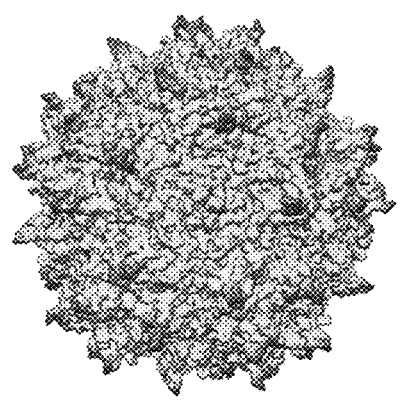
FIGS. 27A-27D show biophysical characterization of AAV-B1.
Figure 27B:
Figure 27C:
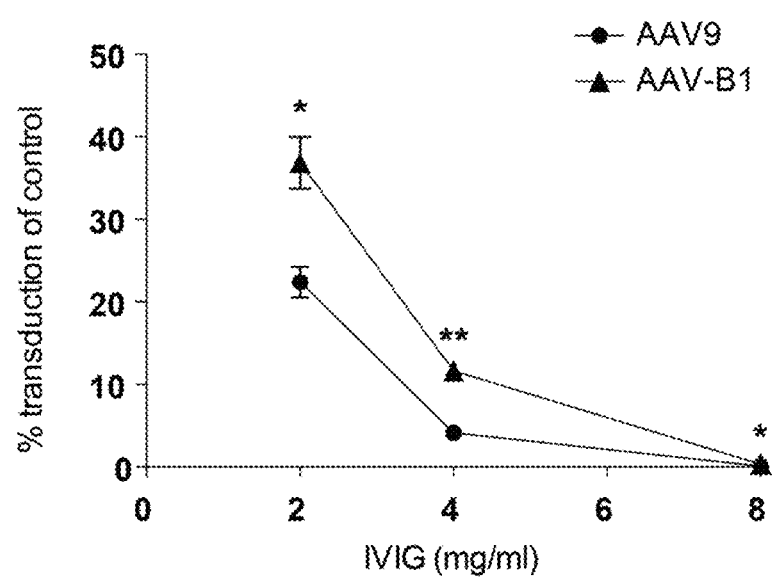
Figure 27D:
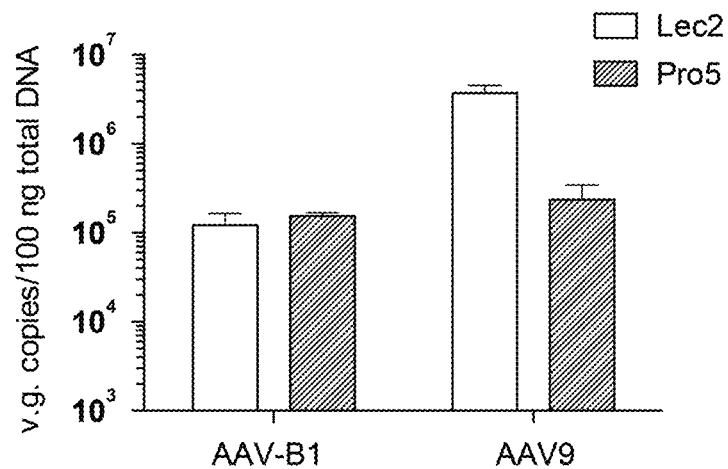

FIG. 24 shows neuronal transduction in cat after systemic delivery of AAV-B1 vectors. Transduction of neurons in the cat brain after systemic delivery of AAV-B1 vector ($3.4\times10^{12}$ vg). Representative images show GFP-positive cells with neuronal morphology in various structures in the brain. Bar=50 μm.

FIG. 25 shows AAV-B1 biodistribution to mouse liver and muscle after intravascular delivery. Native GFP expression in (FIG. 25A) livers of AAV-B1 and AAV9 injected mice ($2\times10^{12}$ vg/mouse) and (FIG. 25D) skeletal muscle (triceps and quadriceps), diaphragm and heart of AAV-B1 injected mice ($5\times10^{11}$ vg/mouse). AAV vector genome content (N=4 animals per group) (FIG. 25B, liver; FIG. 25E muscle groups) and Western blot analysis of GFP expression (N=2 animals per group) (FIG. 25C, liver; FIG. 25F muscle groups) are shown ($5\times10^{11}$ vg/mouse). Signal intensity of GFP was normalized to corresponding β-actin signal intensity for quantitative comparison. *$p<0.05$, **$p<0.01$, by Student's unpaired t-test.

FIG. 26 shows transduction of mouse beta cells, alveolar epithelium and retinal vasculature after intravenous infusion of AAV-B1. GFP expression in FIG. 26A pancreas, FIG. 26D lung, and FIG. 26G retina of AAV-B1 injected mice ($5\times10^{11}$ vg/mouse). White arrow in FIG. 26A indicates GFP-positive insulin-producing beta cells. Inset in FIG. 26G shows individual GFP-positive blood vessels. AAV vector genome content (N=4 animals per group) (FIG. 26B, pancreas; FIG. 26E lung) and FIG. 26C. Western blot analysis of GFP expression (N=2 animals per group) (FIG. 26C, pancreas; FIG. 26E lung) are shown. Signal intensity of GFP was normalized to corresponding β-actin signal intensity for quantitative comparison. *$p<0.05$, ****$p<0.0001$ by Student's unpaired t-test.

FIG. 27 shows biophysical characterization of AAV-B1. FIG. 27A shows a predicted molecular model of AAV-B1 capsid. FIG. 27B shows a surface exposed variable region-IV (VR-IV) of AAV-B1 (left) and AAV8 (right). FIG. 27C shows pooled human IVIg neutralization assay and FIG. 27D shows a CHO cell binding assay of AAV-B1 and AAV9 vectors. Data shown as mean±SEM in FIG. 27C, and as mean±SD in FIG. 27D. Experiment was performed with N=3 biological replicates. *$p<0.05$ by one-way ANOVA.

Figure 28:
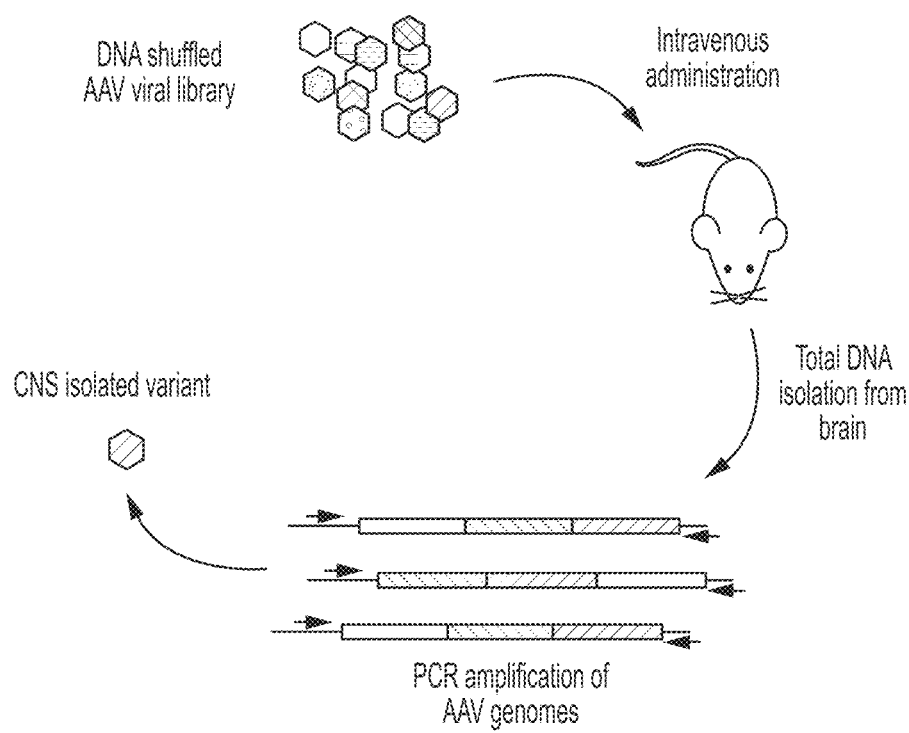
FIG. 28 provides a schematic cartoon of one embodiment of a single round in-vivo biopanning strategy
Figures 29A, 29B:
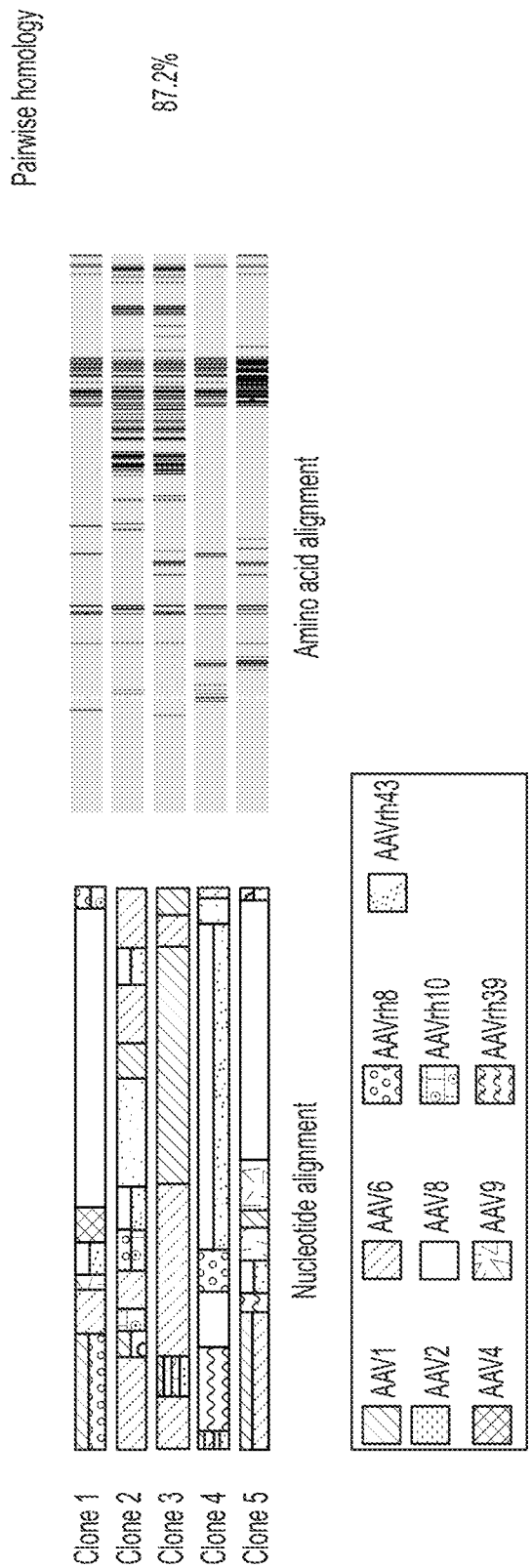
FIGS. 29A-29B show the chimeric nature of packaged viral library.
Figure 30A:
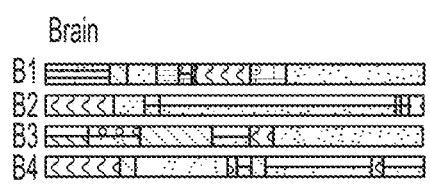
FIG. 30A shows parental capsid contribution to clones 1-5 isolated at random from packaged viral library.
Figure 30C:
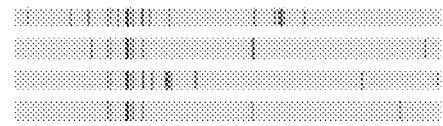
Figure 30B:
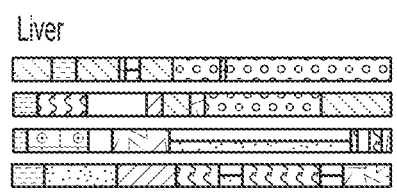
FIG. 30B shows homology between the clones at the amino acid level. Grey areas indicate homology; black lines indicate non-homologous amino acids. % homology is calculated for amino acid composition.
Figure 30D:
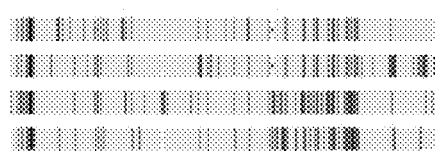

FIG. 28 provides a schematic cartoon of one embodiment of a single round in-vivo biopanning strategy FIG. 29 shows the chimeric nature of packaged viral library. FIG. 30A shows parental capsid contribution to clones 1-5 isolated at random from packaged viral library. FIG. 30B shows homology between the clones at the amino acid level. Grey areas indicate homology; black lines indicate non-homologous amino acids. % homology is calculated for amino acid composition.

FIG. 30 shows the chimeric and homologous nature of brain-resident capsids. Parental capsid contribution to (FIG. 30A) brain-selected capsids AAV-B1, -B2, -B3 and -B4, and (FIG. 30B) 4 liver-resident variants chosen at random. Homology among (FIG. 30C) brain and (FIG. 30D) liver clones at the amino acid level. Grey areas indicate homology; black lines indicate non-homologous amino acids. % homology is calculated for amino acid composition.

Figure 31:
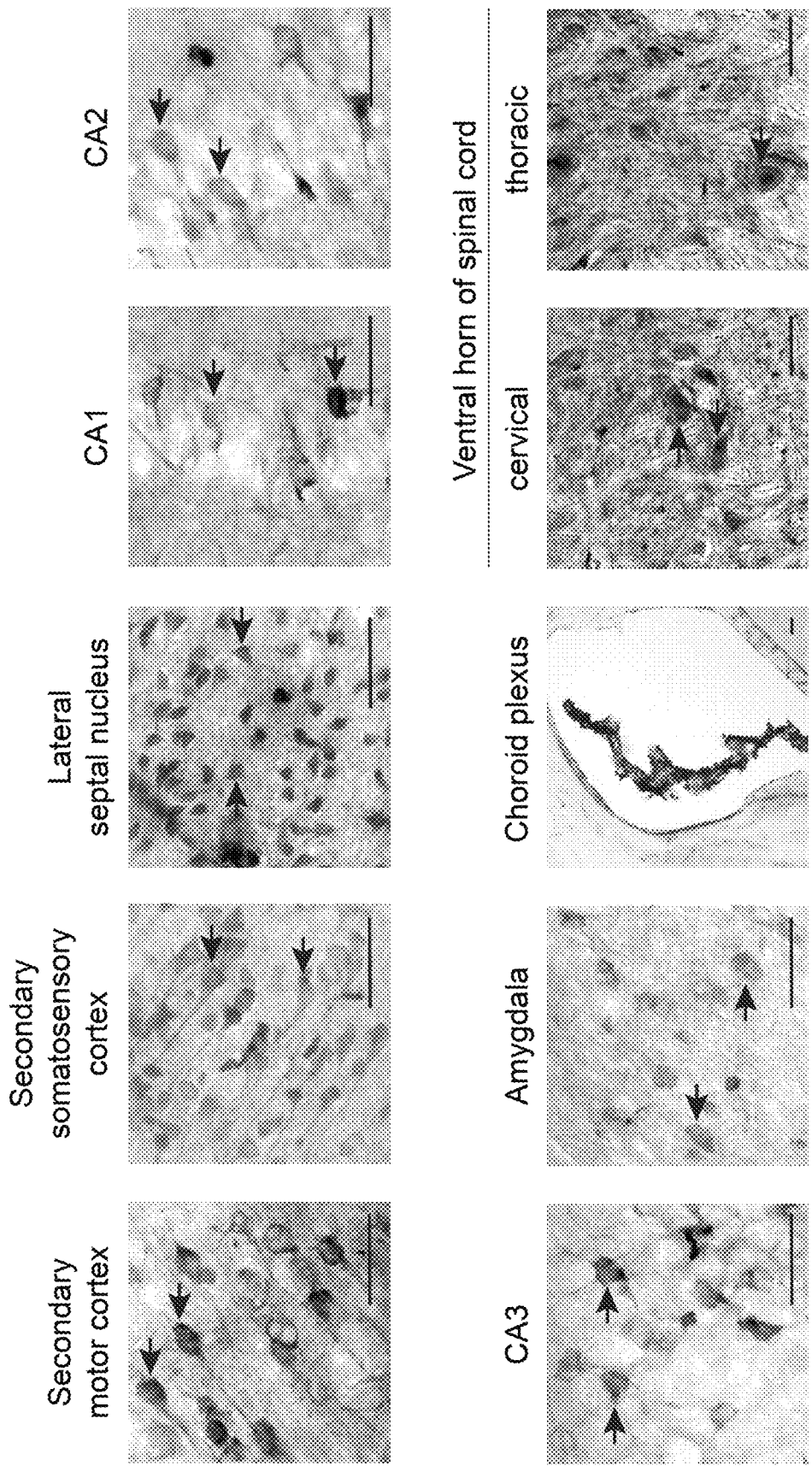
FIG. 31 shows a transduction profile of AAV-B1 vector across multiple CNS regions after systemic delivery. Black arrows indicate examples of GFP-positive neurons. Bar=50 µm.

FIG. 31 shows a transduction profile of AAV-B1 vector across multiple CNS regions after systemic delivery. Black arrows indicate examples of GFP-positive neurons. Bar=50 μm.

Figure 32B:
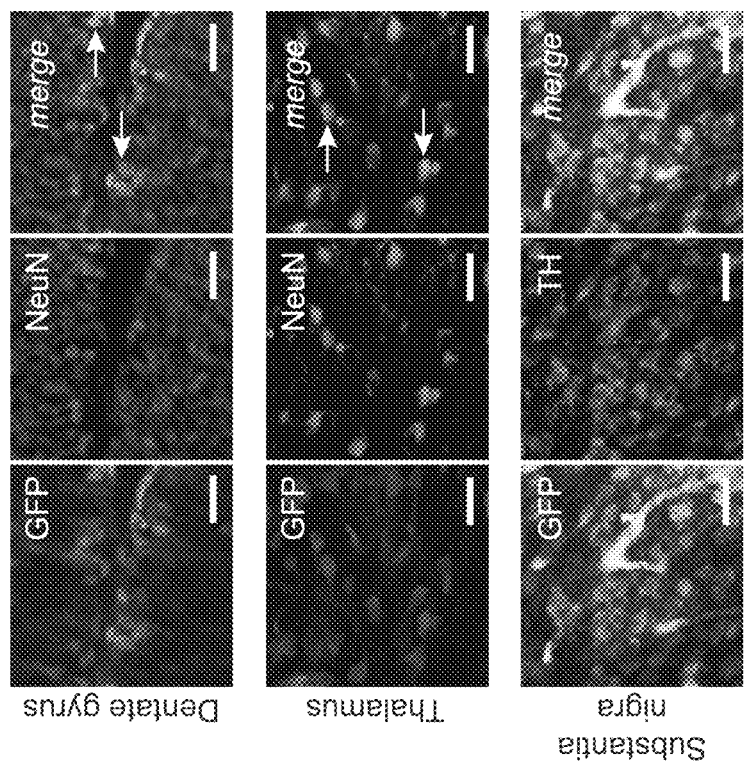
Figure 32A:
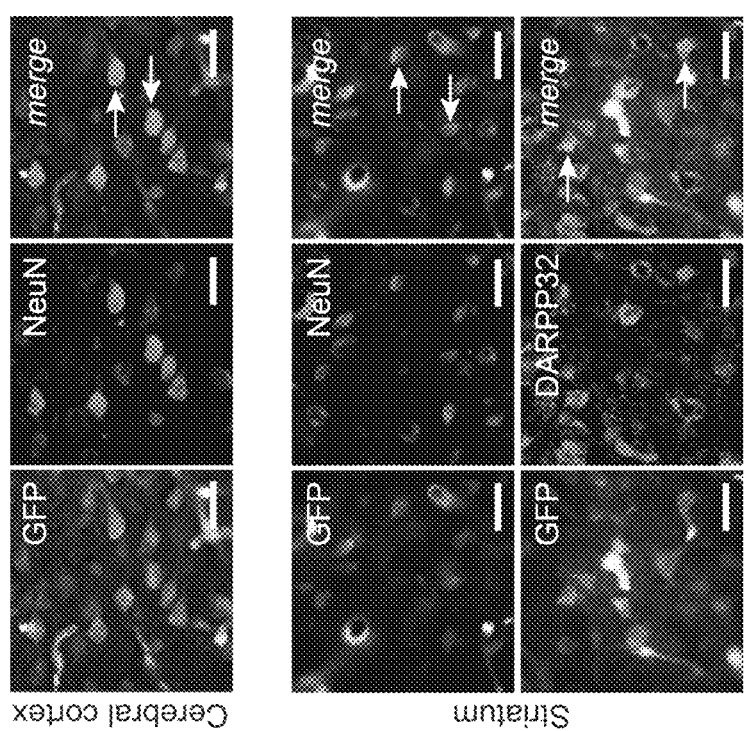

FIG. 32 shows phenotyping of GFP positive cells in CNS after systemic delivery of AAV-B1. Transduced cells were identified by double immunofluorescence staining with antibodies to GFP, pan-neuronal marker NeuN (FIG. 32A, FIG. 32B and FIG. 32D), striatal medium spiny neuron marker DARPP32 (FIG. 32A), dopaminergic neuron marker tyrosine hydroxylase (TH) (FIG. 32B), Purkinje neuron marker calbindin-D-28k (Cal28K) (FIG. 32C), endothelial marker CD31 (FIG. 32E), and mature oligodendrocyte marker APC (FIG. 32F). The large size, morphology and location of GFP-positive neurons in the ventral spinal cord suggest a motor neuron identity. GFP-positive astrocytes (FIG. 32G) were identified based on their morphology. White arrows indicate examples of co-localization. Bar=10 μm.

Figure 33A:
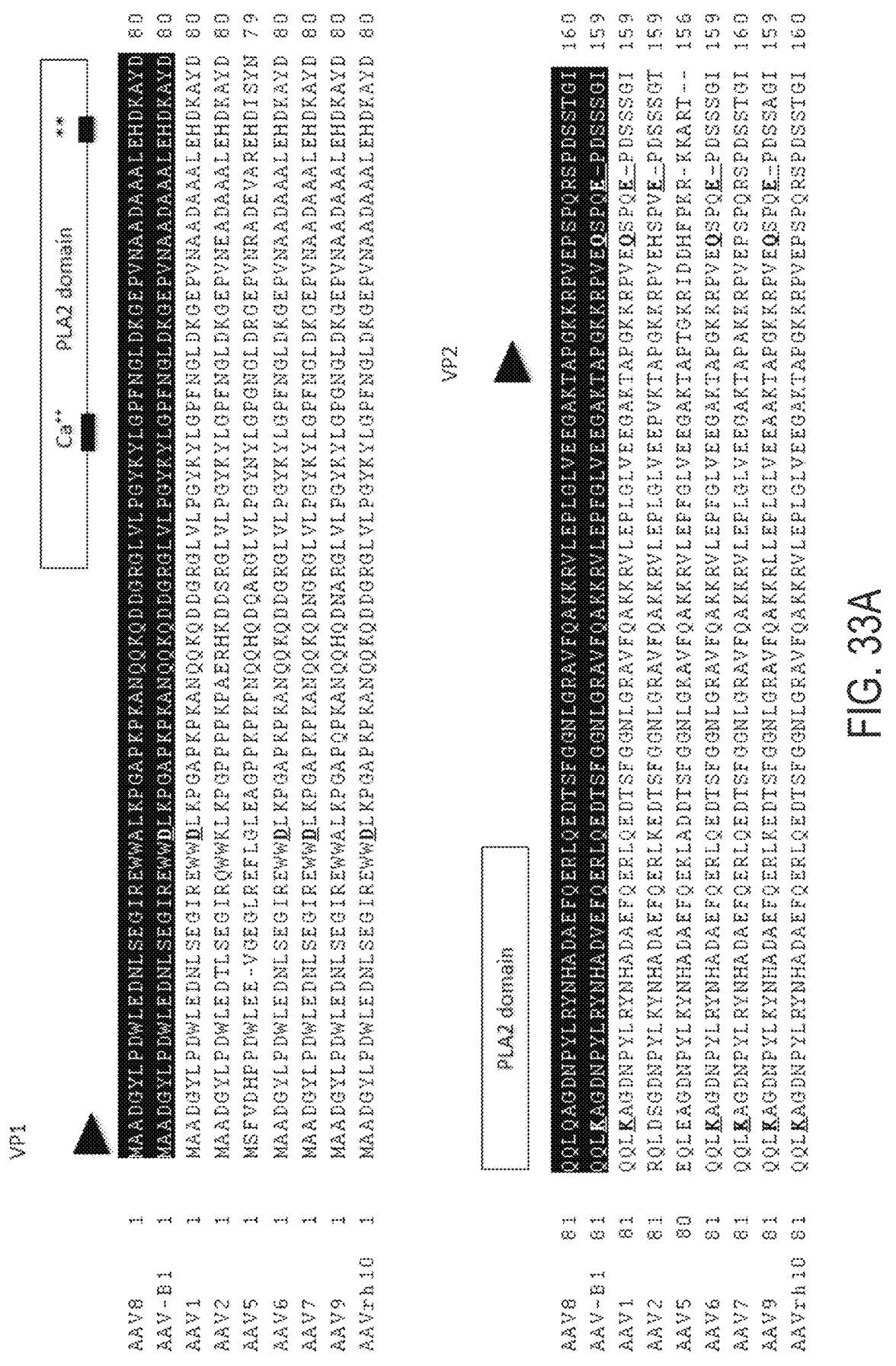

FIG. 33 shows a comparison of AAV-B1 capsid protein sequence to AAV8 and other natural AAV isolates. The top two lines highlight the similarities and differences between amino acid sequences of AAV8 and AAV-B1, with singleton residue variants relative to AAV8 highlighted in red. The residue highlighted in green indicates a variant residue with no corresponding orthologs in the nine AAV species presented in the alignment. Translation start sites for VP1, VP2, and VP3 are indicated with filled triangles. The conserved parvovirus phospholipase A2 domain (approximately residues 44 to 104) in the VP1 unique region with the conserved AAV calcium-binding motif (Y-X-G-P-G/F) and catalytic residues (H-D-X-X-Y) are indicated with filled rectangles. The secondary structural elements are labeled with the corresponding text and the following symbols: β sheets B, C, D, E, F, G, and I are indicated with a horizontal overlined arrow. The positions of the variable loops (VR), I through IX, are indicated. The position of the conserved a helix is indicated with three parallel horizontal lines.

Figures 34A, 34B, 34C:
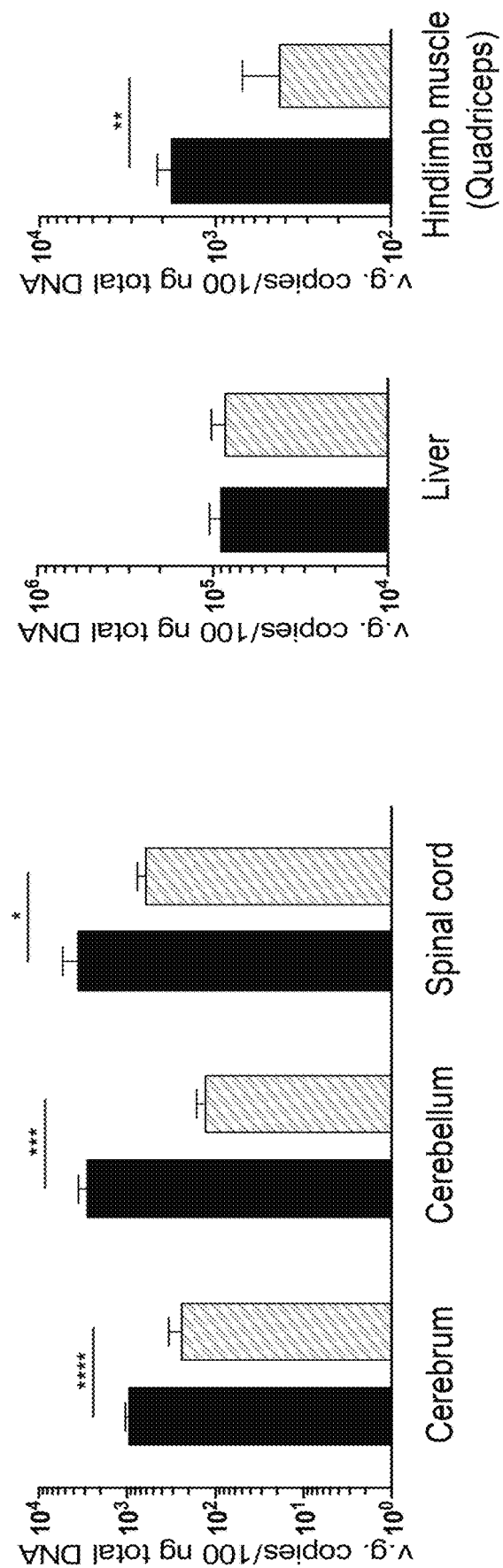
FIGS. 34A-34C show a comparison of biodistribution profile of AAV-B1 and AAV8 after systemic delivery ($5 \times 10^{11}$ vg/mouse). AAV vector genome content (N=4 animals per group) in (FIG. 34A) CNS, (FIG. 34B) liver and (FIG. 34C) skeletal muscle (quadriceps) is shown. $*p<0.05$, $p<0.01$, $*p<0.001$, $****p<0.0001$ by Student's unpaired t-test.

FIG. 34 shows a comparison of biodistribution profile of AAV-B1 and AAV8 after systemic delivery ($5 \times 10^{11}$ vg/mouse). AAV vector genome content (N=4 animals per group) in (FIG. 34A) CNS, (FIG. 34B) liver and (FIG. 34C) skeletal muscle (quadriceps) is shown. $*p<0.05$, $p<0.01$, $*p<0.001$, $****p<0.0001$ by Student's unpaired t-test.

Figure 35A:
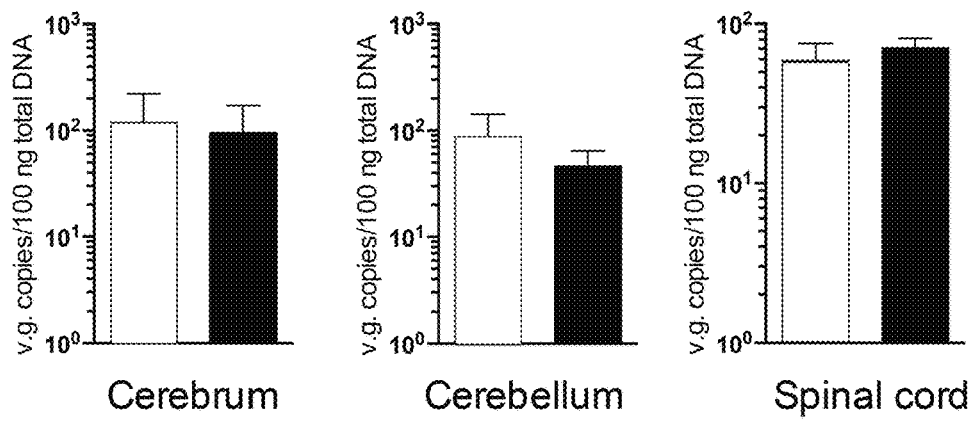
FIGS. 35A-35C show biodistribution profile of AAV-B1 systemically infused at lower dose ($5 \times 10^{10}$ vg/mouse). AAV vector genome content (N=4 animals per group) in (FIG. 35A) CNS, (FIG. 35B) muscle groups and (FIG. 36C) peripheral tissues is shown. $*p<0.05$, $**p<0.01$, by Student's unpaired t-test.
Figure 35B:
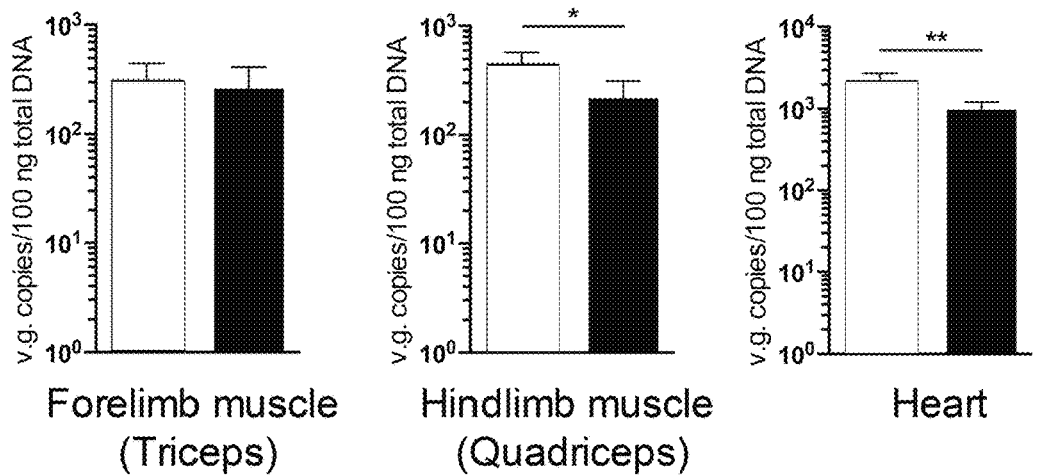
Figure 35C:
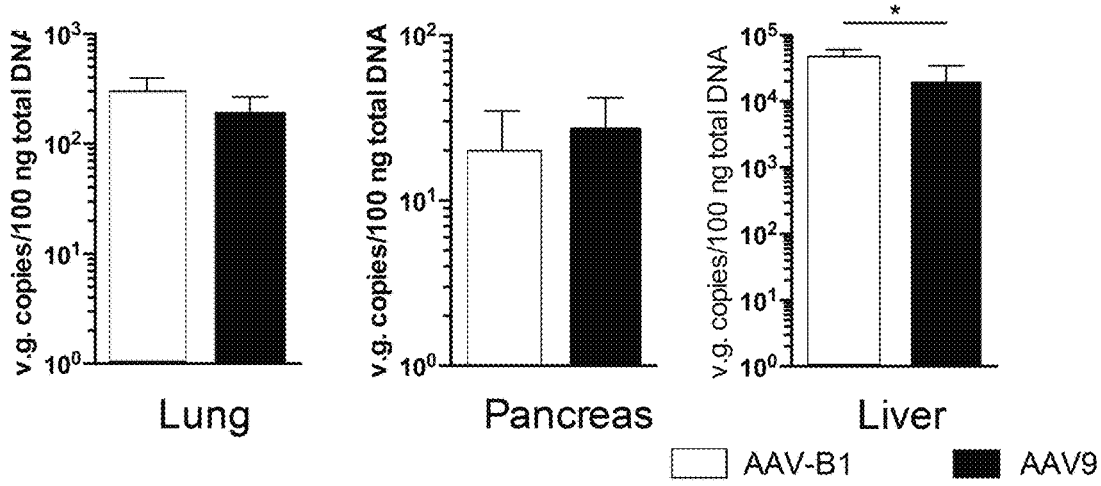

FIG. 35 shows biodistribution profile of AAV-B1 systemically infused at lower dose ($5 \times 10^{10}$ vg/mouse). AAV vector genome content (N=4 animals per group) in (FIG. 35A) CNS, (FIG. 35B) muscle groups and (FIG. 35C) peripheral tissues is shown. $*p<0.05$, $**p<0.01$, by Student's unpaired t-test.

```
SEQUENCE LISTING

>SEQ ID NO: 1; AAV-B1
ATGGCTGCCGATGGTTATCTTCCAGATTGGCTCGAGGACAACCTCTCTGAGGGCATT

CGCGAGTGGTGGGACTTGAAACCTGGAGCCCCGAAGCCCAAAGCCAACCAGCAAA

AGCAGGACGACGGCCGGGGTCTGGTGCTTCCTGGCTACAAGTACCTCGGACCCTTC

AACGGACTCGACAAGGGGGAGCCCGTCAACGCGGCGGACGCAGCGGCCCTCGAGC

ACGACAAGGCCTACGACCAGCAGCTCAAAGCGGGTGACAATCCGTACCTGCGGTAT

AACCACGCCGACGTCGAGTTTCAGGAGCGTCTGCAAGAAGATACGTCTTTTGGGGG

CAACCTCGGGCGAGCAGTCTTCCAGGCCAAGAAGAGGGTTCTCGAACCTTTTGGTC

TGGTTGAGGAAGGCGCTAAGACGGCTCCTGGAAAGAAACGTCCGGTAGAGCAGTC

GCCACAAGAGCCAGACTCCTCCTCGGGCATCGGCAAGAAAGGCCAACAGCCCGCCA

GAAAAAGACTCAATTTTGGCCAGACTGGCGACTCAGAGTCAGTTCCAGACCCTCAA

CCTCTCGGAGAACCTCCAGCAGCGCCCTCTGGTGTGGGACCTAATACAATGGCTGC

AGGCGGTGGCGCACCAATGGCAGACAATAACGAGGGCGCCGACGGAGTGGGTAAT

TCCTCGGGAAATTGGCATTGCGATTCCACATGGATGGGGACAGAGTCATCACCAC

CAGCACCCGAACCTGGGCCCTGCCCACCTACAACAACCACCTCTACAAGCAAATCT

CCAACGGCACCTCGGGAGGAAGCACCAACGACAACACCTATTTTGGCTACAGCACC

CCCTGGGGGTATTTTGATTTCAACAGATTCCACTGCCACTTCTCACCACGTGACTGG

CAGCGACTCATCAACAACAACTGGGGATTCCGGCCAAAAAGACTCAGCTTCAAGCT

CTTCAACATCCAGGTCAAGGAGGTCACGCAGAATGAAGGCACCAAGACCATCGCCA

ATAACCTTACCAGCACGATTCAGGTATTTACGGACTCGGAATACCAGCTGCCATAC

GTCCTCGGCTCCGCGCACCAGGGCTGCCTGCCTCCGTTCCCGGCGGACGTCTTCATG

ATTCCCCAGTACGGCTACCTTACACTGAACAATGGAAGTCAAGCCGTAGGCCGTTC

CTCCTTCTACTGCCTGGAATATTTTCCTTCTCAAATGCTGAGAACGGGCAACAACTT

TGAGTTCAGCTACCAGTTTGAGGACGTGCCTTTTCACAGCAGCTACGCGCACAGCCA

AAGCCTGGACCGGCTGATGAACCCCCTCATCGACCAGTACCTGTACTACCTGTCTCG

GACTCAGTCCACGGGAGGTACCGCAAGAACTCAGCAGTTGCTATTTTCTCAGGCCG

GGCCTAATACAATGGCCAATCAGGCAAAGAACTGGCTGCCAGGACCCTGTTACCGC

CAACAACGCGTCTCAACGACAACCGGGCAAAACAACAATAGCAACTCTGCCTGGAC

TGCTGGGACCAAATACCATCTGAATGGAAGAAATTCATTGGCTAATCCTGGCATCG

CTATGGCAACACACAAAGACGACGAGGAGCGTTTTTTTCCCAGTAACGGGATCCTG

ATTTTTGGCAAACAAAATGCTGCCAGAGACAATGCGGATTACAGCGATGTCATGCT

CACCAGCGAGGAAGAAATCAAAACCACTAACCCTGTGGCTACAGAGGAATACGGT

ATCGTGGCAGATAACTTGCAGCAGCAAAACACGGCTCCTCAAATTGGAACTGTCAA

CAGCCAGGGGCCTTACCCGGTATGGTCTGGCAGAACCGGGACGTGTACCTGCAGG

GTCCCATCTGGGCCAAGATTCCTCACACGGACGGCAACTTCCACCCATCTCCGCTGA
```

SEQUENCE LISTING

```
TGGGCGGCTTTGGCCTGAAACATCCTCCGCCTCAGATCCTGATCAAGAACACGCCTG
TACCTGCGGATCCTCCGACCACCTTCAACCAGTCAAAGCTGAACTCTTTCATCACGC
AATACAGCACCGGACAGGTCAGCGTGGAAATTGAATGGGAGCTACAGAAGGAAAA
CAGCAAGCGCTGGAACCCCGAGATCCAGTACACCTCCAACTACTACAAATCTACAA
GTGTGGACTTTGCTGTTAATACAGAAGGCGTGTACTCTGAACCCCGCCCCATTGGCA
CCCGTTACCTCACCCGTAATCTGTAA

>SEQ ID NO: 2; AAV-B2
ATGGCTGCCGATGGTTATCTTCCAGATTGGCTCGAGGACAACCTCTCTGAGGGCATT
CGCGAGTGGTGGGCGCTGAAACCTGGAGCCCCGAAGCCCAAAGCCAACCAGCAAA
AGCAGGACGACGGCCGGGGTCTGGTGCTTCCTGGCTACAAGTACCTCGGACCCTTC
AACGGACTCGACAAGGGGGAGCCCGTCAACGCGGCGGACGCAGCGGCCCTCGAGC
ACGACAAGGCCTACGACCAGCAGCTCAAAGCGGGTGACAATCCGTACCTGCGGTAT
AACCACGCCGACGCCGAGTTTCAGGAGCGTCTGCAAGAAGATACGTCTTTTGGGGG
CAACCTCGGGCGAGCAGTCTTCCAGGCCAAGAAGCGGGTTCTCGAACCTCTCGGTC
TGGTTGAGGACGGCGCTAAGACGGCTCCTGGAAAGAAGAGACCAGTAGAGCAGTC
ACCCCAAGAACCAGACTCCTCCTCGGGCATCGGCAAGAAAGGCCAACAGCCCGCCA
GAAAAAGACTCAATTTTGGCCAGACTGGCGACTCAGAGTCAGTTCCAGACCCTCAA
CCTCTCGGAGAACCTCCAGCAACCCCCGCTGCTGTGGGACCTACTACAATGGCTTCA
GGCGGTGGCGCACCAATGGCAGACAATAACGAAGGCGCCGACGGAGTGGGTAGTT
CCTCGGGAAATTGGCATTGCGATTCCACATGGCTGGGCGACAGAGTCATCACCACC
AGCACCCGAACCTGGGCCCTGCCCACCTACAACAACCACCTCTACAAGCAAATCTC
CAACGGGACATCGGAGGAGCCACCAACGACAACACCTACTTCGGCTACAGCACCC
CCTGGGGGTATTTTGACTTTAACAGATTCCACTGCCACTTTTCACCACGTGACTGGC
AGCGACTCATCAACAACAACTGGGGATTCCGGCCCAAGAGACTCAGCTTCAAGCTC
TTCAACATCCAGGTCAAGGAGGTCACGCAGAATGAAGGCACCAAGACCATCGCCAA
TAACCTCACCAGCACCATCCAGGTGTTTACGGACTCGGAGTACCAGCTGCCGTACGT
TCTCGGCTCTGCCCACCAGGGCTGCCTGCCTCCGTTCCCGGCGGACGTGTTCATGAT
TCCCCAGTACGGCTACCTAACACTCAACAACGGTAGTCAGGCCGTGGGACGCTCCT
CCTTCTACTGCCTGGAATACTTTCCTTCGCAGATGCTGAGAACCGGCAACAACTTCC
AGTTTACTTACACCTTCGAGGACGTGCCTTTCCACAGCAGCTACGCCCACAGCCAGA
GCTTGGACCGGCTGATGAATCCTCTGATTGACCAGTACCTGTACTACTTGTCTCGGA
CTCAAACAACAGGAGGCACGGCAAATACGCAGACTCTGGGCTTCAGCCAAGGTGG
GCCTAATACAATGGCCAATCAGGCAAAGAACTGGCTGCCAGGACCCTGTTACCGCC
AACAACGCGTCTCAACGACAACCGGGCAAAACAACAATAGCAACTTTGCCTGGACT
GCTGGGACCAAATACCATCTGAATGGAAGAAATTCATTGGCTAATCCTGGCATCGC
TATGGCAACACACAAGGACGACGAGGAGCGTTTTTTTCCCAGTAACGGGATCCTGA
TTTTTGGCAAACAAAATGCTGCCAGAGACAATGCGGATTACAGCGATGTCATGCTC
ACCAGCGAGGAAGAAATCAAAACCACTAACCCTGTGGCTACAGAGGAATACGGTA
TCGTGGCAGATAACTTGCAGCAGCAAAACACGGCTCCTCAAATTGGAACTGTCAAC
```

```
AGCCAGGGGGCCTTACCCGGTATGGTCTGGCAGAACCGGGACGTGTACCTGCAGGG

TCCCATCTGGGCCAAGATTCCTCACACGGACGGCAACTTCCACCCGTCTCCGCTGAT

GGGCGGCTTTGGCCTGAAACATCCTCCGCCTCAGATCCTGATCAAGAACACGCCTGT

ACCTGCGGATCCTCCGACCACCTTCAACCAGTCAAAGCTGAACTCTTTCATCACGCA

ATACAGCACCGGACAGGTCAGCGTGGAAATCGAGTGGGAGCTGCAGAAAGAAAAC

AGCAAGCGCTGGAACCCCGAGATCCAGTACACCTCCAACTACTACAAATCTACAAA

TGTGGACTTTGCTGTCAACACGGAGGGGGTTTATAGCGAGCCTCGCCCCATTGGCAC

CCGTTACCTCACCCGCAACCTGTAA

>SEQ ID NO: 3; AAV-B3
ATGGCTGCCGATGGTTATCTTCCAGATTGGCTCGAGGACAACCTCTCTGAGGGCATT

CGCGAGTGGTGGGCGCTGAAACCTGGAGCCCCGAAGCCCAAAGCCAACCAGCAAA

AGCAGGACGACGGCCGGGGTCTGGTGCTTCCTGGCTACAAGTACCTCGGACCCTTC

AACGGACTCGACAAGGGGGAGCCCGTCAACGCGGCGGACGCAGCGGCCCTCGAGC

ACGACAAGGCCTACGACCAGCAGCTCAAAGCGGGTGACAATCCGTACCTGCGGTAT

AACCACGCCGACGCCGAGTTTCAGGAGCGTCTGCAAGAAGATACGTCTTTTGGGGG

CAACCTCGGGCGAGCAGTCTTCCAGGCCAAGAAGCGGGTTCTCGAACCTCTCGGTC

TGGTTGAGGAAGGCGCTAAGACGGCTCCTGGAAAGAAACGTCCGGTAGAGCAGTC

GCCACAAGAGCCAGACTCCTCCTCGGGCATCGGCAAGACAGGCCAGCAGCCCGCTA

AAAAGAGGCTCAATTTTGGTCAGACTGGCGACTCAGAGTCAGTCCCCGACCCACAA

CCTCTCGGAGAACCTCCAGCAACCCCCGCTGCTGTGGGACCTACTACAATGGCTTCA

GGCGGTGGCGCACCAATGGCAGACAATAACGAAGGCGCCGACGGAGTGGGTAATG

CCTCAGGAAATTGGCATTGCGATTCCACATGGCTGGGCGACAGANTCATCACCACC

AGCACCCGAACATGGGCCTTGCCCACCTATAACAACCACCTCTACAAGCAAATCTC

CAGTGCTTCAACGGGGGCCAGCAACGACAACCACTACTTCGGCTACAGCACCCCCT

GGGGGTATTTTGATTTCAACAGATTCCACTGCCATTTCTCACCACGTGACTGGCAGC

GACTCATCAACAACAATTGGGGATTCCGGCCCAAGAGACTCAACTTCAAGCTCTTC

AACATCCAAGTCAAGGAGGTCACGCAGAATGAAGGCACCAAGACCATCGCCAATA

ACCTCACCAGCACCATCCAGGTGTTTACGGACTCGGAGTACCAGCTGCCGTACGTTC

TCGGCTCTGCCCACCAGGGCTGCCTGCCTCCGTTCCCGGCGGACGTGTTCATGATTC

CCCAGTACGGCTACCTAACACTCAACAACGGTAGTCAGGCCGTGGGACGCTCCTCC

TTCTACTGCCTGGAATATTTTCCATCTCAAATGCTGCGAACTGGAAACAATTTTGAA

TTCAGCTACACCTTCGAGGACGTGCCTTTCCACAGCAGCTACGCACACAGCCAGAG

CTTGGACCGACTGATGAATCCTCTCATCGACCAGTACCTGTACTACTTGTCTCGGAC

TCAAACAACAGGAGGCACGGCAAATACGCAGACTCTGGGCTTCAGCCAAGGTGGG

CCTAATACAATGGCCAATCAGGCAAAGAACTGGCTGCCAGGACCCTGTTACCGCCA

ACAACGCGTCTCAACGACAACCGGGCAAAACAACAATAGCAACTTTGCCTGGACTG

CTGGGACCAAATACCATCTGAATGGAAGAAATTCATTGGCTAATCCTGGCATCGCT

ATGGCAACACACAAAGACGACGAGGAGCGTTTTTTTTCCCAGTAACGGGATCCTGAT

TTTTGGCAAACAAAATGCTGCCAGAGACAATGCGGATTACAGCGATGTCATGCTCA
```

SEQUENCE LISTING

```
CCAGCGAGGAAGAAATCAAAACCACTAACCCTGTGGCTACAGAGGAATACGGTATC

GTGGCAGATAACTTGCAGCAGCAAAACACGGCTCCTCAAATTGGAACTGTCAACAG

CCAGGGGACCTTACCCGGTATGGTCTGGCAGAACCGGGACGTGTACCTGCAGGGTC

CCATCTGGGCCAAGATTCCTCACACGGACGGCAACTTCCACCCGTCTCCGCTGATGG

GCGGCTTTGGCCTGAAACATCCTCCGCCTCAGATCCTGATCAAGAACACGCCTGTAC

CTGCGGATCCTCCGACCACCTTCAACCAGTCAAAGCTGAACTCTTTCATCACGCAAT

ACAGCACCGGACAGGTCAGCGTGGAAATTGAATGGGAGCTACAGAAGGAAAACAG

CAAGCGCTGGAACCCCGAGATCCAGTACACCTCCAATTACTACAAATCTACAAGTG

TGGACTTTGCTGTTAATACAGAAGGCGTGTACTCTGAACCCCGCCCCATTGGCACGC

GTTTCCTCACCCGTAATCTGTAA

>SEQ ID NO: 4; AAV-B4
ATGGCTGCCGATGGTTATCTTCCAGATTGGCTCGAGGACAACCTCTCTGAGGGCATT

CGCGAGTGGTGGGCGCTGAAACCTGGAGCCCCGAAGCCCAAAGCCAACCAGCAAA

AGCAGGACGACGGCCGGGGTCTGGTGCTTCCTGGCTACAAGTACCTCGGACCCTTC

AACGGACTCGACAAGGGGGAGCCCGTCAACGCGGCGGACGCAGCGGCCCTCGAGC

ACGACAAGGCCTACGACCAGCAGCTCAAAGCGGGTGACAATCCGTACCTGCGGTAT

AACCACGCCGACGCCGAGTTTCAGGAGCGTCTGCAAGAAGATACGTCTTTTGGGGG

CAACCTCGGGCAGCAGTCTTCCAGGCCAAGAAGCGGGTTCTCGAACCTCTCGGTC

TGGTTGAGGAAGGCGCTAAGACGGCTCCTGGAAAGAAACGTCCGGTAGAGCAGTC

GCCACAAGAGCCAGACTCCTCCTCGGGCATCGGCAAGACAGGCCAGCAGCCCGCTA

AAAAGAGGCTCAATTTTGGCCAGACTGGCGACTCAGAGTCAGTTCCAGACCCTCAA

CCTCTCGGAGAACCTCCAGCAGCGCCCTCTGGTGTGGGACCTAATACAATGGCTGC

AGGCGGTGGCGCACCAATGGCAGACAATAACGAAGGCGCCGACGGAGTGGGTAGT

TCCTCGGGAAATTGGCATTGCGATTCCACATGGCTGGGCGACAGAGTCATCACCAC

CAGCACCCGAACCTGGGCCCTGCCCACCTACAACAACCACCTCTACAAGCAAATCT

CCAACGGGACATCGGGAGGAGCCACCAACGACAACACCTACTTCGGCTACAGCACC

CCCTGGGGGTATTTTGACTTTAACAGATTCCACTGCCACTTTTCACCACGTGACTGG

CAGCGACTCATCAACAACAACTGGGGATTCCGGCCCAAGAGACTCAGCTTCAAGCT

CTTCAACATCCAGGTCAAGGAGGTCACGCAGAATGAAGGCACCAAGACCATCGCCA

ATAACCTCACCAGCACCATCCAGGTGTTTACGGACTCGGAGTACCAGCTGCCGTAC

GTACTAGGATCCGCTCACCAGGGATGTCTGCCTCCGTTCCCGGCGGACGTGTTCATG

ATTCCCCAGTACGGCTACCTAACACTCAACAACGGTAGTCAGGCCGTGGGACGCTC

CTCCTTCTACTGCCTGGAATATTTTCCATCTCAGATGCTGAGAACGGGCAATAACTT

TACCTTCAGCTACACCTTCGAGGACGTGCCTTTCCACAGCAGCTATGCCCACAGCCA

GAGCTTGGACCGGCTGATGAATCCTCTGATTGACCAGTACCTGTACTACTTGTCTCG

GACTCAAACAACAGGAGGCACGGCAAATACGCAGACTCTGGGCTTCAGCCAAGGT

GGGCCTAATACAATGGCCAATCAGGCAAAGAACTGGCTGCCAGGACCCTGTTACCG

CCAACAACGCGTCTCAACGACAACCGGGCAAAACAACAATAGCAACTTTGCCTGGA

CTGCTGGGACCAAATACCATCTGAATGGAAGAAATTCATTGGCTAATCCTGGCATC
```

```
GCTATGGCAACACACAAAGACGACGAGGAGCGTTTTTTTCCCAGTAACGGGATCCT

GATTTTTGGCAAACAAAATGCTGCCAGAGACAATGCGGATTACAGCGATGTCATGC

TCACCAGCGAGGAAGAAATCAAAACCACTAACCCTGTGGCTACAGAGGAATACGGT

ATCGTGGCAGATAACTTGCAGCAGCAAAACACGGCTCCTCAAATTGGAACTGTCAA

CAGCCAGGGGGCCTTACCCGGTATGGTCTGGCAGAACCGGGACGTGTACCTGCAGG

GTCCCATCTGGGCCAAGATTCCTCACACGGACGGCAACTTCCACCCGTCTCCGCTAA

TGGGAGGATTTGGACTGAAGCACCCACCTCCTCAGATCCTGATCAAGAACACGCCG

GTACCTGCGGATCCTCCGACCACCTTCAACCAGTCAAAGCTGTACTCTTTCATCACG

CAATACAGCACCGGACAGGTCAGCGTGGAAATTGAATGGGAGCTGCAGAAGGAAA

ACAGCAAGCGCTGGAACCCCGAGATCCAATACACCTCCAACTACTACAAATCTACA

AGTGTGGACTTTGCTGTTAATACAGAAGGCGTGTACTCTGAACCCCGCCCCATTGGC

ACCCGTTACCTCACCCGTAATCTGTAA
```

>SEQ ID NO: 5; AAV-B1
MAADGYLPDWLEDNLSEGIREWWDLKPGAPKPKANQQKQDDGRGLVLPGYKYLGPF

NGLDKGEPVNAADAAALEHDKAYDQQLKAGDNPYLRYNHADVEFQERLQEDTSFGG

NLGRAVFQAKKRVLEPFGLVEEGAKTAPGKKRPVEQSPQEPDSSSGIGKKGQQPAR

KRLNFGQTGDSESVPDPQPLGEPPAAPSGVGPNTMAAGGGAPMADNNEGADGVGNS

SGNWHCDSTWMGDRVITTSTRTWALPTYNNHLYKQISNGTSGGSTNDNTYFGYSTP

WGYFDFNRFHCHFSPRDWQRLINNNWGFRPKRLSFKLFNIQVKEVTQNEGTKTIAN

NLTSTIQVFTDSEYQLPYVLGSAHQGCLPPFPADVFMIPQYGYLTLNNGSQAVGRS

SFYCLEYFPSQMLRTGNNFEFSYQFEDVPFHSSYAHSQSLDRLMNPLIDQYLYYLS

RTQSTGGTARTQQLLFSQAGPNTMANQAKNWLPGPCYRQQRVSTTTGQNNNSNSAW

TAGTKYHLNGRNSLANPGIAMATHKDDEERFFPSNGILIFGKQNAARDNADYSDVM

LTSEEEIKTTNPVATEEYGIVADNLQQQNTAPQIGTVNSQGALPGMVWQNRDVYLQ

GPIWAKIPHTDGNFHPSPLMGGFGLKHPPPQILIKNTPVPADPPTTFNQSKLNSFI

TQYSTGQVSVEIEWELQKENSKRWNPEIQYTSNYYKSTSVDFAVNTEGVYSEPRPI

GTRYLTRNL

>SEQ ID NO: 6; AAV-B2
MAADGYLPDWLEDNLSEGIREWWALKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPLGLVEDGAKTAPGKKRPVEQSPQEPDSSSGIGKKGQQPAR

KRLNFGQTGDSESVPDPQPLGEPPATPAAVGPTTMASGGGAPMADNNEGADGVGSS

SGNWHCDSTWLGDRVITTSTRTWALPTYNNHLYKQISNGTSGGATNDNTYFGYSTP

WGYFDFNRFHCHFSPRDWQRLINNNWGFRPKRLSFKLFNIQVKEVTQNEGTKTIAN

NLTSTIQVFTDSEYQLPYVLGSAHQGCLPPFPADVFMIPQYGYLTLNNGSQAVGRS

SFYCLEYFPSQMLRTGNNFQFTYTFEDVPFHSSYAHSQSLDRLMNPLIDQYLYYLS

RTQTTGGTANTQTLGFSQGGPNTMANQAKNWLPGPCYRQQRVSTTTGQNNNSNFAW

TAGTKYHLNGRNSLANPGIAMATHKDDEERFFPSNGILIFGKQNAARDNADYSDVM

LTSEEEIKTTNPVATEEYGIVADNLQQQNTAPQIGTVNSQGALPGMVWQNRDVYLQ

GPIWAKIPHTDGNFHPSPLMGGFGLKHPPPQILIKNTPVPADPPTTFNQSKLNSFI

TQYSTGQVSVEIEWELQKENSKRWNPEIQYTSNYYKSTNVDFAVNTEGVYSEPRPI

GTRYLTRNL

>SEQ ID NO: 7; AAV-B3
MAADGYLPDWLEDNLSEGIREWWALKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPLGLVEEGAKTAPGKKRPVEQSPQEPDSSSGIGKTGQQPAK

KRLNFGQTGDSESVPDPQPLGEPPATPAAVGPTTMASGGGAPMADNNEGADGVGNA

SGNWHCDSTWLGDRXITTSTRTWALPTYNNHLYKQISSASTGASNDNHYFGYSTPW

GYFDFNRFHCHFSPRDWQRLINNNWGFRPKRLNFKLFNIQVKEVTQNEGTKTIANN

LTSTIQVFTDSEYQLPYVLGSAHQGCLPPFPADVFMIPQYGYLTLNNGSQAVGRSS

FYCLEYFPSQMLRTGNNFEFSYTFEDVPFHSSYAHSQSLDRLMNPLIDQYLYYLSR

TQTTGGTANTQTLGFSQGGPNTMANQAKNWLPGPCYRQQRVSTTTGQNNNSNFAWT

AGTKYHLNGRNSLANPGIAMATHKDDEERFFPSNGILIFGKQNAARDNADYSDVML

TSEEEIKTTNPVATEEYGIVADNLQQQNTAPQIGTVNSQGTLPGMVWQNRDVYLQG

PIWAKIPHTDGNFHPSPLMGGFGLKHPPPQILIKNTPVPADPPTTFNQSKLNSFIT

QYSTGQVSVEIEWELQKENSKRWNPEIQYTSNYYKSTSVDFAVNTEGVYSEPRPIG

TRFLTRNL

>SEQ ID NO: 8; AAV-B4
MAADGYLPDWLEDNLSEGIREWWALKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPLGLVEEGAKTAPGKKRPVEQSPQEPDSSSGIGKTGQQPAK

KRLNFGQTGDSESVPDPQPLGEPPAAPSGVGPNTMAAGGGAPMADNNEGADGVGSS

SGNWHCDSTWLGDRVITTSTRTWALPTYNNHLYKQISNGTSGGATNDNTYFGYSTP

WGYFDFNRFHCHFSPRDWQRLINNNWGFRPKRLSFKLFNIQVKEVTQNEGTKTIAN

NLTSTIQVFTDSEYQLPYVLGSAHQGCLPPFPADVFMIPQYGYLTLNNGSQAVGRS

SFYCLEYFPSQMLRTGNNFTFSYTFEDVPFHSSYAHSQSLDRLMNPLIDQYLYYLS

RTQTTGGTANTQTLGFSQGGPNTMANQAKNWLPGPCYRQQRVSTTTGQNNNSNFAW

TAGTKYHLNGRNSLANPGIAMATHKDDEERFFPSNGILIFGKQNAARDNADYSDVM

LTSEEEIKTTNPVATEEYGIVADNLQQQNTAPQIGTVNSQGALPGMVWQNRDVYLQ

GPIWAKIPHTDGNFHPSPLMGGFGLKHPPPQILIKNTPVPADPPTTFNQSKLYSFI

TQYSTGQVSVEIEWELQKENSKRWNPEIQYTSNYYKSTSVDFAVNTEGVYSEPRPI

GTRYLTRNL

>SEQ ID NO: 9; AAV-L1
ATGGCTGCCGATGGTTATCTTCCAGATTGGCTCGAGGACAACCTCTCTGAGGGCATT

CGCGAGTGGTGGGACTTGAAACCTGGAGCCCCGAAACCCAAAGCCAACCAGCAAA

AGCAGGACGACGGCCGGGGTCTGGTGCTTCCTGGCTACAAGTACCTCGGACCCTTC

AACGGACTCGACAAGGGGGAGCCCGTCAACGCGGCGGATGCAGCGGCCCTCGAGC

ACGACAAAGCCTACGACCGGCAGCTCGACAGCGGAGACAACCCCGTACCTCAAGTAC

AACCACGCCGACGCGGAGTTTCAGGAGCGCCTTAAAGAAGATACGTCTTTTGGGGG

-continued

SEQUENCE LISTING

CAACCTCGGACGAGCAGTCTTCCAGGCCAAGAAGAGGGTTCTCGAACCTTTTGGTC

TGGTTGAGGAAGGTGCTAAGACGGCTCCTGGAAAGAAACGTCCGGTAGAGCAGTCG

CCACAAGAGCCAGACTCCTCCTCGGGCATTGGCAAGACAGGCCAGCAGCCCGCTAA

AAAGAGACTCAATTTTGGTCAGACTGGCGACTCAGAGTCAGTCCCCGACCCACAAC

CTCTCGGAGAACCTCCAGCAACCCCCGCTGCTGTGGGACCTACTACAATGGCTTCAG

GTGGTGGCGCACCAGTGGCAGACAATAACGAAGGCGCCGACGGAGTGGGTAGTTC

CTCGGGAAATTGGCATTGCGATTCCACATGGCTGGGCGACAGAGTCATCACCACCA

GCACCCGAACATGGGCCTTGCCCACCTATAACAACCACCTCTACAAGCAAATCTCC

AGTGCTTCGACGGGGGCCAGCAACGACAACCACTACTTCGGCTACAGCACCCCCTG

GGGGTATTTTGATTTCAACAGGTTCCACTGCCATTTCTCACCACGTGACTGGCAGCG

ACTCATCAACAACAATTGGGGATTCCGGCCCAAAAGACTCAACTTCAAGCTGTTCA

ACATCCAGGTCAAGGAAGTCACGACGAACGAAGGCACCAAGACCATCGCCAATAA

TCTCACCAGCACCGTGCAGGTCTTTACGGACTCGGAGTACCAGTTACCGTACGTGCT

AGGATCCGCTCACCAGGGATGTCTGCCTCCGTTCCCGGCGGACGTCTTCATGGTTCC

TCAGTACGGCTATTTAACTTTAAACAATGGAAGCCAAGCCCTGGGACGTTCCTCCTT

CTACTGTCTGGAGTATTTCCCATCGCAGATGCTGAGAACGGGCAACAACTTTACCTT

TAGCTACACCTTCGAGGACGTGCCTTTCCACAGCAGCTACGCGCACAGCCAGAGCC

TGGACAGGCTGATGAATCCCCTCATCGACCAGTACCTGTACTACCTGGTCAGAACG

CAAACGACTGGAACTGGAGGGACGCAGACTCTGGCATTCAGCCAAGCGGGTCCTAG

CTCAATGGCCAACCAGGCTAGAAATTGGGTGCCCGGACCTTGCTACCGGCAGCAGC

GCGTCTCCACGACAACCAACCAGAACAACAACAGCAACTTTGCCTGGACGGGAGCT

GCCAAGTTTAAGCTGAACGGCCGAGACTCTCTAATGAATCCGGGCGTGGCAATGGC

TTCCCACAAGGATGACGACGACCGCTTCTTCCCTTCGAGCGGGGTCCTGATTTTTGG

CAAGCAAGGAGCCGGGAACGATGGAGTGGATTACAGCCAAGTGCTGATTACAGAT

GAGGAAGAAATCAAGGCTACCAACCCCGTGGCCACAGAAGAATATGGAGCAGTGG

CCATCAACAACCAGGCCGCCAATACGCAGGCGCAGACCGGACTCGTGCACAACCAG

GGGGTGATTCCCGGCATGGTGTGGCAGAATAGAGACGTGTACCTGCAGGGTCCCAT

CTGGGCCAAAATTCCTCACACGGACGGCAACTTTCACCCGTCTCCCCTGATGGGCGG

CTTTGGACTGAAGCACCCGCCTCCTCAAATTCTCATCAAGAACACACCGGTTCCAGC

GGACCCGCCGCTTACCTTCAACCAGGCCAAGCTGAACTCTTTCATCACGCAGTACAG

CACCGGACAGGTCAGCGTGGAAATCGAGTGGGAGCTGCAGAAAGAAAACAGCAAA

CGCTGGAATCCAGAGATTCAATACACTTCCAACTACTACAAATCTACAAATGTGGA

CTTTGCTGTCAACACGGAGGGGGTTTATAGCGAGCCTCGCCCCATTGGCACCCGTTA

CCTCACCCGCAACCTGTAA

>SEQ ID NO: 10; AAV-L2
ATGGCTGCCGATGGTTATCTTCCAGATTGGCTCGAGGACACTCTCTCTGAAGGAATA

AGACAGTGGTGGAAGCTCAAACCTGGCCCACCACCACCAAAGCCCGCAGAGCGGC

ATAAGGACGACAGCAGGGGTCTTGTGCTTCCTGGCTACAAGTACCTCGGACCCTTC

AACGGACTCGACAAGGGGGAGCCCGTCAACGCGGCGGACGCAGCGACCCTCGAGC

SEQUENCE LISTING

```
ACGACAAGGCCTACGACCAGCAGCTCAAAGCGGGTGACAATCCGTACCTGCGGTAT

AACCACGCCGACGCCGAGTTTCAGGAGCGTCTGCAAGAAGATACGTCTTTTGGGGG

CNACCTCGGGCGAGCAGTCTTCCAGGCCAAGAAGCGGGTTCTCGAACCTCTCGGTC

TGGTTGAGGAAGCTGCTAAGACGGCTCCTGGAAAGAAGAGACCAGTAGAGCCATC

ACCCCAGCGTTCTCCAGACTCCTCTACGGGCATCGGCAAGAAAGGCCAACAGCCCG

CCAGAAAAGACTCAATTTTGGTCAGACTGGCGACTCAGAGTCAGTTCCAGACCCT

CAACCTCTCGGAGAACCTCCAGCAGCGCCCTCTGGTGTGGGACCTAATACAATGGC

TGCAGGCGGTGGCGCACCAATGGCAGACAATAACGAAGGCGCCGACGGAGTGGGT

AGTTCCTCGGGAAATTGGCATTGCGATTCCACATGGCTGGGCGACAGAGTCATCAC

CACCAGCACCCGAACCTGGGCCCTGCCCACCTACAACAACCACCTCTACAAGCAAA

TCTCCAGTGCTTCAACGGGGGCCAGCAACGACAACCACTACTTCGGCTACAGCACC

CCCTGGGGTATTTTGATTTCAACAGATTCCACTGCCATTTCTCACCACGTGACTGG

CAGCGACTCATCAACAACAATTGGGGATTCCGGCCCAAGAGACTCAACTTCAAGCT

CTTCAACATCCAAGTCAAGGAGGTCACGACGAATGATGGCGTCACGACCATCGCTA

ATAACCTTACCAGCACGGTTCAAGTCTTCTCGGACTCAGACTATCAGCTCCCGTACG

TGCTCGGGTCGGCTCACGAGGGCTGCCTCCCGCCGTTCCCAGCGGACGTTTTCATGA

TTCCTCAGTACGGCTATTTAACTTTAAACAATGGAAGCCAAGCCCTGGGACGTTCCT

CCTTCTACTGTCTGGAGTATTTCCCATCGCAGATGCTGAGAACCGGCAACAACTTTC

AGTTCAGCTACACCTTCGAGGACGTGCCTTTCCACAGCAGCTACGCGCACAGCCAG

AGCCTGGACAGGCTGATGAATCCCCTCATCGACCAGTACCTGTACTACCTGGTCAG

AACGCAAACGACTGGAACTGGAGGGACGCAGACTCTGGCATTCAGCCAAGCGGGT

CCTAGCTCAATGGCCAACCAGGCTAGAAATTGGGTGCCCGGACCTTGCTACCGGCA

GCAGCGCGTCTCCACGACAACCAACCAGAACAACAACAGCAACTTTGCCTGGACGG

GAGCTGCCAAGTTTAAGCTGAACGGCCGAGACTCTCTAATGAATCCGGGCGTGGCA

ATGGCTTCCCACAAGGATGACGACGACCGCTTCTTCCCTTCGAGCGGGGTCCTGATT

TTTGGCAAGCAAGGAGCCGGGAACGATGGAGTGGATTACAGCCAAGTGCTGATTAC

AGATGAGGAAGAAATCAAGGCTACCAACCCCGTAGCCACAGAAGAATATGGAGCA

GTGGCCATCAACAACCAGGCCGCCAATACGCAGGCGCAGACCGGACTCGTGCACAA

CCAGGGGGTGATTCCCGGAATGGTGTGGCAAGACAGAGACGTATACCTGCAGGGTC

CTATTTGGGCCAAAATTCCTCACACGGATGGACACTTTCACCCGTCTCCTCTCATGG

GCGGCTTTGGACTTAAGCACCCGCCTCCTCAGATCCTCATCAAAAACACGCCTGTTC

CTGCGAATCCTCCGGCAGAGTTTTCGGCTACAAAGTTTGCTTCATTCATCACCCAGT

ATTCCACAGGACAAGTGAGCGTGGAGATTGAATGGGAGCTGCAGAAAGAAAACAG

CAAACGCTGGAATCCCGAAGTGCAGTATACATCTAACTATGCAAAATCTGCCAACG

TTGATTTCACTGTGGACAACAATGGACTTTATACTGAGCCTCGCCCCATTGGCACCC

GTTACCTCACCCGTCCCCTGTAA

>SEQ ID NO: 11; AAV-L3
ATGACTGACGGTTACCTTCCAGATTGGCTAGAGGACAACCTCTCTGAAGGCGTTCG

AGAGTGGTGGGCGCTGCAACCTGGAGCCCCGAAGCCCAAAGCCAACCAGCAAAAG
```

```
CAGGACGACGGCCGGGGTCTGGTGCTTCCTGGCTACAAGTACCTCGGACCCTTCAA
CGGACTCGACAAGGGGGAGCCCGTCAACGCGGCGGACGCAGCGGCCCTCGAGCAC
GACAAGGCCTACGACCAGCAGCTCAAAGCGGGTGACAATCCGTACCTGCGGTATAA
CCACGCCGACGCCGAGTTTCAGGAGCGTCTGCAAGAAGATACGTCTTTTGGGGGCA
NCCTCGGGCGAGCAGTCTTCCAGGCCAAGAAGCGGGTTCTCGAACCTCTCGGTCTG
GTTGAGGAAGGCGCTAAGACGGCTCCTGGAAAGAAACGTCCGGTAGAGCCATCACC
CCAGCGTTCTCCAGACTCCTCTACGGGCATCGGCAAGAAAGGCCAACAGCCCGCCA
GAAAAAGACTCAATTTTGGTCAGACTGGCGACTCAGAGTCAGTTCCAGACCCTCAA
CCTCTCGGAGAACCTCCAGCAGCGCCCTCAGGTGTGGGATCTCTTACAATGGCTTCA
GGTGGTGGCGCACCAGTGGCAGACAATAACGAAGGTGCCGATGGAGTGGGTAGTTC
CTCGGGAAATTGGCATTGCGATTCCCAATGGCTGGGGACAGAGTCATCACCACCA
GCACCCGAACCTGGGCCCTGCCCACCTACAACAATCACCTCTACAAGCAAATCTCC
AACAGCACATCTGGAGGATCTTCAAATGACAACGCCTACTTCGGCTACAGCACCCC
CTGGGGTATTTTGACTTCAACAGATTCCACTGCCACTTCTCACCACGTGACTGGCA
GCGACTCATCAACAACAACTGGGGATTCCGGCCCAAGAGACTCAGCTTCAAGCTCT
TCAACATCCAGGTCAAGGAGGTCACGCAGAATGAAGGCACCAAGACCATCGCCAAT
AACCTCACCAGCACCATCCAGGTGTTTACGGACTCGGAGTACCAGCTGCCGTACGTT
CTCGGCTCTGCCCACCAGGGCTGCCTGCCTCCGTTCCCGGCGGACGTGTTCATGATT
CCCCAGTACGGCTACCTAACACTCAACAACGGTAGTCAGGCCGTGGGACGCTCCTC
CTTCTACTGCCTGGAATACTTTCCTTCGCAGATGCTGAGAACCGGCAACAACTTCCA
GTTTACTTACACCTTCGAGGACGTGCCTTTCCACAGCAGCTACGCCCACAGCCAGAG
CTTGGACCGGCTGATGAATCCTCTGATTGACCAGTACCTGTACTACTTGTCTCGGAC
TCAAACAACAGGAGGCACGGCAAATACGCAGACTCTGGGCTTCAGCCAAGGTGGG
CCTAATACAATGGCCAATCAGGCAAAGAACTGGCTGCCAGGACCCTGTTACCGCCA
ACAACGCGTCTCAACGACAACCGGGCAAAACAACAATAGCAACTTTGCCTGGACTG
CTGGGACCAAATACCATCTGAATGGAAGAAATTCATTGGCTAATCCTGGCATCGCT
ATGGCAACACACAAAGACGACGAGGAGCGTTTTTTTCCCAGTAACGGGATCCTGAT
TTTTGGCAAACAAAATGCTGCCAGAGACAATGCGGATTACAGCGATGTCATGCTCA
CCAGCGAGGAAGAAATCAAAACCACTAACCCTGTGGCTACAGAGGAATACGGTATC
GTGGCAGATAACTTGCAGCAGCAAAACACGGCTCCTCAAATTGGAACTGTCAACAG
CCAGGGGGCCTTACCCGGTATGGTCTGGCAGAACGGGACGTGTACCTGCAGGGTC
CCATCTGGGCCAAGATTCCTCACACGGACGGCAACTTCCACCCGTCTCCGCTGATGG
GCGGCTTTGGCCTGAAACATCCTCCGCCTCAGATCCTGATCAAGAACACGCCTGTAC
CTGCGGATCCTCCGACCACCTTAAACCAGGCCAAGCTGAACTCTTTCATCACGCAAT
ACAGCACCGGACAGGTCAGCGTGGAAATTGAATGGGAGCTGCAGAAGGAAAACAG
CAAGCGCTGGAACCCAGAGATTCAGTACACTTCAAACTACTACAAATCTACAAATG
```

| SEQUENCE LISTING |
| --- |

```
TGGACTTTGCTGTCAATACAGAGGGAACTTATAGTGAACCCCGCCCCATTGGCACC

AGATTTCTGACTCGTAATCTGTAA

>SEQ ID NO: 12; AAV-L4
ATGGCTGCCGATGGTTATCTTCCAGATTGGCTCGAGGACACTCTCTCTGAAGGAATA

AGACAGTGGTGGAAGCTCAAACCTGGCCCACCACCACCAAAGCCCGCAGAGCGGC

ATAAGGACGACAGCAGGGGTCTTGTGCTTCCTGGGTACAAGTACCTCGGCCCCTTC

AACGGACTCGACAAGGGGGAGCCCGTCAACGCGGCGGACGCAGCGGCCCTCGAGC

ACGACAAGGCCTACGACCAGCAGCTCGAAGCGGGTGACAATCCGTACCTGCGGTAT

AACCACGCCGACGCCGAGTTTCAGGAGCGTCTGCAAGAAGATACGTCTTTTGGGGG

CANCCTCGGGCGAGCAGTCTTCCAGGCCAAGAAGCGGGTTCTCGAACCTCTCGGTC

TGGTTGAGGAAGGCGCTAAGACGGCTCCTGGAAAGAAGAGACCAGTAGAGCAGTC

ACCCCAAGAACCAGACTCCTCCTCGGGCATCGGCAGGAAAGGCCAACAGCCCGCCA

GAAAAAGACTCAATTTTGGCCAGACTGGCGACTCAGAGTCAGTTCCAGACCCTCAA

CCTCTCGGAGAACCTCCAGCAGCGCCCTCTGGTGTGGGACCTAATACAATGGCTTCA

GGCGGTGGCGCTCCAATGGCAGACAATAACGAAGGCGCCGACGGAGTGGGTAATG

CCTCAGGAAATTGGCATTGCGATTCCACATGGCTGGGCGACAGAGTCATCACCACC

AGCACCCGCACCTGGGCCTTGCCCACCTACAATAACCACCTCTACAAGCAAATCTCC

AGTGCTTCAACGGGGGCCAGCAACGACAACCACTACTTCGGCTACAGCACCCCCTG

GGGGTATTTTGATTTCAACAGATTCCACTGCCACTTTTCACCACGTGACTGGCAGCG

ACTCATCAACAACAATTGGGGATTCCGGCCCAAGAGACTCAACTTCAAACTCTTCA

ACATCCAGGTCAAGGAGGTCACGCAGAATGAAGGCACTAAGACCATCGCCAATAA

CCTTACCAGCACGATTCAGGTATTTACGGACTCGGAATACCAGCTGCCGTACGTCCT

CGGCTCCGCGCACCAGGGCTGCCTGCCTCCGTTCCCGGCGGACGTCTTCATGATTCC

CCAGTACGGCTACCTTACACTGAACAATGGAAGTCAAGCCGTAGGCCGTTCCTCCTT

CTACTGCCTGGAATATTTTCCATCTCAAATGCTGCGAACTGGCAACAACTTCCAGTT

TACCTACACCTTCGAGGACGTGCCTTTCCACAGCAGCTACGCCCACAGCCAGAGCTT

GGACCGGCTGATGAATCCTCTGATTGACCAGTACCTGTACTACTTGTCTCGGACTCA

GTCCACAGGAGGAACTCAAGGTACCCAGCAATTGTTATTTTCTCAAGCTGGGCCTGC

AAACATGTCGGCTCAGGCTAAGAACTGGCTACCTGGACCTTGCTACCGGCAGCAGC

GAGTCTCTACGACACTGTCGCAAAACAACAACAGCAACTTTGCTTGGACTGGTGCC

ACCAAATATCACCTGAACGGAAGAGACTCTTTGGTAAATCCCGGTGTCGCCATGGC

AACCCACAAGGACGACGAGGAACGCTTCTTCCCGTCGAGTGGAGTCCTGATGTTTG

GAAAACAGGGTGCTGGAAGAGACAATGTGGACTACAGCAGCGTTATGCTAACCAG

CGAAGAAGAAATTAAAACCACTAACCCTGTAGCCACAGAACAATACGGTGTGGTGG

TTGATAACTTGCAGCAAACCAATACGGGGCCTATTGTGGGAAATGTCAACAGCCAA

GGAGCCTTACCTGGTATGGTCTGGCAGAACCGGGACGTGTACCTGCAGGGTCCCAT

CTGGGCCAAGATTCCTCACACGGACGGCAACTTCCACCCGTCTCCGCTGATGGGCG

GCTTTGGCCTGAAACATCCTCCGCCTCAGATCCTCATCAAAAACACACCTGTACCTG

CGGATCCTCCAACGGCCTTCAACAAGGACAAGCTGAACTCTTTCATCACCCAGTATT
```

-continued

SEQUENCE LISTING

CTACTGGCCAAGTCAGCGTGGAGATCGAGTGGGAGCTGCAGAAGGAAAACAGCAA

GCGCTGGAACCCGGAGATCCAGTACACTTCCAACTATTACAAGTCTAATAATGTTG

AATTTGCTGTTAATACTGAAGGTGTATATAGTGAACCCCGCCCCATTGGCACCAGAT

ACCTGACTCGTAATCTGTAA

>SEQ ID NO: 13; AAV-L1
MAADGYLPDWLEDNLSEGIREWWDLKPGAPKPKANQQKQDDGRGLVLPGYKYLGPF

NGLDKGEPVNAADAAALEHDKAYDRQLDSGDNPYLKYNHADAEFQERLKEDTSFGG

NLGRAVFQAKKRVLEPFGLVEEGAKTAPGKKRPVEQSPQEPDSSSGIGKTGQQPAK

KRLNFGQTGDSESVPDPQPLGEPPATPAAVGPTTMASGGGAPVADNNEGADGVGSS

SGNWHCDSTWLGDRVITTSTRTWALPTYNNHLYKQISSASTGASNDNHYFGYSTPW

GYFDFNRFHCHFSPRDWQRLINNNWGFRPKRLNFKLFNIQVKEVTTNEGTKTIANN

LTSTVQVFTDSEYQLPYVLGSAHQGCLPPFPADVFMVPQYGYLTLNNGSQALGRSS

FYCLEYFPSQMLRTGNNFTFSYTFEDVPFHSSYAHSQSLDRLMNPLIDQYLYYLVR

TQTTGTGGTQTLAFSQAGPSSMANQARNWVPGPCYRQQRVSTTTNQNNNSNFAWTG

AAKFKLNGRDSLMNPGVAMASHKDDDDRFFPSSGVLIFGKQGAGNDGVDYSQVLIT

DEEEIKATNPVATEEYGAVAINNQAANTQAQTGLVHNQGVIPGMVWQNRDVYLQGP

IWAKIPHTDGNFHPSPLMGGFGLKHPPPQILIKNTPVPADPPLTFNQAKLNSFITQ

YSTGQVSVEIEWELQKENSKRWNPEIQYTSNYYKSTNVDFAVNTEGVYSEPRPIGT

RYLTRNL

>SEQ ID NO: 14; AAV-L2
MAADGYLPDWLEDTLSEGIRQWWKLKPGPPPPKPAERHKDDSRGLVLPGYKYLGPF

NGLDKGEPVNAADAATLEHDKAYDQQLKAGDNPYLRYNHADAEFQERLQEDTSFGG

XLGRAVFQAKKRVLEPLGLVEEAAKTAPGKKRPVEPSPQRSPDSSTGIGKKGQQPA

RKRLNFGQTGDSESVPDPQPLGEPPAAPSGVGPNTMAAGGGAPMADNNEGADGVGS

SSGNWHCDSTWLGDRVITTSTRTWALPTYNNHLYKQISSASTGASNDNHYFGYSTP

WGYFDFNRFHCHFSPRDWQRLINNNWGFRPKRLNFKLFNIQVKEVTTNDGVTTIAN

NLTSTVQVFSDSDYQLPYVLGSAHEGCLPPFPADVFMIPQYGYLTLNNGSQALGRS

SFYCLEYFPSQMLRTGNNFQFSYTFEDVPFHSSYAHSQSLDRLMNPLIDQYLYYLV

RTQTTGTGGTQTLAFSQAGPSSMANQARNWVPGPCYRQQRVSTTTNQNNNSNFAWT

GAAKFKLNGRDSLMNPGVAMASHKDDDDRFFPSSGVLIFGKQGAGNDGVDYSQVLI

TDEEEIKATNPVATEEYGAVAINNQAANTQAQTGLVHNQGVIPGMVWQDRDVYLQG

PIWAKIPHTDGHFHPSPLMGGFGLKHPPPQILIKNTPVPANPPAEFSATKFASFIT

QYSTGQVSVEIEWELQKENSKRWNPEVQYTSNYAKSANVDFTVDNNGLYTEPRPIG

TRYLTRPL

>SEQ ID NO: 15; AAV-L3
MTDGYLPDWLEDNLSEGVREWWALQPGAPKPKANQQKQDDGRGLVLPGYKYLGPFN

GLDKGEPVNAADAAALEHDKAYDQQLKAGDNPYLRYNHADAEFQERLQEDTSFGGX

LGRAVFQAKKRVLEPLGLVEEGAKTAPGKKRPVEPSPQRSPDSSTGIGKKGQQPAR

KRLNFGQTGDSESVPDPQPLGEPPAAPSGVGSLTMASGGGAPVADNNEGADGVGSS

SGNWHCDSQWLGDRVITTSTRTWALPTYNNHLYKQISNSTSGGSSNDNAYFGYSTP

```
WGYFDFNRFHCHFSPRDWQRLINNNWGFRPKRLSFKLFNIQVKEVTQNEGTKTIAN

NLTSTIQVFTDSEYQLPYVLGSAHQGCLPPFPADVFMIPQYGYLTLNNGSQAVGRS

SFYCLEYFPSQMLRTGNNFQFTYTFEDVPFHSSYAHSQSLDRLMNPLIDQYLYYLS

RTQTTGGTANTQTLGFSQGGPNTMANQAKNWLPGPCYRQQRVSTTTGQNNNSNFAW

TAGTKYHLNGRNSLANPGIAMATHKDDEERFFPSNGILIFGKQNAARDNADYSDVM

LTSEEEIKTTNPVATEEYGIVADNLQQQNTAPQIGTVNSQGALPGMVWQNRDVYLQ

GPIWAKIPHTDGNFHPSPLMGGFGLKHPPPQILIKNTPVPADPPTTLNQAKLNSFI

TQYSTGQVSVEIEWELQKENSKRWNPEIQYTSNYYKSTNVDFAVNTEGTYSEPRPI

GTRFLTRNL

>SEQ ID NO: 16; AAV-L4
MAADGYLPDWLEDTLSEGIRQWWKLKPGPPPPKPAERHKDDSRGLVLPGYKYLGPF

NGLDKGEPVNAADAAALEHDKAYDQQLEAGDNPYLRYNHADAEFQERLQEDTSFGG

XLGRAVFQAKKRVLEPLGLVEEGAKTAPGKKRPVEQSPQEPDSSSGIGRKGQQPAR

KRLNFGQTGDSESVPDPQPLGEPPAAPSGVGPNTMASGGGAPMADNNEGADGVGNA

SGNWHCDSTWLGDRVITTSTRTWALPTYNNHLYKQISSASTGASNDNHYFGYSTPW

GYFDFNRFHCHFSPRDWQRLINNNWGFRPKRLNFKLFNIQVKEVTQNEGTKTIANN

LTSTIQVFTDSEYQLPYVLGSAHQGCLPPFPADVFMIPQYGYLTLNNGSQAVGRSS

FYCLEYFPSQMLRTGNNFQFTYTFEDVPFHSSYAHSQSLDRLMNPLIDQYLYYLSR

TQSTGGTQGTQQLLFSQAGPANMSAQAKNWLPGPCYRQQRVSTTLSQNNNSNFAWT

GATKYHLNGRDSLVNPGVAMATHKDDEERFFPSSGVLMFGKQGAGRDNVDYSSVML

TSEEEIKTTNPVATEQYGVVVDNLQQTNTGPIVGNVNSQGALPGMVWQNRDVYLQG

PIWAKIPHTDGNFHPSPLMGGFGLKHPPPQILIKNTPVPADPPTAFNKDKLNSFIT

QYSTGQVSVEIEWELQKENSKRWNPEIQYTSNYYKSNNVEFAVNTEGVYSEPRPIG

TRYLTRNL

>SEQ ID NO: 17; Barcode S4
GTCTCATGCTATTGCTTCGCATCGTCAGAC

>SEQ ID NO: 18; Barcode S5
GCAGGAGTCTTCGGTGCAGTTTGTTACGCA

>SEQ ID NO: 19; Barcode S6
TGATTGGACTAGTCGTGGGAGTTAGCATGC

>SEQ ID NO: 20; Barcode S9
TTATCTGGCGTGTAGGCAGCGGCCTCAGAC

>SEQ ID NO: 21; Barcode S10
TTATACGACTCATATGTGGCATACGTCGTG
```

SEQUENCE LISTING

>SEQ ID NO: 22; Barcode S11
GGAGCCGAGGAAGACTTGTCCGGGGACTGG

>SEQ ID NO: 23; Barcode S12
GCCGGGGTGTTGGTCTTTGTCTACGATGGC

>SEQ ID NO: 3; AAV-B3

What is claimed is:

1. A chimeric AAV capsid protein comprising distinct polypeptide regions derived from at least three different AAV serotypes selected from the group consisting of: AAV1, AAV2, AAV4, AAV5, AAV6, AAV8, AAV9, AAVrh8, AAVrh10, AAVrh39, and AAVrh43, wherein the chimeric AAV capsid protein comprises the sequence as set forth in any one of SEQ ID NOs: 5-8.

2. A rAAV comprising the chimeric AAV capsid protein of claim 1.

3. The rAAV of claim 2, wherein the rAAV targets the CNS tissue of a subject.

4. The rAAV of claim 3, further comprising a transgene, wherein the transgene comprises a CNS-associated gene.

* * * * *

SEQUENCE LISTING

<160> NUMBER OF SEQ ID NOS: 96

<210> SEQ ID NO 1
<211> LENGTH: 2214
<212> TYPE: DNA
<213> ORGANISM: Artificial Sequence
<220> FEATURE:
<223> OTHER INFORMATION: Synthetic Polynucleotide

<400> SEQUENCE: 1

```
atggctgccg atggttatct tccagattgg ctcgaggaca acctctctga gggcattcgc      60
gagtggtggg acttgaaacc tggagccccg aagcccaaag ccaaccagca aaagcaggac     120
gacggccggg gtctggtgct tcctggctac aagtacctcg gacccttcaa cggactcgac     180
aagggggagc ccgtcaacgc ggcggacgca gcggccctcg agcacgacaa ggcctacgac     240
cagcagctca agcgggtga caatccgtac ctgcggtata accacgccga cgtcgagttt     300
caggagcgtc tgcaagaaga tacgtctttt gggggcaacc tcgggcgagc agtcttccag     360
gccaagaaga gggttctcga acctttggt ctggttgagg aaggcgctaa gacggctcct     420
ggaaagaaac gtccggtaga gcagtcgcca caagagccag actcctcctc gggcatcggc     480
aagaaaggcc aacagcccgc cagaaaaaga ctcaattttg gccagactgg cgactcagag     540
tcagttccag accctcaacc tctcggagaa cctccagcag cgccctctgg tgtgggacct     600
aatacaatgg ctgcaggcgg tggcgcacca atggcagaca taacgagggg cgccgacgga     660
gtgggtaatt cctcgggaaa ttggcattgc gattccacat ggatggggga cagagtcatc     720
accaccagca cccgaacctg ggccctgccc acctacaaca accacctcta caagcaaatc     780
tccaacggca cctcgggagg aagcaccaac gacaacacct ttttggcta cagcaccccc     840 tgggggtatt ttgatttcaa cagattccac tgccacttct caccacgtga ctggcagcga     900
ctcatcaaca caactgggg attccggcca aaaagactca gcttcaagct cttcaacatc     960
caggtcaagg aggtcacgca gaatgaaggc accaagacca tcgccaataa ccttaccagc    1020
acgattcagg tatttacgga ctcggaatac cagctgccat acgtcctcgg ctccgcgcac    1080
cagggctgcc tgcctccgtt cccggcggac gtcttcatga ttccccagta cggctacctt    1140
acactgaaca atggaagtca agccgtaggc cgttcctcct tctactgcct ggaatatttt    1200
ccttctcaaa tgctgagaac gggcaacaac tttgagttca gctaccagtt tgaggacgtg    1260
ccttttcaca gcagctacgc gcacagccaa agcctggacc ggctgatgaa ccccctcatc    1320
gaccagtacc tgtactacct gtctcggact cagtccacgg gaggtaccgc aagaactcag    1380
cagttgctat ttctcaggc cgggcctaat acaatggcca atcaggcaaa gaactggctg    1440
ccaggaccct gttaccgcca acaacgcgtc tcaacgacaa ccgggcaaaa caacaatagc    1500
aactctgcct ggactgctgg gaccaaatac catctgaatg gaagaaattc attggctaat    1560
```

| | |
|---|---|
| cctggcatcg ctatggcaac acacaaagac gacgaggagc gttttttccc cagtaacggg | 1620 |
| atcctgattt ttggcaaaca aaatgctgcc agagacaatg cggattacag cgatgtcatg | 1680 |
| ctcaccagcg aggaagaaat caaaaccact aaccctgtgg ctacagagga atacggtatc | 1740 |
| gtggcagata acttgcagca gcaaaacacg gctcctcaaa ttggaactgt caacagccag | 1800 |
| ggggccttac ccggtatggt ctggcagaac cgggacgtgt acctgcaggg tcccatctgg | 1860 |
| gccaagattc ctcacacgga cggcaacttc cacccatctc cgctgatggg cggctttggc | 1920 |
| ctgaaacatc ctccgcctca gatcctgatc aagaacacgc ctgtacctgc ggatcctccg | 1980 |
| accaccttca accagtcaaa gctgaactct ttcatcacgc aatacagcac cggacaggtc | 2040 |
| agcgtggaaa ttgaatggga gctacagaag gaaaacagca agcgctggaa ccccgagatc | 2100 |
| cagtacacct ccaactacta caaatctaca agtgtggact tgctgttaa tacagaaggc | 2160 |
| gtgtactctg aaccccgccc cattggcacc cgttacctca cccgtaatct gtaa | 2214 |

<210> SEQ ID NO 2
<211> LENGTH: 2214
<212> TYPE: DNA
<213> ORGANISM: Artificial Sequence
<220> FEATURE:
<223> OTHER INFORMATION: Synthetic Polynucleotide

<400> SEQUENCE: 2

| | |
|---|---|
| atggctgccg atggttatct tccagattgg ctcgaggaca acctctctga gggcattcgc | 60 |
| gagtggtggg cgctgaaacc tggagccccg aagcccaaag ccaaccagca aaagcaggac | 120 |
| gacggccggg gtctggtgct tcctggctac aagtacctcg gacccttcaa cggactcgac | 180 |
| aagggggagc ccgtcaacgc ggcggacgca gcggccctcg agcacgacaa ggcctacgac | 240 |
| cagcagctca aagcgggtga caatccgtac ctgcggtata accacgccga cgccgagttt | 300 |
| caggagcgtc tgcaagaaga tacgtctttt gggggcaacc tcgggcgagc agtcttccag | 360 |
| gccaagaagc gggttctcga acctctcggt ctggttgagg acggcgctaa gacggctcct | 420 |
| ggaaagaaga gaccagtaga gcagtcaccc caagaaccag actcctcctc gggcatcggc | 480 |
| aagaaaggcc aacagcccgc cagaaaaaga ctcaattttg ccagactggc gactcagag | 540 |
| tcagttccag cccctcaacc tctcggagaa cctccagcaa ccccgctgc tgtgggacct | 600 |
| actacaatgg cttcaggcgg tggcgcacca atggcagaca taacgaagg cgccgacgga | 660 |
| gtgggtagtt cctcgggaaa ttggcattgc gattccacat ggctgggcga cagagtcatc | 720 |
| accaccagca cccgaacctg gcccctgccc acctacaaca accacctcta caagcaaatc | 780 |
| tccaacggga catcggagg agccaccaac acaacacct acttcggcta cagcaccccc | 840 |
| tgggggtatt ttgactttaa cagattccac tgccactttt caccacgtga ctggcagcga | 900 |
| ctcatcaaca caactggg attccggccc aagagactca gcttcaagct cttcaacatc | 960 |
| caggtcaagg aggtcacgca gaatgaaggc accaagacca tcgccaataa cctcaccagc | 1020 |
| accatccagg tgtttacgga ctcggagtac cagctgccgt acgttctcgg ctctgcccac | 1080 |
| cagggctgcc tgcctccgtt cccggcggac gtgttcatga ttccccagta cggctaccta | 1140 |
| acactcaaca acggtagtca ggccgtggga cgctcctcct ctactgcct ggaatacttt | 1200 |
| ccttcgcaga tgctgagaac cggcaacaac ttccagttta cttacacctt cgaggacgtg | 1260 |
| cctttccaca gcagctacgc ccacagccag agcttggacc ggctgatgaa tcctctgatt | 1320 |
| gaccagtacc tgtactactt gtctcggact caaacaacag gaggcacggc aaatacgcag | 1380 |
| actctgggct tcagccaagg tgggcctaat acaatggcca atcaggcaaa gaactggctg | 1440 |

```
ccaggaccct gttaccgcca acaacgcgtc tcaacgacaa ccgggcaaaa caacaatagc    1500
aactttgcct ggactgctgg gaccaaatac catctgaatg gaagaaattc attggctaat    1560
cctggcatcg ctatggcaac acacaaggac gacgaggagc gttttttttcc cagtaacggg   1620 atcctgattt ttggcaaaca aaatgctgcc agagacaatg cggattacag cgatgtcatg    1680
ctcaccagcg aggaagaaat caaaaccact aaccctgtgg ctacagagga atacggtatc    1740
gtggcagata acttgcagca gcaaaacacg gctcctcaaa ttggaactgt caacagccag    1800
ggggccttac ccggtatggt ctggcagaac cgggacgtgt acctgcaggg tcccatctgg    1860
gccaagattc tcacacggga cggcaacttc cacccgtctc cgctgatggg cggctttggc    1920
ctgaaacatc ctccgcctca gatcctgatc aagaacacgc ctgtacctgc ggatcctccg    1980
accaccttca accagtcaaa gctgaactct ttcatcacgc aatacagcac cggacaggtc    2040
agcgtggaaa tcgagtggga gctgcagaaa gaaaacagca agcgctggaa ccccgagatc    2100
cagtacacct ccaactacta caaatctaca aatgtggact tgctgtcaa cacgagggg     2160 gtttatagcg agcctcgccc cattggcacc cgttacctca cccgcaacct gtaa          2214
```

<210> SEQ ID NO 3
<211> LENGTH: 2211
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (715)..(715)
<223> OTHER INFORMATION: n is a, c, g, or t

<400> SEQUENCE: 3

```
atggctgccg atggttatct tccagattgg ctcgaggaca acctctctga gggcattcgc     60
gagtggtggg cgctgaaacc tggagccccg aagcccaaag ccaaccagca aaagcaggac    120
gacggccggg gtctggtgct tcctggctac aagtaccctcg accccttcaa cggactcgac   180 aaggggggagc ccgtcaacgc ggcggacgca gcggcccctcg agcacgacaa ggcctacgac   240
cagcagctca aagcgggtga caatccgtac ctgcggtata accacgccga cgccgagttt    300
caggagcgtc tgcaagaaga tacgtctttt ggggggcaacc tcgggcgagc agtcttccag    360
gccaagaagc gggttctcga acctctcggt ctggttgagg aaggcgctaa gacggctcct    420
ggaaagaaac gtccggtaga gcagtcgcca aagagccag ctcctcctc gggcatcggc      480 aagcacaggcc agcagcccgc taaaaagagg ctcaattttg gtcagactgg cgactcagag    540
tcagtccccg acccacaacc tctcggagaa cctccagcaa ccccgctgc tgtgggacct     600 actacaatgg cttcaggcgg tggcgcacca atggcagaca taacgaagg cgccgacgga     660 gtgggtaatg cctcaggaaa ttggcattgc gattccacat ggctgggcga cagantcatc    720
accaccagca cccgaacatg gccttgccc acctataaca accacctcta caagcaaatc     780
tccagtgctt caacgggggc cagcaacgac aaccactact tcggctacag caccccctgg    840
gggtattttg atttcaacag attccactgc catttctcac cacgtgactg gcagcgactc     900
atcaacaaca attggggatt ccggcccaag agactcaact tcaagctctt caacatccaa    960
gtcaaggagg tcacgcagaa tgaaggcacc aagaccatcg ccaataacct caccagcacc   1020
atccaggtgt ttacggactc ggagtaccag ctgccgtacg ttctcggctc tgcccaccag    1080
ggctgcctgc ctccgttccc ggcggacgtg ttcatgattc cccagtacgg ctacctaaca   1140
```

| | |
|---|---|
| ctcaacaacg gtagtcaggc cgtgggacgc tcctccttct actgcctgga atattttcca | 1200 |
| tctcaaatgc tgcgaactgg aaacaatttt gaattcagct acaccttcga ggacgtgcct | 1260 |
| ttccacagca gctacgcaca cagccagagc ttggaccgac tgatgaatcc tctcatcgac | 1320 |
| cagtacctgt actacttgtc tcggactcaa acaacaggag gcacggcaaa tacgcagact | 1380 |
| ctgggcttca gccaaggtgg gcctaataca atggccaatc aggcaaagaa ctggctgcca | 1440 |
| ggaccctgtt accgccaaca acgcgtctca acgacaaccg gcaaaacaa caatagcaac | 1500 |
| tttgcctgga ctgctgggac caaataccat ctgaatggaa gaaattcatt ggctaatcct | 1560 |
| ggcatcgcta tggcaacaca caaagacgac gaggagcgtt tttttcccag taacgggatc | 1620 |
| ctgattttg gcaaacaaaa tgctgccaga gacaatgcgg attacagcga tgtcatgctc | 1680 |
| accagcgagg aagaaatcaa aaccactaac cctgtggcta cagaggaata cggtatcgtg | 1740 |
| gcagataact tgcagcagca aaacacggct cctcaaattg gaactgtcaa cagccagggg | 1800 |
| accttacccg gtatggtctg gcagaaccgg gacgtgtacc tgcagggtcc catctgggcc | 1860 |
| aagattcctc acacggacgg caacttccac ccgtctccgc tgatgggcgg ctttggcctg | 1920 |
| aaacatcctc cgcctcagat cctgatcaag aacacgcctg tacctgcgga tcctccgacc | 1980 |
| accttcaacc agtcaaagct gaactctttc atcacgcaat acagcaccgg acaggtcagc | 2040 |
| gtggaaattg aatgggagct acagaaggaa aacagcaagc gctggaaccc cgagatccag | 2100 |
| tacacctcca attactacaa atctacaagt gtggactttg ctgttaatac agaaggcgtg | 2160 |
| tactctgaac cccgccccat tggcacgcgt ttcctcaccc gtaatctgta a | 2211 |

<210> SEQ ID NO 4
<211> LENGTH: 2214
<212> TYPE: DNA
<213> ORGANISM: Artificial Sequence
<220> FEATURE:
<223> OTHER INFORMATION: Synthetic Polynucleotide

<400> SEQUENCE: 4

| | |
|---|---|
| atggctgccg atggttatct tccagattgg ctcgaggaca acctctctga gggcattcgc | 60 |
| gagtggtggg cgctgaaacc tggagccccg aagcccaaag ccaaccagca aaagcaggac | 120 |
| gacggccggg gtctggtgct tcctggctac aagtacctcg gacccttcaa cggactcgac | 180 |
| aaggggagc ccgtcaacgc ggcggacgca gcggccctcg agcacgacaa ggcctacgac | 240 |
| cagcagctca aagcgggtga caatccgtac ctgcggtata accacgccga cgccgagttt | 300 |
| caggagcgtc tgcaagaaga tacgtctttt gggggcaacc tcgggcgagc agtcttccag | 360 |
| gccaagaagc gggttctcga acctctcggt ctggttgagg aaggcgctaa gacggctcct | 420 |
| ggaaagaaac gtccggtaga gcagtcgcca aagagccag actcctcctc gggcatcggc | 480 |
| aagacaggcc agcagcccgc taaaaagagg ctcaattttg gccagactgg cgactcagag | 540 |
| tcagttccag accctcaacc tctcggagaa cctccagcag cgccctctgg tgtgggacct | 600 |
| aatacaatgg ctgcaggcgg tggcgcacca atggcagaca taacgaagg cgccgacgga | 660 |
| gtgggtagtt cctcgggaaa ttggcattgc gattccacat ggctgggcga cagagtcatc | 720 |
| accaccagca cccgaacctg ggccctgccc acctacaaca accacctcta caagcaaatc | 780 |
| tccaacggga catcgggagg agccaccaac gacaacacct acttcggcta cagcaccccc | 840 |
| tgggggtatt ttgactttaa cagattccac tgccactttt caccgcgtga ctggcagcga | 900 |
| ctcatcaaca caactggggg attccggccc aagagactgc gcttcaagct cttcaacatc | 960 |
| caggtcaagg aggtcacgca gaatgaaggc accaagacca tcgccaataa cctcaccagc | 1020 |

```
accatccagg tgtttacgga ctcggagtac cagctgccgt acgtactagg atccgctcac   1080
cagggatgtc tgcctccgtt cccggcggac gtgttcatga ttccccagta cggctaccta   1140
acactcaaca acggtagtca ggccgtggga cgctcctcct tctactgcct ggaatatttt   1200
ccatctcaga tgctgagaac gggcaataac tttaccttca gctacacctt cgaggacgtg   1260
cctttccaca gcagctatgc ccacagccag agcttggacc ggctgatgaa tcctctgatt   1320
gaccagtacc tgtactactt gtctcggact caaacaacag gaggcacggc aaatacgcag   1380
actctgggct tcagccaagg tgggcctaat acaatggcca atcaggcaaa gaactggctg   1440
ccaggaccct gttaccgcca acaacgcgtc tcaacgacaa ccgggcaaaa caacaatagc   1500
aactttgcct ggactgctgg gaccaaatac catctgaatg aagaaattc attggctaat    1560 cctggcatcg ctatgcaac acacaaagac gacgaggagc gttttttcc cagtaacggg     1620 atcctgattt ttggcaaaca aaatgctgcc agagacaatg cggattacag cgatgtcatg   1680
ctcaccagcg aggaagaaat caaaaccact aaccctgtgg ctacagagga atacggtatc   1740
gtggcagata acttgcagca gcaaaacacg gctcctcaaa ttggaactgt caacagccag   1800
ggggccttac ccggtatggt ctggcagaac cgggacgtgt acctgcaggg tcccatctgg   1860
gccaagattc ctcacacgga cggcaacttc cacccgtctc cgctaatggg aggatttgga   1920
ctgaagcacc cacctcctca gatcctgatc aagaacacgc cggtacctgc ggatcctccg   1980
accaccttca accagtcaaa gctgtactct ttcatcacgc aatacagcac cggacaggtc   2040
agcgtggaaa ttgaatggga gctgcagaag gaaaacagca agcgctggaa ccccgagatc   2100
caatacacct ccaactacta caatctaca agtgtggact ttgctgttaa tacagaaggc    2160
gtgtactctg aaccccgccc cattggcacc cgttacctca cccgtaatct gtaa          2214

<210> SEQ ID NO 5
<211> LENGTH: 737
<212> TYPE: PRT
<213> ORGANISM: Artificial Sequence
<220> FEATURE:
<223> OTHER INFORMATION: Synthetic Polypeptide

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65              70                  75                  80

Gln Gln Leu Lys Ala Gly Asp Asn Pro Tyr Leu Arg Tyr Asn His Ala
                85                  90                  95

Asp Val Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
```

-continued

```
            145                 150                 155                 160
        Lys Lys Gly Gln Gln Pro Ala Arg Lys Arg Leu Asn Phe Gly Gln Thr
                        165                 170                 175
        Gly Asp Ser Glu Ser Val Pro Asp Pro Gln Pro Leu Gly Glu Pro Pro
                        180                 185                 190
        Ala Ala Pro Ser Gly Val Gly Pro Asn Thr Met Ala Gly Gly Gly
                        195                 200                 205
        Ala Pro Met Ala Asp Asn Asn Glu Gly Ala Asp Gly Val Gly Asn Ser
                        210                 215                 220
        Ser Gly Asn Trp His Cys Asp Ser Thr Trp Met Gly Asp Arg Val Ile
        225                 230                 235                 240
        Thr Thr Ser Thr Arg Thr Trp Ala Leu Pro Thr Tyr Asn Asn His Leu
                        245                 250                 255
        Tyr Lys Gln Ile Ser Asn Gly Thr Ser Gly Ser Thr Asn Asp Asn
                        260                 265                 270
        Thr Tyr Phe Gly Tyr Ser Thr Pro Trp Gly Tyr Phe Asp Phe Asn Arg
                        275                 280                 285
        Phe His Cys His Phe Ser Pro Arg Asp Trp Gln Arg Leu Ile Asn Asn
                        290                 295                 300
        Asn Trp Gly Phe Arg Pro Lys Arg Leu Ser Phe Lys Leu Phe Asn Ile
        305                 310                 315                 320
        Gln Val Lys Glu Val Thr Gln Asn Glu Gly Thr Lys Thr Ile Ala Asn
                        325                 330                 335
        Asn Leu Thr Ser Thr Ile Gln Val Phe Thr Asp Ser Glu Tyr Gln Leu
                        340                 345                 350
        Pro Tyr Val Leu Gly Ser Ala His Gln Gly Cys Leu Pro Pro Phe Pro
                        355                 360                 365
        Ala Asp Val Phe Met Ile Pro Gln Tyr Gly Tyr Leu Thr Leu Asn Asn
                        370                 375                 380
        Gly Ser Gln Ala Val Gly Arg Ser Ser Phe Tyr Cys Leu Glu Tyr Phe
        385                 390                 395                 400
        Pro Ser Gln Met Leu Arg Thr Gly Asn Asn Phe Glu Phe Ser Tyr Gln
                        405                 410                 415
        Phe Glu Asp Val Pro Phe His Ser Ser Tyr Ala His Ser Gln Ser Leu
                        420                 425                 430
        Asp Arg Leu Met Asn Pro Leu Ile Asp Gln Tyr Leu Tyr Tyr Leu Ser
                        435                 440                 445
        Arg Thr Gln Ser Thr Gly Gly Thr Ala Arg Thr Gln Gln Leu Leu Phe
                        450                 455                 460
        Ser Gln Ala Gly Pro Asn Thr Met Ala Asn Gln Ala Lys Asn Trp Leu
        465                 470                 475                 480
        Pro Gly Pro Cys Tyr Arg Gln Gln Arg Val Ser Thr Thr Thr Gly Gln
                        485                 490                 495
        Asn Asn Asn Ser Asn Ser Ala Trp Thr Ala Gly Thr Lys Tyr His Leu
                        500                 505                 510
        Asn Gly Arg Asn Ser Leu Ala Asn Pro Gly Ile Ala Met Ala Thr His
                        515                 520                 525
        Lys Asp Asp Glu Glu Arg Phe Phe Pro Ser Asn Gly Ile Leu Ile Phe
                        530                 535                 540
        Gly Lys Gln Asn Ala Ala Arg Asp Asn Ala Asp Tyr Ser Asp Val Met
        545                 550                 555                 560
        Leu Thr Ser Glu Glu Glu Ile Lys Thr Thr Asn Pro Val Ala Thr Glu
                        565                 570                 575
```

```
Glu Tyr Gly Ile Val Ala Asp Asn Leu Gln Gln Gln Asn Thr Ala Pro
            580                 585                 590
Gln Ile Gly Thr Val Asn Ser Gln Gly Ala Leu Pro Gly Met Val Trp
            595                 600                 605
Gln Asn Arg Asp Val Tyr Leu Gln Gly Pro Ile Trp Ala Lys Ile Pro
            610                 615                 620
His Thr Asp Gly Asn Phe His Pro Ser Pro Leu Met Gly Gly Phe Gly
625                 630                 635                 640
Leu Lys His Pro Pro Gln Ile Leu Ile Lys Asn Thr Pro Val Pro
            645                 650                 655
Ala Asp Pro Pro Thr Thr Phe Asn Gln Ser Lys Leu Asn Ser Phe Ile
            660                 665                 670
Thr Gln Tyr Ser Thr Gly Gln Val Ser Val Glu Ile Glu Trp Glu Leu
            675                 680                 685
Gln Lys Glu Asn Ser Lys Arg Trp Asn Pro Glu Ile Gln Tyr Thr Ser
            690                 695                 700
Asn Tyr Tyr Lys Ser Thr Ser Val Asp Phe Ala Val Asn Thr Glu Gly
705                 710                 715                 720
Val Tyr Ser Glu Pro Arg Pro Ile Gly Thr Arg Tyr Leu Thr Arg Asn
            725                 730                 735
Leu

<210> SEQ ID NO 6
<211> LENGTH: 737
<212> TYPE: PRT
<213> ORGANISM: Artificial Sequence
<220> FEATURE:
<223> OTHER INFORMATION: Synthetic Polypeptide

<400> SEQUENCE: 6

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Lys Pro
            20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Leu Glu His Asp Lys Ala Tyr Asp
65              70                  75                  80
Gln Gln Leu Lys Ala Gly Asp Asn Pro Tyr Leu Arg Tyr Asn His Ala
            85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Asp Gly Ala Lys Thr Ala Pro Gly Lys Lys Arg
    130                 135                 140
Pro Val Glu Gln Ser Pro Gln Glu Pro Asp Ser Ser Gly Ile Gly
145                 150                 155                 160
Lys Lys Gly Gln Gln Pro Ala Arg Lys Arg Leu Asn Phe Gly Gln Thr
            165                 170                 175
Gly Asp Ser Glu Ser Val Pro Asp Pro Gln Pro Leu Gly Glu Pro Pro
            180                 185                 190
```

```
Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Ser Ser
        210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Ala Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Ala Asn Thr Gln Thr Leu Gly Phe
        450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
            500                 505                 510

Asn Gly Arg Asn Ser Leu Ala Asn Pro Gly Ile Ala Met Ala Thr His
        515                 520                 525

Lys Asp Asp Glu Glu Arg Phe Phe Pro Ser Asn Gly Ile Leu Ile Phe
530                 535                 540

Gly Lys Gln Asn Ala Ala Arg Asp Asn Ala Asp Tyr Ser Asp Val Met
545                 550                 555                 560

Leu Thr Ser Glu Glu Glu Ile Lys Thr Thr Asn Pro Val Ala Thr Glu
            565                 570                 575

Glu Tyr Gly Ile Val Ala Asp Asn Leu Gln Gln Asn Thr Ala Pro
        580                 585                 590

Gln Ile Gly Thr Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
```

```
                610                 615                 620
His Thr Asp Gly Asn Phe His Pro Ser Pro Leu Met Gly Gly Phe Gly
625                 630                 635                 640

Leu Lys His Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
                660                 665                 670

Thr Gln Tyr Ser Thr Gly Gln Val Ser Val Glu Ile Glu Trp Glu Leu
                675                 680                 685

Gln Lys Glu Asn Ser Lys Arg Trp Asn Pro Glu Ile Gln Tyr Thr Ser
                690                 695                 700

Asn Tyr Tyr Lys Ser Thr Asn Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 7
<211> LENGTH: 736
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (239)..(239)
<223> OTHER INFORMATION: Xaa can be any naturally occurring amino acid

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
                50                  55                  60

Val Asn Ala Ala Asp Ala Ala Leu Glu His Asp Lys Ala Tyr Asp
65              70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
                130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
                195                 200                 205

Ala Pro Met Ala Asp Asn Asn Glu Gly Ala Asp Gly Val Gly Asn Ala
```

```
              210                 215                 220
Ser Gly Asn Trp His Cys Asp Ser Thr Trp Leu Gly Asp Arg Xaa Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
                275                 280                 285

His Cys His Phe Ser Pro Arg Asp Trp Gln Arg Leu Ile Asn Asn Asn
                290                 295                 300

Trp Gly Phe Arg Pro Lys Arg Leu Asn Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
                340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
                370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Ser Arg
                435                 440                 445

Thr Gln Thr Thr Gly Gly Thr Ala Asn Thr Gln Thr Leu Gly Phe Ser
                450                 455                 460

Gln Gly Gly Pro Asn Thr Met Ala Asn Gln Ala Lys Asn Trp Leu Pro
465                 470                 475                 480

Gly Pro Cys Tyr Arg Gln Gln Arg Val Ser Thr Thr Thr Gly Gln Asn
                485                 490                 495

Asn Asn Ser Asn Phe Ala Trp Thr Ala Gly Thr Lys Tyr His Leu Asn
                500                 505                 510

Gly Arg Asn Ser Leu Ala Asn Pro Gly Ile Ala Met Ala Thr His Lys
                515                 520                 525

Asp Asp Glu Glu Arg Phe Phe Pro Ser Asn Gly Ile Leu Ile Phe Gly
                530                 535                 540

Lys Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ala Asp Asn Leu Gln Gln Gln Asn Thr Ala Pro Gln
                580                 585                 590

Ile Gly Thr Val Asn Ser Gln Gly Thr Leu Pro Gly Met Val Trp Gln
                595                 600                 605

Asn Arg Asp Val Tyr Leu Gln Gly Pro Ile Trp Ala Lys Ile Pro His
                610                 615                 620

Thr Asp Gly Asn Phe His Pro Ser Pro Leu Met Gly Gly Phe Gly Leu
625                 630                 635                 640
```

```
Lys His Pro Pro Gln Ile Leu Ile Lys Asn Thr Pro Val Pro Ala
            645                 650                 655

Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Ser Val Asp Phe Ala Val Asn Thr Glu Gly Val
705                 710                 715                 720

Tyr Ser Glu Pro Arg Pro Ile Gly Thr Arg Phe Leu Thr Arg Asn Leu
                725                 730                 735

<210> SEQ ID NO 8
<211> LENGTH: 737
<212> TYPE: PRT
<213> ORGANISM: Artificial Sequence
<220> FEATURE:
<223> OTHER INFORMATION: Synthetic Polypeptide

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Pro Asn Thr Met Ala Ala Gly Gly Gly
        195                 200                 205

Ala Pro Met Ala Asp Asn Asn Glu Gly Ala Asp Gly Val Gly Ser Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ala Thr Asn Asp Asn
            260                 265                 270
```

```
Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Arg Thr Gln Thr Thr Gly Gly Thr Ala Asn Thr Gln Thr Leu Gly Phe
            450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
            500                 505                 510

Asn Gly Arg Asn Ser Leu Ala Asn Pro Gly Ile Ala Met Ala Thr His
            515                 520                 525

Lys Asp Asp Glu Glu Arg Phe Phe Pro Ser Asn Gly Ile Leu Ile Phe
530                 535                 540

Gly Lys Gln Asn Ala Ala Arg Asp Asn Ala Asp Tyr Ser Asp Val Met
545                 550                 555                 560

Leu Thr Ser Glu Glu Glu Ile Lys Thr Thr Asn Pro Val Ala Thr Glu
                565                 570                 575

Glu Tyr Gly Ile Val Ala Asp Asn Leu Gln Gln Asn Thr Ala Pro
            580                 585                 590

Gln Ile Gly Thr Val Asn Ser Gln Gly Ala Leu Pro Gly Met Val Trp
            595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Tyr Ser Phe Ile
            660                 665                 670

Thr Gln Tyr Ser Thr Gly Gln Val Ser Val Glu Ile Glu Trp Glu Leu
            675                 680                 685
```

| | | | | | | | | | | | |
|---|---|---|---|---|---|---|---|---|---|---|---|
| Gln | Lys | Glu | Asn | Ser | Lys | Arg | Trp | Asn | Pro | Glu | Ile | Gln | Tyr | Thr | Ser |
| | 690 | | | | 695 | | | | 700 | | |

Gln Lys Glu Asn Ser Lys Arg Trp Asn Pro Glu Ile Gln Tyr Thr Ser
    690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 9
<211> LENGTH: 2208
<212> TYPE: DNA
<213> ORGANISM: Artificial Sequence
<220> FEATURE:
<223> OTHER INFORMATION: Synthetic Polynucleotide

<400> SEQUENCE: 9

| | |
|---|---|
| atggctgccg atggttatct tccagattgg ctcgaggaca acctctctga gggcattcgc | 60 |
| gagtggtggg acttgaaacc tggagccccg aaacccaaag ccaaccagca aaagcaggac | 120 |
| gacggccggg gtctggtgct tcctggctac aagtacctcg gacccttcaa cggactcgac | 180 |
| aaggggagc cgtcaacgc ggcggatgca gcggccctcg agcacgacaa agcctacgac | 240 |
| cggcagctcg acagcggaga caacccgtac ctcaagtaca accacgccga cgcggagttt | 300 |
| caggagcgcc ttaaagaaga tacgtctttt gggggcaacc tcggacgagc agtcttccag | 360 |
| gccaagaaga gggttctcga accttttggt ctggttgagg aaggtgctaa gacggctcct | 420 |
| ggaaagaaac gtccggtaga gcagtcgcca aagagccag actcctcctc gggcattggc | 480 |
| aagacaggcc agcagcccgc taaaaagaga ctcaattttg gtcagactgg cgactcagag | 540 |
| tcagtccccg acccacaacc tctcggagaa cctccagcaa cccccgctgc tgtgggacct | 600 |
| actacaatgg cttcaggtgg tggcgcacca gtggcagaca taacgaagg cgccgacgga | 660 |
| gtgggtagtt cctcgggaaa ttggcattgc gattccacat ggctgggcga cagagtcatc | 720 |
| accaccagca cccgaacatg ggccttgccc acctataaca accacctcta caagcaaatc | 780 |
| tccagtgctt cgacggggc cagcaacgac aaccactact cggctacag cacccccctgg | 840 |
| gggtattttg atttcaacag gttccactgc catttctcac cacgtgactg gcagcgactc | 900 |
| atcaacaaca attggggatt ccggcccaaa agactcaact tcaagctgtt caacatccag | 960 |
| gtcaaggaag tcacgacgaa cgaaggcacc aagaccatcg ccataatct caccagcacc | 1020 |
| gtgcaggtct ttacggactc ggagtaccag ttaccgtacg tgctaggatc cgctcaccag | 1080 |
| ggatgtctgc ctccgttccc ggcggacgtc ttcatggttc ctcagtacgg ctatttaact | 1140 |
| ttaaacaatg gaagccaagc cctgggacgt tcctccttct actgtctgga gtatttccca | 1200 |
| tcgcagatgc tgagaacggg caacaacttt acctttagct acaccttcga ggacgtgcct | 1260 |
| ttccacagca gctacgcgca gccagagc ctggacaggc tgatgaatcc cctcatcgac | 1320 |
| cagtacctgt actacctggt cagaacgcaa acgactggaa ctggagggac gcagactctg | 1380 |
| gcattcagcc aagcgggtcc tagctcaatg gccaaccagg ctagaaattg ggtgcccgga | 1440 |
| ccttgctacc ggcagcagcg cgtctccacg acaaccaacc agaacaacaa cagcaacttt | 1500 |
| gcctggacgg gagctgccaa gtttaagctg aacggccgag actctctaat gaatccgggc | 1560 |
| gtggcaatgg cttcccacaa ggatgacgac gaccgcttct tcccttcgag cggggtcctg | 1620 |
| attttttggca gcaaggagc cgggaacgat ggagtggatt acagccaagt gctgattaca | 1680 |
| gatgaggaag aaatcaaggc taccaacccc gtggccacag aagaatatgg agcagtggcc | 1740 |

-continued

| | |
|---|---|
| atcaacaacc aggccgccaa tacgcaggcg cagaccggac tcgtgcacaa ccaggggtg | 1800 |
| attcccggca tggtgtggca gaatagagac gtgtacctgc agggtcccat ctgggccaaa | 1860 |
| attcctcaca cggacggcaa cttttcaccc gtctccctga tgggcggctt tggactgaag | 1920 |
| cacccgcctc ctcaaattct catcaagaac acaccggttc cagcggaccc gccgcttacc | 1980 |
| ttcaaccagg ccaagctgaa ctctttcatc acgcagtaca gcaccggaca ggtcagcgtg | 2040 |
| gaaatcgagt gggagctgca gaaagaaaac agcaaacgct ggaatccaga gattcaatac | 2100 |
| acttccaact actacaaatc tacaaatgtg gactttgctg tcaacacgga gggggtttat | 2160 |
| agcgagcctc gccccattgg caccgttac ctcacccgca acctgtaa | 2208 |

<210> SEQ ID NO 10
<211> LENGTH: 2211
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (337)..(337)
<223> OTHER INFORMATION: n is a, c, g, or t

<400> SEQUENCE: 10

| | |
|---|---|
| atggctgccg atggttatct tccagattgg ctcgaggaca ctctctctga aggaataaga | 60 |
| cagtggtgga agctcaaacc tggcccacca ccaccaaagc ccgcagagcg cataaggac | 120 |
| gacagcaggg gtcttgtgct tcctggctac aagtacctcg acccttcaa cggactcgac | 180 |
| aagggggagc ccgtcaacgc ggcggacgca gcgaccctcg agcacgacaa ggcctacgac | 240 |
| cagcagctca aagcgggtga caatccgtac ctgcggtata accacgccga cgccgagttt | 300 |
| caggagcgtc tgcaagaaga tacgtctttt gggggcnacc tcgggcgagc agtcttccag | 360 |
| gccaagaagc gggttctcga acctctcggt ctggttgagg aagctgctaa gacggctcct | 420 |
| ggaaagaaga gaccagtaga gccatcaccc cagcgttctc cagactcctc tacgggcatc | 480 |
| ggcaagaaag ccaacagcc cgccagaaaa agactcaatt ttggtcagac tggcgactca | 540 |
| gagtcagttc cagaccctca acctctcgga gaacctccag cagcgccctc tggtgtggga | 600 |
| cctaatacaa tggctgcagg cggtggcgca ccaatggcag acaataacga aggcgccgac | 660 |
| ggagtgggta gttcctcggg aaattggcat tgcgattcca catggctggg cgacagagtc | 720 |
| atcaccacca gcacccgaac ctgggccctg cccacctaca acaaccacct ctacaagcaa | 780 |
| atctccagtg cttcaacggg ggccagcaac gacaaccact acttcggcta cagcacccc | 840 |
| tgggggtatt ttgatttcaa cagattccac tgccatttct caccacgtga ctggcagcga | 900 |
| ctcatcaaca caattggggg attccggccc aagagactca acttcaagct cttcaacatc | 960 |
| caagtcaagg aggtcacgac gaatgatggc gtcacgacca tcgctaataa ccttaccagc | 1020 |
| acggttcaag tcttctcgga ctcagactat cagctcccgt acgtgctcgg tcggctcac | 1080 |
| gagggctgcc tcccgccgtt cccagcggac gtttcatga ttcctcagta cggctattta | 1140 |
| actttaaaca atggaagcca agccctggga cgttcctcct tctactgtct ggagtatttc | 1200 |
| ccatcgcaga tgctgagaac cggcaacaac tttcagttca gctacacctt cgaggacgtg | 1260 |
| cctttccaca gcagctacgc gcacagccag agcctggaca ggctgatgaa tcccctcatc | 1320 |
| gaccagtacc tgtactacct ggtcagaacg caaacgactg gaactggagg gacgcagact | 1380 |
| ctggcattca gccaagcggg tcctagctca atggccaacc aggctagaaa ttgggtgccc | 1440 |
| ggaccttgct accggcagca gcgcgtctcc acgacaacca accagaacaa caacagcaac | 1500 |

```
tttgcctgga cgggagctgc caagtttaag ctgaacggcc gagactctct aatgaatccg   1560
ggcgtggcaa tggcttccca caaggatgac gacgaccgct tcttcccttc gagcggggtc   1620 ctgattttg gcaagcaagg agccgggaac gatggagtgg attacagcca agtgctgatt    1680
acagatgagg aagaaatcaa ggctaccaac cccgtagcca cagaagaata tggagcagtg   1740
gccatcaaca accaggccgc caatacgcag gcgcagaccg gactcgtgca caaccagggg   1800
gtgattcccg gaatggtgtg gcaagacaga gacgtatacc tgcagggtcc tatttgggcc   1860
aaaattcctc acacggatgg acactttcac ccgtctcctc tcatgggcgg ctttggactt   1920 aagcaccccgc ctcctcagat cctcatcaaa aacacgcctg ttcctgcgaa tcctccggca  1980
gagttttcgg ctacaaagtt tgcttcattc atcacccagt attccacagg acaagtgagc   2040
gtggagattg aatgggagct gcagaaagaa aacagcaaac gctggaatcc gaagtgcag    2100 tatacatcta actatgcaaa atctgccaac gttgatttca ctgtggacaa caatggactt   2160
tatactgagc ctcgccccat tggcacccgt tacctcaccc gtcccctgta a             2211
```

<210> SEQ ID NO 11
<211> LENGTH: 2214
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (335)..(335)
<223> OTHER INFORMATION: n is a, c, g, or t

<400> SEQUENCE: 11

```
atgactgacg gttaccttcc agattggcta gaggacaacc tctctgaagg cgttcgagag    60
tggtgggcgc tgcaacctgg agccccgaag cccaaagcca accagcaaaa gcaggacgac   120
ggccggggtc tggtgcttcc tggctacaag tacctcggac ccttcaacgg actcgacaag   180
ggggagcccg tcaacgcggc ggacgcagcg ccctcgagc acgacaaggc ctacgaccag    240
cagctcaaag cgggtgacaa tccgtacctg cggtataacc acgccgacgc cgagtttcag   300
gagcgtctgc aagaagatac gtcttttggg ggcancctcg ggcgagcagt cttccaggcc   360
aagaagcggg ttctcgaacc tctcggtctg gttgaggaag cgctaagac ggctcctgga    420 aagaaacgtc cggtagagcc atcacccccag cgttctccag actcctctac gggcatcggc   480
aagaaaggcc aacagcccgc cagaaaaaga ctcaattttg gtcagactgg cgactcagag   540
tcagttccag accctcaacc tctcggagaa cctccagcag cgcccctcagg tgtgggatct   600 cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc    840 tgggggtatt ttgacttcaa cagattccac tgccactct caccacgtga ctggcagcga    900
ctcatcaaca caactggggg attccggccc aagagactca gcttcaagct cttcaacatc   960
caggtcaagg aggtcacgca gaatgaaggc accaagacca tcgccaataa cctcaccagc  1020
accatccagg tgtttacgga ctcggagtac cagctgccgt acgttctcgg ctctgcccac  1080
cagggctgcc tgcctccgtt cccggcgac gtgttcatga ttcccagta cggctaccta   1140 acactcaaca acggtagtca ggccgtggga cgctcctcct tctactgcct ggaatacttt  1200
```

```
ccttcgcaga tgctgagaac cggcaacaac ttccagttta cttacacctt cgaggacgtg    1260
cctttccaca gcagctacgc ccacagccag agcttggacc ggctgatgaa tcctctgatt    1320
gaccagtacc tgtactactt gtctcggact caaacaacag gaggcacggc aaatacgcag    1380
actctgggct tcagccaagg tgggcctaat acaatggcca atcaggcaaa gaactggctg    1440
ccaggaccct gttaccgcca caacgcgtc tcaacgacaa ccgggcaaaa caacaatagc    1500
aactttgcct ggactgctgg gaccaaatac catctgaatg gaagaaattc attggctaat    1560
cctggcatcg ctatggcaac acacaaagac gacgaggagc gttttttcc cagtaacggg    1620 atcctgattt ttggcaaaca aaatgctgcc agagacaatg cggattacag cgatgtcatg    1680
ctcaccagcg aggaagaaat caaaaccact aaccctgtgg ctacagagga atacggtatc    1740
gtggcagata acttgcagca gcaaaacacg gctcctcaaa ttggaactgt caacagccag    1800
ggggccttac ccggtatggt ctggcagaac cgggacgtgt acctgcaggg tcccatctgg    1860
gccaagattc ctcacacgga cggcaacttc cacccgtctc cgctgatggg cggctttggc    1920
ctgaaacatc ctccgcctca gatcctgatc aagaacacgc ctgtacctgc ggatcctccg    1980
accaccttaa accaggccaa gctgaactct ttcatcacgc aatacagcac cggacaggtc    2040
agcgtggaaa ttgaatggga gctgcagaag gaaaacagca gcgctggaa cccagagatt    2100 cagtacactt caaactacta caaatctaca aatgtggact tgctgtcaa tacagaggga    2160 acttatagtg aaccccgccc cattggcacc agatttctga ctcgtaatct gtaa          2214

<210> SEQ ID NO 12
<211> LENGTH: 2211
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (338)..(338)
<223> OTHER INFORMATION: n is a, c, g, or t

<400> SEQUENCE: 12
atggctgccg atggttatct tccagattgg ctcgaggaca ctctctctga aggaataaga     60
cagtggtgga agctcaaacc tggcccacca ccaccaaagc ccgcagagcg gcataaggac    120
gacagcaggg gtcttgtgct tcctgggtac aagtacctcg gcccttcaa cggactcgac    180 aaggggagc ccgtcaacgc ggcggacgca gcggccctcg agcacgacaa ggcctacgac    240
cagcagctcg aagcgggtga caatccgtac ctgcggtata accacgccga cgccgagttt    300
caggagcgtc tgcaagaaga tacgtctttt gggggcancc tcgggcgagc agtcttccag    360
gccaagaagc gggttctcga acctctcggt ctggttgagg aaggcgctaa gacggctcct    420
ggaaagaaga gaccagtaga gcagtcaccc caagaaccag actcctcctc gggcatcggc    480
aggaaaggcc aacagcccgc cagaaaaaga ctcaatttg ccagactgg cgactcagag    540 tcagttccag accctcaacc tctcggagaa cctccagcag cgccctctgg tgtgggacct    600
aatacaatgg cttcaggcgg tggcgctcca atggcagaca taacgaagg cgccgacgga    660 gtgggtaatg cctcaggaaa ttggcattgc gattccacat ggctgggcga cagagtcatc    720
accaccagca cccgcacctg gccttgcccc acctacaata accacctcta caagcaaatc    780
tccagtgctt caacgggggc cagcaacgac aaccactact cggctacag cacccctgg    840 gggtattttg atttcaacag attccactgc cactttcac cacgtgactg gcagcgactc    900
atcaacaaca ttggggatt ccggcccaag agactcaact tcaaactctt caacatccag    960
```

-continued

```
gtcaaggagg tcacgcagaa tgaaggcact aagaccatcg ccaataacct taccagcacg    1020
attcaggtat ttacggactc ggaataccag ctgccgtacg tcctcggctc cgcgcaccag    1080
ggctgcctgc ctccgttccc ggcggacgtc ttcatgattc cccagtacgg ctaccttaca    1140
ctgaacaatg gaagtcaagc cgtaggccgt cctccttct actgcctgga atattttcca    1200
tctcaaatgc tgcgaactgg caacaacttc cagtttacct acaccttcga ggacgtgcct    1260
ttccacagca gctacgccca cagccagagc ttggaccggc tgatgaatcc tctgattgac    1320
cagtacctgt actacttgtc tcggactcag tccacaggag gaactcaagg tacccagcaa    1380
ttgttatttt ctcaagctgg gcctgcaaac atgtcggctc aggctaagaa ctggctacct    1440
ggaccttgct accggcagca gcgagtctct acgacactgt cgcaaaacaa caacagcaac    1500
tttgcttgga ctggtgccac caaatatcac ctgaacggaa gagactcttt ggtaaatccc    1560
ggtgtcgcca tggcaaccca aaggacgac gaggaacgct tcttcccgtc gagtggagtc    1620
ctgatgtttg gaaaacaggg tgctggaaga gacaatgtgg actacagcag cgttatgcta    1680
accagcgaag aagaaattaa aaccactaac cctgtagcca cagaacaata cggtgtggtg    1740
gttgataact tgcagcaaac caatacgggg cctattgtgg gaaatgtcaa cagccaagga    1800
gccttacctg gtatggtctg gcagaaccgg gacgtgtacc tgcagggtcc catctgggcc    1860
aagattcctc acacggacgg caacttccac ccgtctccgc tgatgggcgg ctttggcctg    1920
aaacatcctc cgcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a             2211
```

<210> SEQ ID NO 13
<211> LENGTH: 735
<212> TYPE: PRT
<213> ORGANISM: Artificial Sequence
<220> FEATURE:
<223> OTHER INFORMATION: Synthetic Polypeptide

<400> SEQUENCE: 13

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140
```

```
Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
            165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Val Ala Asp Asn Asn Glu Gly Ala Asp Gly Val Gly Ser Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Glu Gly Thr Lys Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Val Pro Gln Tyr Gly Tyr Leu Thr Leu Asn Asn Gly
    370                 375                 380

Ser Gln Ala Leu Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Val Arg
            435                 440                 445

Thr Gln Thr Thr Gly Thr Gly Gly Thr Gln Thr Leu Ala Phe Ser Gln
            450                 455                 460

Ala Gly Pro Ser Ser Met Ala Asn Gln Ala Arg Asn Trp Val Pro Gly
465                 470                 475                 480

Pro Cys Tyr Arg Gln Gln Arg Val Ser Thr Thr Thr Asn Gln Asn Asn
                485                 490                 495

Asn Ser Asn Phe Ala Trp Thr Gly Ala Ala Lys Phe Lys Leu Asn Gly
            500                 505                 510

Arg Asp Ser Leu Met Asn Pro Gly Val Ala Met Ala Ser His Lys Asp
            515                 520                 525

Asp Asp Asp Arg Phe Phe Pro Ser Ser Gly Val Leu Ile Phe Gly Lys
    530                 535                 540

Gln Gly Ala Gly Asn Asp Gly Val Asp Tyr Ser Gln Val Leu Ile Thr
545                 550                 555                 560
```

Asp Glu Glu Glu Ile Lys Ala Thr Asn Pro Val Ala Thr Glu Glu Tyr
            565                 570                 575

Gly Ala Val Ala Ile Asn Asn Gln Ala Ala Asn Thr Gln Ala Gln Thr
        580                 585                 590

Gly Leu Val His Asn Gln Gly Val Ile Pro Gly Met Val Trp Gln Asn
        595                 600                 605

Arg Asp Val Tyr Leu Gln Gly Pro Ile Trp Ala Lys Ile Pro His Thr
        610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asp
                645                 650                 655

Pro Pro Leu Thr Phe Asn Gln Ala Lys Leu Asn Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Tyr Lys Ser Thr Asn Val Asp Phe Ala Val Asn Thr Glu Gly Val Tyr
705                 710                 715                 720

Ser Glu Pro Arg Pro Ile Gly Thr Arg Tyr Leu Thr Arg Asn Leu
                725                 730                 735

<210> SEQ ID NO 14
<211> LENGTH: 736
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (113)..(113)
<223> OTHER INFORMATION: Xaa can be any naturally occurring amino acid

<400> SEQUENCE: 14

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Thr Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Xaa Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

```
Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
            210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asn
            370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
            405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
            435                 440                 445

Arg Thr Gln Thr Thr Gly Thr Gly Gly Thr Gln Thr Leu Ala Phe Ser
            450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
            515                 520                 525

Asp Asp Asp Asp Arg Phe Phe Pro Ser Ser Gly Val Leu Ile Phe Gly
            530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590
```

```
Thr Gly Leu Val His Asn Gln Gly Val Ile Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735
```

<210> SEQ ID NO 15
<211> LENGTH: 737
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (112)..(112)
<223> OTHER INFORMATION: Xaa can be any naturally occurring amino acid

<400> SEQUENCE: 15

```
Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln Lys Gln Asp Asp Gly Arg Gly Leu Val Leu Pro Gly
            35                  40                  45

Tyr Lys Tyr Leu Gly Pro Phe Asn Gly Leu Asp Lys Gly Glu Pro Val
50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Arg Tyr Asn His Ala Asp
            85                  90                  95

Ala Glu Phe Gln Glu Arg Leu Gln Glu Asp Thr Ser Phe Gly Gly Xaa
            100                 105                 110

Leu Gly Arg Ala Val Phe Gln Ala Lys Lys Arg Val Leu Glu Pro Leu
            115                 120                 125

Gly Leu Val Glu Glu Gly Ala Lys Thr Ala Pro Gly Lys Lys Arg Pro
            130                 135                 140

Val Glu Pro Ser Pro Gln Arg Ser Pro Asp Ser Ser Thr Gly Ile Gly
145                 150                 155                 160

Lys Lys Gly Gln Gln Pro Ala Arg Lys Arg Leu Asn Phe Gly Gln Thr
            165                 170                 175

Gly Asp Ser Glu Ser Val Pro Asp Pro Gln Pro Leu Gly Glu Pro Pro
            180                 185                 190

Ala Ala Pro Ser Gly Val Gly Ser Leu Thr Met Ala Ser Gly Gly Gly
            195                 200                 205
```

```
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Asn Ser Thr Ser Gly Ser Ser Asn Asp Asn
                260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Ser Phe Lys Leu Phe Asn Ile
305                 310                 315                 320
Gln Val Lys Glu Val Thr Gln Asn Glu Gly Thr Lys Thr Ile Ala Asn
                325                 330                 335
Asn Leu Thr Ser Thr Ile Gln Val Phe Thr Asp Ser Glu Tyr Gln Leu
            340                 345                 350
Pro Tyr Val Leu Gly Ser Ala His Gln Gly Cys Leu Pro Pro Phe Pro
        355                 360                 365
Ala Asp Val Phe Met Ile Pro Gln Tyr Gly Tyr Leu Thr Leu Asn Asn
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Thr Tyr Thr
                405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Arg Thr Gln Thr Thr Gly Gly Thr Ala Asn Thr Gln Thr Leu Gly Phe
    450                 455                 460
Ser Gln Gly Gly Pro Asn Thr Met Ala Asn Gln Ala Lys Asn Trp Leu
465                 470                 475                 480
Pro Gly Pro Cys Tyr Arg Gln Gln Arg Val Ser Thr Thr Thr Gly Gln
                485                 490                 495
Asn Asn Asn Ser Asn Phe Ala Trp Thr Ala Gly Thr Lys Tyr His Leu
            500                 505                 510
Asn Gly Arg Asn Ser Leu Ala Asn Pro Gly Ile Ala Met Ala Thr His
        515                 520                 525
Lys Asp Asp Glu Glu Arg Phe Phe Pro Ser Asn Gly Ile Leu Ile Phe
    530                 535                 540
Gly Lys Gln Asn Ala Ala Arg Asp Asn Ala Asp Tyr Ser Asp Val Met
545                 550                 555                 560
Leu Thr Ser Glu Glu Glu Ile Lys Thr Thr Asn Pro Val Ala Thr Glu
            565                 570                 575
Glu Tyr Gly Ile Val Ala Asp Asn Leu Gln Gln Gln Asn Thr Ala Pro
        580                 585                 590
Gln Ile Gly Thr Val Asn Ser Gln Gly Ala Leu Pro Gly Met Val Trp
    595                 600                 605
Gln Asn Arg Asp Val Tyr Leu Gln Gly Pro Ile Trp Ala Lys Ile Pro
610                 615                 620
```

```
His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
            645                 650                 655

Ala Asp Pro Pro Thr Thr Leu Asn Gln Ala Lys Leu Asn Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
690                 695                 700

Asn Tyr Tyr Lys Ser Thr Asn Val Asp Phe Ala Val Asn Thr Glu Gly
705                 710                 715                 720

Thr Tyr Ser Glu Pro Arg Pro Ile Gly Thr Arg Phe Leu Thr Arg Asn
            725                 730                 735

Leu

<210> SEQ ID NO 16
<211> LENGTH: 736
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (113)..(113)
<223> OTHER INFORMATION: Xaa can be any naturally occurring amino acid

<400> SEQUENCE: 16

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Glu Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Xaa Leu Gly Arg Ala Val Phe Gln Ala Lys Lys Arg Val Leu Glu Pro
    115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Arg Lys Gly Gln Gln Pro Ala Arg Lys Arg Leu Asn Phe Gly Gln Thr
            165                 170                 175

Gly Asp Ser Glu Ser Val Pro Asp Pro Gln Pro Leu Gly Glu Pro Pro
        180                 185                 190

Ala Ala Pro Ser Gly Val Gly Pro Asn Thr Met Ala Ser Gly Gly Gly
    195                 200                 205

Ala Pro Met Ala Asp Asn Asn Glu Gly Ala Asp Gly Val Gly Asn Ala
210                 215                 220
```

```
Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
        450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
            485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Val Ala Met Ala Thr His Lys
            515                 520                 525

Asp Asp Glu Glu Arg Phe Phe Pro Ser Ser Gly Val Leu Met Phe Gly
530                 535                 540

Lys Gln Gly Ala Gly Arg Asp Asn Val Asp Tyr Ser Ser Val Met Leu
545                 550                 555                 560

Thr Ser Glu Glu Glu Ile Lys Thr Thr Asn Pro Val Ala Thr Glu Gln
            565                 570                 575

Tyr Gly Val Val Val Asp Asn Leu Gln Gln Thr Asn Thr Gly Pro Ile
        580                 585                 590

Val Gly Asn Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
```

```
                    645                 650                 655
Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 17
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 17
gtctcatgct attgcttcgc atcgtcagac                                    30

<210> SEQ ID NO 18
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 18
gcaggagtct tcggtgcagt ttgttacgca                                    30

<210> SEQ ID NO 19
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 19
tgattggact agtcgtggga gttagcatgc                                    30

<210> SEQ ID NO 20
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 20
ttatctggcg tgtaggcagc ggcctcagac                                    30

<210> SEQ ID NO 21
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 21
ttatacgact catatgtggc atacgtcgtg                                    30

<210> SEQ ID NO 22

```
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 22
ggagccgagg aagacttgtc cggggactgg                               30

<210> SEQ ID NO 23
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 23
gccggggtgt tggtctttgt ctacgatggc                               30

<210> SEQ ID NO 24
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 24
gggtcgttag cgtcctcctg attcgtattc                               30

<210> SEQ ID NO 25
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 25
ttattgttgt ttggcgtgtt gtgtgccttt                               30

<210> SEQ ID NO 26
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 26
tcgtccttcg cgtgcgggta cgtttctgga                               30

<210> SEQ ID NO 27
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 27
ttctatgcgt gttacgcaga agctgttgaa                               30

<210> SEQ ID NO 28
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 28
```
gccttcgctt actgcgaatt gggatattta                                30

<210> SEQ ID NO 29
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 29
gtctgggcat cttactcatg ttgatggtcc                                30

<210> SEQ ID NO 30
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 30
gatgactgag cctatgtgga tgcattgtcc                                30

<210> SEQ ID NO 31
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 31
gacgttgcct aatcgtagta cgacgcctcg                                30

<210> SEQ ID NO 32
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 32
ggatcttgat actaatatta attattgtgt                                30

<210> SEQ ID NO 33
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 33
gcggtctgcg ttgtcgttga ttaggattgg                                30

<210> SEQ ID NO 34
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 34
gcatgcgaac cttttgttgg ctagtaggac                                30

<210> SEQ ID NO 35
<211> LENGTH: 30
<212> TYPE: DNA

<210> SEQ ID NO 35
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 35
ggttgcggcg cgggggactg gtcattagaa                                30

<210> SEQ ID NO 36
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 36
tgtgaaggtt atgctgcctt agagttttaa                                30

<210> SEQ ID NO 37
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 37
ggagcggtat atttgtggtc atcttacgca                                30

<210> SEQ ID NO 38
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 38
tctggctcat gcgaagttgc tggctcgggt                                30

<210> SEQ ID NO 39
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 39
gacggatagg gatgctccgc ttcatcagac                                30

<210> SEQ ID NO 40
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 40
gcctgttcct gagactcagc aggattagct                                30

<210> SEQ ID NO 41
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 41
gtctgggctt cagtattgtt ggtttctgca                                30

```
<210> SEQ ID NO 42
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 42
ttcgtcgtat gcgaggcctc cggatgagat                                          30

<210> SEQ ID NO 43
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 43
gtggccgcat gaggattaga agactaggac                                          30

<210> SEQ ID NO 44
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 44
gtggccgcat gaggattaga agactag                                             27

<210> SEQ ID NO 45
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 45
tcgtctgcat cttgatgctg atcttcctag                                          30

<210> SEQ ID NO 46
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 46
tcatgcgatt cctagtagtc ctggtccgtc                                          30

<210> SEQ ID NO 47
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 47
ttctgtttgg tgtgctttga atactgagtc                                          30

<210> SEQ ID NO 48
<211> LENGTH: 30
<212> TYPE: DNA
<213> ORGANISM: Artificial Sequence
<220> FEATURE:
```

<223> OTHER INFORMATION: Synthetic Polynucleotide

<400> SEQUENCE: 48
tgcgggtagt tcgtagttgc cgacgaagag                                                30

<210> SEQ ID NO 49
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 49
ggatggtccg tcgctgagga atcctccgtg                                                30

<210> SEQ ID NO 50
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 50
taagcagcct cgggttcgga agcgtgggga                                                30

<210> SEQ ID NO 51
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 51
gcctcagctt tgtcctgctg cgccggcgta                                                30

<210> SEQ ID NO 52
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 52
ggcgcagttt ccgatggatc agtgttgttt                                                30

<210> SEQ ID NO 53
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 53
tcggatgcag ttgagtcgtt agctgtgga                                                 29

<210> SEQ ID NO 54
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 54
ttatgttcgg gatgcgcggt atacggatta                                                30

```
<210> SEQ ID NO 55
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 55
tcagcgtccg gctacgccta ctagtaagca                              30

<210> SEQ ID NO 56
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 56
tttttattct tggtggccgg tggagcggca                              30

<210> SEQ ID NO 57
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 57
gatatctgct cgtatgaggc ctccttggtg                              30

<210> SEQ ID NO 58
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 58
ggtgcctcag agtcctgttt ttcgtactcg                              30

<210> SEQ ID NO 59
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 59
gacttcttat cattcgtcgc gtagtgatgc                              30

<210> SEQ ID NO 60
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 60
ttggtgggag taggcgtgtt ctgggactct                              30

<210> SEQ ID NO 61
<211> LENGTH: 30
<212> TYPE: DNA
<213> ORGANISM: Artificial Sequence
<220> FEATURE:
<223> OTHER INFORMATION: Synthetic Polynucleotide
```

```
<400> SEQUENCE: 61
tatttatcat ctgtagttta aggctattat                               30

<210> SEQ ID NO 62
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 62
ttcgcatagg cgtaatttgc gtctgactcc                               30

<210> SEQ ID NO 63
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 63
tacttagact tgtctgaggg tgccgcgtaa                               30

<210> SEQ ID NO 64
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 64
gcttttgcgg atttatccgg ttaatacggc                               30

<210> SEQ ID NO 65
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 65
tcgtcgtcgg acgcgggttg cggggtctat                               30

<210> SEQ ID NO 66
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 66
tagtgtacgc agttgtcggc gcttagtag                                29

<210> SEQ ID NO 67
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 67
tgatcggagt tatattcgtg cggcgccgt                                29

<210> SEQ ID NO 68
<211> LENGTH: 30
```

```
<212> TYPE: DNA
<213> ORGANISM: Artificial Sequence
<220> FEATURE:
<223> OTHER INFORMATION: Synthetic Polynucleotide

<400> SEQUENCE: 68
tgtgccgttt ggtagttagg atctggggtc                                30

<210> SEQ ID NO 69
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 69
tgctgatatt attgggatga gtcttactg                                 29

<210> SEQ ID NO 70
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 70
gccgaagaag actcatatgt cggggtcgag                                30

<210> SEQ ID NO 71
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 71
taggtctagg tctgggactc attagtagga                                30

<210> SEQ ID NO 72
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 72
tacgcgtcct agtctgggtt cgtggatgag                                30

<210> SEQ ID NO 73
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 73
ggtgctgggt acgaagccgt ctacgcttcc                                30

<210> SEQ ID NO 74
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 74
```
tattccttat tcttgggaga ttagtaagtc                                               30

<210> SEQ ID NO 75
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 75
tcagacgaat cagaagtatg gttagtagca                                               30

<210> SEQ ID NO 76
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 76
tgcttagtat aatctgatgc gtacgtcgta                                               30

<210> SEQ ID NO 77
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 77
tcatggtgag cggaatacat gctacgagtg t                                             31

<210> SEQ ID NO 78
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 78
gctgagtttg gttatttcgg tttgggctac                                               30

<210> SEQ ID NO 79
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 79
taatatggtg gcgcgggagg ttcggatggc                                               30

<210> SEQ ID NO 80
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 80
gctgatgccg cttaggacgc aggttccgag                                               30

<210> SEQ ID NO 81
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 81
ggagttgcgg ttggcgtttg gttagttgcg         30

<210> SEQ ID NO 82
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 82
taggatgccg tagttttctt agcgggcgc          29

<210> SEQ ID NO 83
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 83
gggtaagggt tggcttcggg ctgtttcggt         30

<210> SEQ ID NO 84
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 84
gtatagtttg aagtatgata gtgcggggtt t        31

<210> SEQ ID NO 85
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 85
gcatcggagt agtctgtagc agctgtcgca         30

<210> SEQ ID NO 86
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 86
tagtccgacg cctgtggtta attttcttac         30

<210> SEQ ID NO 87
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 87
ttctgatcat gcgacgaggg cgaagactag         30

-continued

<210> SEQ ID NO 88
<211> LENGTH: 738
<212> TYPE: PRT
<213> ORGANISM: Artificial Sequence
<220> FEATURE:
<223> OTHER INFORMATION: Synthetic Polypeptide

<400> SEQUENCE: 88

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365
```

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
                435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
                515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
                595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 89
<211> LENGTH: 736
<212> TYPE: PRT
<213> ORGANISM: Artificial Sequence
<220> FEATURE:
<223> OTHER INFORMATION: Synthetic Polypeptide

```
<400> SEQUENCE: 89

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415
```

```
Glu Val Pro Phe His Ser Ser Tyr Ala His Ser Gln Ser Leu Asp
    420                 425                 430

Arg Leu Met Asn Pro Leu Ile Asp Gln Tyr Leu Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 90
<211> LENGTH: 735
<212> TYPE: PRT
<213> ORGANISM: Artificial Sequence
<220> FEATURE:
<223> OTHER INFORMATION: Synthetic Polypeptide

<400> SEQUENCE: 90

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Ala Glu Arg His Lys Asp Asp Ser Arg Gly Leu Val Leu Pro
            35                  40                  45
```

```
Gly Tyr Lys Tyr Leu Gly Pro Phe Asn Gly Leu Asp Lys Gly Glu Pro
 50                  55                  60

Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
        130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460
```

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
    595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 91
<211> LENGTH: 724
<212> TYPE: PRT
<213> ORGANISM: Artificial Sequence
<220> FEATURE:
<223> OTHER INFORMATION: Synthetic Polypeptide

<400> SEQUENCE: 91

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
            85                  90                  95

```
Ala Glu Phe Gln Glu Lys Leu Ala Asp Asp Thr Ser Phe Gly Gly Asn
                100                 105                 110
Leu Gly Lys Ala Val Phe Gln Ala Lys Lys Arg Val Leu Glu Pro Phe
            115                 120                 125
Gly Leu Val Glu Glu Gly Ala Lys Thr Ala Pro Thr Gly Lys Arg Ile
        130                 135                 140
Asp Asp His Phe Pro Lys Arg Lys Lys Ala Arg Thr Glu Glu Asp Ser
145                 150                 155                 160
Lys Pro Ser Thr Ser Ser Asp Ala Glu Ala Gly Pro Ser Gly Ser Gln
                165                 170                 175
Gln Leu Gln Ile Pro Ala Gln Pro Ala Ser Ser Leu Gly Ala Asp Thr
            180                 185                 190
Met Ser Ala Gly Gly Gly Gly Pro Leu Gly Asp Asn Asn Gln Gly Ala
        195                 200                 205
Asp Gly Val Gly Asn Ala Ser Gly Asp Trp His Cys Asp Ser Thr Trp
210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
            260                 265                 270
Phe Asp Phe Asn Arg Phe His Ser His Trp Ser Pro Arg Asp Trp Gln
        275                 280                 285
Arg Leu Ile Asn Asn Tyr Trp Gly Phe Arg Pro Arg Ser Leu Arg Val
        290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
            340                 345                 350
Leu Pro Ala Phe Pro Pro Gln Val Phe Thr Leu Pro Gln Tyr Gly Tyr
        355                 360                 365
Ala Thr Leu Asn Arg Asp Asn Thr Glu Asn Pro Thr Glu Arg Ser Ser
        370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
            420                 425                 430
Gln Tyr Leu Tyr Arg Phe Val Ser Thr Asn Asn Thr Gly Gly Val Gln
        435                 440                 445
Phe Asn Lys Asn Leu Ala Gly Arg Tyr Ala Asn Thr Tyr Lys Asn Trp
450                 455                 460
Phe Pro Gly Pro Met Gly Arg Thr Gln Gly Trp Asn Leu Gly Ser Gly
465                 470                 475                 480
Val Asn Arg Ala Ser Val Ser Ala Phe Ala Thr Thr Asn Arg Met Glu
                485                 490                 495
Leu Glu Gly Ala Ser Tyr Gln Val Pro Pro Gln Pro Asn Gly Met Thr
            500                 505                 510
Asn Asn Leu Gln Gly Ser Asn Thr Tyr Ala Leu Glu Asn Thr Met Ile
```

```
                515                 520                 525
Phe Asn Ser Gln Pro Ala Asn Pro Gly Thr Thr Ala Thr Tyr Leu Glu
530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
            595                 600                 605

Ala Lys Ile Pro Glu Thr Gly Ala His Phe His Pro Ser Pro Ala Met
            610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
                660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
            690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 92
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 92

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160
```

```
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Thr Pro Ala Ala Val Gly Pro Thr Thr Met Ala Ser Gly Gly Gly
        195                 200                 205
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
                260                 265                 270
Tyr Phe Gly Tyr Ser Thr Pro Trp Gly Tyr Phe Asp Phe Asn Arg Phe
            275                 280                 285
His Cys His Phe Ser Pro Arg Asp Trp Gln Arg Leu Ile Asn Asn Asn
        290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
                340                 345                 350
Tyr Val Leu Gly Ser Ala His Gln Gly Cys Leu Pro Pro Phe Pro Ala
            355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Asp Val Pro Phe His Ser Ser Tyr Ala His Ser Gln Ser Leu Asp
                420                 425                 430
Arg Leu Met Asn Pro Leu Ile Asp Gln Tyr Leu Tyr Tyr Leu Asn Arg
            435                 440                 445
Thr Gln Asn Gln Ser Gly Ser Ala Gln Asn Lys Asp Leu Leu Phe Ser
    450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
                500                 505                 510
Gly Arg Glu Ser Ile Ile Asn Pro Gly Thr Ala Met Ala Ser His Lys
            515                 520                 525
Asp Asp Lys Asp Lys Phe Phe Pro Met Ser Gly Val Met Ile Phe Gly
    530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
```

```
Phe Gly Thr Val Ala Val Asn Leu Gln Ser Ser Thr Asp Pro Ala
            580                 585                 590

Thr Gly Asp Val His Val Met Gly Ala Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

<210> SEQ ID NO 93
<211> LENGTH: 737
<212> TYPE: PRT
<213> ORGANISM: Artificial Sequence
<220> FEATURE:
<223> OTHER INFORMATION: Synthetic Polypeptide

<400> SEQUENCE: 93

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205
```

```
Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225             230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
                260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
        450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
```

```
                625                 630                 635                 640
Leu Lys His Pro Pro Gln Ile Leu Ile Lys Asn Thr Pro Val Pro
                645                 650                 655
Ala Asn Pro Pro Glu Val Phe Thr Pro Ala Lys Phe Ala Ser Phe Ile
                660                 665                 670
Thr Gln Tyr Ser Thr Gly Gln Val Ser Val Glu Ile Glu Trp Glu Leu
                675                 680                 685
Gln Lys Glu Asn Ser Lys Arg Trp Asn Pro Glu Ile Gln Tyr Thr Ser
                690                 695                 700
Asn Phe Glu Lys Gln Thr Gly Val Asp Phe Ala Val Asp Ser Gln Gly
705                 710                 715                 720
Val Tyr Ser Glu Pro Arg Pro Ile Gly Thr Arg Tyr Leu Thr Arg Asn
                725                 730                 735
Leu

<210> SEQ ID NO 94
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 94

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
                20                  25                  30
Lys Ala Asn Gln Gln His Gln Asp Asn Ala Arg Gly Leu Val Leu Pro
            35                  40                  45
Gly Tyr Lys Tyr Leu Gly Pro Gly Asn Gly Leu Asp Lys Gly Glu Pro
        50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Leu Leu Glu Pro
            115                 120                 125
Leu Gly Leu Val Glu Glu Ala Ala Lys Thr Ala Pro Gly Lys Lys Arg
        130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
                180                 185                 190
Ala Ala Pro Ser Gly Val Gly Ser Leu Thr Met Ala Ser Gly Gly Gly
            195                 200                 205
Ala Pro Val Ala Asp Asn Asn Glu Gly Ala Asp Gly Val Gly Ser Ser
        210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
```

```
Tyr Lys Gln Ile Ser Asn Ser Thr Ser Gly Gly Ser Asn Asp Asn
            260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Tyr Gln Leu
            340                 345                 350

Pro Tyr Val Leu Gly Ser Ala His Glu Gly Cys Leu Pro Phe Pro
            355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670
```

```
Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 95
<211> LENGTH: 738
<212> TYPE: PRT
<213> ORGANISM: Artificial Sequence
<220> FEATURE:
<223> OTHER INFORMATION: Synthetic Polypeptide

<400> SEQUENCE: 95

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
290                 295                 300
```

```
Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
```

```
                      725              730              735
Asn Leu

<210> SEQ ID NO 96
<211> LENGTH: 1559
<212> TYPE: DNA
<213> ORGANISM: Artificial sequence
<220> FEATURE:
<223> OTHER INFORMATION: Synthetic polynucleotide

<400> SEQUENCE: 96
acggagtggg tarttcctcg ggaaattggc attgcgattc cacatggctg ggcgacagag     60
tcatcaccac cagcacccga acctgggccc tgcccaccta caacaaccac ctctacaagc    120
aaatctccaa cgggacatcg ggaggagcca ccaacgacaa cacctacttc ggctacagca    180
ccccctgggg gtattttgay ttyaacagat tccactgcca cttytcacca cgtgactggc    240
agcgactcat caacaacaac tggggattcc ggcccaagag actcagcttc aagctcttca    300
acatccaggt caaggaggtc acgcagaatg aaggcaccaa gaccatcgcc aataacctca    360
ccagcaccat ccaggtgttt acggactcgg agtaccagct gccgtacgtt ctcggctcyg    420
cccaccaggg ctgcctgcct ccgttcccgg cggacgtgtt catgattccc cagtacggct    480
acctaacact caacaacggt agtcaggccg tgggacgctc ctccttctac tgcctggaat    540
attttccwtc tcaratgctg agaacgggca caaactttga gttcagctac accttcgagg    600
acgtgccttt ccacagcagc tacgcccaca gccagagctt ggaccggctg atgaatcctc    660
tsatygacca gtacctgtac tacttgtctc ggactcaaac aacaggaggc acggcaaata    720
cgcagactct gggcttcagc caaggtgggc ctaatacaat ggccaatcag gcaaagaact    780
ggctgccagg accctgttac cgccaacaac gcgtctcaac gacaaccggg caaaacaaca    840
atagcaactt tgcctggact gctgggacca ataccatct gaatggaaga aattcattgg    900
ctaatcctgg catcgctatg gcaacacaca aagacgacga ggagcgtttt tttcccagta    960
acgggatcct gattttggc aaacaaaatg ctgccagaga caatgcggat tacagcgatg   1020
tcatgctcac cagcgaggaa gaaatcaaaa ccactaaccc tgtggctaca gaggaatacg   1080
gtatcgtggc agataacttg cagcagcaaa acacggctcc tcaaattgga actgtcaaca   1140 gccaggggc cttacccggt atggtctggc agaaccggga cgtgtacctg cagggtccca   1200
tctgggccaa gattcctcac acggacggca acttccaccc gtctccgctg atgggcggct   1260
ttggcctgaa acatcctccg cctcagatcc tgatcaagaa cacgcctgta cctgcggatc   1320
ctccgaccac cttcaaccag tcaaagctga actctttcat cacgcaatac agcaccggac   1380
aggtcagcgt ggaaattgaa tgggagctrc agaaggaaaa cagcaagcgc tggaacccccg   1440 agatccagta cacctccaac tactacaaat ctacaagtgt ggactttgct gttaatacag   1500
aaggcgtgta ctctgaaccc cgccccattg gcacccgtta cctcacccgt aatctgtaa    1559
```